US008008525B2

(12) United States Patent
Fukatsu et al.

(10) Patent No.: US 8,008,525 B2
(45) Date of Patent: *Aug. 30, 2011

(54) RECEPTOR FUNCTION REGULATING AGENT

(75) Inventors: Kohji Fukatsu, Osaka (JP); Ryo Fujii, Osaka (JP); Makoto Kobayashi, Osaka (JP); Jinichi Yonemori, Osaka (JP); Toshio Tanaka, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 928 days.

This patent is subject to a terminal disclaimer.

(21) Appl. No.: 10/580,906

(22) PCT Filed: Nov. 26, 2004

(86) PCT No.: PCT/JP2004/017996
§ 371 (c)(1),
(2), (4) Date: May 26, 2006

(87) PCT Pub. No.: WO2005/051373
PCT Pub. Date: Jun. 9, 2005

(65) Prior Publication Data
US 2008/0167378 A1 Jul. 10, 2008

(30) Foreign Application Priority Data
Nov. 26, 2003 (JP) ................... 2003-394848

(51) Int. Cl.
*C07C 59/56* (2006.01)
(52) U.S. Cl. ........ 562/472; 562/405; 562/465; 562/470; 562/471
(58) Field of Classification Search .................. None
See application file for complete search history.

(56) References Cited

U.S. PATENT DOCUMENTS
7,238,716 B2 * 7/2007 Momose et al. ............... 514/340

FOREIGN PATENT DOCUMENTS

| | | |
|---|---|---|
| EP | 1431267 | 6/2004 |
| JP | 11-29533 | 2/1999 |
| JP | 2002-265457 | 9/2002 |
| WO | WO 97/31907 | 9/1997 |
| WO | WO 99/11255 | 3/1999 |
| WO | WO 9911255 A1 * | 3/1999 |
| WO | WO 00/64876 | 11/2000 |
| WO | WO 01/00603 | 1/2001 |
| WO | WO 01/55085 | 8/2001 |
| WO | WO 02/053547 | 7/2002 |
| WO | WO 02/067868 | 9/2002 |
| WO | WO 02067868 A2 * | 9/2002 |
| WO | WO 02/083616 | 10/2002 |
| WO | WO 03/016254 | 2/2003 |
| WO | WO 03070686 A1 * | 8/2003 |
| WO | WO 03/099793 | 12/2003 |
| WO | WO 2004/022551 | 3/2004 |
| WO | WO 2004/041266 | 5/2004 |
| WO | WO 2004/065960 | 8/2004 |
| WO | 2005/016862 | 2/2005 |
| WO | 2005/092316 | 10/2005 |
| WO | 2005/092317 | 10/2005 |

OTHER PUBLICATIONS

M.E.Wolff, in Burger's Medicinal Chemistry and Drug Discovery, 1995, pp. 975-977.*
G.S.Banker and C.T.Rhodes, in Modern Pharmaceuticals, 1996, pp. 451 and 596.*
Nihon Keizai Shimbun, Morning Paper, May 28, 2004. pp. 017 ( English Translation provided).
Holzforschung (1991), 45 (Supp., Lignin and Pulping Chemistry), 9-14 "*On the Mechanism of Formation of Non-Cycle Benzyl Ethers During Lignin Biosynthesis*".
Strehlke et al.,European Journal of Medicinal Chemistry (1979), 14(3), 238-242 "*Antifungale Imidazolverbindungen IV (I) Benzyläther von (Imidazolyläthyl)—und (Imadazolylpropyl)—phenolen*".
Genomic Drug Discovery Forum 7th Symposium, Nov. 15, 2004 and English translation thereof.
Pharmaceutical Sciences World Congress Abstracts, May 30-Jun. 3, 2004.
The Yomiuri Shimbun (Osaka), Protein that shapes life Nov. 12, 2003 and English translation thereof.
International Search Report mailed Mar. 22, 2005.
Database CA [Online] Chemical Abstracts Service, XP-002460907, Database accession No. 1983:53319 (Kuchar, et al., "Benzyloxyarylaliphatic acids: synthesis and quantitative relations between structure and anti-inflammatory activity" Collection of Czechoslovak Chemical Communications (1982), 47(9)).

* cited by examiner

*Primary Examiner* — Sudhakar Katakam
(74) *Attorney, Agent, or Firm* — Hamre, Schumann, Mueller & Larson, P.C.

(57) ABSTRACT

An agent for regulating 14273 receptor function, which is useful as a preventing or treating drug for diabetes mellitus, hyperlipidemia or the like, is provided. An agent for regulating 14273 receptor function comprising a compound containing an aromatic ring and a group capable of releasing a cation.

5 Claims, 8 Drawing Sheets

Palmitoleic acid

Linoleic acid

γ-Linolenic acid

Arachidonic acid

RECEPTOR FUNCTION REGULATING AGENT

TECHNICAL FIELD

The present invention relates to a 14273 receptor (GPR120) function regulating agent comprising a carboxylic acid containing an aromatic ring or a derivative thereof, and a novel compound having a 14273 receptor function regulating effect.

BACKGROUND ART

Description on the amino acid sequence of 14273 receptor derived from human, and DNA encoding the same amino acid sequence is described (WO 2000/00611).

From the fact that 14273 receptor knock-out mice gained weight, the pharmaceutical agents for the obesity, diabetes mellitus, and the like (WO 2002/67868).

A carboxylic acid containing an aromatic ring or a derivative thereof is known to have a variety of physiological activities.

There are known alkanoic acid derivatives which have a blood glucose reducing effect, a blood lipid reducing effect, a blood insulin reducing effect, an insulin resistance improving effect, an insulin sensitivity enhancing effect and the like, and thus are useful as a preventing and/or treating agent for diabetes mellitus, hyperlipidemia and the like (WO 2002/053547).

A useful compound as a hypoglycemic agent, a hypolipidemic agent, and a preventing and/or treating agent for diabetes mellitus, hyperlipidemia and the like, is known (WO 99/11255).

Triarylic acid derivatives useful as a preventing and/or treating agent for diabetes mellitus, hyperlipidemia and the like, are known (WO 2000/64876).

Thiazole derivatives and oxazole derivatives which are useful PPARδ agonists as an agent for prevention and/or treatment of Type I or II diabetes mellitus, hyperlipidemia and the like, are known (WO 2001/00603).

Substituted 4-hydroxy-phenylalkanoic acid derivatives, which are useful PPARδ agonists as an agent for prevention and/or treatment of Type I or II diabetes mellitus, hyperlipidemia and the like, are known (WO 97/31907).

ω-Aryl-α-substituted aliphatic acid derivatives, which are useful PPARγ agonists as an agent for improving insulin resistance, hypoglycemic, hypolipidemic, or a preventing and/or treating diabetes mellitus, hyperlipidemia and the like, are known (WO 02/083616).

Propionic acid derivatives which are useful as a preventing and/or treating agent for PPARγ-related diseases, or a preventing and/or treating agent for Type I or II diabetes mellitus, hyperlipidemia and the like, are known (JP-A No. 2000-80086).

A compound useful for the peroxidase hydrogen peroxide assay system is described (JP-A No. 11-29533).

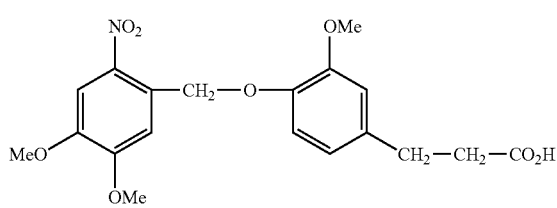

Furthermore, the following compounds are known:

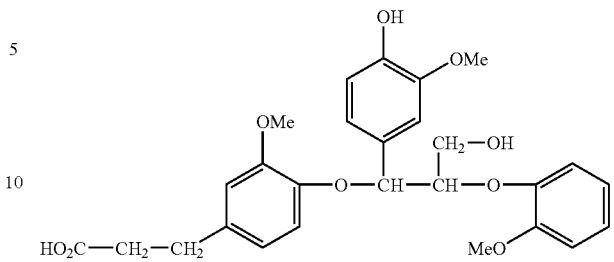

(Holzforschung (1991), 45 (Suppl., Lignin and Pulping Chemistry), 9-14. 1).

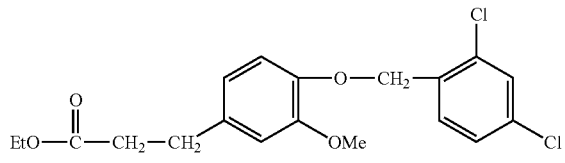

(European Journal of Medicinal Chemistry (1979), 14 (3), 238-42).

It is reported that substances stimulating GPR120 serve as drugs for overeating or obesity, while substances suppressing GPR120 have potential to be used for the treatment of anorexia (Yomiuri Shimbun (Osaka), Nov. 12, 2003, a morning paper p. 32).

DISCLOSURE OF THE INVENTION

Up to date, no low molecular weight synthetic agonist or antagonist for 14273 receptor (GPR120) has been known. Thus, development of an excellent 14273 receptor function regulating agent is highly desired.

It is an object of the present invention to provide a 14273 receptor function regulating agent which is useful as a preventing and/or treating drug for diabetes mellitus, hyperlipidemia, obesity, anorexia and the like, and a novel compound having a 14273 receptor function regulating effect.

The inventors of the invention devotedly conducted various researches, and as a result, found that a carboxylic acid containing an aromatic ring or a derivative thereof has unexpectedly excellent 14273 receptor agonist activity based on the specific chemical structure of the compound, and further has excellent properties as a medicine, such as stability and the like, thus being a safe as well as useful drug as a preventing and/or treating drug for 14273 receptor-related morbid conditions or diseases in a mammal. The invention was completed based on this finding.

Thus, the invention provides:

[1] an agent for regulating 14273 receptor function comprising a compound having an aromatic ring and a group capable of releasing a cation;

[2] the agent according to [1], wherein the compound is a carboxylic acid containing two or more aromatic rings, or a derivative thereof;

[3] the agent according to [1], wherein the compound is represented by the formula:

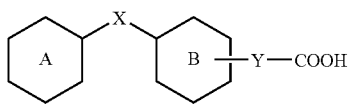
(I)

wherein ring A is an aromatic ring optionally having substituent(s); ring B is an aromatic ring optionally having substituent(s) in addition to —Y—COOH; X and Y are each a spacer; and —Y—COOH is substituted at any position on ring B, or a salt thereof or a prodrug thereof;

[4] an agent for preventing or treating diabetes mellitus, hyperlipidemia, obesity or anorexia, comprising a 14273 receptor function regulating drug having an aromatic ring and a group capable of releasing a cation;

[5] an agent for regulating stress comprising a compound having an aromatic ring and a group capable of releasing a cation;

[6] a compound represented by the formula:

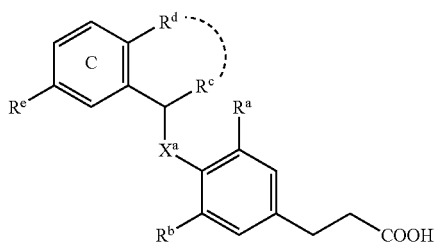
(II)

wherein $R^a$ is a hydrogen atom, a fluorine atom, a chlorine atom, a hydrocarbon group optionally having substituent(s), a heterocyclic group optionally having substituent(s), a hydroxy group optionally having substituent(s), a carboxyl group optionally having substituent(s), an acyl group, or an amino group optionally having substituent(s);

$R^b$ is a hydrogen atom, a fluorine atom, a chlorine atom, a hydrocarbon group optionally having substituent(s), a heterocyclic group optionally having substituent(s), a hydroxy group optionally having substituent(s), a carboxyl group optionally having substituent(s), an acyl group, or an amino group optionally having substituent(s), with the proviso that when one of $R^a$ and $R^b$ is a hydrogen atom, then the other should not be a hydrogen atom;

$R^c$ is a hydrogen atom, a hydrocarbon group optionally having substituent(s), or a heterocyclic group optionally having substituent(s);

$R^d$ is a hydrogen atom, a fluorine atom, a chlorine atom, a hydrocarbon group optionally having substituent(s), a heterocyclic group optionally having substituent(s), a hydroxy group optionally having substituent(s), a carboxyl group optionally having substituent(s), an acyl group, or an amino group optionally having substituent(s), or $R^c$ and $R^d$ are optionally bonded to each other to form a ring optionally having substituent(s);

$R^e$ is a hydrogen atom, a fluorine atom, a chlorine atom, a hydrocarbon group optionally having substituent(s), a heterocyclic group optionally having substituent(s), a hydroxy group optionally having substituent(s), a carboxyl group optionally having substituent(s), an acyl group, or an amino group optionally having substituent(s), with the proviso that when one of $R^d$ and $R^e$ is a hydrogen atom, then the other should not be a hydrogen atom;

$X^a$ is an oxygen atom, or a methylene group optionally having substituent(s); and ring C is a benzene ring optionally having further substituent(s), or a salt thereof, except
(i) 3,5-difluoro-4-[(2,3-dihydro-1H-inden-1-yl)oxy]benzenepropanoic acid, (ii) 3-chloro-4-[(2,3-dihydro-1H-inden-1-yl)oxy]benzenepropanoic acid, (iii) 4-([1,1'-biphenyl]-3-ylmethoxy)-3-chlorobenzenepropanoic acid, (iv) 4-[(4,5-dimethoxy-2-nitrophenyl)methoxy]-3-methoxybenzenepropanoic acid, and (v) 4-[3-hydroxy-1-(4-hydroxy-3-methoxyphenyl)-2-(2-methoxyphenoxy)propoxy]-3-methoxybenzenepropanoic acid;

[7] the compound according to [6], wherein ring C is a benzene ring represented by the formula:

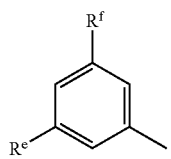

wherein $R^f$ is a hydrocarbon group optionally having substituent(s), or a hydroxy group optionally having substituent(s); and $R^e$ is a hydroxy group optionally having substituent(s);

[8] the compound according to [6], wherein $R^d$ and $R^e$ are each a hydrogen atom, a fluorine atom, a chlorine atom, an alkyl group optionally having substituent(s) free of a benzene ring, an alkenyl group optionally having substituent(s) free of a benzene ring, an alkynyl group optionally having substituent(s) free of a benzene ring, a cycloalkyl group optionally having substituent(s) free of a benzene ring, a heterocyclic group optionally having substituent(s) free of a benzene ring, an alkoxy group optionally having substituent(s) free of a benzene ring, a heterocyclyloxy group optionally having substituent(s) free of a benzene ring, a carboxyl group optionally having substituent(s) free of a benzene ring, an acyl group free of a benzene ring, or an amino group optionally having substituent(s) free of a benzene ring;

when one of $R^d$ and $R^e$ is a hydrogen atom, then the other should not be a hydrogen atom; and ring C is a benzene ring optionally having further substituent(s) free of a benzene ring;

[9] the compound according to [6], wherein at least one of $R^a$ and $R^b$ is a fluorine atom, a chlorine atom, or an alkoxy group optionally having substituent(s);

$R^c$ is a hydrogen atom;

$R^d$ and $R^e$ are each a hydrogen atom, or an alkoxy group optionally having substituent(s) free of a benzene ring;

when one of $R^d$ and $R^e$ is a hydrogen atom, then the other should not be a hydrogen atom;

$X^a$ is an oxygen atom; and ring C is a benzene ring optionally having substituent(s) free of a benzene ring;

[10] the compound according to [6], wherein at least one of $R^a$ and $R^b$ is a fluorine atom, a chlorine atom, a $C_{1-6}$ alkyl group, or a $C_{1-6}$ alkoxy group; $R^c$ is a hydrogen atom; $X^a$ is an oxygen atom; $R^d$ is a hydrogen atom; and $R^e$ is a $C_{6-14}$ aryloxy group optionally having substituent(s);

[11] the compound according to [6], wherein $R^a$ is a fluorine atom, a chlorine atom, or a $C_{1-6}$ alkoxy group;

$R^b$ is a hydrogen atom, or a fluorine atom;

$R^c$ is a hydrogen atom, or a $C_{1-6}$ alkyl group;

$X^a$ is an oxygen atom;

ring C is a benzene ring optionally having, in addition to $R^d$ and $R^e$, further substituent(s) selected from the group consisting of (i) a $C_{1-6}$ alkyl group, (ii) a hydroxy group, (iii) a $C_{1-6}$ alkoxy group optionally having substituent(s) selected from the group consisting of hydroxy, amino, $C_{1-6}$ alkoxy-carbonyl-amino, carboxy, $C_{1-6}$ alkoxy-carbonyl, carbamoyl, mono-$C_{1-6}$ alkyl-carbamoyl, di-$C_{1-6}$ alkyl-carbamoyl, tri-$C_{1-6}$ alkylsilyloxy, and a 5- to 7-membered heterocyclic group containing, in addition to carbon atom(s), 1 to 4 heteroatoms of one or two kinds selected from a nitrogen atom, a sulfur atom and an oxygen atom, (iv) a $C_{6-14}$ aryloxy group, and (v) a $C_{7-16}$ aralkyloxy group; and (1) when $R^d$ is a hydrogen atom, then $R^e$ should be (i) a hydroxy group, (ii) a $C_{1-6}$ alkoxy group optionally having substituent(s) selected from the group consisting of $C_{1-6}$ alkoxy, carboxy, $C_{1-6}$ alkoxy-carbonyl, $C_{1-6}$ alkyl-carbonyl, carbamoyl, mono-$C_{1-6}$ alkyl-carbamoyl and di-$C_{1-6}$ alkyl-carbamoyl, (iii) a $C_{2-6}$ alkynyloxy group, (iv) a $C_{3-7}$ cycloalkyloxy group, (v) a $C_{6-14}$ aryloxy group optionally having substituent(s) selected from the group consisting of a halogen atom, $C_{1-6}$ alkyl, $C_{1-6}$ alkoxy and $C_{1-6}$ alkyl-carbonyl, or (vi) a 5- to 10-membered heterocyclyl-oxy group containing, in addition to carbon atom(s), 1 to 4 heteroatoms of one or two kinds selected from a nitrogen atom, a sulfur atom and an oxygen atom;

(2) when $R^e$ is a hydrogen atom, then $R^d$ should be (i) a $C_{1-6}$ alkyl group, (ii) a $C_{6-14}$ aryl group, (iii) a $C_{1-6}$ alkoxy group optionally having substituent(s) with a 5- to 7-membered heterocyclic group containing, in addition to carbon atom(s), 1 to 4 heteroatoms of one or two kinds selected from a nitrogen atom, a sulfur atom and an oxygen atom, (iv) a $C_{3-7}$ cycloalkyloxy group, (v) a $C_{6-14}$ aryloxy group optionally having substituent(s) selected from the group consisting of a halogen atom and optionally halogenated $C_{1-6}$ alkyl, (vi) a $C_{7-16}$ aralkyloxy group, or (vii) a 5- to 7-membered heterocyclic group containing, in addition to carbon atom(s), 1 to 4 heteroatoms of one or two kinds selected from a nitrogen atom, a sulfur atom and an oxygen atom;

[12] the compound according to [6], wherein $R^a$ is a fluorine atom, a chlorine atom, or a $C_{1-6}$ alkoxy group;

$R^b$ is a hydrogen atom or a fluorine atom;

$R^c$ is a hydrogen atom;

$R^d$ is a hydrogen atom, or a $C_{6-14}$ aryl group;

$R^e$ is a hydrogen atom, a $C_{1-6}$ alkoxy group, or a $C_{6-14}$ aryloxy group;

when one of $R^d$ and $R^e$ is a hydrogen atom, then the other should not be a hydrogen atom;

$X^a$ is an oxygen atom; and ring C is a benzene ring having no substituent other than $R^d$ and $R^e$;

[13] the compound according to [7], wherein $R^f$ is (i) a $C_{1-6}$ alkyl group, (ii) a hydroxy group, (iii) a $C_{1-6}$ alkoxy group optionally having substituent(s) selected from the group consisting of hydroxy, amino, $C_{1-6}$ alkoxy-carbonyl-amino, carboxy, $C_{1-6}$ alkoxy-carbonyl, carbamoyl, mono-$C_{1-6}$ alkyl-carbamoyl, di-$C_{1-6}$ alkyl-carbamoyl, tri-$C_{1-6}$ alkylsilyloxy, and a 5- to 7-membered heterocyclic group containing, in addition to carbon atom(s), 1 to 4 heteroatoms of one or two kinds selected from a nitrogen atom, a sulfur atom and an oxygen atom, (iv) a $C_{6-14}$ aryloxy group, or (v) a $C_{7-16}$ aralkyloxy group; and $R^e$ is a $C_{1-6}$ alkoxy group, or a $C_{6-14}$ aryloxy group;

[14] 3,5-difluoro-4-[(3-phenoxyphenyl)methoxy]-benzenepropanoic acid, or 3-fluoro-4-[(3-phenoxyphenyl)methoxy]benzenepropanoic acid, or a salt thereof;

[15] 3-(4-{([3-(4-chlorophenoxy)benzyl]oxy}-3,5-difluorophenyl)propanoic acid, 3-(3,5-difluoro-4-{[3-(4-fluorophenoxy)benzyl]oxy}phenyl)propanoic acid, 3-(3,5-difluoro-4-{[3-(4-methylphenoxy)benzyl]oxy}phenyl) propanoic acid, 3-(3-fluoro-4-{[3-(2-fluorophenoxy)benzyl]oxy}phenyl)-propanoic acid, 3-(3-fluoro-4-{[3-(3-fluorophenoxy)benzyl]-oxy}phenyl)propanoic acid, 3-(3-fluoro-4-{[3-(4-fluorophenoxy)benzyl]oxy}phenyl) propanoic acid, 3-(3-fluoro-4-{[3-(4-chlorophenoxy)benzyl]oxy}phenyl)propanoic acid, 3-(3-fluoro-4-{[3-(4-methylphenoxy)benzyl]oxy}phenyl)propanoic acid, 3-{3-methyl-4-[(3-phenoxybenzyl)oxy]phenyl}propanoic acid, or 3-(4-{[3-(4-fluorophenoxy)benzyl]oxy}-3-methylphenyl) propanoic acid, or a salt thereof;

[16] a prodrug of the compound according to [6], except ethyl 4-[(2,4-dichlorophenyl)methoxy]-3-methoxybenzenepropanoate;

[17] the prodrug according to [16], which is an ester form of the carboxylic acid;

[18] a pharmaceutical agent comprising the compound according to [6], or a salt thereof, or a prodrug thereof;

[19] a method of regulating the function of 14273 receptor, comprising administering, to a mammal, an effective amount of a compound having an aromatic ring and a group capable of releasing a cation;

[20] a method of preventing or treating diabetes mellitus, hyperlipidemia, obesity or anorexia, comprising regulating the function of 14273 receptor by administering, to a mammal, an effective amount of a compound having an aromatic ring and a group capable of releasing a cation;

[21] a method of regulating stress, comprising administering, to a mammal, an effective amount of a compound having an aromatic ring and a group capable of releasing a cation;

[22] use of a compound having an aromatic ring and a group capable of releasing a cation, for the production of an agent for regulating 14723 receptor function;

[23] use of a 14273 receptor function regulating drug having an aromatic ring and a group capable of releasing a cation, for the production of an agent for the prevention or treatment of diabetes mellitus, hyperlipidemia, obesity or anorexia;

[24] use of a compound having an aromatic ring and a group capable of releasing a cation, for the production of a stress regulating agent;

[25] a method of screening for a ligand, agonist or antagonist for a 14273 receptor, comprising using a 14273 receptor, or a partial peptide thereof or a salt thereof, and a compound having an aromatic ring and a group capable of releasing a cation; and

[26] a kit for screening for a ligand, agonist or antagonist for a 14273 receptor, comprising a 14273 receptor, or a partial peptide thereof or a salt thereof, and a compound having an aromatic ring and a group capable of releasing a cation.

Furthermore, the invention provides:

[27] the agent according to [1] above, comprising a compound represented by the formula:

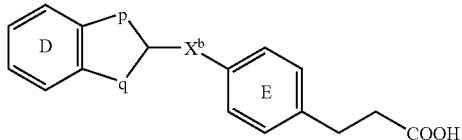

(III)

wherein ring D is a benzene ring optionally having substituent(s); ring E is a phenylene group optionally having substituent(s); $X^b$ is a spacer other than an alkylene group; and p and q are each a $C_{0-4}$ carbon chain optionally having substituent(s), or a salt thereof or a prodrug thereof;

[28] the agent according to [27] above, wherein the formula:

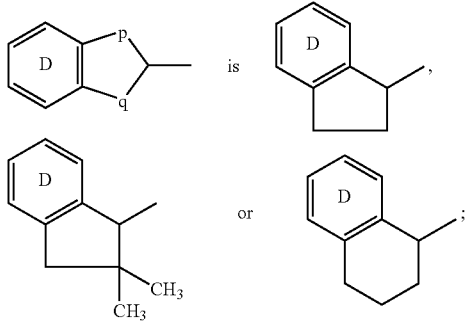

the substituent optionally possessed by ring D is (1) a halogen atom, (2) a $C_{1-6}$ alkyl group, (3) a $C_{1-6}$ alkoxy group, (4) a $C_{6-14}$ aryl group optionally substituted with a halogen atom, $C_{1-6}$ alkyl or $C_{1-6}$ alkoxy, (5) a $C_{6-14}$ aryloxy group, or (6) a $C_{7-16}$ aralkyloxy group;

the substituent optionally possessed by ring E is a halogen atom or a $C_{1-6}$ alkyl group; and the spacer represented by $X^b$ is an oxygen atom;

[29] the agent according to [1] above, which is a compound represented by the formula:

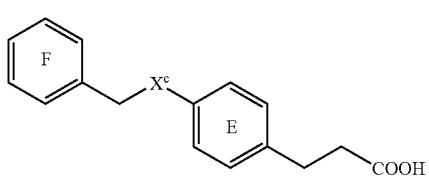

(IV)

wherein ring F is a benzene ring optionally having substituent(s); ring E is a phenylene group optionally having substituent(s); and $X^c$ is an oxygen atom or a methylene group optionally having substituent(s), or a salt thereof or a prodrug thereof;

[30] the agent according to [1] above, which is represented by the formula:

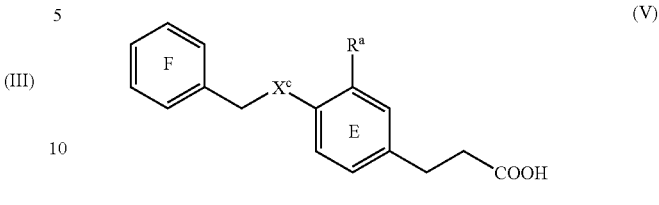

(V)

wherein $R^a$ is a hydrogen atom, a fluorine atom, a chlorine atom, a hydrocarbon group optionally having substituent(s), a heterocyclic group optionally having substituent(s), a hydroxy group optionally having substituent(s), a carboxyl group optionally having substituent(s), an acyl group, or an amino group optionally having substituent(s); and other symbols are as defined in [28] above;

[31] the agent according to [27] above, wherein the formula:

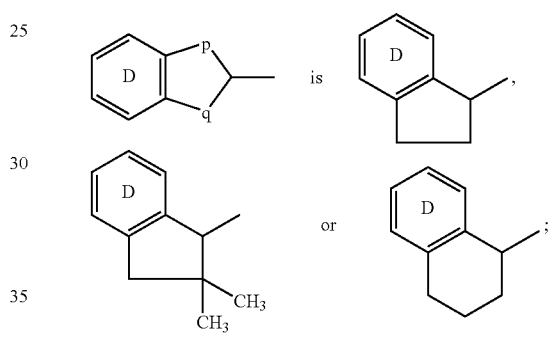

the substituent optionally possessed by ring D is a halogen atom, a $C_{1-6}$ alkyl group, or a $C_{1-6}$ alkoxy group; the substituent optionally possessed by ring E is a halogen atom; and the spacer represented by $X^b$ is an oxygen atom;

[32] the agent according to [29] above, wherein ring F is a benzene ring optionally having substituent(s) selected from the group consisting of (i) a $C_{1-6}$ alkyl group, (ii) a $C_{6-14}$ aryl group optionally having substituent(s) selected from the group consisting of $C_{1-6}$ alkyl and $C_{1-6}$ alkoxy, (iii) a hydroxy group, (iv) a $C_{1-6}$ alkoxy group optionally having substituent(s) selected from the group consisting of hydroxy, $C_{1-6}$ alkoxy, amino, $C_{1-6}$ alkoxy-carbonyl-amino, carboxy, $C_{1-6}$ alkoxy-carbonyl, $C_{1-6}$ alkyl-carbonyl, carbamoyl, mono-$C_{1-6}$ alkyl-carbamoyl, di-$C_{1-6}$ alkyl-carbamoyl, tri-$C_{1-6}$ alkylsilyloxy, and a 5- to 7-membered heterocyclic group containing, in addition to carbon atom(s), 1 to 4 heteroatoms of one or two kinds selected from a nitrogen atom, a sulfur atom and an oxygen atom, (v) a $C_{2-6}$ alkynyloxy group, (vi) a $C_{3-8}$ cycloalkyloxy group, (vii) a $C_{6-14}$ aryloxy group optionally having substituent(s) selected from the group consisting of a halogen atom, optionally halogenated $C_{1-6}$ alkyl, $C_{1-6}$ alkoxy, and $C_{1-6}$ alkyl-carbonyl, (viii) a $C_{7-16}$ aralkyloxy group, (ix) a 5- to 7-membered heterocyclyl-oxy group containing, in addition to carbon atom(s), 1 to 4 heteroatoms of one or two kinds selected from a nitrogen atom, a sulfur atom and an oxygen atom, (x) a 5- to 7-membered heterocyclic group containing, in addition to carbon atom(s), 1 to 4 heteroatoms of one or two kinds selected from a nitrogen atom, a sulfur atom and an oxygen atom, and (xi) a $C_{1-3}$ alkylenedioxy group;
ring E is a phenylene group optionally having substituent(s) selected from the group consisting of a halogen atom, $C_{1-6}$ alkyl and $C_{1-6}$ alkoxy; and
$X^c$ is an oxygen atom;

[33] the agent according to [29] above, wherein
ring F is a benzene ring optionally having substituent(s) selected from the group consisting of (i) $C_{1-6}$ alkyl, (ii) $C_{6-14}$ aryl optionally having substituent(s) selected from the group consisting of $C_{1-6}$ alkyl and $C_{1-6}$ alkoxy, (iii) $C_{7-15}$ aralkyl, (iv) $C_{1-6}$ alkoxy, and (v) $C_{6-14}$ aryloxy;
ring E is a phenylene group optionally having substituent(s) selected from a halogen atom and $C_{1-6}$ alkoxy (preferably, a halogen atom); and
$X^c$ is an oxygen atom;

[34] the agent according to [29] above, wherein $R^a$ is a hydrogen atom, a halogen atom, a $C_{1-6}$ alkyl group, or a $C_{1-6}$ alkoxy group; and other symbols are as defined in [33] above;

[35] the agent according to [29] above, wherein $R^a$ is a hydrogen atom, a fluorine atom, a chlorine atom, a methyl group or a methoxy group; and other symbols are as defined in [33] above;

[36] the agent according to [3] above, wherein
ring A is (1) a benzene ring or a naphthalene ring (preferably, a benzene ring) optionally having substituent(s) selected from the group consisting of
 (i) a $C_{1-6}$ alkyl group,
 (ii) a $C_{6-14}$ aryl group (preferably, a phenyl group) optionally having substituent(s) selected from $C_{1-6}$ alkyl and $C_{1-6}$ alkoxy,
 (iii) a hydroxy group,
 (iv) a $C_{1-6}$ alkoxy group optionally having substituent(s) selected from the group consisting of hydroxy, $C_{1-6}$ alkoxy, amino, $C_{1-6}$ alkoxy-carbonyl-amino, carboxy, $C_{1-6}$ alkoxy-carbonyl, $C_{1-6}$ alkyl-carbonyl, carbamoyl, mono-$C_{1-6}$ alkyl-carbamoyl, di-$C_{1-6}$ alkyl-carbamoyl, tri-$C_{1-6}$ alkylsilyloxy, and a 5- to 7-membered heterocyclic group containing, in addition to carbon atom(s), 1 to 4 heteroatoms of one or two kinds selected from a nitrogen atom, a sulfur atom and an oxygen atom,
 (v) a $C_{2-6}$ alkynyloxy group,
 (vi) a $C_{3-8}$ cycloalkyloxy group,
 (vii) a $C_{6-14}$ aryloxy group optionally having substituent(s) selected from the group consisting of a halogen atom, optionally halogenated $C_{1-6}$ alkyl, $C_{1-6}$ alkoxy and $C_{1-6}$ alkyl-carbonyl,
 (viii) a $C_{7-16}$ aralkyloxy group,
 (ix) a 5- to 7-membered heterocyclyl-oxy group containing, in addition to carbon atom(s), 1 to 4 heteroatoms of one or two kinds selected from a nitrogen atom, a sulfur atom and an oxygen atom,
 (x) a 5- to 7-membered heterocyclic group containing, in addition to carbon atom(s), 1 to 4 heteroatoms of one or two kinds selected from a nitrogen atom, a sulfur atom and an oxygen atom, and
 (xi) a $C_{1-3}$ alkylenedioxy group, or (2)

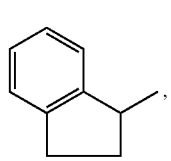, 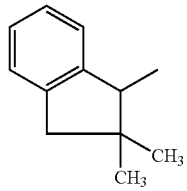 or

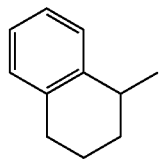

optionally having, on the benzene ring, substituent(s) selected from the group consisting of (i) a halogen atom, (ii) $C_{1-6}$ alkyl, and (iii) $C_{1-6}$ alkoxy;
ring B is a benzene ring optionally having, in addition to —Y—COOH, substituent(s) selected from the group consisting of a halogen atom, $C_{1-6}$ alkyl and $C_{1-6}$ alkoxy;
X is a bond, —$(CH_2)_m{}^1$—O— (wherein $m^1$ is an integer of 0 to 3), —CH($CH_3$)—O—, —CONH— or —S—$(CH_2)_m{}^3$—O— (wherein $m^3$ is an integer of 1 to 3);
Y is a methylene group or an ethylene group; and
—Y—COOH substitutes at any position on ring B;

[37] The agent according to [3] above, wherein
ring A is (i) a benzene ring or a naphthalene ring (preferably, a benzene ring) optionally having substituent(s) selected from the group consisting of (1) a $C_{6-14}$ aryl group (preferably, a phenyl group) optionally having substituent(s) selected from the group consisting of $C_{1-6}$ alkyl and $C_{1-6}$ alkoxy, (2) a $C_{6-14}$ aryloxy group (preferably, a phenoxy group) optionally substituted with $C_{1-6}$ alkyl, (3) a $C_{7-15}$ aralkyl group (preferably, a benzyl group), and (4) a $C_{1-6}$ alkoxy group, or (ii)

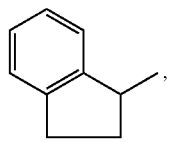, 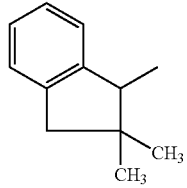 or

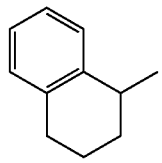

optionally having, on the benzene ring, substituent(s) selected from the group consisting of a halogen atom, $C_{1-6}$ alkyl and $C_{1-6}$ alkoxy;
ring B is a benzene ring optionally having, in addition to —Y—COOH, substituent(s) selected from the group consisting of a halogen atom, $C_{1-6}$ alkyl and $C_{1-6}$ alkoxy;
X is a bond, —$(CH_2)_m{}^1$—O— (wherein $m^1$ is an integer of 0 to 3), —CH($CH_3$)—O—, —CONH— or —S—$(CH_2)_m{}^3$—O— (wherein $m^3$ is an integer of 1 to 3);

Y is a methylene group or an ethylene group; and
—Y—COOH substitutes at any position on ring B;

[37] the agent according to [3] above, wherein ring A is (i) a benzene ring optionally having substituent(s) selected from the group consisting of (1) a $C_{6-14}$ aryl group (preferably, a phenyl group) optionally having substituent(s) selected from the group consisting of $C_{1-6}$ alkyl and $C_{1-6}$ alkoxy, (2) a $C_{6-14}$ aryloxy group (preferably, a phenoxy group) optionally having $C_{1-6}$ alkyl, (3) a $C_{7-15}$ aralkyl group (preferably, a benzyl group), and (4) a $C_{1-6}$ alkoxy group, or (ii)

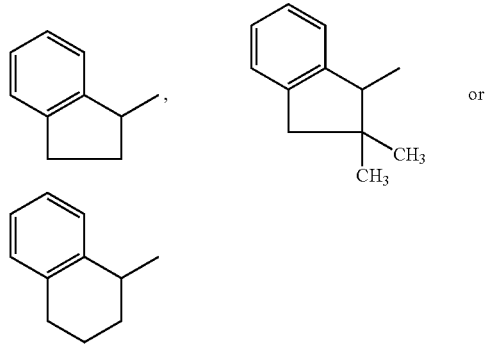

optionally having, on the benzene ring, substituent(s) selected from the group consisting of a halogen atom, $C_{1-6}$ alkyl and $C_{1-6}$ alkoxy;

ring B is a benzene ring optionally having, in addition to —Y—COOH, substituent(s) selected from the group consisting of a halogen atom, $C_{1-6}$ alkyl and $C_{1-6}$ alkoxy;

X is —O—, —CH$_2$—O—, or —CH(CH$_3$)—O—;

Y is a methylene group or an ethylene group (preferably, an ethylene group); and —Y—COOH substitutes at the para-position of a phenyl group of
ring B;

[39] a compound represented by the formula:

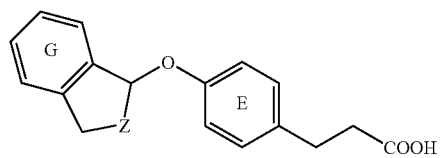

(VI)

wherein Z is a $C_{1-3}$ alkylene group having substituent(s); ring G is a benzene ring having substituent(s); and ring E is a benzene ring optionally having substituent(s),
or a salt thereof;

[40] the compound according to [39] above, wherein Z is a methylene group having one or two $C_{1-3}$ alkyl;
ring G is a benzene ring having substituent(s) selected from the group consisting of $C_{1-6}$ alkyl, $C_{1-6}$ alkoxy and a halogen atom; and
ring E is an unsubstituted benzene ring,
or a salt thereof;

[41] a prodrug of the compound according to [39] above, or a salt thereof;

[42] a pharmaceutical agent comprising the compound according to [39] above, or a salt thereof or a prodrug thereof;

[43] The agent according to [1] above, comprising a compound represented by the formula:

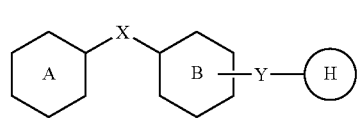

(VII)

wherein ring A is an aromatic ring optionally having substituent(s); ring B is an aromatic ring optionally having substituent(s) in addition to

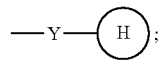

X and Y are each a spacer; and

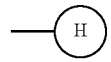

is a group capable of releasing a cation,
or a salt thereof or a prodrug thereof;

[44] the agent according to [1], [2], [4] or [5] above, wherein the aromatic ring is an aromatic hydrocarbon ring having 6 to 14 carbon atoms, or a 5- to 14-membered (monocyclic, bicyclic or tricyclic), preferably 5- to 10-membered, more preferably 5- or 6-membered, aromatic heterocyclic ring containing, in addition to carbon atom(s), 1 to 4 heteroatoms of one or two kinds selected from a nitrogen atom, a sulfur atom and an oxygen atom;
the group capable of releasing a cation is (1) a 5-membered heterocyclic group capable of releasing a cation, which contains 1 to 4 ring-constituting atoms selected from a nitrogen atom, an oxygen atom and a sulfur atom, (2) a carboxyl group, (3) a sulfonic acid group, (4) a sulfamoyl group optionally mono-substituted with a $C_{1-4}$ alkyl group, (5) a phosphonic acid group, (6) a carbamoyl group optionally mono-substituted with a $C_{1-4}$ alkyl group (e.g., methyl, ethyl, propyl, butyl, isobutyl, tert-butyl, etc.), (7) a $C_{2-7}$ alkylsulfonylthiocarbamoyl group (e.g., methylsulfonylthiocarbamoyl, ethylsulfonylthiocarbamoyl, etc.), or (8) a trifluoromethanesulfonyl amide group (—NHSO$_2$CF$_3$);

[45] the agent according to [3] above, wherein the aromatic ring optionally having substituent(s), which is represented by ring A, is
(1) a hydrocarbon ring having 6 to 14 carbon atoms, or
(2) a 5- to 14-membered (monocyclic, bicyclic or tricyclic), preferably 5- to 10-membered, more preferably 5- or 6-membered, aromatic heterocyclic ring containing, in addition to carbon atom(s), 1 to 4 heteroatoms of one or two kinds selected from a nitrogen atom, a sulfur atom and an oxygen atom,
each optionally having substituent(s) selected from the group (hereinafter simply referred to as Substituent Group A) consisting of:
(i) oxo;
(ii) a halogen atom;
(iii) $C_{1-3}$ alkylenedioxy;
(iv) nitro;
(v) cyano;
(vi) optionally esterified carboxyl;

(vii) $C_{1-6}$ alkyl optionally having substituent(s) selected from the group (hereinafter simply referred to as Substituent Group B) consisting of a halogen atom; hydroxy; nitro; cyano; amino; a 5- to 7-membered heterocyclic group containing, in addition to carbon atom(s), 1 to 4 heteroatoms of one or two kinds selected from a nitrogen atom, a sulfur atom and an oxygen atom (said heterocyclic group is optionally substituted with a halogen atom, hydroxy, amino, optionally halogenated $C_{1-6}$ alkyl, formyl, $C_{1-6}$ alkyl-carbonyl, $C_{6-14}$ aryl-carbonyl, $C_{7-16}$ aralkyl-carbonyl, 5- to 7-membered heterocyclyl-carbonyl containing, in addition to carbon atom(s), 1 to 4 heteroatoms of one or two kinds selected from a nitrogen atom, a sulfur atom and an oxygen atom, mono- or di-$C_{1-6}$ alkylamino, mono- or di-$C_{6-14}$ arylamino, $C_{3-8}$ cycloalkyl, $C_{1-6}$ alkoxy, $C_{1-6}$ alkylthio, $C_{1-6}$ alkylsulfinyl, $C_{1-6}$ alkylsulfonyl, the above-mentioned optionally esterified carboxyl (particularly, $C_{1-6}$ alkoxy-carbonyl), carbamoyl, thiocarbamoyl, mono-$C_{1-6}$ alkyl-carbamoyl, di-$C_{1-6}$ alkyl-carbamoyl, or mono- or di-$C_{6-14}$ aryl-carbamoyl); formyl; $C_{1-6}$ alkyl-carbonyl, $C_{6-14}$ aryl-carbonyl; $C_{7-16}$ aralkyl-carbonyl; 5- to 7-membered heterocyclyl-carbonyl containing, in addition to carbon atom(s), 1 to 4 heteroatoms of one or two kinds selected from a nitrogen atom, a sulfur atom and an oxygen atom; mono- or di-$C_{1-6}$ alkylamino; mono- or di-$C_{6-14}$ arylamino; formylamino; mono- or di-$C_{1-6}$ alkyl-carbonyl-amino, mono- or di-$C_{1-6}$ alkoxy-carbonyl-amino; $C_{3-8}$ cycloalkyl; optionally halogenated $C_{1-6}$ alkoxy; $C_{1-6}$ alkylthio; $C_{1-6}$ alkylsulfinyl; $C_{1-6}$ alkylsulfonyl; the above-mentioned optionally esterified carboxyl (particularly, $C_{1-6}$)-alkoxy-carbonyl; carbamoyl; thiocarbamoyl; mono-$C_{1-6}$ alkyl-carbamoyl; di-$C_{1-6}$ alkyl-carbamoyl; mono- or di-$C_{6-14}$ aryl-carbamoyl; mono- or di-5- to 7-membered heterocyclylcarbamoyl containing, in addition to carbon atom(s), 1 to 4 heteroatoms of one or two kinds selected from a nitrogen atom, a sulfur atom and an oxygen atom; and $C_{1-6}$ alkyl-carbonylamino optionally substituted with carboxy;

(viii) $C_{2-6}$ alkenyl optionally substituted with substituent(s) selected from the Substituent Group B above;

(ix) $C_{2-6}$ alkynyl optionally substituted with substituent(s) selected from the Substituent Group B above;

(x) $C_{3-8}$ cycloalkyl optionally having substituent(s) selected from the group (hereinafter simply referred to as Substituent Group C) consisting of a halogen atom; hydroxy; nitro; cyano; amino; the above-mentioned optionally substituted $C_{1-6}$ alkyl; the above-mentioned optionally substituted $C_{2-6}$ alkenyl; the above-mentioned optionally substituted $C_{2-6}$ alkynyl; formyl; $C_{1-6}$ alkyl-carbonyl; $C_{6-14}$ aryl-carbonyl; $C_{7-16}$ aralkyl-carbonyl; 5- to 7-membered heterocyclyl-carbonyl containing, in addition to carbon atom(s), 1 to 4 heteroatoms of one or two kinds selected from a nitrogen atom, a sulfur atom and an oxygen atom; $C_{6-14}$ aryl (said $C_{6-14}$ aryl is optionally substituted with a halogen atom, hydroxy, amino, optionally halogenated $C_{1-6}$ alkyl, formyl, $C_{1-6}$ alkyl-carbonyl, $C_{6-14}$ aryl-carbonyl, $C_{7-16}$ aralkyl-carbonyl, 5- to 7-membered heterocyclyl-carbonyl containing, in addition to carbon atom(s), 1 to 4 heteroatoms of one or two kinds selected from a nitrogen atom, a sulfur atom and an oxygen atom, mono- or di-$C_{1-6}$ alkylamino, mono- or di-$C_{6-14}$ arylamino, formylamino; mono- or di-$C_{1-6}$ alkyl-carbonyl-amino, mono- or di-$C_{1-6}$ alkoxy-carbonyl-amino; $C_{3-8}$ cycloalkyl, $C_{1-6}$ alkoxy, $C_{1-6}$ alkylthio, $C_{1-6}$ alkylsulfinyl, $C_{1-6}$ alkylsulfonyl, the above-mentioned optionally esterified carboxyl (particularly, $C_{1-6}$ alkoxy-carbonyl), carbamoyl, thiocarbamoyl, mono-$C_{1-6}$ alkyl-carbamoyl, di-$C_{1-6}$ alkyl-carbamoyl, or mono- or di-$C_{6-14}$ aryl-carbamoyl); $C_{6-14}$ aryloxy (said $C_{6-14}$ aryloxy is optionally substituted with a halogen atom, hydroxy, amino, optionally halogenated $C_{1-6}$ alkyl, formyl, $C_{1-6}$ alkyl-carbonyl, $C_{6-14}$ aryl-carbonyl, $C_{7-16}$ aralkyl-carbonyl, 5- to 7-membered heterocyclyl-carbonyl containing, in addition to carbon atom(s), 1 to 4 heteroatoms of one or two kinds selected from a nitrogen atom, a sulfur atom and an oxygen atom, mono- or di-$C_{1-6}$ alkylamino, mono- or di-$C_{6-14}$ arylamino, formylamino; mono- or di-$C_{1-6}$ alkyl-carbonyl-amino, mono- or di-$C_{1-6}$ alkoxy-carbonyl-amino; $C_{3-8}$ cycloalkyl, $C_{1-6}$ alkoxy, $C_{1-6}$ alkylthio, $C_{1-6}$ alkylsulfinyl, $C_{1-6}$ alkylsulfonyl, the above-mentioned optionally esterified carboxyl (particularly, $C_{1-6}$ alkoxy-carbonyl), carbamoyl, thiocarbamoyl, mono-$C_{1-6}$ alkyl-carbamoyl, di-$C_{1-6}$ alkyl-carbamoyl, or mono- or di-$C_{6-14}$ aryl-carbamoyl); $C_{7-16}$ aralkyloxy (said $C_{7-16}$ aralkyloxy is optionally substituted with a halogen atom, hydroxy, amino, optionally halogenated $C_{1-6}$ alkylformyl, $C_{1-6}$ alkyl-carbonyl, $C_{6-14}$ aryl-carbonyl, $C_{7-16}$ aralkyl-carbonyl, 5- to 7-membered heterocyclyl-carbonyl containing, in addition to carbon atom(s), 1 to 4 heteroatoms of one or two kinds selected from a nitrogen atom, a sulfur atom and an oxygen atom, mono- or di-$C_{1-6}$ alkylamino, mono- or di-$C_{6-14}$ arylamino, $C_{3-8}$ cycloalkyl, $C_{1-6}$ alkoxy, $C_{1-6}$ alkylthio, $C_{1-6}$ alkylsulfinyl, $C_{1-6}$ alkylsulfonyl, the above-mentioned optionally esterified carboxyl (particularly, $C_{1-6}$ alkoxy-carbonyl), carbamoyl, thiocarbamoyl, mono-$C_{1-6}$ alkyl-carbamoyl, di-$C_{1-6}$ alkyl-carbamoyl, or mono- or di-$C_{6-14}$ aryl-carbamoyl); a 5- to 7-membered heterocyclic group containing, in addition to carbon atom(s), 1 to 4 heteroatoms of one or two kinds selected from a nitrogen atom, a sulfur atom and an oxygen atom (said heterocyclic group is optionally substituted with a halogen atom, hydroxy, amino, formyl, $C_{1-6}$ alkyl-carbonyl, $C_{6-14}$ aryl-carbonyl, $C_{7-16}$ aralkyl-carbonyl, a 5- to 7-membered heterocyclyl-carbonyl group containing, in addition to carbon atom(s), 1 to 4 heteroatoms of one or two kinds selected from a nitrogen atom, a sulfur atom and an oxygen atom, mono- or di-$C_{1-6}$ alkylamino, mono- or di-$C_{6-14}$ arylamino, $C_{3-8}$ cycloalkyl, $C_{1-6}$ alkoxy, $C_{1-6}$ alkylthio, $C_{1-6}$ alkylsulfinyl, $C_{1-6}$ alkylsulfonyl, the above-mentioned optionally esterified carboxyl (particularly, $C_{1-6}$ alkoxy-carbonyl), carbamoyl, thiocarbamoyl, mono-$C_{1-6}$ alkyl-carbamoyl, di-$C_{1-6}$ alkyl-carbamoyl, or mono- or di-$C_{6-14}$ aryl-carbamoyl); mono- or di-lower ($C_{1-6}$) alkylamino; mono- or di-$C_{6-14}$ arylamino; $C_{3-8}$ cycloalkyl; the above-mentioned optionally substituted $C_{1-6}$ alkoxy; $C_{1-6}$ alkylthio; $C_{1-6}$ alkylsulfinyl; $C_{1-6}$ alkylsulfonyl; the above-mentioned optionally esterified carboxyl (particularly, $C_{1-6}$ alkoxy-carbonyl); carbamoyl; thiocarbamoyl; mono-$C_{1-6}$ alkyl-carbamoyl; di-$C_{1-6}$ alkyl-carbamoyl; mono- or di-$C_{6-14}$ aryl-carbamoyl; and mono- or di-5- to 7-membered heterocyclylcarbamoyl containing, in addition to carbon atom(s), 1 to 4 heteroatoms of one or two kinds selected from a nitrogen atom, a sulfur atom and an oxygen atom;

(xi) $C_{1-6}$ alkoxy optionally substituted with substituent(s) selected from the Substituent Group B above;

(xii) $C_{2-6}$ alkenyloxy optionally substituted with substituent(s) selected from the Substituent Group B above;

(xiii) $C_{2-6}$ alkynyloxy optionally substituted with substituent(s) selected from the Substituent Group B above;

(xiv) $C_{3-8}$ cycloalkyloxy optionally substituted with substituent(s) selected from the Substituent Group C above;

(xv) hydroxy;

(xvi) mercapto;

(xvii) $C_{1-6}$ alkylthio optionally substituted with substituent(s) selected from the Substituent Group B above;

(xviii) formyl;

(xix) $C_{1-6}$ alkyl-carbonyl optionally substituted with substituent(s) selected from the Substituent Group B above;

(xx) $C_{3-8}$ cycloalkyl-carbonyl optionally substituted with substituent(s) selected from the Substituent Group C above;

(xxi) $C_{1-6}$ alkylsulfonyl optionally substituted with substituent(s) selected from the Substituent Group B above;

(xxii) $C_{1-6}$ alkylsulfinyl optionally substituted with substituent(s) selected from the Substituent Group B above;

(xxiii) amino optionally having substituent(s) selected from the group consisting of the above-mentioned optionally substituted $C_{1-6}$ alkyl, the above-mentioned optionally substituted $C_{2-6}$ alkenyl, the above-mentioned optionally substituted $C_{2-6}$ alkynyl, the above-mentioned optionally substituted $C_{3-8}$ cycloalkyl, the above-mentioned optionally substituted $C_{6-14}$ aryl, the above-mentioned optionally substituted lower alkoxy, the above-mentioned optionally substituted $C_{6-14}$ aryl-carbonyl, formyl, the above-mentioned lower ($C_{1-6}$) alkyl-carbonyl, the above-mentioned optionally substituted $C_{3-8}$ cycloalkyl-carbonyl, the above-mentioned optionally substituted lower ($C_{1-6}$) alkoxy-carbonyl, the above-mentioned optionally substituted lower ($C_{1-6}$) alkylsulfonyl, and the above-mentioned optionally substituted $C_{6-14}$ arylsulfonyl [e.g., amino, mono- or di-$C_{1-6}$ alkylamino optionally substituted with substituent(s) selected from the Substituent Group B above, mono- or di-$C_{3-8}$ cycloalkylamino optionally substituted with substituent(s) selected from the Substituent Group C above, mono- or di-$C_{6-14}$ arylamino optionally substituted with substituent(s) selected from the Substituent Group C above, mono- or di-$C_{7-16}$ aralkylamino optionally substituted with substituent(s) selected from the Substituent Group C above, $C_{6-14}$ arylcarbonylamino optionally substituted with substituent(s) selected from the Substituent Group C above, formylamino; $C_{1-6}$ alkyl-carbonylamino optionally substituted with substituent(s) selected from the Substituent Group B above; $C_{3-8}$ cycloalkyl-carbonylamino optionally substituted with substituent(s) selected from the Substituent Group C above; $C_{1-6}$ alkoxy-carbonylamino optionally substituted with substituent(s) selected from the Substituent Group B above; $C_{1-6}$ alkylsulfonylamino optionally substituted with substituent(s) selected from the Substituent Group B above; and $C_{6-14}$ arylsulfonylamino optionally substituted with substituent(s) selected from the Substituent Group C above];

(xxiv) $C_{1-6}$ alkyl-carbonyloxy optionally substituted with substituent(s) selected from the Substituent Group B above;

(xxv) $C_{1-6}$ alkoxy-carbonyloxy optionally substituted with substituent(s) selected from the Substituent Group B above;

(xxvi) mono-$C_{1-6}$ alkyl-carbamoyloxy optionally substituted with substituent(s) selected from the Substituent Group B above;

(xxvii) di-$C_{1-6}$ alkyl-carbamoyloxy optionally substituted with substituent(s) selected from the Substituent Group B above;

(xxviii) sulfo;

(xxix) sulfamoyl;

(xxx) sulfinamoyl;

(xxxi) sulfenamoyl;

(xxxii) 5- to 7-membered heterocyclylcarbonyl containing, in addition to carbon atom(s), 1 to 4 heteroatoms of one or two kinds selected from a nitrogen atom, a sulfur atom and an oxygen atom, which is optionally substituted with substituent(s) selected from the Substituent Group C above;

(xxxiii) $C_{6-14}$ aryloxy optionally substituted with substituent(s) selected from the Substituent Group C above;

(xxxiv) $C_{7-16}$ aralkyloxy optionally substituted with substituent(s) selected from the Substituent Group C above;

(xxxv) $C_{6-14}$ arylthio optionally substituted with substituent(s) selected from the Substituent Group C above;

(xxxvi) $C_{7-16}$ aralkylthio optionally substituted with substituent(s) selected from the Substituent Group C above;

(xxxvii) $C_{6-14}$ aryl-carbonyl optionally substituted with substituent(s) selected from the Substituent Group C above;

(xxxviii) $C_{7-16}$ aralkyl-carbonyl optionally substituted with substituent(s) selected from the Substituent Group C above;

(xxxix) $C_{6-14}$ aryl-carbonylamino optionally substituted with substituent(s) selected from the Substituent Group C above;

(xxxx) $C_{6-14}$ aryl-carbonyloxy optionally substituted with substituent(s) selected from the Substituent Group C above;

(xxxxi) mono- or di-$C_{6-14}$ aryl-carbamoyloxy optionally substituted with substituent(s) selected from the Substituent Group C above;

(xxxxii) $C_{6-14}$ arylsulfonyl optionally substituted with substituent(s) selected from the Substituent Group C above;

(xxxxiii) $C_{6-14}$ arylsulfinyl optionally substituted with substituent(s) selected from the Substituent Group C above;

(xxxxiv) $C_{6-14}$ arylsulfonylamino optionally substituted with substituent(s) selected from the Substituent Group C above;

(xxxxv) heterocyclyloxy optionally substituted with substituent(s) selected from the Substituent Group C above (preferably, aromatic heterocyclyloxy optionally substituted with substituent(s) selected from the Substituent Group C above);

(xxxxvi) $C_{6-14}$ aryl optionally having substituent(s) selected from the group (hereinafter simply referred to as Substituent Group G) consisting of a halogen atom; hydroxy; nitro; cyano; the above-mentioned optionally substituted $C_{1-6}$ alkyl; the above-mentioned optionally substituted $C_{2-6}$ alkenyl; the above-mentioned optionally substituted $C_{2-6}$ alkynyl; the above-mentioned optionally substituted $C_{3-8}$ cycloalkyl; the above-mentioned optionally substituted $C_{1-6}$ alkoxy; the above-mentioned optionally substituted $C_{1-6}$ alkylthio; mercapto; the above-mentioned $C_{1-6}$ alkylthio; formyl; the above-mentioned optionally substituted $C_{1-6}$ alkyl-carbonyl; the above-mentioned optionally substituted $C_{3-8}$ cycloalkyl-carbonyl; the above-mentioned optionally substituted $C_{1-6}$ alkylsulfonyl; the above-mentioned optionally substituted $C_{1-6}$ alkylsulfinyl; amino; the above-mentioned optionally substituted mono- or di-lower alkylamino; the above-mentioned optionally substituted mono- or di-$C_{3-8}$ cycloalkylamino; the above-mentioned optionally substituted mono- or di-$C_{6-14}$ arylamino; the above-mentioned optionally substituted mono- or di-$C_{7-16}$ aralkylamino; the above-mentioned optionally substituted $C_{6-14}$ aryl-carbonylamino; formylamino; the above-mentioned optionally substituted $C_{1-6}$ alkyl-carbonylamino; the above-mentioned optionally substituted $C_{3-8}$ cycloalkyl-carbonylamino; the above-mentioned optionally substituted $C_{1-6}$ alkoxy-carbonylamino; the above-mentioned optionally substituted $C_{1-6}$ alkylsulfonylamino; the above-mentioned optionally substituted $C_{6-14}$ arylsulfonylamino; the above-mentioned optionally substituted $C_{1-6}$ alkyl-carbonyloxy; the above-mentioned optionally substituted $C_{1-6}$ alkoxy-carbonyloxy; the above-mentioned optionally substituted mono-lower $C_{1-6}$ alkyl carbamoyloxy; the above-mentioned optionally substituted di-$C_{1-6}$ alkyl-carbamoyloxy; sulfo; sulfamoyl; sulfinamoyl; sulfenamoyl; the above-mentioned optionally substituted 5- to 7-membered heterocyclylcarbonyl containing, in addition to carbon atom(s), 1 to 4 heteroatoms of one or two kinds selected from a nitrogen atom, a sulfur atom and an oxygen atom; the above-mentioned optionally substituted $C_{6-14}$ aryloxy; the above-mentioned optionally substituted $C_{7-16}$ aralkyloxy; the above-mentioned optionally substituted $C_{6-14}$ arylthio; the above-mentioned optionally substituted $C_{7-16}$ aralkylthio; the above-mentioned optionally substituted $C_{6-14}$ aryl-carbonyl; the above-mentioned optionally substituted $C_{7-16}$ aralkyl-carbonyl; the above-mentioned optionally substituted $C_{6-14}$ aryl-carbonylamino; the above-mentioned optionally substituted $C_{6-14}$ aryl-carbonyloxy; the above-mentioned optionally substituted mono- or di-$C_{6-14}$ aryl-carbamoyloxy; the above-mentioned optionally substituted $C_{6-14}$ arylsulfonyl; the above-mentioned optionally substituted $C_{6-14}$ arylsulfinyl; the above-mentioned optionally substituted $C_{6-14}$ arylsulfonylamino; the above-mentioned optionally substituted heterocyclyloxy (preferably, optionally substituted aromatic heterocyclyloxy); the above-mentioned optionally esterified carboxyl; carbamoyl; thiocarbamoyl; mono-$C_{1-6}$ alkyl-carbamoyl; di-$C_{1-6}$ alkyl-carbamoyl; mono- or di-$C_{6-14}$ aryl-carbamoyl; mono- or di-5- to 7-membered heterocyclylcarbamoyl containing, in addition to carbon atom(s), 1 to 4 heteroatoms of one or two kinds selected from a nitrogen atom, a sulfur atom and an oxygen atom; and a 5- to 7-membered heterocyclic group containing, in addition to carbon atom(s), 1 to 4 heteroatoms of one or species selected from a nitrogen atom, a sulfur atom and an oxygen atom (said heterocyclic group is optionally substituted with a halogen atom, hydroxy, amino, optionally halogenated $C_{1-6}$ alkyl, mono- or di-$C_{1-6}$ alkylamino, mono- or di-$C_{6-14}$ arylamino, $C_{3-8}$ cycloalkyl, $C_{1-6}$ alkoxy, $C_{1-6}$ alkoxy-carbonyl, $C_{1-6}$ alkylthio, $C_{1-6}$ alkylsulfinyl, $C_{1-6}$ alkylsulfonyl, the above-mentioned optionally esterified carboxyl, carbamoyl, thiocarbamoyl, mono-$C_{1-6}$ alkyl-carbamoyl, di-$C_{1-6}$ alkyl-carbamoyl, or mono- or di-$C_{6-14}$ aryl-carbamoyl);

(xxxxvii) $C_{7-16}$ aralkyl optionally substituted with substituent(s) selected from the Substituent Group G above;

(xxxxviii) $C_{6-14}$ aryl-$C_{2-6}$ alkenyl optionally substituted with substituent(s) selected from the Substituent Group G above;

(xxxxix) a 5- to 14-membered, preferably 5- to 10-membered, more preferably 5- to 7-membered (monocyclic, bicyclic or tricyclic) heterocyclic group containing, in addition to carbon atom(s), 1 to 4 heteroatoms of one or two kinds selected from a nitrogen atom, a sulfur atom and an oxygen atom, which optionally has substituent(s) selected from the group (hereinafter simply referred to as Substituent Group H) consisting of a halogen atom; hydroxy; nitro; cyano; the above-mentioned optionally substituted $C_{1-6}$ alkyl; the above-mentioned optionally substituted $C_{2-6}$ alkenyl; the above-mentioned optionally substituted $C_{2-6}$ alkynyl; the above-mentioned optionally substituted $C_{3-8}$ cycloalkyl; the above-mentioned optionally substituted $C_{1-6}$ alkoxy; mercapto; the above-mentioned optionally substituted $C_{1-6}$ alkylthio; formyl; the above-mentioned optionally substituted $C_{1-6}$ alkyl-carbonyl; the above-mentioned optionally substituted $C_{3-8}$ cycloalkyl-carbonyl; the above-mentioned optionally substituted $C_{1-6}$ alkylsulfonyl; the above-mentioned optionally substituted $C_{1-6}$ alkylsulfinyl; amino; the above-mentioned optionally substituted mono- or di-$C_{1-6}$ alkylamino; the above-mentioned optionally substituted mono- or di-$C_{3-8}$ cycloalkylamino; the above-mentioned optionally substituted mono- or di-$C_{6-14}$ arylamino; the above-mentioned optionally substituted mono- or di-$C_{7-16}$ aralkylamino; the above-mentioned optionally substituted $C_{6-14}$ aryl-carbonylamino; formylamino; the above-mentioned optionally substituted $C_{1-6}$ alkyl-carbonylamino; the above-mentioned optionally substituted $C_{3-8}$ cycloalkyl-carbonylamino; the above-mentioned optionally substituted $C_{1-6}$ alkoxy-carbonylamino; the above-mentioned optionally substituted $C_{1-6}$ alkylsulfonylamino; the above-mentioned optionally substituted $C_{6-14}$ arylsulfonylamino; the above-mentioned optionally substituted $C_{1-6}$ alkyl-carbonyloxy; the above-mentioned optionally substituted $C_{1-6}$ alkoxy-carbonyloxy; the above-mentioned optionally substituted mono-$C_{1-6}$ alkyl-carbamoyloxy; the above-mentioned optionally substituted di-$C_{1-6}$ alkyl-carbamoyloxy; sulfo; sulfamoyl; sulfinamoyl; sulfenamoyl; the above-mentioned optionally substituted 5- to 7-membered heterocyclylcarbonyl containing, in addition to carbon atom(s), 1 to 4 heteroatoms of one or two kinds selected from a nitrogen atom, a sulfur atom and an oxygen atom; the above-mentioned optionally substituted $C_{6-14}$ aryloxy; the above-mentioned optionally substituted $C_{7-16}$ aralkyloxy; the above-mentioned optionally substituted $C_{6-14}$ arylthio; the above-mentioned optionally substituted $C_{7-16}$ aralkylthio; the above-mentioned optionally substituted $C_{6-14}$ aryl-carbonyl; the above-mentioned optionally substituted $C_{7-16}$ aralkyl-carbonyl; the above-mentioned optionally substituted $C_{6-14}$ aryl-carbonylamino; the above-mentioned optionally substituted $C_{6-14}$ aryl-carbonyloxy; the above-mentioned optionally substituted mono- or di-$C_{6-14}$ aryl-carbamoyloxy; the above-mentioned optionally substituted $C_{6-14}$ arylsulfonyl; the above-mentioned optionally substituted $C_{6-14}$ arylsulfinyl; the above-mentioned optionally substituted $C_{6-14}$ arylsulfonylamino; the above-mentioned optionally substituted heterocyclyloxy (preferably, optionally substituted aromatic heterocyclyloxy); the above-mentioned optionally esterified carboxyl; carbamoyl; thiocarbamoyl; mono-$C_{1-6}$ alkyl-carbamoyl; di-$C_{1-6}$ alkyl-carbamoyl; mono- or di-$C_{6-14}$ aryl-carbamoyl; mono- or di-5- to 7-membered heterocyclylcarbamoyl containing, in addition to carbon atom(s), 1 to 4 heteroatoms of one or two kinds selected from a nitrogen atom, a sulfur atom and an oxygen atom; the above-mentioned optionally substituted $C_{6-14}$ aryl; the above-mentioned optionally substituted $C_{7-16}$ aralkyl; and a 5- to 7-membered heterocyclic group containing, in addition to carbon atom(s), 1 to 4 heteroatoms of one or two kinds selected from a nitrogen atom, a sulfur atom and an oxygen atom (said heterocyclic group is optionally substituted with a halogen atom, hydroxy, amino, optionally halogenated $C_{1-6}$ alkyl, mono- or di-$C_{1-6}$ alkylamino, mono- or di-$C_{6-14}$ arylamino, $C_{3-8}$ cycloalkyl, $C_{1-6}$ alkoxy, $C_{1-6}$ alkoxy-carbonyl, $C_{1-6}$ alkylthio, $C_{1-6}$ alkylsulfinyl, $C_{1-6}$ alkylsulfonyl, the above-mentioned optionally esterified carboxyl, carbamoyl, thiocarbamoyl, mono-$C_{1-6}$ alkyl-carbamoyl, di-$C_{1-6}$ alkyl-carbamoyl, mono- or di-$C_{6-14}$ aryl-carbamoyl or the like)

(xxxxx) thiocarbamoyl;

(xxxxxi) substituent(s) selected from a carbamoyl group optionally substituted with one or two substituents selected from the group consisting of the above-mentioned optionally substituted $C_{1-6}$ alkyl, the above-mentioned optionally substituted $C_{2-6}$ alkenyl, the above-mentioned optionally substituted $C_{2-6}$ alkynyl, the above-mentioned optionally substituted $C_{3-8}$ cycloalkyl, the above-mentioned optionally substituted $C_{6-14}$ aryl, the above-mentioned optionally substituted heterocyclic group, the above-mentioned optionally substituted $C_{1-6}$ alkoxy, the above-mentioned optionally substituted $C_{6-14}$ aryl-carbonyl, formyl, the above-mentioned $C_{1-6}$ alkyl-carbonyl, the above-mentioned optionally substituted $C_{3-8}$ cycloalkyl-carbonyl, the above-mentioned optionally substituted $C_{1-6}$ alkoxy-carbonyl, the above-mentioned lower ($C_{1-6}$) alkylsulfonyl, and the above-mentioned optionally substituted $C_{6-14}$ arylsulfonyl; and (xxxxxii) a group having two or more (e.g., 2 or 3) of these substituents bound thereto;

ring B is (1) a hydrocarbon ring having 6 to 14 carbon atoms, or (2) a 5- to 14-membered (monocyclic, bicyclic or tricyclic), preferably 5- to 10-membered, more preferably 5- or 6-membered, aromatic heterocyclic ring containing, in addition to carbon atom(s), 1 to 4 heteroatoms of one or two kinds selected from a nitrogen atom, a sulfur atom and an oxygen atom, each of which is optionally substituted with substituent(s) selected from the Substituent Group A above, in addition to

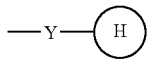

or —Y—COOH;

the spacer represented by X or Y is a $C_{1-13}$ alkylene group or a $C_{2-13}$ alkenylene group, each optionally substituted with substituent(s) selected from the group consisting of a $C_{1-6}$ alkyl group, an oxo group and a $C_{6-14}$ aryl group, wherein —C— of the $C_{1-13}$ alkylene group or $C_{2-13}$ alkenylene group is optionally replaced by —O—, —N— or —S—;

[43] a compound described above,
wherein
the hydrocarbon group optionally having substituent(s) is a $C_{1-6}$ alkyl group, a $C_{2-6}$ alkenyl group, a $C_{2-6}$ alkynyl group, a $C_{3-8}$ cycloalkyl group, a $C_{6-14}$ aryl group, or a $C_{7-16}$ aralkyl group, each optionally substituted with substituent(s) selected from the Substituent Group A above;

the heterocyclic group optionally having substituent(s) is a 5- to 14-membered, preferably 5- to 10-membered, more preferably 5- to 7-membered, (monocyclic, bicyclic or tricyclic) heterocyclic group containing, in addition to carbon atom(s), 1 to 4 heteroatoms of one or two kinds selected from a nitrogen atom, a sulfur atom and an oxygen atom, which is optionally substituted with substituent(s) selected from the Substituent Group E above;

the hydroxy group optionally having substituent(s) is a hydroxy group, the above-mentioned optionally substituted $C_{1-6}$ alkoxy group, the above-mentioned optionally substituted $C_{1-6}$ alkyl-carbonyloxy group, the above-mentioned optionally substituted $C_{1-6}$ alkoxy-carbonyloxy group, the above-mentioned optionally substituted mono-$C_{1-6}$ alkyl-carbamoyloxy group, the above-mentioned optionally substituted di-$C_{1-6}$ alkyl-carbamoyloxy group, the above-mentioned optionally substituted $C_{6-14}$ aryloxy group, the above-mentioned optionally substituted $C_{7-16}$ aralkyloxy group, the above-mentioned optionally substituted $C_{6-14}$ aryl-carbonyloxy group, the above-mentioned optionally substituted mono- or di-$C_{6-14}$ aryl-carbamoyloxy group, or the above-mentioned optionally substituted aromatic heterocyclyloxy group;

the carboxyl group optionally having substituent(s) is a carboxyl group optionally having substituent(s) selected from the above-mentioned optionally substituted $C_{1-6}$ alkyl, the above-mentioned optionally substituted $C_{6-14}$ aryl, and the above-mentioned optionally substituted $C_{7-16}$ aralkyl;

the acyl group is a formyl group, the above-mentioned optionally substituted $C_{1-6}$ alkyl-carbonyl group, the above-mentioned optionally substituted $C_{3-8}$ cycloalkyl-carbonyl group, the above-mentioned optionally substituted $C_{6-14}$ aryl-carbonyl group, the above-mentioned optionally substituted $C_{7-16}$ aralkyl-carbonyl group, $C_{1-6}$ alkylsulfonyl, the above-mentioned optionally substituted $C_{6-14}$ arylsulfonyl group, $C_{1-6}$ alkylsulfinyl, the above-mentioned optionally substituted $C_{6-14}$ arylsulfinyl, sulfo, sulfamoyl, sulfinamoyl, sulfenamoyl, or the above-mentioned optionally substituted 5- to 7-membered heterocyclylcarbonyl containing, in addition to carbon atom(s), 1 to 4 heteroatoms of one or two kinds selected from a nitrogen atom, a sulfur atom and an oxygen atom;

the amino group optionally having substituent(s) is an amino group optionally substituted by substituent(s) selected from the group consisting of the above-mentioned optionally substituted $C_{1-6}$ alkyl, the above-mentioned optionally substituted $C_{2-6}$ alkenyl, the above-mentioned optionally substituted $C_{2-6}$ alkynyl, the above-mentioned optionally substituted $C_{3-8}$ cycloalkyl, the above-mentioned optionally substituted $C_{6-14}$ aryl, the above-mentioned optionally substituted lower alkoxy, the above-mentioned optionally substituted $C_{6-14}$ aryl-carbonyl, formyl, the above-mentioned lower ($C_{1-6}$) alkyl-carbonyl, the above-mentioned optionally substituted $C_{3-8}$ cycloalkyl-carbonyl, the above-mentioned optionally substituted lower ($C_{1-6}$) alkoxy-carbonyl, the above-mentioned optionally substituted lower ($C_{1-6}$) alkylsulfonyl, and the above-mentioned optionally substituted $C_{6-14}$ arylsulfonyl;

the methylene group optionally having substituent(s) is a methylene group optionally having substituent(s) selected from a $C_{1-6}$ alkyl group, an oxo group, and a $C_{6-14}$ aryl group;

the substituent optionally further possessed by the benzene ring of ring C is a substituent selected from the Substituent Group A above;

the alkyl group optionally having substituent(s) free of a benzene ring is a $C_{1-6}$ alkyl group optionally having substituent(s) selected from the group (hereinafter simply referred to as Substituent Group D) consisting of a halogen atom; hydroxy; nitro; cyano; amino; a mono- or di-5- to 7-membered heterocyclic group containing, in addition to carbon atom(s), 1 to 4 heteroatoms of one or two kinds selected from a nitrogen atom, a sulfur atom and an oxygen atom (said heterocyclic group is optionally substituted with a halogen atom, hydroxy, amino, optionally halogenated $C_{1-6}$ alkyl, mono- or di-$C_{1-6}$ alkylamino, $C_{3-8}$ cycloalkyl, $C_{1-6}$ alkoxy, $C_{1-6}$ alkoxy-carbonyl, $C_{1-6}$ alkylthio, $C_{1-6}$ alkylsulfinyl, $C_{1-6}$ alkylsulfonyl, the above-mentioned optionally esterified carboxyl, carbamoyl, thiocarbamoyl, mono-$C_{1-6}$ alkyl-carbamoyl, or di-$C_{1-6}$ alkyl-carbamoyl); mono- or di-$C_{1-6}$ alkylamino; $C_{3-8}$ cycloalkyl; optionally halogenated $C_{1-6}$ alkoxy; $C_{1-6}$ alkoxy-carbonyl; $C_{1-6}$ alkylthio; $C_{1-6}$ alkylsulfinyl; $C_{1-6}$ alkylsulfonyl; the above-mentioned optionally esterified carboxyl; carbamoyl; thiocarbamoyl; mono-$C_{1-6}$ alkyl-carbamoyl; di-$C_{1-6}$ alkyl-carbamoyl; mono- or di-5- to 7-membered heterocyclylcarbamoyl containing, in addition to carbon atom(s), 1 to 4 heteroatoms of one or two kinds selected from a nitrogen atom, a sulfur atom and an oxygen atom; and $C_{1-6}$ alkyl-carbonylamino optionally substituted with carboxy;

the alkenyl group optionally having substituent(s) free of a benzene ring is a $C_{2-6}$ alkenyl group optionally substituted with substituent(s) selected from the Substituent Group D above;

the alkynyl group optionally having substituent(s) free of a benzene ring is a $C_{2-6}$ alkynyl group optionally substituted with substituent(s) selected from the Substituent Group D above;

the cycloalkyl group optionally having substituent(s) free of a benzene ring is a $C_{3-8}$ cycloalkyl group optionally having substituent(s) selected from the group (hereinafter simply referred to as Substituent Group E) consisting of a halogen atom; hydroxy; nitro; cyano; amino; $C_{1-6}$ alkyl optionally substituted with substituent(s) selected from the Substituent Group D above; $C_{2-6}$ alkenyl optionally substituted with substituent(s) selected from the Substituent Group D above; $C_{2-6}$ alkynyl optionally substituted with substituent(s) selected from the Substituent Group D above; a 5- to 7-membered heterocyclic group containing, in addition to carbon atom(s), 1 to 4 heteroatoms of one or two kinds selected from a nitrogen atom, a sulfur atom and an oxygen atom (said heterocyclic group is optionally substituted with a halogen atom, hydroxy, amino, mono- or di-$C_{1-6}$ alkylamino, $C_{3-8}$ cycloalkyl, $C_{1-6}$ alkoxy, $C_{1-6}$ alkoxy-carbonyl, $C_{1-6}$ alkylthio, $C_{1-6}$ alkylsulfinyl, $C_{1-6}$ alkylsulfonyl, the above-mentioned optionally esterified carboxyl, carbamoyl, thiocarbamoyl, mono-$C_{1-6}$ alkyl-carbamoyl, di-$C_{1-6}$ alkyl-carbamoyl or the like); mono- or di-$C_{1-6}$ alkylamino; $C_{3-8}$ cycloalkyl; $C_{1-6}$ alkoxy optionally substituted with substituent(s) selected from the Substituent Group D above; $C_{1-6}$ alkoxy-carbonyl; $C_{1-6}$ alkylthio; $C_{1-6}$ alkylsulfinyl; $C_{1-6}$ alkylsulfonyl; the above-mentioned optionally esterified carboxyl; carbamoyl; thiocarbamoyl; mono-$C_{1-6}$ alkyl-carbamoyl; di-$C_{1-6}$ alkyl-carbamoyl; and mono- or di-5- to 7-membered heterocyclyl-carbamoyl containing, in addition to carbon atom(s), 1 to 4 heteroatoms of one or two kinds selected from a nitrogen atom, a sulfur atom and an oxygen atom;

the heterocyclic group optionally having substituent(s) free of a benzene ring is a 5- to 14-membered, preferably 5- to 10-membered, more preferably 5- to 7-membered, (monocyclic, bicyclic or tricyclic) heterocyclic group containing, in addition to carbon atom(s), 1 to 4 heteroatoms of one or two kinds selected from a nitrogen atom, a sulfur atom and an oxygen atom, which is optionally substituted with substituent(s) selected from the Substituent Group E above;

the alkoxy group optionally having substituent(s) free of a benzene ring is a $C_{1-6}$ alkoxy group optionally substituted with substituent(s) selected from the Substituent Group D above;

the heterocyclyloxy group optionally having substituent(s) free of a benzene ring is a 5- to 14-membered, preferably 5- to 10-membered, more preferably 5- to 7-membered, (monocyclic, bicyclic or tricyclic) heterocyclyl-oxy group containing, in addition to carbon atom(s), 1 to 4 heteroatoms of one or two kinds selected from a nitrogen atom, a sulfur atom and an oxygen atom, which is optionally substituted with substituent(s) selected from the Substituent Group E above;

the carboxyl group optionally having substituent(s) free of a benzene ring is carboxyl optionally having $C_{1-6}$ alkyl optionally substituted with substituent(s) selected from the Substituent Group D above;

the acyl group free of a benzene ring is formyl, $C_{1-6}$ alkyl-carbonyl optionally substituted with substituent(s) selected from the Substituent Group D above, $C_{3-8}$ cycloalkyl-carbonyl optionally substituted with substituent(s) selected from the Substituent Group E above, $C_{1-6}$ alkylsulfonyl, $C_{1-6}$ alkyl-sulfinyl, sulfo, sulfamoyl, sulfinamoyl, sulfenamoyl, or 5- to 7-membered heterocyclylcarbonyl containing, in addition to carbon atom(s), 1 to 4 heteroatoms of one or two kinds selected from a nitrogen atom, a sulfur atom and an oxygen atom, which is optionally substituted with substituent(s) selected from the Substituent Group E above;

the amino group optionally having substituent(s) free of a benzene ring is amino, mono- or di-$C_{1-6}$ alkylamino optionally substituted with substituent(s) selected from the Substituent Group D above, formylamino, $C_{1-6}$ alkyl-carbonylamino optionally substituted with substituent(s) selected from the Substituent Group D above, $C_{3-8}$ cycloalkyl-carbonylamino optionally substituted with substituent(s) selected from the Substituent Group E above, $C_{1-6}$ alkoxy-carbonylamino optionally substituted with substituent(s) selected from the Substituent Group D above, or $C_{1-6}$ alkylsulfonylamino optionally substituted with substituent(s) selected from the Substituent Group D above;

the substituent free of a benzene ring, which is optionally further possessed by the benzene ring of ring C, is a substituent selected from the group (hereinafter simply referred to as Substituent Group F) consisting of oxo; a halogen atom; $C_{1-3}$ alkylenedioxy; nitro; cyano; optionally esterified carboxyl; $C_{1-6}$ alkyl optionally substituted with substituent(s) selected from the Substituent Group D above; $C_{2-6}$ alkenyl optionally substituted with substituent(s) selected from the Substituent Group D above; $C_{2-6}$ alkynyl optionally substituted with substituent(s) selected from the Substituent Group D above; $C_{3-8}$ cycloalkyl optionally substituted with substituent(s) selected from the Substituent Group E above; $C_{1-6}$ alkoxy optionally substituted with substituent(s) selected from the Substituent Group D above; hydroxy; mercapto; $C_{1-6}$ alkylthio optionally substituted with substituent(s) selected from the Substituent Group D above; formyl; $C_{1-6}$ alkyl-carbonyl optionally substituted with substituent(s) selected from the Substituent Group D above; $C_{3-8}$ cycloalkyl-carbonyl optionally substituted with substituent(s) selected from the Substituent Group E above; $C_{1-6}$ alkylsulfonyl optionally substituted with substituent(s) selected from the Substituent Group D above; $C_{1-6}$ alkylsulfinyl optionally substituted with substituent(s) selected from the Substituent Group D above; amino, mono- or di-$C_{1-6}$ alkylamino optionally substituted with substituent(s) selected from the Substituent Group D above, formylamino; $C_{1-6}$ alkyl-carbonylamino optionally substituted with substituent(s) selected from the Substituent Group D above; $C_{3-8}$ cycloalkyl-carbonylamino optionally substituted with substituent(s) selected from the Substituent Group E above; $C_{1-6}$ alkoxy-carbonylamino optionally substituted with substituent(s) selected from the Substituent Group D above; $C_{1-6}$ alkylsulfonylamino optionally substituted with substituent(s) selected from the Substituent Group D above; $C_{1-6}$ alkyl-carbonyloxy optionally substituted with substituent(s) selected from the Substituent Group D above; $C_{1-6}$ alkoxy-carbonyloxy optionally substituted with substituent(s) selected from the Substituent Group D above; mono-$C_{1-6}$ alkyl-carbamoyloxy optionally having substituent(s) selected from Substituent Group D above; di-$C_{1-6}$ alkyl-carbamoyloxy optionally substituted with substituent(s) selected from the Substituent Group D above; sulfo; sulfamoyl; sulfinamoyl; sulfenamoyl; and 5- to 7-membered heterocyclylcarbonyl containing, in addition to carbon atom(s), 1 to 4 heteroatoms of one or two kinds selected from a nitrogen atom, a sulfur atom and an oxygen atom, which is optionally substituted with substituent(s) selected from the Substituent Group E above;

the alkoxy group optionally having substituent(s) is a $C_{1-6}$ alkoxy group optionally substituted with substituent(s) selected from the Substituent Group B above;

the alkoxy group optionally having substituent(s) free of a benzene ring is a $C_{1-6}$ alkoxy group optionally substituted with substituent(s) selected from the Substituent Group D above;

the benzene ring optionally having substituent(s) is a benzene ring optionally substituted with substituent(s) selected from the Substituent Group A above;

the phenylene group optionally having substituent(s) is a phenylene group optionally substituted with substituent(s) selected from the Substituent Group A above;

the spacer other than an alkylene group is (1) a $C_{1-13}$ alkylene group optionally substituted with substituent(s) selected from the group consisting of a $C_{1-6}$ alkyl group, an oxo group and a $C_{6-14}$ aryl group, wherein —C— of the $C_{1-13}$ alkylene group is replaced by —O—, —N— or —S—, or (2) a $C_{2-13}$ alkenylene group optionally substituted with substituent(s) selected from the group consisting of a $C_{1-6}$ alkyl group, an oxo group and a $C_{6-14}$ aryl group, wherein —C— of the $C_{2-13}$ alkenylene group is replaced by —O—, —N— or —S—;

the $C_{0-4}$ carbon chain optionally having substituent(s) is a $C_{1-4}$ alkylene group optionally having substituent(s) selected from the Substituent Group A above;

the methylene group optionally having substituent(s) is a methylene group optionally having substituent(s) selected from a $C_{1-6}$ alkyl group, an oxo group and a $C_{6-14}$ aryl group;

the $C_{1-3}$ alkylene group having substituent(s) is a $C_{1-3}$ alkylene group substituted with substituent(s) selected from the Substituent Group A above;

the benzene ring having substituent(s) is a benzene ring substituted having substituent(s) selected from the Substituent Group A above; and the $C_{6-14}$ aryloxy group optionally having substituent(s) is a $C_{6-14}$ aryloxy group optionally substituted with substituent(s) selected from the Substituent Group C above, or a salt thereof;

[46] a commercial package comprising the agent for the prophylaxis or treatment of diabetes mellitus, hyperlipidemia, obesity or anorexia according to [4] above, and a written matter relating to the agent, said written matter describing that the agent for the prophylaxis or treatment can or should be used for the prevention or treatment of diabetes mellitus, hyperlipidemia, obesity or anorexia;

[47] a commercial package comprising the stress regulating agent according to [5] above, and a written matter relating to the regulating agent, said written matter describing that the regulating agent can or should be used for relieving the stress; and the like.

The compound of the invention or a prodrug thereof has excellent 14273 receptor function regulating effect and thus can be used as a preventing and/or treating agent for diabetes mellitus, hyperlipidemia, obesity, anorexia or the like, or a stress regulating agent.

Further, when the compound of the invention or a prodrug thereof is used as a surrogate ligand, it is possible to screen 14273 receptor agonists or 14273 receptor antagonists with good efficiency.

BEST MODE FOR CARRYING OUT THE INVENTION

Figure 1:
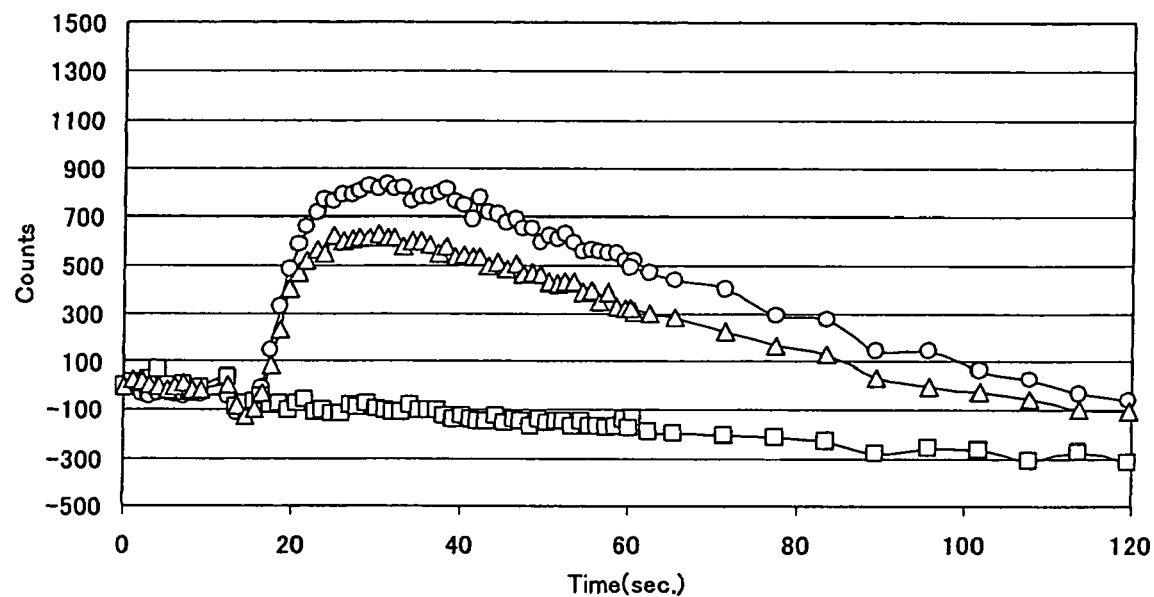
FIG. 1 shows the results of investigation on the change in the intracellular $Ca^{2+}$ concentration when 30 μM of palmitoleic acid was added. The term Counts on the ordinate indicates the fluorescence intensity indicating the intracellular $Ca^{2+}$ concentration, while the term Time (sec.) on the abscissa indicates the time passage (seconds) after sample addition. Symbol ○ indicates CHO-K1 cells expressing human 14273, symbol Δ indicates CHO-K1 cells expressing mouse 14273, and symbol □ indicates control CHO-K1 cells which do not express 14273.

The compound used for the present invention is a compound containing an aromatic ring and a group capable of releasing a cation; preferably a carboxylic acid containing an aromatic ring, or a derivative thereof; more preferably a carboxylic acid containing two or more aromatic rings, or a derivative thereof; and specifically Compound (I), Compound (II), Compound (III), Compound (IV), Compound (V), Compound (VI) and Compound (VII) described above. Compound (II) and Compound (VI) are new compounds.

In the present specification, an aromatic ring refers to an aromatic hydrocarbon ring or an aromatic heterocyclic ring.

For the aromatic hydrocarbon ring, a hydrocarbon ring having 6 to 14 carbon atoms, such as a benzene ring, a naphthalene ring or the like, is used, and among them, a benzene ring is preferably used.

For the aromatic heterocyclic ring, for example, a 5- to 14-membered (monocyclic, bicyclic or tricyclic), preferably 5- to 10-membered, and more preferably 5- or 6-membered, aromatic heterocyclic ring containing, in addition to carbon atoms, 1 to 4 heteroatoms of one or two kinds selected from a nitrogen atom, a sulfur atom and an oxygen atom is used. The "5- to 14-membered (preferably, 5- to 10-membered) aromatic heterocyclic ring" may be exemplified by an aromatic heterocyclic ring such as thiophene, furan, oxazole, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine or the like, or a ring formed by condensation of such a ring (preferably, monocyclic ring) with one or a plurality (preferably, one or two) of aromatic rings (e.g., benzene ring, etc.), and the like. Among these, aromatic heterocyclic rings having no basicity are preferred, and examples thereof include aromatic heterocyclic rings such as thiophene, benzo[b]thiophene, benzo[b]furan, benzoxazole, benzothiazole, benzisothiazole, naphtho[2,3-b]thiophene, furan, indole, carbazole, thiazole, isothiazole, isoxazole and the like, or a ring formed by condensation of such a ring (preferably, monocyclic ring) with one or a plurality of (preferably, one or two) aromatic rings (e.g., a benzene ring, etc.) having no basicity, and the like.

In the present specification, the group capable of releasing a cation may be a group which is capable of releasing a cation chemically (for example, through a chemical reaction such as oxidation, reduction, hydrolysis or the like, etc.) or biologically, that is, under physiological conditions (for example, through an in vivo reaction such as oxidation, reduction, hydrolysis by an in vivo enzyme or the like, etc.), or a group which can be converted thereto.

The group capable of releasing a cation may be exemplified by (1) a 5-membered heterocyclic group capable of releasing a cation, (2) a carboxyl group, (3) a sulfonic acid group, (4) a sulfamoyl group which may be mono-substituted with a $C_{1-4}$ alkyl group, (5) a phosphonic acid group, (6) a carbamoyl group which may be mono-substituted with a $C_{1-4}$ alkyl group (e.g., methyl, ethyl, propyl, butyl, isobutyl, tert-butyl, etc.), (7) a $C_{2-7}$ alkylsulfonylthiocarbamoyl group (e.g., methylsulfonylthiocarbamoyl, ethylsulfonylthiocarbamoyl, etc.), or (8) a trifluoromethanesulfonic acid amide group ($-NHSO_2CF_3$), or the like.

The 5-membered heterocyclic group capable of releasing a cation is a 5-membered heterocyclic group having 1 to 4 atoms selected from N, O and S as the ring-constituting atom, or the like, and may be exemplified by

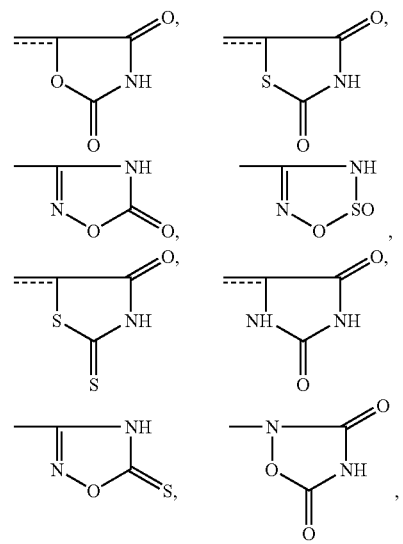

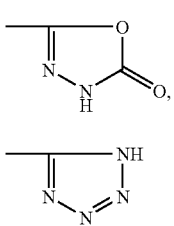
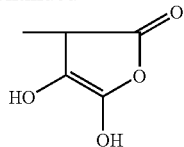

and the like.

Among these,

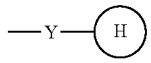

is preferred, and particularly,

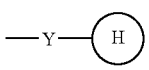

is preferred.

The group capable of releasing a cation is particularly preferably a carboxyl group.

With respect to Compound (I) and Compound (VII), ring A is an aromatic ring which may be substituted.

The aromatic ring represented by ring A is preferably a benzene ring, or an aromatic heterocyclic ring having no basicity, such as thiophene, benzo[b]thiophene, benzo[b]furan, benzoxazole, benzothiazole, benzisothiazole, naphtho[2,3-b]thiophene, furan, indole, carbazole, thiazole, isothiazole, isoxazole or the like, and particularly, a benzene ring is suitable.

With respect to Compound (I) and Compound (VII), ring B is an aromatic ring which may be further substituted with substituent(s), in addition to

—Y—(H)

or —Y—COOH.

The aromatic ring represented by ring B is preferably a benzene ring, or an aromatic heterocyclic ring having no basicity, such as thiophene, benzo[b]thiophene, benzo[b]furan, benzoxazole, benzothiazole, benzisothiazole, naphtho[2,3-b]thiophene, furan, indole, carbazole, thiazole, isothiazole, isoxazole or the like, and particularly, a benzene ring is suitable.

The above-mentioned substituent which may be carried by ring A, and the substituent which may be carried by ring B in addition to

—Y—(H)

or —Y—COOH, may be exemplified by substituent(s) selected from oxo; a halogen atom (e.g., fluorine, chlorine, bromine, iodine, etc.); $C_{1-3}$ alkylenedioxy (e.g., methylenedioxy, ethylenedioxy, etc.); nitro; cyano; carboxyl which may be esterified; lower ($C_{1-6}$) alkyl which may be substituted; lower ($C_{2-6}$) alkenyl which may be substituted; lower ($C_{2-6}$) alkynyl which may be substituted; $C_{3-8}$ cycloalkyl which may be substituted; lower ($C_{1-6}$) alkoxy which may be substituted; lower ($C_{2-6}$) alkenyloxy which may be substituted; lower ($C_{2-6}$) alkynyloxy which may be substituted; $C_{3-8}$ cycloalkyloxy which may be substituted; hydroxyl; mercapto; lower ($C_{1-6}$) alkylthio which may be substituted; formyl; lower ($C_{1-6}$) alkyl-carbonyl which may be substituted; $C_{3-8}$ cycloalkyl-carbonyl which may be substituted; lower ($C_{1-6}$) alkylsulfonyl (e.g., methylsulfonyl, ethylsulfonyl, etc.) which may be substituted; lower ($C_{1-6}$) alkylsulfinyl (e.g., methylsulfinyl, ethylsulfinyl, etc.) which may be substituted; amino [e.g., amino, mono- or di-lower ($C_{1-6}$) alkylamino which may be substituted, mono- or di-$C_{3-8}$ cycloalkylamino which may be substituted, mono- or di-$C_{6-14}$ arylamino which may be substituted, mono- or di-$C_{7-16}$ aralkylamino which may be substituted, $C_{6-14}$ aryl-carbonylamino which may be substituted, formylamino; lower ($C_{1-6}$) aralkyl-carbonyl-amino which may be substituted; $C_{3-8}$ cycloaralkyl-carbonyl-amino which may be substituted; lower ($C_{1-6}$) alkoxy-carbonyl-amino which may be substituted; lower ($C_{1-6}$) alkylsulfonylamino which may be substituted; $C_{6-14}$ arylsulfonylamino (e.g., phenylsulfonylamino, 2-naphthylsulfonylamino, 1-naphthylsulfonylamino, etc.) which may be substituted]; lower ($C_{1-6}$) alkyl-carbonyloxy which may be substituted; lower ($C_{1-6}$) alkoxy-carbonyloxy which may be substituted; mono-lower ($C_{1-6}$) alkyl-carbamoyloxy which may be substituted; di-lower ($C_{1-6}$) alkyl-carbamoyloxy which may be substituted; sulfo; sulfamoyl; sulfinamoyl; sulfenamoyl; 5- to 7-membered heterocyclylcarbonyl containing, in addition to carbon atoms, 1 to 4 heteroatoms of one or two kinds selected from a nitrogen atom, a sulfur atom and an oxygen atom, which may be substituted; $C_{6-14}$ aryloxy which may be substituted; $C_{7-16}$ aralkyloxy which may be substituted; $C_{6-14}$ arylthio which may be substituted; $C_{7-16}$ aralkylthio which may be substituted; $C_{6-14}$ aryl-carbonyl which may be substituted; $C_{7-16}$ aralkyl-carbonyl which may be substituted; $C_{6-14}$ aryl-carbonylamino which may be substituted; $C_{6-14}$ aryl-carbonyloxy which may be substituted; mono- or di-$C_{6-14}$ arylcarbamoyloxy which may be substituted; $C_{6-14}$ arylsulfonyl which may be substituted; $C_{6-14}$ arylsulfinyl which may be substituted; $C_{6-14}$ arylsulfonylamino which may be substituted; heterocyclyloxy which may be substituted (preferably, aromatic heterocyclyloxy which may be substituted); $C_{6-14}$ aryl which may be substituted; $C_{7-16}$ aralkyl which may be substituted; $C_{6-14}$ aryl-$C_{2-6}$ alkenyl which may be substituted; a heterocyclic group which may be substituted; thiocarbamoyl; and a carbamoyl group which may be substituted; and substituent(s) selected from the groups in which two or more (e.g., 2 or 3) of these substituents are combined; and the like (hereinafter, simply referred to as Substituent Group A). Ring A may have 1 to 5, preferably 1 to 3, of the above-mentioned substituents on substitutable positions, and when there are two or more substituents, they may be identical or different.

The "optionally esterified carboxyl" in the Substituent Group A may be exemplified by carboxyl, $C_{1-6}$ alkoxy-carbonyl (e.g., methoxycarbonyl, ethoxycarbonyl, propoxycarbonyl, tert-butoxycarbonyl, etc.) which may be substituted, $C_{6-14}$ aryloxycarbonyl (e.g., phenoxycarbonyl, etc.) which may be substituted, $C_{7-16}$ aralkyloxycarbonyl (e.g., benzyloxycarbonyl, phenethyloxycarbonyl, etc.) which may be substituted, or the like.

The "lower ($C_{1-6}$) alkyl" of the "optionally substituted lower ($C_{1-6}$) alkyl" in the Substituent Group A may be exemplified by methyl, ethyl, propyl, isopropyl, butyl, isobutyl, sec-butyl, tert-butyl, pentyl, isopentyl, neopentyl, hexyl, or the like.

The "lower ($C_{2-6}$) alkenyl" of the "optionally substituted lower ($C_{2-6}$) alkenyl" in the Substituent Group A may be exemplified by vinyl, propenyl, isopropenyl, 2-buten-1-yl, 4-penten-1-yl, 5-hexen-1-yl, or the like.

The "lower ($C_{2-6}$) alkynyl" of the "optionally substituted lower ($C_{2-6}$) alkynyl" in the Substituent Group A may be exemplified by 2-butyn-1-yl, 4-pentyn-1-yl, 5-hexyn-1-yl, or the like.

The "lower ($C_{1-6}$) alkoxy" of the "optionally substituted lower ($C_{1-6}$) alkoxy" in the Substituent Group A may be exemplified by methoxy, ethoxy, propoxy, isopropoxy, butoxy, isobutoxy, sec-butoxy, pentyloxy, hexyloxy, or the like.

The "lower ($C_{1-6}$) alkylthio" of the "optionally substituted lower ($C_{1-6}$) alkylthio" in the Substituent Group A may be exemplified by methylthio, ethylthio, propylthio, isopropylthio, butylthio, sec-butylthio, tert-butylthio, or the like.

The "lower ($C_{1-6}$) alkyl-carbonyl" of the "optionally substituted lower ($C_{1-6}$) alkyl-carbonyl" in the Substituent Group A may be exemplified by acetyl, propionyl, pivaloyl, or the like.

The "mono- or di-lower ($C_{1-6}$) alkylamino" of the "optionally substituted mono- or di-lower ($C_{1-6}$) alkylamino" in the Substituent Group A may be exemplified by methylamino, ethylamino, propylamino, dimethylamino, diethylamino, or the like.

The "lower ($C_{1-6}$) aralkyl-carbonyl-amino" of the "optionally substituted lower ($C_{1-6}$) aralkyl-carbonyl-amino" in the Substituent Group A may be exemplified by acetylamino, propionylamino, pivaloylamino, or the like.

The "lower ($C_{1-6}$) alkoxy-carbonyl-amino" of the "optionally substituted lower ($C_{1-6}$) alkoxy-carbonyl-amino" in the Substituent Group A may be exemplified by methoxycarbonylamino, ethoxycarbonylamino, propoxycarbonylamino, butoxycarbonylamino, or the like.

The "lower ($C_{1-6}$) alkylsulfonylamino" of the "optionally substituted lower ($C_{1-6}$) alkylsulfonylamino" in the Substituent Group A may be exemplified by methylsulfonylamino, ethylsulfonylamino, or the like.

The "lower ($C_{1-6}$) alkyl-carbonyloxy" of the "optionally substituted lower ($C_{1-6}$) alkyl-carbonyloxy" in the Substituent Group A may be exemplified by acetoxy, propionyloxy, or the like.

The "lower ($C_{1-6}$) alkoxy-carbonyloxy" of the "optionally substituted lower ($C_{1-6}$) alkoxy-carbonyloxy" in the Substituent Group A may be exemplified by methoxycarbonyloxy, ethoxycarbonyloxy, propoxycarbonyloxy, butoxycarbonyloxy, or the like.

The "mono-lower ($C_{1-6}$) alkyl-carbamoyloxy" of the "optionally substituted mono-lower ($C_{1-6}$) alkyl-carbamoyloxy" in the Substituent Group A may be exemplified by methylcarbamoyloxy, ethylcarbamoyloxy, or the like.

The "di-lower ($C_{1-6}$) alkyl-carbamoyloxy" of the "optionally substituted di-lower ($C_{1-6}$) alkyl-carbamoyloxy" in the Substituent Group A may be exemplified by dimethylcarbamoyloxy, diethylcarbamoyloxy, or the like.

These "lower alkyl group", "lower alkenyl", "lower alkynyl", "lower alkoxy", "lower alkenyloxy", "lower alkynyloxy", "lower alkylthio", "lower alkyl-carbonyl", "$C_{1-6}$ alkoxy-carbonyl", "lower alkylsulfonyl", "lower alkylsulfinyl", "mono- or di-lower ($C_{1-6}$) alkylamino", "lower aralkyl-carbonyl-amino", "lower alkoxy-carbonyl-amino", "lower alkylsulfonylamino", "lower alkyl-carbonyloxy", "lower alkoxy-carbonyloxy", "mono-lower alkyl-carbamoyloxy" and "di-lower alkyl-carbamoyloxy" may respectively have 1 to 5 substituents selected from, for example, a halogen atom (e.g., a fluorine atom, a chlorine atom, a bromine atom, an iodine atom); hydroxyl; nitro; cyano; amino; a 5- to 7-membered heterocyclic group containing, in addition to carbon atoms, 1 to 4 heteroatoms of one or two kinds selected from a nitrogen atom, a sulfur atom and an oxygen atom (e.g., furyl, pyridyl, thienyl, piperidino, piperazino, morpholino, etc.) (this heterocyclic group may be substituted with a halogen atom, hydroxyl, amino, lower ($C_{1-6}$) alkyl which may be halogenated, formyl, $C_{1-6}$ alkyl-carbonyl, $C_{6-14}$ aryl-carbonyl, $C_{7-16}$ aralkyl-carbonyl, a 5- to 7-membered heterocyclylcarbonyl group containing, in addition to carbon atoms, 1 to 4 heteroatoms of one or two kinds selected from a nitrogen atom, a sulfur atom and an oxygen atom, mono- or di-lower ($C_{1-6}$) alkylamino, mono- or di-$C_{6-14}$ arylamino, $C_{3-8}$ cycloalkyl, lower ($C_{1-6}$) alkoxy, lower ($C_{1-6}$) alkylthio, lower ($C_{1-6}$) alkylsulfinyl, lower ($C_{1-6}$) alkylsulfonyl, the above-mentioned carboxyl (particularly, lower ($C_{1-6}$) alkoxy-carbonyl) which may be esterified, carbamoyl, thiocarbamoyl, mono-lower ($C_{1-6}$) alkyl-carbamoyl, di-lower ($C_{1-6}$) alkyl-carbamoyl, mono- or di-$C_{6-14}$ arylcarbamoyl, or the like); formyl; $C_{1-6}$ alkyl-carbonyl; $C_{6-14}$ aryl-carbonyl; $C_{7-16}$ aralkyl-carbonyl; a 5- to 7-membered heterocyclylcarbonyl group containing, in addition to carbon atoms, 1 to 4 heteroatoms of one or two kinds selected from a nitrogen atom, a sulfur atom and an oxygen atom; mono- or di-lower ($C_{1-6}$) alkylamino; mono- or di-$C_{6-14}$ arylamino; formylamino; mono- or di-$C_{1-6}$ aralkyl-carbonyl-amino, mono- or di-$C_{1-6}$ alkoxy-carbonyl-amino; $C_{3-8}$ cycloalkyl; lower ($C_{1-6}$) alkoxy which may be halogenated; lower ($C_{1-6}$) alkylthio; lower ($C_{1-6}$) alkylsulfinyl; lower ($C_{1-6}$) alkylsulfonyl; the above-mentioned carboxyl (particularly, lower ($C_{1-6}$) alkoxy-carbonyl) which may be esterified; carbamoyl; thiocarbamoyl; mono-lower ($C_{1-6}$) alkyl-carbamoyl (e.g., methylcarbamoyl, ethylcarbamoyl, etc.); di-lower ($C_{1-6}$) alkyl-carbamoyl (e.g., dimethylcarbamoyl, diethylcarbamoyl, ethylmethylcarbamoyl, etc.); mono- or di-$C_{6-14}$ arylcarbamoyl (e.g., phenylcarbamoyl, 1-naphthylcarbamoyl, 2-naphthylcarbamoyl, etc.); mono- or di-5- to 7-membered heterocyclylcarbamoyl containing, in addition to carbon atoms, 1 to 4 heteroatoms of one or two kinds selected from a nitrogen atom, a sulfur atom and an oxygen atom (e.g., 2-pyridylcarbamoyl, 3-pyridylcarbamoyl, 4-pyridylcarbamoyl, 2-thienylcarbamoyl, 3-thienylcarbamoyl, etc.); $C_{1-6}$ aralkyl-carbonyl-amino (e.g., acetylamino, propionylamino) which may be substituted with carboxyl; tri-$C_{1-6}$ alkylsilyloxy (tert-butyldimethylsilyloxy); and the like (hereinafter, Substituent Group B), on substitutable positions.

The "$C_{3-8}$ cycloalkyl" of the "optionally substituted $C_{3-8}$ cycloalkyl" in the Substituent Group A may be exemplified by cyclopropyl, cyclobutyl, cyclopentyl, cyclohexyl, or the like.

The "$C_{3-8}$ cycloalkyl-carbonyl" of the "optionally substituted $C_{3-8}$ cycloalkyl-carbonyl" in the Substituent Group A may be exemplified by cyclopropylcarbonyl, cyclopentylcarbonyl, cyclohexylcarbonyl, or the like.

The "mono- or di-$C_{3-8}$ cycloalkylamino" of the "optionally substituted mono- or di-$C_{3-8}$ cycloalkylamino" in the Substituent Group A may be exemplified by cyclopropylamino, cyclopentylamino, cyclohexylamino, or the like.

The "$C_{3-8}$ cycloaralkyl-carbonyl-amino" of the "optionally substituted $C_{3-8}$ cycloaralkyl-carbonyl-amino" in the Substituent Group A may be exemplified by cyclopropylcarbonylamino, cyclopentylcarbonylamino, cyclohexylcarbonylamino, or the like.

The "5- to 7-membered heterocyclylcarbonyl containing, in addition to carbon atoms, 1 to 4 heteroatoms of one or two kinds selected from a nitrogen atom, a sulfur atom and an oxygen atom" of the "optionally substituted 5- to 7-membered heterocyclylcarbonyl containing, in addition to carbon atom(s), 1 to 4 heteroatoms of one or two kinds selected from a nitrogen atom, a sulfur atom and an oxygen atom" in the Substituent Group A may be exemplified by nicotinoyl, isonicotinoyl, thenoyl, furoyl, morpholinocarbonyl, thiomorpholinocarbonyl, piperazine-1-ylcarbonyl, pyrrolidin-1-ylcarbonyl, or the like.

The "$C_{6-14}$ aryloxy" of the "optionally substituted $C_{6-14}$ aryloxy" in the Substituent Group A may be exemplified by phenyloxy, 1-naphthyloxy, 2-naphthyloxy, or the like.

The "$C_{7-16}$ aralkyloxy" of the "optionally substituted $C_{7-16}$ aralkyloxy" in the substituent Group A may be exemplified by benzyloxy, phenethyloxy, or the like.

The "$C_{6-14}$ arylthio" of the "optionally substituted $C_{6-14}$ arylthio" in the Substituent Group A may be exemplified by phenylthio, 1-naphthylthio, 2-naphthylthio, or the like.

The "$C_{7-16}$ aralkylthio" of the "optionally substituted $C_{7-16}$ aralkylthio" in the Substituent Group A may be exemplified by benzylthio, phenethylthio, or the like.

The "$C_{6-14}$ aryl-carbonyl" of the "optionally substituted $C_{6-14}$ aryl-carbonyl" in the Substituent Group A may be exemplified by benzoyl, 1-naphthoyl, 2-naphthoyl, or the like.

The "$C_{7-16}$ aralkyl-carbonyl" of the "optionally substituted $C_{7-16}$ aralkyl-carbonyl" in the Substituent Group A may be exemplified by phenylacetyl, 3-phenylpropionyl, or the like.

The "mono- or di-$C_{6-14}$ arylamino" of the "optionally substituted mono- or di-$C_{6-14}$ arylamino" in the Substituent Group A may be exemplified by phenylamino, diphenylamino, or the like.

The "mono- or di-$C_{7-16}$ aralkylamino" of the "optionally substituted mono- or di-$C_{7-16}$ aralkylamino" in the Substituent Group A may be exemplified by benzylamino, or the like.

The "$C_{6-14}$ aryl-carbonylamino" of the "optionally substituted $C_{6-14}$ aryl-carbonylamino" in the Substituent Group A may be exemplified by benzoylamino, naphthoylamino, or the like.

The "$C_{6-14}$ arylsulfonylamino" of the "optionally substituted $C_{6-14}$ arylsulfonylamino" in the Substituent Group A may be exemplified by phenylsulfonylamino, 2-naphthylsulfonylamino, 1-naphthylsulfonylamino, or the like.

The "$C_{6-14}$ aryl-carbonylamino" of the "optionally substituted $C_{6-14}$ aryl-carbonylamino" in the Substituent Group A may be exemplified by benzoylamino, naphthoylamino, or the like.

The "$C_{6-14}$ aryl-carbonyloxy" of the "optionally substituted $C_{6-14}$ aryl-carbonyloxy" in the Substituent Group A may be exemplified by benzoyloxy, naphthylcarbonyloxy, or the like.

The "mono- or di-$C_{6-14}$ arylcarbamoyloxy" of the "optionally substituted mono- or di-$C_{6-14}$ arylcarbamoyloxy" in the Substituent Group A may be exemplified by phenylcarbamoyloxy, naphthylcarbamoyloxy, or the like.

The "$C_{6-14}$ arylsulfonyl" of the "optionally substituted $C_{6-14}$ arylsulfonyl" in the Substituent Group A may be exemplified by phenylsulfonyl, 1-naphthylsulfonyl, 2-naphthylsulfonyl, or the like.

The "$C_{6-14}$ arylsulfinyl" of the "optionally substituted $C_{6-14}$ arylsulfinyl" in the Substituent Group A may be exemplified by phenylsulfinyl, 1-naphthylsulfinyl, 2-naphthylsulfinyl, or the like.

The "$C_{6-14}$ arylsulfonylamino" of the "optionally substituted $C_{6-14}$ arylsulfonylamino" in the Substituent Group A may be exemplified by phenylsulfonylamino, or the like.

The "heterocyclyloxy" of the "optionally substituted heterocyclyloxy" in the Substituent Group A may be exemplified by 5- to 10-membered heterocyclic-oxy containing, in addition to carbon atoms, 1 to 4 heteroatoms of one or two kinds selected from a nitrogen atom, a sulfur atom and an oxygen atom, or the like. For the heterocyclic moiety, the same one as the "heterocyclic group" of the "optionally substituted heterocyclic group" to be described below can be used.

The "aromatic heterocyclyloxy" of the "optionally substituted aromatic heterocyclyloxy" in the Substituent Group A may be exemplified by 5- to 10-membered aromatic heterocyclic-oxy containing, in addition to carbon atoms, 1 to 4 heteroatoms of one or two kinds selected from a nitrogen atom, a sulfur atom and an oxygen atom, and the like, and specifically, pyrazinyloxy and the like can be used.

These "$C_{3-8}$ cycloalkyl", "$C_{3-8}$ cycloalkyloxy", "$C_{3-8}$ cycloalkyl-carbonyl", "mono- or di-$C_{3-8}$ cycloalkylamino", "$C_{3-8}$ cycloaralkyl-carbonyl-amino", "5- to 7-membered heterocyclylcarbonyl containing, in addition to carbon atoms, 1 to 4 heteroatoms of one or two kinds selected from a nitrogen atom, a sulfur atom and an oxygen atom", "$C_{6-14}$ aryloxy", "$C_{7-16}$ aralkyloxy", "$C_{6-14}$ arylthio", "$C_{7-16}$ aralkylthio", "$C_{6-14}$ aryl-carbonyl", "$C_{7-16}$ aralkyl-carbonyl", "$C_{6-14}$ aryloxycarbonyl", "$C_{7-16}$ aralkyloxycarbonyl", "mono- or di-$C_{6-14}$ arylamino", "mono- or di-$C_{7-16}$ aralkylamino", "$C_{6-14}$ arylsulfonylamino", "$C_{6-14}$ aryl-carbonylamino", "$C_{6-14}$ aryl-carbonyloxy", "mono- or di-$C_{6-14}$ arylcarbamoyloxy", "$C_{6-14}$ arylsulfonyl", "$C_{6-14}$ arylsulfinyl", "$C_{6-14}$ arylsulfonylamino", "heterocyclyloxy", and "aromatic heterocyclyloxy" may respectively have 1 to 5 substituents selected from a halogen atom (e.g., a fluorine atom, a chlorine atom, a bromine atom, an iodine atom); hydroxyl; nitro; cyano; amino; the above-mentioned lower alkyl which may be substituted; the above-mentioned lower alkenyl which may be substituted; the above-mentioned lower alkynyl which may be substituted; formyl; $C_{1-6}$ alkyl-carbonyl; $C_{6-14}$ aryl-carbonyl; $C_{7-16}$ aralkyl-carbonyl; a 5- to 7-membered heterocyclylcarbonyl group containing, in addition to carbon atoms, 1 to 4 heteroatoms of one or two kinds selected from a nitrogen atom, a sulfur atom and an oxygen atom; $C_{6-14}$ aryl (this $C_{6-14}$ aryl may be substituted with a halogen atom, hydroxyl, amino, lower ($C_{1-6}$) alkyl which may be halogenated, formyl, $C_{1-6}$ alkyl-carbonyl, $C_{6-14}$ aryl-carbonyl, $C_{7-16}$ aralkyl-carbonyl, a 5- to 7-membered heterocyclylcarbonyl group containing, in addition to carbon atoms, 1 to 4 heteroatoms of one or two kinds selected from a nitrogen atom, a sulfur atom and an oxygen atom, mono- or di-lower ($C_{1-6}$) alkylamino, mono- or di-$C_{6-14}$ arylamino, formylamino; mono- or di-$C_{1-6}$ aralkyl-carbonyl-amino, mono- or di-$C_{1-6}$ alkoxy-carbonyl-amino; $C_{3-8}$ cycloalkyl, lower ($C_{1-6}$) alkoxy, lower ($C_{1-6}$) alkylthio, lower ($C_{1-6}$) alkylsulfinyl, lower ($C_{1-6}$) alkylsulfonyl, the above-mentioned carboxyl (particularly, lower ($C_{1-6}$) alkoxy-carbonyl) which may be esterified, carbamoyl, thiocarbamoyl, mono-lower ($C_{1-6}$) alkyl-carbamoyl, di-lower ($C_{1-6}$) alkyl-carbamoyl, mono- or di-$C_{6-14}$ arylcarbamoyl, or the like); $C_{6-14}$ aryloxy (this $C_{6-14}$ aryloxy may be substituted with a halogen atom, hydroxyl, amino, lower ($C_{1-6}$) alkyl which may be halogenated, formyl, $C_{1-6}$ alkyl-carbonyl, $C_{6-14}$ aryl-carbonyl, $C_{7-16}$ aralkyl-carbonyl, a 5- to 7-membered heterocyclylcarbonyl group containing, in addition to carbon atoms, 1 to 4 heteroatoms of one or two kinds selected from a nitrogen atom, a sulfur atom and an oxygen atom, mono- or di-lower ($C_{1-6}$) alkylamino, mono- or di-$C_{6-14}$ arylamino, formylamino; mono- or di-$C_{1-6}$ aralkyl-carbonyl-amino, mono- or di-$C_{1-6}$ alkoxy-carbonyl-amino; $C_{3-8}$ cycloalkyl, lower ($C_{1-6}$) alkoxy, lower ($C_{1-6}$) alkylthio, lower ($C_{1-6}$) alkylsulfinyl, lower ($C_{1-6}$) alkylsulfonyl, the above-mentioned carboxyl (particularly, lower ($C_{1-6}$) alkoxy-carbonyl) which may be esterified, carbamoyl, thiocarbamoyl, mono-lower ($C_{1-6}$) alkyl-carbamoyl, di-lower ($C_{1-6}$) alkylcarbamoyl, mono- or di-$C_{6-14}$ arylcarbamoyl, or the like); $C_{7-16}$ aralkyloxy (this $C_{7-16}$ aralkyloxy may be substituted with a halogen atom, hydroxyl, amino, lower ($C_{1-6}$) alkyl-formyl which may be halogenated, $C_{1-6}$ alkyl-carbonyl, $C_{6-14}$ aryl-carbonyl, $C_{7-16}$ aralkyl-carbonyl, a 5- to 7-membered heterocyclylcarbonyl group containing, in addition to carbon atoms, 1 to 4 heteroatoms of one or two kinds selected from a nitrogen atom, a sulfur atom and an oxygen atom, mono- or di-lower ($C_{1-6}$) alkylamino, mono- or di-$C_{6-14}$ arylamino, $C_{3-8}$ cycloalkyl, lower ($C_{1-6}$) alkoxy, lower ($C_{1-6}$) alkylthio, lower ($C_{1-6}$) alkylsulfinyl, lower ($C_{1-6}$) alkylsulfonyl, the above-mentioned carboxyl (particularly, lower ($C_{1-6}$) alkoxy-carbonyl) which may be esterified, carbamoyl, thiocarbamoyl, mono-lower ($C_{1-6}$) alkyl-carbamoyl, di-lower ($C_{1-6}$) alkyl-carbamoyl, mono- or di-$C_{6-14}$ arylcarbamoyl, or the like); a 5- to 7-membered heterocyclic group (e.g., furyl, pyridyl, thienyl, piperidino, piperazino, morpholino, etc.) containing, in addition to carbon atoms, 1 to 4 heteroatoms of one or two kinds selected from a nitrogen atom, a sulfur atom and an oxygen atom (this heterocyclic group may be substituted with a halogen atom, hydroxyl, amino, formyl, $C_{1-6}$ alkyl-carbonyl, $C_{6-14}$ aryl-carbonyl, $C_{7-16}$ aralkyl-carbonyl, a 5- to 7-membered heterocyclylcarbonyl group containing, in addition to carbon atoms, 1 to 4 heteroatoms of one or two kinds selected from a nitrogen atom, a sulfur atom and an oxygen atom, mono- or di-lower ($C_{1-6}$) alkylamino, mono- or di-$C_{6-14}$ arylamino, $C_{3-8}$ cycloalkyl, lower ($C_{1-6}$) alkoxy, lower ($C_{1-6}$) alkylthio, lower ($C_{1-6}$) alkylsulfinyl, lower ($C_{1-6}$) alkylsulfonyl, the above-mentioned carboxyl (particularly, lower ($C_{1-6}$) alkoxy-carbonyl) which may be esterified, carbamoyl, thiocarbamoyl, mono-lower ($C_{1-6}$) alkyl-carbamoyl, di-lower ($C_{1-6}$) alkyl-carbamoyl, mono- or di-$C_{6-14}$ arylcarbamoyl, or the like); mono- or di-lower ($C_{1-6}$) alkylamino; mono- or di-$C_{6-14}$ arylamino; $C_{3-8}$ cycloalkyl; the above-mentioned lower ($C_{1-6}$) alkoxy which may be substituted; lower ($C_{1-6}$) alkylthio; lower ($C_{1-6}$) alkylsulfinyl; lower ($C_{1-6}$) alkylsulfonyl; the above-mentioned carboxyl (particularly, lower ($C_{1-6}$) alkoxy-carbonyl) which may be esterified; carbamoyl; thiocarbamoyl; mono-lower ($C_{1-6}$) alkyl-carbamoyl (e.g., methylcarbamoyl, ethylcarbamoyl, etc.); di-lower ($C_{1-6}$) alkyl-carbamoyl (e.g., dimethylcarbamoyl, diethylcarbamoyl, ethylmethylcarbamoyl, etc.); mono- or di-$C_{6-14}$ arylcarbamoyl (e.g., phenylcarbamoyl, 1-naphthylcarbamoyl, 2-naphthylcarbamoyl, etc.); mono- or di-5- to 7-membered heterocyclylcarbamoyl (e.g., 2-pyridylcarbamoyl, 3-pyridylcarbamoyl, 4-pyridylcarbamoyl, 2-thienylcarbamoyl, 3-thienylcarbamoyl, etc.) containing, in addition to carbon atoms, 1 to 4 heteroatoms of one or two kinds selected from a nitrogen atom, a sulfur atom and an oxygen atom; tri-$C_{1-6}$ alkylsilyloxy (tert-butyldimethylsilyloxy); and the like (hereinafter, Substituent Group C), on substitutable positions.

The "$C_{6-14}$ aryl" of the "optionally substituted $C_{6-14}$ aryl" in the Substituent Group A may be exemplified by phenyl, 1-naphthyl, 2-naphthyl, 2-biphenylyl, 3-biphenylyl, 4-biphenylyl, 2-anthryl, or the like. This $C_{6-14}$ aryl may be partially saturated, and the partially saturated $C_{6-14}$ aryl may be exemplified by tetrahydronaphthyl or the like.

The "$C_{7-16}$ aralkyl" of the "optionally substituted $C_{7-16}$ aralkyl" in the Substituent Group A may be exemplified by benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl), or the like.

The "$C_{6-14}$ aryl-$C_{2-6}$ alkenyl" of the "optionally substituted $C_{6-14}$ aryl-$C_{2-6}$ alkenyl" in the Substituent Group A may be exemplified by styryl or the like.

These "$C_{6-14}$ aryl", "$C_{7-16}$ aralkyl" and "$C_{6-14}$ aryl-$C_{2-6}$ alkenyl" may be substituted with 1 to 5 substituents selected from, for example, a halogen atom; hydroxyl; nitro; cyano; the above-mentioned lower alkyl which may be substituted; the above-mentioned lower alkenyl which may be substituted; the above-mentioned lower alkynyl which may be substituted; the above-mentioned $C_{3-8}$ cycloalkyl which may be substituted; the above-mentioned lower alkoxy which may be substituted; the above-mentioned lower alkylthio which may be substituted; mercapto; the above-mentioned lower alkylthio which may be substituted; formyl; the above-mentioned lower alkyl-carbonyl which may be substituted; the above-mentioned $C_{3-8}$ cycloalkyl-carbonyl which may be substituted; the above-mentioned lower alkylsulfonyl which may be substituted; the above-mentioned lower alkylsulfinyl which may be substituted; amino, the above-mentioned mono- or di-lower alkylamino which may be substituted; the above-mentioned mono- or di-$C_{3-8}$ cycloalkylamino which may be substituted; the above-mentioned mono- or di-$C_{6-14}$ arylamino which may be substituted; the above-mentioned mono- or di-$C_{7-16}$ aralkylamino which may be substituted; the above-mentioned $C_{6-14}$ aryl-carbonylamino which may be substituted; formylamino; the above-mentioned lower aralkyl-carbonyl-amino which may be substituted; the above-mentioned $C_{3-8}$ cycloaralkyl-carbonyl-amino which may be substituted; the above-mentioned lower alkoxy-carbonyl-amino which may be substituted; the above-mentioned lower alkylsulfonylamino which may be substituted; the above-mentioned $C_{6-14}$ arylsulfonylamino which may be substituted; the above-mentioned lower alkyl-carbonyloxy which may be substituted; the above-mentioned lower alkoxy-carbonyloxy which may be substituted; the above-mentioned mono-lower alkyl-carbamoyloxy which may be substituted; the above-mentioned di-lower alkyl-carbamoyloxy which may be substituted; sulfo; sulfamoyl; sulfinamoyl; sulfenamoyl; the above-mentioned 5- to 7-membered heterocyclylcarbonyl containing, in addition to carbon atoms, 1 to 4 heteroatoms of one or two kinds selected from a nitrogen atom, a sulfur atom and an oxygen atom, which may be substituted; the above-mentioned $C_{6-14}$ aryloxy which may be substituted; the above-mentioned $C_{7-16}$ aralkyloxy which may be substituted; the above-mentioned $C_{6-14}$ arylthio which may be substituted; the above-mentioned $C_{7-16}$ aralkylthio which may be substituted; the above-mentioned $C_{6-14}$ aryl-carbonyl which may be substituted; the above-mentioned $C_{7-16}$ aralkyl-carbonyl which may be substituted; the above-mentioned $C_{6-14}$ aryl-carbonylamino which may be substituted; the above-mentioned $C_{6-14}$ aryl-carbonyloxy; the above-mentioned mono- or di-$C_{6-14}$ arylcarbamoyloxy which may be substituted; the above-mentioned $C_{6-14}$ arylsulfonyl which may be substituted; the above-mentioned $C_{6-14}$ arylsulfinyl; the above-mentioned $C_{6-14}$ arylsulfonylamino which may be substituted; the above-mentioned heterocyclyloxy which may be substituted (preferably, aromatic heterocyclyloxy which may be substituted); the above-mentioned carboxyl which may be esterified; carbamoyl; thiocarbamoyl; mono-lower ($C_{1-6}$) alkyl-carbamoyl; di-lower ($C_{1-6}$) alkyl-carbamoyl; mono- or di-$C_{6-14}$ arylcarbamoyl; mono- or di-5- to 7-membered heterocyclylcarbamoyl containing, in addition to carbon atoms, 1 to 4 heteroatoms of one or two kinds selected from a nitrogen atom, a sulfur atom and an oxygen atom; a 5- to 7-membered heterocyclic group (e.g., furyl, pyridyl, thienyl, piperidino, piperazino, morpholino, etc.) containing, in addition to carbon atoms, 1 to 4 heteroatoms of one or two kinds selected from a nitrogen atom, a sulfur atom and an oxygen atom (this heterocyclic group may be substituted with a halogen atom, hydroxyl, amino, lower ($C_{1-6}$) alkyl which may be halogenated, mono- or di-lower ($C_{1-6}$) alkylamino, mono- or di-$C_{6-14}$ arylamino, $C_{3-8}$ cycloalkyl, lower ($C_{1-6}$) alkoxy, lower ($C_{1-6}$) alkoxy-carbonyl, lower ($C_{1-6}$) alkylthio, lower ($C_{1-6}$) alkylsulfinyl, lower ($C_{1-6}$) alkylsulfonyl, the above-mentioned carboxyl which may be esterified, carbamoyl, thiocarbamoyl, mono-lower ($C_{1-6}$) alkyl-carbamoyl, di-lower ($C_{1-6}$) alkyl-carbamoyl, mono- or di-$C_{6-14}$ arylcarbamoyl, or the like); and the like (hereinafter, Substituent Group G), on substitutable positions.

The "heterocyclic group" of the "optionally substituted heterocyclic group" in the Substituent Group A may be preferably exemplified by a 5- to 14-membered, preferably 5- to 10-membered, and more preferably 5- to 7-membered (monocyclic, bicyclic or tricyclic) heterocyclic group containing, in addition to carbon atom(s), 1 to 4 heteroatoms of one or two kinds selected from a nitrogen atom, a sulfur atom and an oxygen atom, preferably (i) a 5- to 14-membered (preferably, 5- to 10-membered) aromatic heterocyclic group, (ii) a 5- to 10-membered non-aromatic heterocyclic group, or (iii) a monovalent group obtained by eliminating any one hydrogen atom from a 7- to 10-membered bridged heterocyclic ring. Among them, a 5-membered aromatic heterocyclic group is preferably used. Specifically, an aromatic heterocyclic group such as, for example, thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), indolyl (e.g., 1-indolyl, 2-indolyl, 3-indolyl), 2-benzothiazolyl, benzo[b]thienyl (e.g., 2-benzo[b]thienyl, 3-benzo[b]thienyl), benzo[b]furanyl (e.g., 2-benzo[b]furanyl, 3-benzo[b]furanyl) or the like; a non-aromatic heterocyclic group such as, for example, pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino or the like; or the like.

The heterocyclic group may be substituted with 1 to 5 substituents selected from, for example, a halogen atom; hydroxyl; nitro; cyano; the above-mentioned lower alkyl which may be substituted; the above-mentioned lower alkenyl which may be substituted; the above-mentioned lower alkynyl which may be substituted; the above-mentioned $C_{3-8}$ cycloalkyl which may be substituted; the above-mentioned lower alkoxy which may be substituted; mercapto; the above-mentioned lower alkylthio which may be substituted; formyl; the above-mentioned lower alkyl-carbonyl which may be substituted; the above-mentioned $C_{3-8}$ cycloalkyl-carbonyl which may be substituted; the above-mentioned lower alkylsulfonyl which may be substituted; the above-mentioned lower alkylsulfinyl which may be substituted; amino; the above-mentioned mono- or di-lower alkylamino which may be substituted; the above-mentioned mono- or di-$C_{3-8}$ cycloalkylamino which may be substituted; the above-mentioned mono- or di-$C_{6-14}$ arylamino which may be substituted; the above-mentioned mono- or di-$C_{7-16}$ aralkylamino which may be substituted; the above-mentioned $C_{6-14}$ arylcarbonylamino which may be substituted; formylamino; the above-mentioned lower aralkyl-carbonyl-amino which may be substituted; the above-mentioned $C_{3-8}$ cycloaralkyl-carbonyl-amino which may be substituted; the above-mentioned lower alkoxy-carbonyl-amino which may be substituted; the above-mentioned lower alkylsulfonylamino which may be substituted; the above-mentioned $C_{6-14}$ arylsulfonylamino which may be substituted; the above-mentioned lower alkyl-carbonyloxy which may be substituted; the above-mentioned lower alkoxy-carbonyloxy which may be substituted; the above-mentioned mono-lower alkyl-carbamoyloxy which may be substituted; the above-mentioned di-lower alkyl-carbamoyloxy which may be substituted; sulfo; sulfamoyl; sulfinamoyl; sulfenamoyl; the above-mentioned 5- to 7-membered heterocyclylcarbonyl containing, in addition to carbon atoms, 1 to 4 heteroatoms of one or two kinds selected from a nitrogen atom, a sulfur atom and an oxygen atom, which may be substituted; the above-mentioned $C_{6-14}$ aryloxy which may be substituted; the above-mentioned $C_{7-16}$ aralkyloxy which may be substituted; the above-mentioned $C_{6-14}$ arylthio which may be substituted; the above-mentioned $C_{7-16}$ aralkylthio which may be substituted; the above-mentioned $C_{6-14}$ aryl-carbonyl which may be substituted; the above-mentioned $C_{7-16}$ aralkyl-carbonyl which may be substituted; the above-mentioned $C_{6-14}$ aryl-carbonylamino which may be substituted; the above-mentioned $C_{6-14}$ aryl-carbonyloxy which may be substituted; the above-mentioned mono- or di-$C_{6-14}$ arylcarbamoyloxy which may be substituted; the above-mentioned $C_{6-14}$ arylsulfonyl which may be substituted; the above-mentioned $C_{6-14}$ arylsulfinyl which may be substituted; the above-mentioned $C_{6-14}$ arylsulfonylamino which may be substituted; the above-mentioned heterocyclyloxy which may be substituted (preferably, aromatic heterocyclyloxy which may be substituted); the above-mentioned carboxyl which may be esterified; carbamoyl; thiocarbamoyl; mono-lower ($C_{1-6}$) alkyl-carbamoyl; di-lower ($C_{1-6}$) alkyl-carbamoyl; mono- or di-$C_{6-14}$ arylcarbamoyl; mono- or di-5- to 7-membered heterocyclylcarbamoyl containing, in addition to carbon atoms, 1 to 4 heteroatoms of one or two kinds selected from a nitrogen atom, a sulfur atom and an oxygen atom; the above-mentioned $C_{6-14}$ aryl which may be substituted; the above-mentioned $C_{7-16}$ aralkyl which may be substituted; a 5- to 7-membered heterocyclic group containing, in addition to carbon atoms, 1 to 4 heteroatoms of one or two kinds selected from a nitrogen atom, a sulfur atom and an oxygen atom (e.g., furyl, pyridyl, thienyl, piperidino, piperazino, morpholino, etc.) (this heterocyclic group may be substituted with a halogen atom, hydroxyl, amino, lower ($C_{1-6}$) alkyl which may be halogenated, mono- or di-lower ($C_{1-6}$) alkylamino, mono- or di-$C_{6-14}$ arylamino, $C_{3-8}$ cycloalkyl, lower ($C_{1-6}$) alkoxy, lower ($C_{1-6}$) alkoxy-carbonyl, lower ($C_{1-6}$) alkylthio, lower ($C_{1-6}$) alkylsulfinyl, lower ($C_{1-6}$) alkylsulfonyl, the above-mentioned carboxyl which may be esterified, carbamoyl, thiocarbamoyl, mono-lower ($C_{1-6}$) alkyl-carbamoyl, di-lower ($C_{1-6}$) alkyl-carbamoyl, mono- or di $C_{6-14}$ arylcarbamoyl, or the like); and the like (hereinafter, Substituent Group H), on substitutable positions.

The "optionally substituted carbamoyl group" in the Substituent Group A may be exemplified by a carbamoyl group which may be substituted with one or two substituents selected from the above-mentioned lower alkyl which may be substituted, the above-mentioned lower alkenyl which may be substituted, the above-mentioned lower alkynyl which may be substituted, the above-mentioned $C_{3-8}$ cycloalkyl which may be substituted, the above-mentioned $C_{6-14}$ aryl which may be substituted, the above-mentioned heterocyclic group which may be substituted, the above-mentioned lower alkoxy which may be substituted, the above-mentioned $C_{6-14}$ aryl-carbonyl which may be substituted, formyl, the above-mentioned $C_{1-6}$ alkyl-carbonyl, the above-mentioned $C_{3-8}$ cycloalkyl-carbonyl which may be substituted, the above-mentioned $C_{1-6}$ alkoxy-carbonyl which may be substituted, the above-mentioned lower ($C_{1-6}$) alkylsulfonyl which may be substituted, the above-mentioned $C_{6-14}$ arylsulfonyl which may be substituted, and the like, and specifically may be exemplified by carbamoyl; mono-$C_{1-6}$ alkyl-carbamoyl (e.g., methylcarbamoyl, ethylcarbamoyl, etc.); di-$C_{1-6}$ alkyl-carbamoyl (e.g., dimethylcarbamoyl, diethylcarbamoyl, ethylmethylcarbamoyl, etc.); $C_{1-6}$ alkyl ($C_{1-6}$ alkoxy)-carbamoyl (e.g., methyl(methoxy)carbamoyl, ethyl(methoxy)carbamoyl); mono- or di-$C_{6-14}$ arylcarbamoyl (e.g., phenylcarbamoyl, 1-naphthylcarbamoyl, 2-naphthylcarbamoyl, etc.); mono- or di-5- to 7-membered heterocyclylcarbamoyl containing, in addition to carbon atoms, 1 to 4 heteroatoms of one or two kinds selected from a nitrogen atom, a sulfur atom and an oxygen atom (e.g., 2-pyridylcabamoyl, 3-pyridylcarbamoyl, 4-pyridylcarbamoyl, 2-thienylcarbamoyl, 3-thienylcarbamoyl, etc.), $C_{6-14}$ aryl-carbonylcarbamoyl, $C_{1-6}$ alkyl-carbonylcarbamoyl, $C_{3-8}$ cycloalkyl-carbonylcarbamoyl, $C_{1-6}$ alkoxy-carbonylcarbamoyl, or the like. Also, the "optionally substituted carbamoyl group" may be exemplified by 5- to 7-membered cyclic carbamoyl (e.g., 1-pyrrolidinylcarbonyl, 1-piperidinylcarbonyl, hexamethyleneiminocarbonyl) or the like.

The "optionally substituted amino" in the Substituent Group A may be exemplified by amino which may be substituted with one or two substituents selected from the above-mentioned lower alkyl which may be substituted, the above-mentioned lower alkenyl which may be substituted, the above-mentioned lower alkynyl which may be substituted, the above-mentioned $C_{3-8}$ cycloalkyl which may be substituted, the above-mentioned $C_{6-14}$ aryl which may be substituted, the above-mentioned lower alkoxy which may be substituted, the above-mentioned $C_{6-14}$ aryl-carbonyl, formyl, the above-mentioned lower ($C_{1-6}$) alkyl-carbonyl, the above-mentioned $C_{3-8}$ cycloalkyl-carbonyl which may be substituted, the above-mentioned lower ($C_{1-6}$) alkoxy-carbonyl which may be substituted, the above-mentioned lower ($C_{1-6}$) alkylsulfonyl which may be substituted, the above-mentioned $C_{6-14}$ arylsulfonyl which may be substituted, and the like. Among these, the above-mentioned amino, mono- or di-lower ($C_{1-6}$) alkylamino which may be substituted, mono- or di-$C_{6-14}$ arylamino which may be substituted, mono- or di-$C_{7-16}$ aralkylamino which may be substituted, $C_{6-14}$ aryl-carbonylamino which may be substituted, formylamino; lower ($C_{1-6}$) aralkyl-carbonyl-amino which may be substituted; $C_{3-8}$ cycloalkyl-carbonyl-amino which may be substituted; lower ($C_{1-6}$) alkoxy-carbonyl-amino which may be substituted; lower ($C_{1-6}$) alkylsulfonylamino which may be substituted; $C_{6-14}$ arylsulfonylamino which may be substituted, and the like are preferably used.

With respect to Compound (I) and Compound (VII), X and Y are each a spacer, and this spacer may be exemplified by an alkylene group which may be substituted or an alkenylene group which may be substituted, in which —C— of the alkylene group or alkenylene group may be substituted by —O—, —N— or —S—. The position where —C— of the alkylene group or alkenylene group is substituted by —O—, —N— or —S— may be any one of at the terminal or in the chain of the alkylene group or alkenylene group, but inter alia, the "optionally substituted alkylene group, in which —C— of the alkylene group may be substituted by —O—, —N— or —S—" is preferred.

The "alkylene group" of the "optionally substituted alkylene group" as the spacer may be exemplified by a $C_{1-13}$ alkylene group (e.g., methylene, ethylene, propylene, butylene, etc.), and among them, a $C_{1-6}$ alkylene group is preferred.

The "alkenylene group" of the "optionally substituted alkenylene group" as the spacer may be exemplified by a $C_{2-13}$ alkenylene group (e.g., vinylene, propenylene, isopropenylene, 2-buten-1-ylene, 4-penten-1-ylene, 5-hexen-1-ylene), and among them, a $C_{2-6}$ alkenylene group (e.g., vinylene, propenylene, isopropenylene, 2-buten-1-ylene, 4-penten-1-ylene, 5-hexen-1-ylene) is preferred.

For the substituent for the "alkylene group" or "alkenylene group", a $C_{1-6}$ alkyl group (e.g., methyl, ethyl, propyl, isopropyl, butyl, isobutyl, sec-butyl, tert-butyl, pentyl, isopentyl, neopentyl, hexyl), an oxo group, a $C_{6-14}$ aryl group (e.g., phenyl), and the like are preferably used, and among these, a $C_{1-6}$ alkyl group (e.g., methyl), an oxo group and the like are preferred, while an oxo group is particularly preferred. The number of substituents is, for example, 1 to 3.

With respect to Compound (III), $X^b$ is a spacer other than an alkylene group, and this spacer may be exemplified by an "optionally substituted alkylene group, in which —C— of the alkylene group is substituted by —O—, —N— or —S—", or an "optionally substituted alkenylene group, in which —C— of the alkenylene group is substituted by —O—, —N— or —S—". Among these, the "optionally substituted alkylene group, in which —C— of the alkylene group is substituted by —O—, —N— or —S—" is preferred. Specifically, among the above-mentioned spacers represented by X or Y, those other than an alkylene group are used.

For the spacer represented by X or $X^b$, (i) —$X^1$—$W^2$—$X^2$— (wherein $X^1$ and $X^2$ are each a bond or a $C_{1-6}$ alkylene group which may be substituted; $W^2$ is —O—, —N($R^4$)—, —CO—N($R^5$)—, —S—; and $R^4$ and $R^5$ are each a hydrogen atom or a $C_{1-6}$ alkyl group), or (ii) —$W^3$—$X^3$—$W^4$— (wherein $X^3$ is a $C_{1-6}$ alkylene group which may be substituted; $W^3$ and $W^4$ are each —O—, —N($R^4$)—, —CO—N($R^5$)—, or —S—; and $R^4$ and $R^5$ are each a hydrogen atom or a $C_{1-6}$ alkyl group) is preferred.

The "$C_{1-6}$ alkylene group" of the "optionally substituted $C_{1-6}$ alkylene group" represented by $X^1$, $X^2$ or $X^3$ may be exemplified by methylene, ethylene, propylene, butylene, pentylene or hexylene, and among these, a $C_{1-4}$ alkylene group such as methylene, ethylene, propylene or butylene is preferred.

The substituent of the "$C_{1-6}$ alkylene group" is preferably a $C_{1-6}$ alkyl group (e.g., methyl, ethyl, propyl, isopropyl, butyl, isobutyl, sec-butyl, tert-butyl, pentyl, isopentyl, neopentyl, hexyl), a $C_{6-14}$ aryl group (e.g., phenyl), or the like. The number of substituents is, for example, 1 to 3.

The $C_{1-6}$ alkyl group represented by $R^4$ or $R^5$ may be exemplified by methyl, ethyl, propyl, isopropyl, butyl, isobutyl, sec-butyl, tert-butyl, pentyl, isopentyl, neopentyl or hexyl.

$W^2$ is preferably —O— or the like.

$W^3$ and $W^4$ are each preferably —S— or the like.

Among these, the spacer represented by X or $X^b$ is preferably —$X^1$—O—$X^2$— (wherein $X^1$ and $X^2$ are each a bond, or a $C_{1-6}$ alkylene group which may be substituted), and particularly, especially —$X^1$—O— (wherein $X^1$ is a bond or a $C_{1-6}$ alkylene group which may be substituted) is suitable.

$X^1$ is preferably a bond or a $C_{1-6}$ alkylene group (particularly, a $C_{1-4}$ alkylene group) which may be substituted with substituent(s) selected from $C_{1-6}$ alkyl and $C_{6-14}$ aryl.

For the combination of $X^1$ and $X^2$, the case of both being bonds, and the case of either one being a bond, are preferred.

More specifically, the spacer represented by X or $X^b$ is preferably (i) a bond, (ii) —$X^1$—O— (wherein $X^1$ is a bond or a $C_{1-6}$ alkylene group which may be substituted), (iii) —$N(R^4)$—$X^3$—O— (wherein $X^3$ is a $C_{1-6}$ alkylene group which may be substituted; and $R^4$ is a hydrogen atom or a $C_{1-6}$ alkyl group), (iv) —S—$X^3$—O— (wherein $X^3$ is a $C_{1-6}$ alkylene group which may be substituted), (v) —$N(R^4)$—$X^3$— (wherein $X^3$ is a $C_{1-6}$ alkylene group which may be substituted; and $R^4$ is a hydrogen atom or a $C_{1-6}$ alkyl group), (vi) —CO—$N(R^5)$— (wherein $R^5$ is a hydrogen atom or a $C_{1-6}$ alkyl group), (vii) —$X^3$—S— (wherein $X^3$ is a $C_{1-6}$ alkylene group which may be substituted), (viii) —S—$X^3$—S— (wherein $X^3$ is a $C_{1-6}$ alkylene group which may be substituted), or the like.

$X^b$ is particularly preferably —O—.

Y is preferably —$W^5$—$Y^1$— (wherein $Y^1$ is a $C_{1-6}$ alkylene group which may be substituted; $W^5$ is a bond, —O—, —$N(R^6)$—, —CO—$N(R^7)$— or —S—; and $R^6$ and $R^7$ are each a hydrogen atom or a $C_{1-6}$ alkyl group), or the like.

The "$C_{1-6}$ alkylene group" of the "optionally substituted $C_{1-6}$ alkylene group" represented by $Y^1$ may be exemplified by methylene, ethylene, propylene, butylene, pentylene or hexylene, and among these, a $C_{1-4}$ alkylene group such as methylene, ethylene, propylene or butylene is preferred.

The $C_{1-6}$ alkyl group represented by $R^6$ or $R^7$ may be exemplified by methyl, ethyl, propyl, isopropyl, butyl, isobutyl, sec-butyl, tert-butyl, pentyl, isopentyl, neopentyl or hexyl.

$W^5$ is preferably a bond or —O—, and particularly preferably a bond.

In particular, Y is preferably (i) a $C_{1-6}$ alkylene group which may be substituted, or (ii) —O—$Y^1$— (wherein $Y^1$ is a $C_{1-6}$ alkylene group which may be substituted), and among these, a $C_{1-6}$ alkylene group which may be substituted (e.g., methylene, ethylene, propylene) is preferred, and particularly an ethylene group which may be substituted is suitable. Further, the $C_{1-6}$ alkylene group represented by Y or $Y^1$ is preferably unsubstituted.

With respect to Compound (I), —Y—COOH may be bound to ring B at any position, but when ring B is a benzene ring (phenyl group), these rings are preferably bound to the para-position relative to X to which these rings are bound.

With respect to Compound (III), Compound (IV) and Compound (V), ring E is a phenylene group which may be substituted. The substituent which may be carried by the phenylene group represented by ring E may be exemplified by the substituents selected from the above-mentioned Substituent Group A, and among them, a halogen atom, a hydroxyl group, a $C_{1-6}$ alkyl, a $C_{1-6}$ alkoxy and the like are preferably used. The number of substituents is, for example, 1 to 3, and preferably 1 to 2.

With respect to Compound (III), Compound (IV) and Compound (V), ring E is preferably substituted at the meta-position to —$CH_2CH_2COOH$, and the substituent is preferably a halogen atom (e.g., fluorine, chlorine, bromine, iodine), a $C_{1-6}$ alkyl group (e.g., methyl, ethyl, propyl), a $C_{1-6}$ alkoxy group (e.g., methoxy, ethoxy, propoxy), or the like.

With respect to Compound (III), ring D is a benzene ring which may be substituted. The substituent which may be carried by the benzene ring represented by ring D may be exemplified by the substituents selected from the above-mentioned Substituent Group A. The number of substituents is, for example, 1 to 3.

With respect to Compound (III), p and q are each a carbon chain having 0 to 4 carbon atoms which may be substituted.

Here, the carbon chain having 0 to 4 carbon atoms may be exemplified by a bond, a $C_{1-4}$ alkylene group (e.g., methylene, ethylene, etc.), or the like, and among them, a $C_{1-4}$ alkylene group (e.g., methylene, ethylene, etc.) is preferred. In particular, methylene and ethylene are preferred, and methylene is particularly preferred.

The partial structural formula:

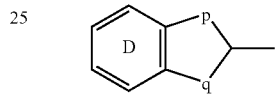

is preferably

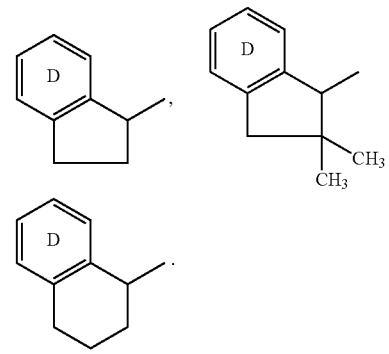

The substituent which may be carried by the carbon chain having 0 to 4 carbon atoms may be exemplified by the substituents selected from the above-mentioned Substituent Group A. The number of substituents is, for example, 1 to 3.

The substituent which may be carried by ring D is preferably (1) a halogen atom (e.g., a fluorine atom, a chlorine atom, a bromine atom), (2) a $C_{1-6}$ alkyl group (e.g., a $C_{1-3}$ alkyl group such as methyl, etc.), (3) a $C_{1-6}$ alkoxy group (e.g., a $C_{1-3}$ alkoxy group such as methoxy, etc.), (4) a $C_{6-14}$ aryl group (e.g., a phenyl group) which may be substituted with a halogen atom (e.g., fluorine atom, chlorine atom), $C_{1-6}$ alkyl (e.g., $C_{1-3}$ alkyl such as methyl, etc.), or $C_{1-6}$ alkoxy (e.g., $C_{1-3}$ alkoxy such as methoxy, etc.), (5) a $C_{6-14}$ aryloxy group (e.g., a phenoxy group), or (6) a $C_{7-16}$ aralkyloxy group (e.g., a benzyloxy group, a phenylethyloxy group, a phenylpropyloxy group, a phenylbutyloxy group). The number of substituents is, for example, 1 to 3.

The substituent which may be carried by ring E is preferably a halogen atom (e.g., a fluorine atom, a chlorine atom), a $C_{1-6}$ alkyl group (e.g., a $C_{1-3}$ alkyl group such as methyl, etc.), or a $C_{1-6}$ alkoxy group (e.g., a $C_{1-3}$ alkoxy group such as methoxy, etc.), but ring E is more preferably unsubstituted.

The spacer represented by $X^b$ is preferably an oxygen atom.

With respect to Compound (II), the "hydrocarbon group optionally having substituent(s)" represented by $R^a$ or $R^b$ may be exemplified by the lower ($C_{1-6}$) alkyl which may be substituted, lower ($C_{2-6}$) alkenyl which may be substituted, lower ($C_{2-6}$) alkynyl which may be substituted, $C_{3-8}$ cycloalkyl which may be substituted, $C_{6-14}$ aryl which may be substituted, $C_{7-16}$ aralkyl which may be substituted, or the like, which have been described to belong to the Substituent Group A.

The "optionally substituted heterocyclic group" represented by $R^a$ or $R^b$ may be exemplified by the same group as the "optionally substituted heterocyclic group" that has been described to belong to the Substituent Group A.

The "optionally substituted hydroxyl group" represented by $R^a$ or $R^b$ may be exemplified by the hydroxyl, lower ($C_{1-6}$) alkoxy which may be substituted, lower ($C_{1-6}$) alkyl-carbonyloxy which may be substituted, lower ($C_{1-6}$) alkoxy-carbonyloxy which may be substituted, mono-lower ($C_{1-6}$) alkyl-carbamoyloxy which may be substituted, di-lower ($C_{1-6}$) alkyl-carbamoyloxy which may be substituted, $C_{6-14}$ aryloxy which may be substituted, $C_{7-16}$ aralkyloxy which may be substituted, $C_{6-14}$ aryl-carbonyloxy which may be substituted, mono- or di-$C_{6-14}$ arylcarbamoyloxy which may be substituted, aromatic heterocyclyloxy which may be substituted, or the like, which have been described to belong to the Substituent Group A.

The "carboxyl group optionally having substituent(s)" represented by $R^a$ or $R^b$ may be exemplified by the carboxyl group which may be substituted with substituent(s) selected from $C_{1-6}$ alkyl which may be substituted, $C_{6-14}$ aryl which may be substituted, $C_{7-16}$ aralkyl which may be substituted, and the like, which has been described to belong to the Substituent Group A. Specific examples thereof include carboxyl, $C_{1-6}$ alkoxy-carbonyl (e.g., methoxycarbonyl, ethoxycarbonyl, propoxycarbonyl, tert-butoxycarbonyl, etc.), $C_{6-14}$ aryloxycarbonyl (e.g., phenoxycarbonyl, etc.), $C_{7-16}$ aralkyloxycarbonyl (e.g., benzyloxycarbonyl, phenethyloxycarbonyl, etc.), and the like.

The "acyl group" represented by $R^a$ or $R^b$ may be exemplified by the formyl, lower ($C_{1-6}$) alkyl-carbonyl which may be substituted, $C_{3-8}$ cycloalkyl-carbonyl which may be substituted, $C_{6-14}$ aryl-carbonyl which may be substituted, $C_{7-16}$ aralkyl-carbonyl which may be substituted, lower ($C_{1-6}$) alkylsulfonyl, $C_{6-14}$ arylsulfonyl which may be substituted, lower ($C_{1-6}$) alkylsulfinyl, $C_{6-14}$ arylsulfinyl which may be substituted, sulfo, sulfamoyl, sulfinamoyl, sulfenamoyl, 5- to 7-membered heterocyclylcarbonyl containing, in addition to carbon atoms, 1 to 4 heteroatoms of one or two kinds selected from a nitrogen atom, a sulfur atom and an oxygen atom, which may be substituted, or the like, which have been described to belong to the Substituent Group A.

The "amino group optionally having substituent(s)" represented by $R^a$ or $R^b$ may be exemplified by the amino, mono- or di-lower ($C_{1-6}$) alkylamino which may be substituted, mono- or di-$C_{6-14}$ arylamino which may be substituted, mono- or di-$C_{7-16}$ aralkylamino which may be substituted, $C_{6-14}$ aryl-carbonylamino which may be substituted, formylamino; lower ($C_{1-6}$) alkyl-carbonyl-amino which may be substituted; $C_{3-8}$ cycloalkyl-carbonyl-amino which may be substituted; lower ($C_{1-6}$) alkoxy-carbonyl-amino which may be substituted; lower ($C_{1-6}$) alkylsulfonylamino which may be substituted; $C_{6-14}$ arylsulfonylamino which may be substituted, or the like, which have been described to belong to the Substituent Group A.

In addition, when one of $R^a$ and $R^b$ is a hydrogen atom, the other is not a hydrogen atom.

The "hydrocarbon group optionally having substituent(s)" represented by $R^c$ may be exemplified by the same group as the "hydrocarbon group optionally having substituent(s)" represented by $R^a$ or $R^b$.

The "optionally substituted heterocyclic group" represented by $R^c$ may be exemplified by the same group as the "optionally substituted heterocyclic group" which has been described to belong to the Substituent Group A.

The "hydrocarbon group optionally having substituent(s)" represented by $R^d$ or $R^e$ may be exemplified by the same group as the "hydrocarbon group optionally having substituent(s)" represented by $R^a$ or $R^b$.

The "optionally substituted heterocyclic group" represented by $R^d$ or $R^e$ may be exemplified by the same group as the "optionally substituted heterocyclic group" which has been described to belong to the Substituent Group A.

The "optionally substituted hydroxyl group" represented by $R^d$ or $R^e$ may be exemplified by the same group as the "optionally substituted hydroxyl group" represented by $R^a$ or $R^b$.

The "optionally substituted carboxyl group" represented by $R^d$ or $R^e$ may be exemplified by the same group as the "carboxyl group optionally having substituent(s)" represented by $R^a$ or $R^b$.

The "acyl group" represented by $R^d$ or $R^e$ may be exemplified by the same group as the "acyl group" represented by $R^a$ or $R^b$.

The "amino group optionally having substituent(s)" represented by $R^d$ or $R^e$ may be exemplified by the same group as the "amino group optionally having substituent(s)" represented by $R^a$ or $R^b$.

In addition, when one of $R^d$ and $R^e$ is a hydrogen atom, the other is not a hydrogen atom.

The "optionally substituted ring" which may be formed by $R^c$ and $R^d$ that are bonded to each other, may be exemplified by a 5- to 7-membered ring which may contain, in addition to carbon atoms, 1 to 3 heteroatoms selected from a nitrogen atom, an oxygen atom and a sulfur atom, or the like. Inter alia, a 5- to 7-membered carbon ring is preferred.

The "methylene group optionally having substituent(s)" represented by $X^a$ may be exemplified by a methylene group which may be substituted with substituent(s) selected from a $C_{1-6}$ alkyl group (e.g., methyl, ethyl, propyl, isopropyl, butyl, isobutyl, sec-butyl, tert-butyl, pentyl, isopentyl, neopentyl, hexyl), an oxo group, a $C_{6-14}$ aryl group (e.g., phenyl) or the like.

$X^a$ is preferably an oxygen atom.

The substituent which may be further carried by the benzene ring represented by ring C, may be exemplified by the substituents selected from the Substituent Group A.

In addition, Compound (II) does not include (i) 3,5-difluoro-4-[(2,3-dihydro-1H-inden-1-yl)oxy]benzenepropanoic acid, (ii) 3-chloro-4-[(2,3-dihydro-1H-inden-1-yl)oxy]benzenepropanoic acid, (iii) 4-([1,1'-biphenyl]-3-ylmethoxy)-3-chlorobenzenepropanoic acid, (iv) 4-[(4,5-dimethoxy-2-nitrophenyl)methoxy]-3-methoxybenzenepropanoic acid, and (v) 4-[3-hydroxy-1-(4-hydroxy-3-methoxyphenyl)-2-(2-methoxyphenoxy)propoxy]-3-methoxybenzenepropanoic acid.

$R^d$ and $R^e$ are each preferably a hydrogen atom, a fluorine atom, a chlorine atom, an alkyl group (e.g., a $C_{1-6}$ alkyl group) which may be substituted with substituent(s) free of a benzene ring, an alkenyl group (e.g., a $C_{2-6}$ alkenyl group) which may be substituted with substituent(s) free of a benzene ring, a cycloalkyl group (e.g., a $C_{3-8}$ cycloalkyl group) which may be substituted with substituent(s) free of a benzene ring, an alkynyl group (e.g., a $C_{2-6}$ alkynyl group) which may be substituted with substituent(s) free of a benzene ring, a heterocyclic group which may be substituted with substituent(s) free of a benzene ring, an alkoxy group (e.g., a $C_{1-6}$ alkoxy group) which may be substituted with substituent(s) free of a benzene ring, a heterocyclyloxy group which may be substituted with substituent(s) free of a benzene ring, a carboxyl group which may be substituted with substituent(s) free of a benzene ring, an acyl group free of a benzene ring, or an amino group which may be substituted with substituent(s) free of a benzene ring.

Here, the alkyl group (e.g., $C_{1-6}$ alkyl group) which may be substituted with substituent(s) free of a benzene ring, the alkenyl group (e.g., $C_{2-6}$ alkenyl group) which may be substituted with substituent(s) free of a benzene ring, the cycloalkyl group (e.g., $C_{3-8}$ cycloalkyl group) which may be substituted with substituent(s) free of a benzene ring, the alkynyl group (e.g., $C_{2-6}$ alkynyl group) which may be substituted with substituent(s) free of a benzene ring, the heterocyclic group which may be substituted with substituent(s) free of a benzene ring, the alkoxy group (e.g., $C_{1-6}$ alkoxy group) which may be substituted with substituent(s) free of a benzene ring, the heterocyclyloxy group which may be substituted with substituent(s) free of a benzene ring, the carboxyl group which may be substituted with substituent(s) free of a benzene ring, the acyl group free of a benzene ring, and the amino group which may be substituted with substituent(s) free of a benzene ring refer to the above-described $C_{1-6}$ alkyl group which may be substituted, the $C_{2-6}$ alkenyl group which may be substituted, the $C_{3-8}$ cycloalkyl group which may be substituted, $C_{2-6}$ alkynyl group which may be substituted, the heterocyclic group which may be substituted, the $C_{1-6}$ alkoxy group which may be substituted, the heterocyclyloxy group which may be substituted, the carboxyl group which may be substituted, the acyl group, and the amino group which may be substituted, respectively, the substituent moieties of which have no benzene ring. More specifically, substituent(s) free of a benzene ring is substituent(s) having no phenyl group, and preferably, in addition to the substituent having no phenyl group, substituent(s) which does not contain a fused ring having a benzene skeleton (for example, a naphthalene ring, a fused ring of a benzene ring with a $C_{5-8}$ cycloalkyl ring, a fused ring of a benzene ring with a 5- to 10-membered (preferably, 5- to 7-membered) heterocyclic ring containing 1 to 4 heteroatoms of one or two kinds selected from a nitrogen atom, a sulfur atom and an oxygen atom, in addition to carbon atoms)).

More preferably, the "substituent free of a benzene ring" of the "alkyl group (e.g., a $C_{1-6}$ alkyl group) optionally substituted with substituent(s) free of a benzene ring", the "alkenyl group (e.g., a $C_{2-6}$ alkenyl group) optionally substituted with substituent(s) free of a benzene ring", the "alkynyl group (e.g., a $C_{2-6}$ alkynyl group) optionally substituted with substituent(s) free of a benzene ring", or the "alkoxy group (e.g., a $C_{1-6}$ alkoxy group) optionally substituted with substituent(s) free of a benzene ring", may be exemplified by the substituents selected from a halogen atom; hydroxyl; nitro; cyano; amino; a 5- to 7-membered heterocyclic group containing, in addition to carbon atoms, 1 to 4 heteroatoms of one or two kinds selected from a nitrogen atom, a sulfur atom and an oxygen atom (this heterocyclic group may be substituted with a halogen atom, hydroxyl, amino, lower ($C_{1-6}$) alkyl which may be halogenated, mono- or di-lower ($C_{1-6}$) alkylamino, $C_{3-8}$ cycloalkyl, lower ($C_{1-6}$) alkoxy, lower ($C_{1-6}$) alkoxy-carbonyl, lower ($C_{1-6}$) alkylthio, lower ($C_{1-6}$) alkylsulfinyl, lower ($C_{1-6}$ alkylsulfonyl, the above-mentioned carboxyl which may be esterified, carbamoyl, thiocarbamoyl, mono-lower ($C_{1-6}$) alkyl-carbamoyl, di-lower ($C_{1-6}$) alkyl-carbamoyl, or the like); mono- or di-lower ($C_{1-6}$) alkylamino; $C_{3-8}$ cycloalkyl; lower ($C_{1-6}$) alkoxy which may be halogenated; lower ($C_{1-6}$) alkoxy-carbonyl; lower ($C_{1-6}$) alkylthio; lower ($C_{1-6}$) alkylsulfinyl; lower ($C_{1-6}$) alkylsulfonyl; the above-mentioned carboxyl which may be esterified; carbamoyl; thiocarbamoyl; mono-lower ($C_{1-6}$) alkyl-carbamoyl; di-lower ($C_{1-6}$) alkyl-carbamoyl; mono- or di-5- to 7-membered heterocyclylcarbamoyl containing, in addition to carbon atoms, 1 to 4 heteroatoms of one or two kinds selected from a nitrogen atom, a sulfur atom and an oxygen atom; $C_{1-6}$ aralkyl-carbonyl-amino which may be substituted with carboxyl, and the like (hereinafter, Substituent Group D).

The "substituent free of a benzene ring" of the "cycloalkyl group (e.g., $C_{3-8}$ cycloalkyl group) optionally substituted with substituent(s) free of a benzene ring", "heterocyclic group optionally substituted with substituent(s) free of a benzene ring", or "heterocyclyloxy group optionally substituted with substituent(s) free of a benzene ring" may be exemplified by substituents selected from a halogen atom; hydroxyl; nitro; cyano; amino; lower ($C_{1-6}$) alkyl which may be substituted with substituent(s) selected from the Substituent Group D; lower ($C_{2-6}$) alkenyl which may be substituted with substituent(s) selected from the Substituent Group D; lower ($C_{2-6}$) alkynyl which may be substituted with substituent(s) selected from the Substituent Group D; a 5- to 7-membered heterocyclic group containing, in addition to carbon atoms, 1 to 4 heteroatoms of one or two kinds selected from a nitrogen atom, a sulfur atom and an oxygen atom (this heterocyclic group may be substituted with substituent(s) selected from a halogen atom, hydroxyl, amino, mono- or di-lower ($C_{1-6}$) alkylamino, $C_{3-8}$ cycloalkyl, lower ($C_{1-6}$) alkoxy, lower ($C_{1-6}$) alkoxy-carbonyl, lower ($C_{1-6}$) alkylthio, lower ($C_{1-6}$) alkylsulfinyl, lower ($C_{1-6}$ alkylsulfonyl, the above-mentioned carboxyl which may be esterified, carbamoyl, thiocarbamoyl, mono-lower ($C_{1-6}$) alkyl-carbamoyl, di-lower ($C_{1-6}$) alkyl-carbamoyl or the like); mono- or di-lower ($C_{1-6}$) alkylamino; $C_{3-8}$ cycloalkyl; lower ($C_{1-6}$) alkoxy which may be substituted with substituent(s) selected from the Substituent Group D; lower ($C_{1-6}$) alkoxy-carbonyl; lower ($C_{1-6}$) alkylthio; lower ($C_{1-6}$) alkylsulfinyl; lower ($C_{1-6}$) alkylsulfonyl; the above-mentioned carboxyl which may be esterified; carbamoyl; thiocarbamoyl; mono-lower ($C_{1-6}$) alkyl-carbamoyl; di-lower ($C_{1-6}$) alkyl-carbamoyl; mono- or di-5- to 7-membered heterocyclylcarbamoyl containing, in addition to carbon atoms, 1 to 4 heteroatoms of one or two kinds selected from a nitrogen atom, a sulfur atom and an oxygen atom, and the like (hereinafter, Substituent Group E).

The "carboxyl group optionally substituted with substituent(s) free of a benzene ring" may be exemplified by a carboxyl group which may be substituted with $C_{1-6}$ alkyl which may be substituted with substituent(s) selected from the Substituent Group D, and specific examples thereof include carboxyl, $C_{1-6}$ alkoxy-carbonyl (e.g., methoxycarbonyl, ethoxycarbonyl, propoxycarbonyl, tert-butoxycarbonyl, etc.), and the like.

The "acyl group free of a benzene ring" may be exemplified by formyl, lower ($C_{1-6}$) alkyl-carbonyl which may be substituted with substituent(s) selected from the Substituent Group D, $C_{3-8}$ cycloalkyl-carbonyl which may be substituted with substituent(s) selected from the Substituent Group E, lower ($C_{1-6}$) alkylsulfonyl, lower ($C_{1-6}$) alkylsulfinyl, sulfo, sulfamoyl, sulfinamoyl, sulfenamoyl, 5- to 7-membered heterocyclylcarbonyl containing, in addition to carbon atoms, 1 to 4 heteroatoms of one or two kinds selected from a nitrogen atom, a sulfur atom and an oxygen atom, which may be substituted with substituent(s) selected from the Substituent Group E, or the like.

The "amino group optionally substituted with substituent(s) free of a benzene ring" may be exemplified by amino, mono- or di-lower ($C_{1-6}$) alkylamino which may be substituted with substituent(s) selected from the Substituent Group D, formylamino, lower ($C_{1-6}$) aralkyl-carbonyl-amino which may be substituted with substituent(s) selected from the Substituent Group D, $C_{3-8}$ cycloaralkyl-carbonyl-amino which may be substituted with substituent(s) selected from the Substituent Group E, lower ($C_{1-6}$) alkoxy-carbonyl-amino which may be substituted with substituent(s) selected from the Substituent Group D, lower ($C_{1-6}$) alkylsulfonylamino which may be substituted with substituent(s) selected from the Substituent Group D, or the like.

When one of $R^d$ and $R^e$ is a hydrogen atom, the other is not a hydrogen atom.

Ring C is further preferably a benzene ring which may be substituted with substituent(s) free of a benzene ring.

The "substituent free of a benzene ring" which may be carried by the benzene ring represented by ring C may be exemplified by those free of a benzene ring among the substituents of the Substituent Group A. Specific examples thereof include oxo; a halogen atom; $C_{1-3}$ alkylenedioxy; nitro; cyano; carboxyl which may be esterified; lower ($C_{1-6}$) alkyl which may be substituted with substituent(s) selected from the Substituent Group D; lower ($C_{2-6}$) alkenyl which may be substituted with substituent(s) selected from the Substituent Group D; lower ($C_{2-6}$) alkynyl which may be substituted with substituent(s) selected from the Substituent Group D; $C_{3-8}$ cycloalkyl which may be substituted with substituent(s) selected from the Substituent Group E; lower ($C_{1-6}$) alkoxy which may be substituted with substituent(s) selected from the Substituent Group D; hydroxyl; mercapto; lower ($C_{1-6}$) alkylthio which may be substituted with substituent(s) selected from the Substituent Group D; formyl; lower ($C_{1-6}$) alkyl-carbonyl which may be substituted with substituent(s) selected from the Substituent Group D; $C_{3-8}$ cycloalkyl-carbonyl which may be substituted with substituent(s) selected from the Substituent Group E; lower ($C_{1-6}$) alkylsulfonyl which may be substituted with substituent(s) selected from the Substituent Group D; lower ($C_{1-6}$) alkyl-sulfinyl which may be substituted with substituent(s) selected from the Substituent Group D; amino, mono- or di-lower ($C_{1-6}$) alkylamino which may be substituted with substituent(s) selected from the Substituent Group D, formylamino; lower ($C_{1-6}$) aralkyl-carbonyl-amino which may be substituted with substituent(s) selected from the Substituent Group D; $C_{3-8}$ cycloaralkyl-carbonyl-amino which may be substituted with substituent(s) selected from the Substituent Group E; lower ($C_{1-6}$) alkoxy-carbonyl-amino which may be substituted with substituent(s) selected from the Substituent Group D; lower ($C_{1-6}$) alkylsulfonylamino which may be substituted with substituent(s) selected from the Substituent Group D; lower ($C_{1-6}$) alkyl-carbonyloxy which may be substituted with substituent(s) selected from the Substituent Group D; lower ($C_{1-6}$) alkoxy-carbonyloxy which may be substituted with substituent(s) selected from the Substituent Group D; mono-lower ($C_{1-6}$) alkyl-carbamoyloxy which may be substituted with substituent(s) selected from the Substituent Group D; di-lower ($C_{1-6}$) alkyl-carbamoyloxy which may be substituted with substituent(s) selected from the Substituent Group D; sulfo; sulfamoyl; sulfinamoyl; sulfenamoyl; 5- to 7-membered heterocyclylcarbonyl containing, in addition to carbon atoms, 1 to 4 heteroatoms of one or two kinds selected from a nitrogen atom, a sulfur atom and an oxygen atom, which may be substituted with substituent(s) selected from the Substituent Group E, and the like (hereinafter, Substituent Group F).

Compound (II) is preferably such that $R^a$ is a fluorine atom, a chlorine atom, a $C_{1-6}$ alkyl group or a $C_{1-6}$ alkoxy group;

$R^b$ is a hydrogen atom or a fluorine atom;

$R^c$ is a hydrogen atom or a $C_{1-6}$ alkyl group;

$X^a$ is an oxygen atom;

ring C is a benzene ring which may be substituted with substituent(s) selected from the group consisting of (i) a $C_{1-6}$ alkyl group, (ii) a hydroxyl group, (iii) a $C_{1-6}$ alkoxy group which may be substituted with substituent(s) selected from the group consisting of hydroxyl, amino, $C_{1-6}$ alkoxy-carbonyl-amino, carboxyl, $C_{1-6}$ alkoxy-carbonyl, carbamoyl, mono-$C_{1-6}$ alkyl-carbamoyl, di-$C_{1-6}$ alkyl-carbamoyl, and a 5- to 7-membered heterocyclic group containing, in addition to carbon atoms, 1 to 4 heteroatoms of one or two kinds selected from a nitrogen atom, a sulfur atom and an oxygen atom, (iv) a $C_{6-14}$ aryloxy group, and (v) a $C_{7-16}$ aralkyloxy group, in addition to $R^d$ and $R^e$;

(1) when $R^d$ is a hydrogen atom, $R^e$ is (i) a hydroxyl group, (ii) a $C_{1-6}$ alkoxy group which may be substituted with substituent(s) selected from the group consisting of $C_{1-6}$ alkoxy, carboxyl, $C_{1-6}$ alkoxy-carbonyl, $C_{1-6}$ alkyl-carbonyl, carbamoyl, mono-$C_{1-6}$ alkyl-carbamoyl, and di-$C_{1-6}$ alkyl-carbamoyl, (iii) a $C_{2-6}$ alkynyloxy group, (iv) a $C_{3-8}$ cycloalkyloxy group, (v) a $C_{6-14}$ aryloxy group which may be substituted with substituent(s) selected from the group consisting of a halogen atom, $C_{1-6}$ alkyl, $C_{1-6}$ alkoxy and $C_{1-6}$ alkyl-carbonyl, or (vi) a 5- to 10-membered heterocyclic-oxy group containing, in addition to the carbon atoms, 1 to 4 heteroatoms of one or two kinds selected from a nitrogen atom, a sulfur atom and an oxygen atom;

(2) when $R^e$ is a hydrogen atom, $R^d$ is (i) a $C_{1-6}$ alkyl group, (ii) a $C_{6-14}$ aryl group, (iii) a $C_{1-6}$ alkoxy group which may be substituted with a 5- to 7-membered heterocyclic group containing, in addition to carbon atoms, 1 to 4 heteroatoms of one or two kinds selected from a nitrogen atom, a sulfur atom and an oxygen atom, (iv) a $C_{3-8}$ cycloalkyloxy group, (v) a $C_{6-14}$ aryloxy group which may be substituted with substituent(s) selected from the group consisting of a halogen atom and $C_{1-6}$ alkyl which may be halogenated, (vi) a $C_{7-16}$ aralkyloxy group, or (vii) a 5- to 7-membered heterocyclic group containing, in addition to carbon atoms, 1 to 4 heteroatoms of one or two kinds selected from a nitrogen atom, a sulfur atom and an oxygen atom; and when one of $R^d$ and $R^e$ is a hydrogen atom, the other is preferably not a hydrogen atom.

Compound (II) is also preferably such that at least one of $R^a$ and $R^b$ is a fluorine atom, a chlorine atom or an alkoxy group which may be substituted; $R^c$ is a hydrogen atom; $R^d$ and $R^e$ are each a hydrogen atom or an alkoxy group which may be substituted with substituent(s) free of a benzene ring; when at least one of $R^d$ and $R^e$ is a hydrogen atom, the other should not be a hydrogen atom; $X^a$ is an oxygen atom; and ring C is a benzene ring which may be substituted with substituent(s) free of a benzene ring. Inter alia, Compound (II) is particularly preferably such that $R^a$ is a fluorine atom, a chlorine atom or a $C_{1-6}$ alkoxy group (e.g., methoxy, ethoxy, propoxy, isopropoxy); $R^b$ is a hydrogen atom or a fluorine atom; $R^c$ is a hydrogen atom; $R^d$ is a hydrogen atom; $R^e$ is a $C_{6-14}$ aryl group (e.g., phenyl), a $C_{1-6}$ alkoxy group (e.g., methoxy, ethoxy, propoxy, isopropoxy), or a $C_{6-14}$ aryloxy group (e.g., phenoxy) $X^a$ is an oxygen atom; and ring C is a benzene ring having no substituent other than $R^d$ and $R^e$.

Compound (II) is also preferably such that $R^e$ is a $C_{6-14}$ aryloxy group (e.g., phenoxy) which may be substituted, and is also particularly preferably such that at least one of $R^a$ and $R^b$ is a fluorine atom, a chlorine atom, a $C_{1-6}$ alkyl group (e.g., methyl), or a $C_{1-6}$ alkoxy group (e.g., methoxy); $R^c$ is a hydrogen atom; $X^a$ is an oxygen atom; $R^d$ is a hydrogen atom; $R^e$ is a $C_{6-14}$ aryloxy group (e.g., phenoxy) which may be substituted with substituent(s) selected from the group consisting of a halogen atom, $C_{1-6}$ alkyl, $C_{1-6}$ alkoxy, $C_{1-6}$ alkyl-carbonyl and the like.

Compound (II) is also preferably such that ring C is a benzene ring represented by the formula:

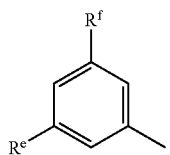

wherein $R^f$ is a hydrocarbon group which may be substituted, or a hydroxyl group which may be substituted; and $R^e$ is a hydroxyl group which may be substituted.

The "hydrocarbon group optionally having substituent(s)" represented by $R^f$ may be exemplified by the same group as the "hydrocarbon group optionally having substituent(s)" represented by $R^a$ or $R^b$.

The "optionally substituted hydroxyl group" represented by $R^e$ or $R^f$ may be exemplified by the same group as the "optionally substituted hydroxyl group" represented by $R^a$ or $R^b$.

In this case, $R^f$ is preferably (i) a $C_{1-6}$ alkyl group, (ii) a hydroxyl group, (iii) a $C_{1-6}$ alkoxy group which may be substituted with substituent(s) selected from the group consisting of hydroxyl, amino, $C_{1-6}$ alkoxy-carbonyl-amino, carboxyl, $C_{1-6}$ alkoxy-carbonyl, carbamoyl, mono-$C_{1-6}$ alkyl-carbamoyl, di-$C_{1-6}$ alkyl-carbamoyl, tri-$C_{1-6}$ alkylsilyloxy and a 5- to 7-membered heterocyclic group containing, in addition to carbon atoms, 1 to 4 heteroatoms of one or two kinds selected from a nitrogen atom, a sulfur atom and an oxygen atom, (iv) a $C_{6-14}$ aryloxy group, or (v) a $C_{7-16}$ aralkyloxy group, and Re is preferably a $C_{1-6}$ alkoxy group or a $C_{6-14}$ aryloxy group.

More specifically, Compound (II) is preferably, for example, 3,5-difluoro-4-[(3-phenoxyphenyl)methoxy]benzenepropanoic acid, 3-fluoro-4-[(3-phenoxyphenyl)methoxy]benzenepropanoic acid, 3-(4-{[3-(4-chlorophenoxy)benzyl]oxy}-3,5-difluorophenyl)propanoic acid, 3-(3,5-difluoro-4-{[3-(4-fluorophenoxy)benzyl]oxy}phenyl)propanoic acid, 3-(3,5-difluoro-4-{[3-(4-methylphenoxy)benzyl]oxy}phenyl)propanoic acid, 3-(3-fluoro-4-{[3-(2-fluorophenoxy)benzyl]oxy}phenyl)propanoic acid, 3-(3-fluoro-4-{[3-(3-fluorophenoxy)benzyl]oxy}phenyl)propanoic acid, 3-(3-fluoro-4-{[3-(4-fluorophenoxy)benzyl]oxy}phenyl)propanoic acid, 3-(3-fluoro-4-{[3-(4-chlorophenoxy)benzyl]oxy}phenyl)propanoic acid, 3-(3-fluoro-4-{[3-(4-methylphenoxy)benzyl]oxy}phenyl)propanoic acid, 3-{3-methyl-4-[(3-phenoxybenzyl)oxy]phenyl}propanoic acid, or 3-(4-{[3-(4-fluorophenoxy)benzyl]oxy}-3-methylphenyl)propanoic acid, or a salt thereof.

For Compound (IV), ring F is a benzene ring which may be substituted, and the substituent of the benzene ring may be exemplified by the substituents selected from the Substituent Group A.

The "methylene group optionally having substituent(s)" represented by $X^c$ may be exemplified by the same group as the "methylene group optionally having substituent(s)" represented by $X^a$.

Ring F is preferably a benzene ring which may be substituted with substituent(s) selected from the group consisting of
(i) a $C_{1-6}$ alkyl group,
(ii) a $C_{6-14}$ aryl group which may be substituted with substituent(s) selected from the group consisting of $C_{1-6}$ alkyl and $C_{1-6}$ alkoxy,
(iii) a hydroxyl group,
(iv) a $C_{1-6}$ alkoxy group which may be substituted with substituent(s) selected from the group consisting of hydroxyl, $C_{1-6}$ alkoxy, amino, $C_{1-6}$ alkoxy-carbonyl-amino, carboxyl, $C_{1-6}$ alkoxy-carbonyl, $C_{1-6}$ alkyl-carbonyl, carbamoyl, mono-$C_{1-6}$ alkyl-carbamoyl, di-$C_{1-6}$ alkyl-carbamoyl, tri-$C_{1-6}$ alkylsilyloxy, and a 5- to 7-membered heterocyclic group containing, in addition to carbon atoms, 1 to 4 heteroatoms of one or two kinds selected from a nitrogen atom, a sulfur atom and an oxygen atom,
(v) a $C_{2-6}$ alkynyloxy group,
(vi) a $C_{3-8}$ cycloalkyloxy group,
(vii) a $C_{6-14}$ aryloxy group which may be substituted with substituent(s) selected from the group consisting of a halogen atom, $C_{1-6}$ alkyl which may be halogenated, $C_{1-6}$ alkoxy and $C_{1-6}$ alkyl-carbonyl,
(viii) a $C_{7-16}$ aralkyloxy group,
(ix) a 5- to 7-membered heterocyclyloxy group containing, in addition to carbon atoms, 1 to 4 heteroatoms of one or two kinds selected from a nitrogen atom, a sulfur atom and an oxygen atom,
(x) a 5- to 7-membered heterocyclic group containing, in addition to carbon atoms, 1 to 4 heteroatoms of one or two kinds selected from a nitrogen atom, a sulfur atom and an oxygen atom,
(xi) a $C_{1-3}$ alkylenedioxy group, and the like. Inter alia, ring F is preferably a benzene ring which may be substituted with substituent(s) selected from the group consisting of (i) $C_{1-6}$ alkyl (e.g., methyl, ethyl, propyl, isopropyl), (ii) $C_{6-14}$ aryl (e.g., phenyl, naphthyl) which may be substituted with substituent(s) selected from the group consisting of $C_{1-6}$ alkyl (e.g., methyl, ethyl) and $C_{1-6}$ alkoxy (e.g., methoxy), (iii) $C_{7-15}$ aralkyl (e.g., benzyl), (iv) $C_{1-6}$ alkoxy (e.g., methoxy, ethoxy, propoxy, isopropoxy), and (v) $C_{6-14}$ aryloxy (e.g., phenoxy), and the like.

Ring E is preferably a phenylene group which may be substituted with substituent(s) selected from the group consisting of a halogen atom (e.g., fluorine, chlorine), $C_{1-6}$ alkyl (e.g., methyl), $C_{1-6}$ alkoxy (e.g., methoxy) and the like, preferably substituent(s) selected from the group consisting of a halogen atom and $C_{1-6}$ alkoxy, and particularly preferably a halogen atom.

$X^c$ is preferably an oxygen atom.

For Compound (V), $R^a$ has the same meaning as $R^a$ of Compound (II). Other symbols are the same as those of Compound (IV).

$R^a$ is preferably a hydrogen atom, a halogen atom, a $C_{1-6}$ alkyl group, a $C_{1-6}$ alkoxy group, or the like. Among them, $R^a$ is preferably a hydrogen atom, a fluorine atom, a chlorine atom, a methyl group or a methoxy group, and particularly preferably a halogen atom such as a fluorine atom. Other symbols are preferably the same as those of Compound (IV).

For Compound (VI), the "$C_{1-3}$ alkylene group" of the $C_{1-3}$ alkylene group which is substituted in Z, is preferably methylene, ethylene or propylene. Among them, the $C_{1-3}$ alkylene group is preferably methylene or ethylene, and particularly methylene is suitable.

The substituent carried by the "$C_{1-3}$ alkylene group" may be exemplified by the substituents selected from the Substituent Group A, and among them, a $C_{1-6}$ alkyl group (e.g., methyl, ethyl, propyl, isopropyl, butyl, isobutyl, sec-butyl, tert-butyl, pentyl, isopentyl, neopentyl, and hexyl) is preferred, and particularly a $C_{1-3}$ alkyl group such as methyl is suitable.

Ring G is a substituted benzene ring, and the substituent of the benzene ring may be exemplified by the substituents selected from the Substituent Group A.

Ring E has the meaning as described above.

Z is preferably a methylene group having one or two $C_{1-3}$ alkyl (e.g., methyl, ethyl), and particularly preferably a methylene group having two methyl.

Ring G is preferably a benzene ring substituted with substituent(s) selected from the group consisting of $C_{1-6}$ alkyl (e.g., methyl, ethyl, propyl, and isopropyl), $C_{1-6}$ alkoxy (e.g., methoxy, ethoxy, propoxy, isopropoxy) and a halogen atom (e.g., fluorine atom, chlorine atom).

Compound (III) is preferably such that

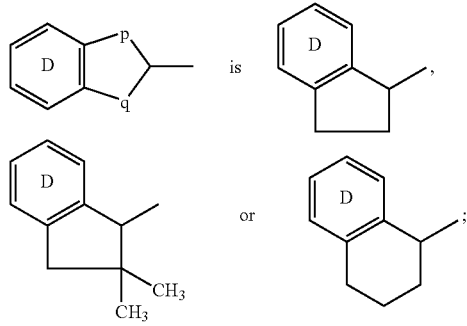

the substituent which may be carried by ring D is a halogen atom or a $C_{1-6}$ alkyl group;

the substituent which may be carried b ring E is a halogen atom;

the spacer represented by $X^b$ is an oxygen atom.

Compound (I) is preferably such that ring A is (1) a benzene ring or a naphthalene ring (preferably, a benzene ring) which may be substituted with substituent(s) selected from the group consisting of (i) a $C_{1-6}$ alkyl group, (ii) a $C_{6-14}$ aryl group (preferably, a phenyl group) which may be substituted with substituent(s) selected from the group consisting of $C_{1-6}$ alkyl and $C_{1-6}$ alkoxy, (iii) a hydroxyl group, (iv) a $C_{1-6}$ alkoxy group which may be substituted with substituent(s) selected from the group consisting of hydroxyl, $C_{1-6}$ alkoxy, amino, $C_{1-6}$ alkoxy-carbonyl-amino, carboxyl, $C_{1-6}$ alkoxy-carbonyl, $C_{1-6}$ alkyl-carbonyl, carbamoyl, mono-$C_{1-6}$ alkyl-carbamoyl, di-$C_{1-6}$ alkyl-carbamoyl, tri-$C_{1-6}$ alkyl-silyloxy, and a 5- to 7-membered heterocyclic group containing, in addition to carbon atoms, 1 to 4 heteroatoms of one or two kinds selected from a nitrogen atom, a sulfur atom and an oxygen atom, (v) a $C_{2-6}$ alkynyloxy group, (vi) a $C_{3-8}$ cycloalkyloxy group, (vii) a $C_{6-14}$ aryloxy group which may be substituted with substituent(s) selected from the group consisting of a halogen atom, $C_{1-6}$ alkyl which may be halogenated, $C_{1-6}$ alkoxy and $C_{1-6}$ alkyl-carbonyl, (viii) a $C_{7-16}$ aralkyloxy group, (ix) a 5- to 7-membered heterocyclic-oxy group containing, in addition to carbon atoms, 1 to 4 heteroatoms of one or two kinds selected from a nitrogen atom, a sulfur atom and an oxygen atom, (x) a 5- to 7-membered heterocyclic group containing, in addition to carbon atoms, 1 to 4 heteroatoms of one or two kinds selected from a nitrogen atom, a sulfur atom and an oxygen atom, and (xi) a $C_{1-3}$ alkylenedioxy group, or (2)

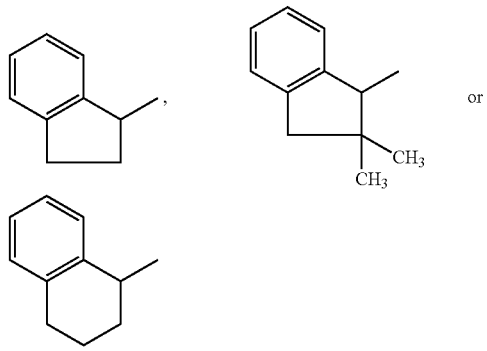

which may have substituent(s) selected from the group consisting of (i) a halogen atom, (ii) $C_{1-6}$ alkyl, and (iii) $C_{1-6}$ alkoxy, on the benzene ring;

ring B is a benzene ring which may be further substituted with substituent(s) selected from the group consisting of a halogen atom, $C_{1-6}$ alkyl and $C_{1-6}$ alkoxy, in addition to —Y—COOH;

X is a bond, —$(CH_2)_{m^1}$—O— (wherein $m^1$ is an integer from 0 to 3), —$CH(CH_3)$—O—, —CONH— or —S—$(CH_2)_{m^3}$—O— (wherein $m^3$ is an integer from 1 to 3);

Y is a methylene group or an ethylene group; and

—Y—COOH is substituted at an arbitrary position on ring B.

Furthermore, Compound (I) is also preferably such that ring A is (i) a benzene ring or a naphthalene ring (preferably, a benzene ring) which may be substituted with substituent(s) selected from the group consisting of (1) a $C_{6-14}$ aryl group (preferably, a phenyl group) which may be substituted with substituent(s) selected from the group consisting of $C_{1-6}$ alkyl and $C_{1-6}$ alkoxy, (2) a $C_{6-14}$ aryloxy group (preferably, a phenoxy group) which may be substituted with $C_{1-6}$ alkyl, (3) a $C_{7-15}$ aralkyl group (preferably, a benzyl group), and (4) a $C_{1-6}$ alkoxy group, or (ii)

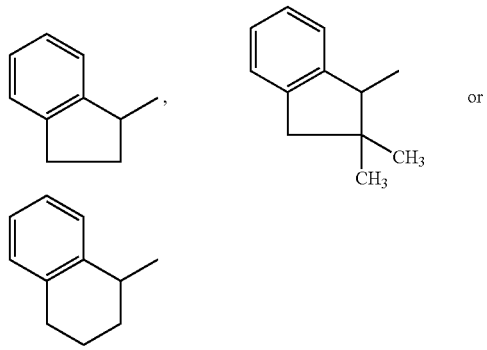

which may have substituent(s) selected from the group consisting of a halogen atom, $C_{1-6}$ alkyl and $C_{1-6}$ alkoxy, on the benzene ring;

ring B is a benzene ring which may be further substituted with substituent(s) selected from the group consisting of a halogen atom, $C_{1-6}$ alkyl and $C_{1-6}$ alkoxy, in addition to —Y—COOH;

X is a bond, —$(CH_2)_{m^1}$—O— (wherein $m^1$ is an integer from 0 to 3), —CH($CH_3$)—O—, —CONH— or —S— $(CH_2)_{m^3}$—O— (wherein $m^3$ is an integer from 1 to 3);

Y is a methylene group or an ethylene group; and

—Y—COOH is substituted at an arbitrary position on ring B.

Moreover, Compound (I) is also preferably such that ring A is (i) a benzene ring which may be substituted with substituent(s) selected from the group consisting of (1) a $C_{6-14}$ aryl group (preferably, a phenyl group) which may be substituted with substituent(s) selected from the group consisting of $C_{1-6}$ alkyl and $C_{1-6}$ alkoxy, (2) a $C_{6-14}$ aryloxy group (preferably, a phenoxy group) which may be substituted with $C_{1-6}$ alkyl, (3) a $C_{7-15}$ aralkyl group (preferably, a benzyl group), and (4) a $C_{1-6}$ alkoxy group, or (ii)

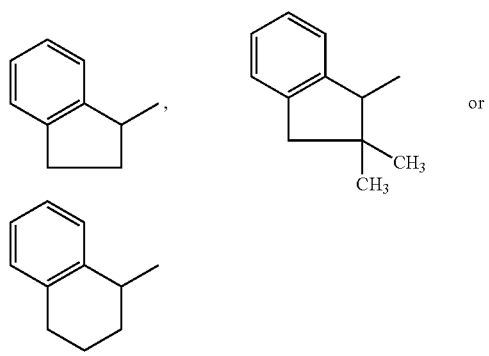

which may have substituent(s) selected from the group consisting of a halogen atom, $C_{1-6}$ alkyl and $C_{1-6}$ alkoxy, on the benzene ring;

ring B is a benzene ring which may be further substituted with substituent(s) selected from the group consisting of a halogen atom, $C_{1-6}$ alkyl and $C_{1-6}$ alkoxy, in addition to —Y—COOH;

X is —O—, —$CH_2$—O— or —CH($CH_3$)—O— (preferably, —O— or —$CH_2$—O—);

Y is a methylene group or an ethylene group (preferably, an ethylene group); and —Y—COOH is substituted at the para position of the phenyl group on ring B.

Furthermore, as the compound used in the invention, use can be made of the compounds described in JP-A No. 2002-265457, JP-A No. 2002-212171, JP-A No. 2001-226350, JP-A No. 2001-199971, JP-A No. 2000-198772, JP-A No. 2000-80086, JP-A No. 2000-34266, JP-A No. 9-323983, JP-A No. 8-311065 and the like.

Salts of the compounds of the invention include a metal salt, an ammonium salt, a salt with an organic base, a salt with an inorganic acid, a salt with an organic acid, a salt with a basic or acidic amino acid, etc. Preferable examples of the metal salt include an alkali metal salt such as sodium salt, potassium salt, etc.; an alkaline earth metal salt such as calcium salt, magnesium salt, barium, etc.; aluminum salt; etc. Preferable examples of the salt with an organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferable examples of the salt with an inorganic acid include a salt with hydrochloric acid, hydrobromic acid, nitric acid, sulfuric acid, phosphoric acid, etc. Preferable examples of the salt with an organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferable examples of the salt with a basic amino acid include a salt with arginine, lysine, ornithine, etc. Preferable examples of the salt with an acidic amino acid include a salt with aspartic acid, glutamic acid, etc.

Among those listed above, a pharmacologically acceptable salt is preferred. For example, when the compound has an acidic functional group, preferred are an inorganic salt such as an alkali metal salt such as sodium salt and potassium salt, etc., an alkaline earth metal salt such as calcium salt and magnesium salt, barium, etc., and an ammonium salt, and when the compound of the invention has a basic functional group, preferred are a salt with an inorganic acid such as hydrochloric acid, hydrobromic acid, nitric acid, sulfuric acid and phosphoric acid, etc., a salt with an organic acid such as acetic acid, phthalic acid, fumaric acid, oxalic acid, tartaric acid, maleic acid, citric acid, succinic acid, methanesulfonic acid and p-toluenesulfonic acid, etc.

The prodrug of Compound (I), Compound (II), Compound (III), Compound (IV), Compound (V), Compound (VI) or Compound (VII), or a salt thereof of the invention (hereinafter, simply referred to as Compound (A) of the invention) means a compound which is converted to Compound (A) of the invention under the physiological condition or with a reaction by an enzyme, a gastric acid, etc. in the living body, that is, a compound which is converted to the compound of the invention by enzymatic oxidation, reduction, hydrolysis, etc.; and a compound which is converted to Compound (A) of the invention with hydrolysis, etc by gastric acid, etc.

Examples of the prodrug of Compound (A) of the invention include a compound wherein an amino group of Compound (A) of the invention is substituted with acyl, alkyl, phosphoric acid, etc. (e.g., a compound wherein an amino group of Compound (A) of the invention is substituted with eicosanyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc); a compound wherein an hydroxy group of Compound (A) of the invention is substituted with acyl, alkyl, phosphoric acid, boric acid, etc. (e.g., a compound wherein an hydroxy group of Compound (A) of the invention is substituted with acetyl, palmitoyl, propanoyl, pivaloyl, succinyl, fumaryl, alanyl, dimethylaminomethylcarbonyl, etc.); a compound wherein a carboxyl group of Compound (A) of the invention is substituted with ester, amide, etc. (e.g., a compound wherein a carboxyl group of Compound (A) of the invention is modified with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. Of these, a compound wherein a carboxyl group of Compound (A) of the invention is esterified by a $C_{1-6}$ alkyl group such as methyl, ethyl, tert-butyl and the like can be preferably used. These compounds can be manufactured by per se known methods from Compound (A) of the invention.

The prodrug of Compound (A) of the invention is preferably ester of carboxylic acid, specifically, a compound wherein the carboxyl group of Compound (I), Compound (II), Compound (III), Compound (IV), Compound (V), Compound (VI) of the invention is esterified with a $C_{1-6}$ alkyl group such as methyl, ethyl and tert-butyl is preferably used.

For example, a compound represented by the formula:

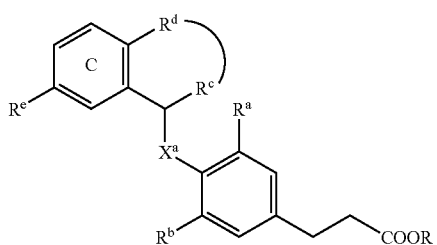

(II')

wherein R represents a $C_{1-6}$ alkyl group (for example, methyl, ethyl, and tert-butyl) and other symbols are the same as described above, or a salt thereof and the like can be used.

In addition, the prodrug of Compound (A) of the invention may be a compound which is converted into Compound (A) of the invention under the physiological conditions as described in "Pharmaceutical Development", Vol. 7 (Molecular Design), pp. 163-198 published in 1990 by Hirokawa Publishing Co.

Hereinafter, a method of producing the compound or the salt thereof of the invention will be explained.

In the following Reaction Schemes, each symbol of the compounds has the same meaning as described above unless otherwise stated. The compounds in Reaction Scheme include salts thereof, and the salts are, for example, ones as defined in the compound of the invention.

The product may be isolated from the reaction mixture by an ordinary method, and easily purified by ordinary means of separation such as recrystallization, distillation, chromatography, etc., though it may be used in next reaction as the reaction solution as it is, or as the crude product.

Compound (II) of the invention can be produced, for example, according to the method represented by the following Reaction scheme 1 or a method analogous thereto.

In addition, Compound (IV) and Compound (V) of the invention can be produced similarly to Compound (II).

Compound (I') or (II') is commercially, easily available, and further can be produced according to per se known methods or a method analogous thereto.

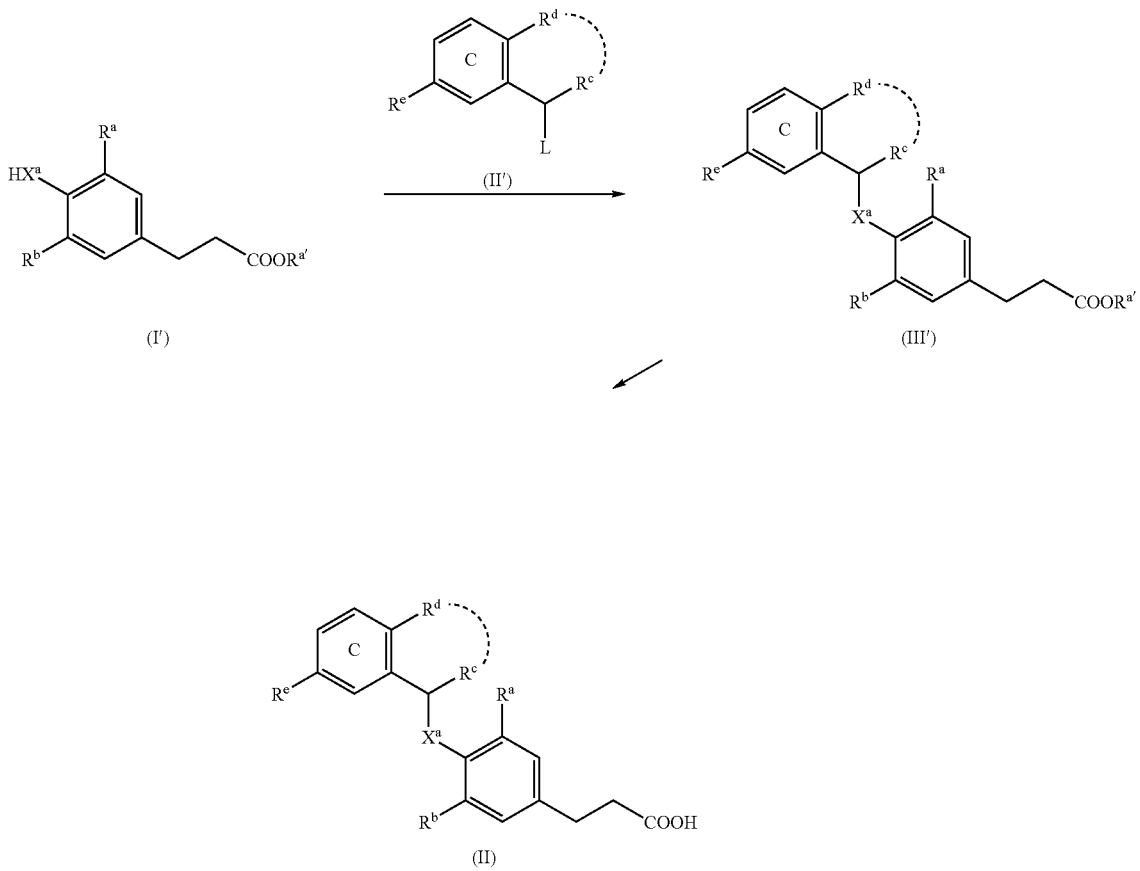

Compound (III') [wherein $R^{a'}$ is a hydrocarbon group optionally having substituent(s).] wherein $X^a$ is oxygen atom can be produced by condensation of Compound (I') [wherein $R^{a'}$ is the same as described above.] and Compound (II') [wherein L is a leaving group.] under the presence of a base.

The "hydrocarbon group optionally having substituent(s)" represented by $R^{a'}$ is preferably the "lower ($C_{1-6}$) alkyl which may be substituted", the "lower ($C_{2-6}$) alkenyl which may be substituted", the "lower ($C_{2-6}$) alkynyl which may be substituted", the "$C_{3-8}$ cycloalkyl which may be substituted", the "$C_{6-14}$ aryl which may be substituted" and the "$C_{7-16}$ aralkyl which may be substituted" and the like, which are exemplified in the above-mentioned substituent Group A.

The "leaving group" represented by L includes, for example, a hydroxy group, a halogen atom (for example, fluorine, chlorine, bromine, and iodine), $C_{1-6}$ alkylsulfonyloxy group which may be halogenated (for example, methanesulfonyloxy, ethanesulfonyloxy, trichloromethanesulfonyloxy and the like), $C_{6-10}$ arylsulfonyloxy group optionally having substituent(s) and the like. The "$C_{6-10}$ arylsulfonyloxy group optionally having substituent(s)" includes, for example, a $C_{6-10}$ arylsulfonyloxy group (for example, phenylsulfonyloxy, naphthylsulfonyloxy and the like) which may have 1 to 3 substituents which are selected from a $C_{1-6}$ alkyl group (for example, methyl, ethyl and the like), a $C_{1-6}$ alkoxy group (for example, methoxy, ethoxy and the like) and nitro and the like, and specific examples include phenylsulfonyloxy, m-nitrophenylsulfonyloxy, p-toluenesulfonyloxy and the like.

The base used in the present reaction includes inorganic bases such as sodium hydroxide, potassium hydroxide, lithium hydroxide and barium hydroxide, basic salts such as sodium carbonate, potassium carbonate, cesium carbonate, sodium hydrocarbonate, sodium acetate and ammonium acetate, aromatic amines such as pyridine and lutidine, tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine and N-methylmorpholine, alkali metal hydrides such as sodium hydride and potassium hydride, metal amides such as sodium amide, lithium diisopropylamide and lithium hexamethyldisilazide, metal alkoxides such as sodium methoxide, sodium ethoxide, sodium tert-butoxide and potassium tert-butoxide, and the like. These bases are used about 1 to 10 moles, preferably about 1 to 3 moles to 1 mole of Compound (I').

The present reaction is advantageously carried out with use of a solvent inert to a reaction. Such solvent are not particularly limited if the reaction proceeds, and includes preferably, for example, alcohols such as methanol, ethanol, 1-propanol, 2-propanol and tert-butyl alcohol, ethers such as diethyl ether, diisopropyl ether, diphenyl ether, tetrahydrofuran, 1,4-dioxane and 1,2-dimethoxyethane, carbohydrates such as benzene, toluene, cyclohexane and hexane, amides such as N,N-dimethylformamide, N,N-dimethylacetoamide and hexamethylphosphoric triamide, halogenated carbohydrates such as dichloromethane, chloroform, carbon tetrachloride and 1,2-dichloroethane, nitriles such as acetonitrile and propionitrile, esters such as methyl acetate, ethyl acetate and butyl acetate, sulfoxides such as dimethylsulfoxide, water or a mixed solvent thereof.

The reaction time is usually about 10 minutes to about 12 hours, preferably about 20 minutes to about 6 hours. The reaction temperature is usually about −50 to about 150° C., preferably about −20 to about 100° C.

Compound (III') wherein $X^a$ is an oxygen atom can be also produced by condensation of Compound (I') and Compound (II') wherein L is a hydroxy group, if desired, under the presence of a dehydrating agent.

The dehydrating agent which may be used in the present reaction includes, for example, an acidic catalyst such as hydrochloric acid, sulfuric acid, phosphoric acid, potassium hydrosulfate, oxalic acid, p-toluenesulfonic acid, 10-camphor sulfonic acid and boron trifluoride ether complex, a basic catalyst such as sodium hydroxide and potassium hydroxide and the like. Furthermore, for example, carbodiimides such as N,N'-dicyclohexylcarbodiimide, alumina, sodium dioxide, phosphorus oxychloride, thionyl chloride, methanesulfonyl chloride and the like may be also used. These acid and base are used in an amount of about 0.1 to 10 moles, preferably about 0.1 to 5.0 moles, to 1 mole of Compound (I').

The present reaction is advantageously carried out without a solvent or with use of a solvent inert to a reaction. Such solvent is not particularly limited if the reaction proceeds, and includes preferably, for example, alcohols such as methanol, ethanol and propanol, ethers such as diethyl ether, tetrahydrofuran, dioxane and 1,2-dimethoxyethane, organic acids such as formic acid and acetic acid, carbohydrates such as benzene, toluene, cyclohexane and hexane, amides such as N,N-dimethylformamide and N,N-dimethylacetoamide, sulfoxides such as dimethylsulfoxide or a mixed solvent thereof and the like.

The reaction time is usually 30 minutes to 24 hours, preferably 30 minutes to 5 hours. The reaction temperature is usually 0 to 200° C., preferably 0 to 150° C.

Compound (III') wherein $X^a$ is an oxygen atom can be also produced by condensation of Compound (I') and Compound (II') wherein L is a hydroxy group with use of Mitsunobu reaction (Synthesis, 1981, 1-27).

The reaction is carried out by reacting Compound (I') and Compound (II') wherein L is a hydroxy group under the presence of azodicarboxylates (for example, diethyl azodicarboxylate, diisopropyl azodicarboxylate, 1,1'-(azodicarbonyl)dipiperidine and the like) and phosphines (for example, triphenylphosphine, tributylphosphine and the like).

Compound (II') is used in an amount of about 1 to about 5 moles, preferably about 1 to about 2 moles, to 1 mole of Compound (I').

The "azodicarboxylates" and "phosphines" are used in an amount of about 1 to about 5 moles, preferably about 1 to about 2 moles, respectively to 1 mole of Compound (I').

The present reaction is advantageously carried out with use of a solvent inert to a reaction. Such solvent are not particularly limited if the reaction proceeds, and includes preferably, for example, ethers such as diethyl ether, diisopropyl ether, diphenyl ether, tetrahydrofuran, 1,4-dioxane and 1,2-dimethoxyethane, carbohydrates such as benzene, toluene, cyclohexane and hexane, amides such as N,N-dimethylformamide, N,N-dimethylacetoamide and hexamethylphosphoric triamide, halogenated carbohydrates such as dichloromethane, chloroform, carbon tetrachloride and 1,2-dichloroethane, nitriles such as acetonitrile and propionitrile, ketones such as acetone and ethylmethylketone, sulfoxides such as dimethylsulfoxide or a mixed solvent thereof and the like.

The reaction time is usually about 5 minutes to about 48 hours, preferably about 10 minutes to about 24 hours. The reaction temperature is usually about −20 to about 200° C., preferably about 0 to about 100° C.

Compound (II) is produced by hydrolyzing the ester group of Compound (III') with use of acid or base. For acidic hydrolysis, there are generally used mineral acids such as hydrochloric acid and sulfuric acid or Lewis acids such as boron trichloride and boron tribromide, combination of Lewis acid and thiol or sulfide, organic acids such as trifluoroacetic acid and p-toluenesulfonic acid. For alkaline hydrolysis, there are used inorganic bases such as sodium hydroxide, potassium hydroxide and barium hydroxide, basic salts such as sodium carbonate and potassium carbonate, metal alkoxides such as sodium methoxide, sodium ethoxide and potassium tertiary butoxide, organic bases such as triethylamine, imidazole and formamidine and the like. These acid and base are used in an amount of about 0.5 to 10 moles, preferably about 0.5 to 6 moles, to 1 mole of Compound (III').

The present reaction is advantageously carried out without a solvent or with use of a solvent inert to a reaction. Such solvent are not particularly limited if the reaction proceeds, and includes preferably, for example, alcohols such as methanol, ethanol and propanol, aromatic carbohydrates such as benzene and toluene, saturated carbohydrates such as cyclohexane and hexane, organic acids such as formic acid and acetic acid, ethers such as tetrahydrofuran, dioxane and 1,2-dimethoxyethane, amides such as N,N-dimethylformamide and N,N-dimethylacetoamide, halogenated carbohydrates such as dichloromethane, chloroform, carbon tetrachloride and 1,2-dichloroethane, nitrites such as acetonitrile and propionitrile, ketones such as acetone and methylethylketone, sulfoxides such as dimethylsulfoxide, water or a mixed solvent thereof and the like.

The reaction time is usually 10 minutes to 60 hours, preferably 10 minutes to 12 hours. The reaction temperature is usually −10 to 200° C., preferably 0 to 120° C.

Compound (III) of the invention can be produced, for example, according to the method represented by the following Reaction scheme 2 or a method analogous thereto.

In addition, Compound (VI) of the invention can be produced similarly to Compound (III).

Compounds (IV'), (V'), (VI') and (VII') are commercially, easily available, and further can be produced according to per se known methods or a method analogous thereto.

tylaluminum hydride, tributyltin hydride, etc., complex metal hydrides such as lithium aluminum hydride, sodium borohydride, etc., borane complexes such as borane tetrahydrofuran complex, borane dimethylsulfide, etc., alkylboranes such as thexyl borane, disiamylborane, etc., diborane, or metals such as zinc, aluminum, tin, iron, etc., alkali metals (sodium, lithium, etc.)/liquid ammonia (batch reduction), etc. The reducing agent is used, for example, in an amount of about 1 to about 10 moles, preferably about 1 to about 5 moles, respectively to 1 mole of Compound (IV') in the case of metal hydrides or metal hydrogen complex compounds, about 1 to about 10 moles, preferably about 1 to about 5 moles to 1 mole of Compound (IV') in the case of borane complexes, alkylboranes or diborane, and about 1 to about 20 equivalents, preferably about 1 to about 5 equivalents in the case of metals. Lewis acids may be also used in the present reaction, if desired. The "Lewis acids" includes, for example, aluminum chloride, aluminum bromide, titanium chloride (IV), tin chloride (II), zinc chloride, boron trichloride, boron tribromide, boron trifluoride and the like. The Lewis acid is used in an amount of about 1 to about 10 moles, preferably about 1 to about 5 moles to 1 mole of Compound (IV').

In addition, it is also reduced by hydrogenation reaction, and in this case, for example, a catalyst such as carbon palladium, platinum oxide (IV), Raney nickel, Raney cobalt and the like can be used. The catalyst is used in an amount of about 5 to about 1000% by weight, preferably about 10 to about 300% by weight to 1 mole of Compound (IV'). Various hydrogen sources may be used instead of gas hydrogen. The "hydrogen source" includes formic acid, ammonium formate, triethylammonium formate, sodium phosphinate, hydrazine and the like. The hydrogen source is used in an amount of about 1 to about 10 moles, preferably about 1 to about 5 moles, respectively to 1 mole of Compound (IV').

The present reaction is advantageously carried out with use of a solvent inert to a reaction. Such solvent is not particularly limited if the reaction proceeds, and includes preferably, for

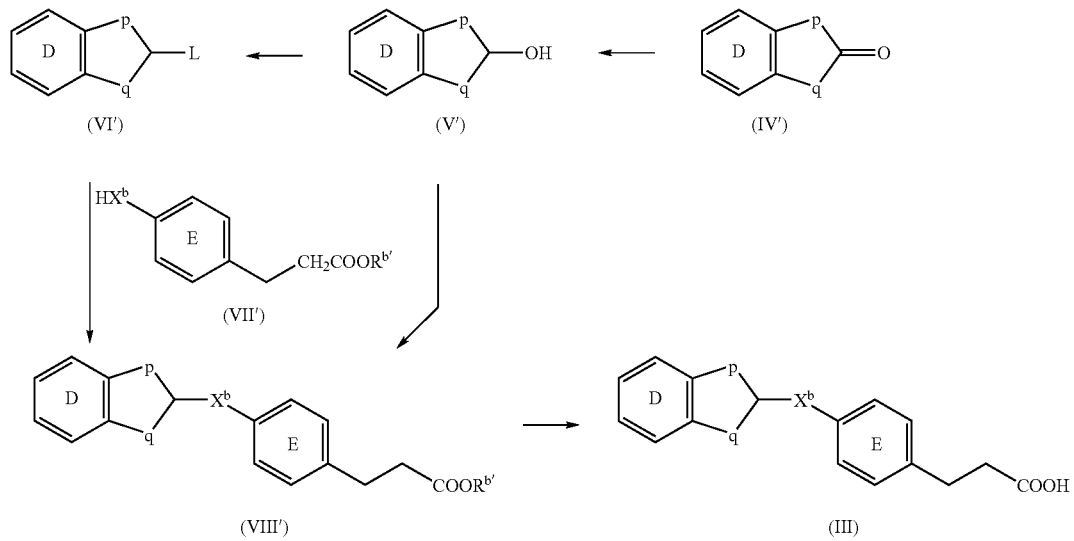

Reaction scheme 2

Compound (V') can be produced by reduction of the carbonyl group of Compound (IV').

The reducing agent which is used in reduction includes, for example, metal hydrides such as aluminum hydride, diisobuexample, alcohols such as methanol, ethanol, 1-propanol, 2-propanol and tert-butyl alcohol, ethers such as diethyl ether, diisopropyl ether, diphenyl ether, tetrahydrofuran, 1,4-dioxane and 1,2-dimethoxyethane, carbohydrates such as benzene, toluene, cyclohexane and hexane, amides such as N,N-dimethylformamide, N,N-dimethylacetoamide and hexamethylphosphoric triamide, organic acids such as formic acid, acetic acid, propionic acid, trifluoroacetic acid and methanesulfonic acid or a mixed solvent thereof and the like.

The reaction time varies depending on kind or amount of the reducing agent used or activity and amount of the catalyst, but it is usually about 1 hour to about 100 hours, preferably about 1 hour to about 50 hours. The reaction temperature is usually about −20 to about 120° C., preferably about 0 to about 80° C. When a hydrogenation catalyst is used, the hydrogen pressure is usually about 1 to about 100 atmospheres.

Compound (VI') [wherein L represents a leaving group] can be produced by converting the hydroxy group of Compound (V') to the "leaving group".

The "leaving group" represented by L includes, for example, a halogen atom such as fluorine, chlorine, bromine and iodine, $C_{1-6}$ alkylsulfonyloxy group which may be halogenated, such as methanesulfonyloxy, ethanesulfonyloxy and trichloromethanesulfonyloxy, $C_{6-10}$ arylsulfonyloxy group optionally having substituent(s) and the like. The "$C_{6-10}$ arylsulfonyloxy group optionally having substituent(s)" includes, for example, a $C_{6-10}$ arylsulfonyloxy group such as phenylsulfonyloxy and naphthylsulfonyloxy which may have 1 to 3 substituents which are selected from a $C_{1-6}$ alkyl group such as methyl and ethyl, a $C_{1-6}$ alkoxy group such as methoxy and ethoxy and nitro, and the like, and specific examples include phenylsulfonyloxy, m-nitrophenylsulfonyloxy, p-toluenesulfonyloxy and the like.

When the "leaving group" represented by L is a halogen atom, a halogenating agent which is used in halogenation includes, for example, thionyl halides such as thionyl chloride and thionyl bromide, phosphoryl halides such as phosphoryl chloride and phosphoryl bromide, phosphorus halides such as phosphorus pentachloride, phosphorus trichloride, phosphorus pentabromide and phosphorus tribromide, oxalyl halides such as oxalyl chloride, phosgene and the like. The halogenating agent is used in an amount of about 0.1 to about 30 moles, preferably about 0.2 to about 10 moles, and further preferably about 1 to about 10 moles to 1 mole of Compound (V').

The present reaction is carried out under the presence of a base, if desired. The "base" includes tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine and N-methylmorpholine and the like. The base is used in an amount of about 1 to about 20 moles, preferably about 1 to about 10 moles to 1 mole of Compound (V').

The present reaction is advantageously carried out without a solvent or with use of a solvent inert to a reaction. Such solvent are not particularly limited if the reaction proceeds, and includes preferably, for example, carbohydrates such as benzene, toluene, cyclohexane and hexane, ethers such as diethyl ether, diisopropyl ether, diphenyl ether, tetrahydrofuran, 1,4-dioxane and 1,2-dimethoxyethane, amides such as N,N-dimethylformamide, N,N-dimethylacetoamide and hexamethylphosphoric triamide, halogenated carbohydrates such as dichloromethane, chloroform, carbon tetrachloride and 1,2-dichloroethane or a mixed solvent thereof and the like.

The reaction time is usually about 10 minutes to about 12 hours, preferably about 10 minutes to about 5 hours. The reaction temperature is usually about −10 to about 200° C., preferably about −10 to about 120° C.

When the "leaving group" represented by L is $C_{1-6}$ alkylsulfonyloxy group which may be halogenated or $C_{6-10}$ arylsulfonyloxy group optionally having substituent(s), the sulfonylation agent includes, for example, $C_{1-6}$ alkylsulfonyl halide such as methanesulfonyl chloride, $C_{6-10}$ arylsulfonyl halide such as sulfonyl chlorobenzene and p-toluenesulfonyl chloride and the like. The sulfonylation agent is used in an amount of about 1 to about 20 moles, preferably about 1 to about 10 moles to 1 mole of Compound (V').

The present reaction is advantageously carried out without a solvent or with use of a solvent inert to a reaction. Such solvent are not particularly limited if the reaction proceeds, and includes preferably, for example, carbohydrates such as benzene, toluene, cyclohexane and hexane, ethers such as diethyl ether, diisopropyl ether, diphenyl ether, tetrahydrofuran, 1,4-dioxane and 1,2-dimethoxyethane, halogenated carbohydrates such as dichloromethane, chloroform, carbon tetrachloride and 1,2-dichloroethane, esters such as methyl acetate, ethyl acetate and butyl acetate or a mixed solvent thereof and the like.

The present reaction is carried out under the presence of a base, if desired. The "base" includes tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine and N-methylmorpholine, inorganic bases such as sodium hydroxide, potassium hydroxide, lithium hydroxide and barium hydroxide, basic salts such as sodium carbonate, potassium carbonate, cesium carbonate, sodium hydrocarbonate, sodium acetate and ammonium acetate and the like. The base is used in an amount of about 1 to about 20 moles, preferably about 1 to about 10 moles to 1 mole of Compound (V').

The reaction time is usually about 10 minutes to about 12 hours, preferably about 10 minutes to about 5 hours. The reaction temperature is usually about −30 to about 150° C., preferably about −20 to about 100° C.

Compound (VIII') [wherein $R^{b'}$ is a hydrocarbon group optionally having substituent(s)] can be produced by condensation of Compound (VI') and Compound (VII') [wherein $R^{b'}$ represents the same as described above] under the presence of a base, when $X^b$ is an oxygen atom or sulfur atom.

The "hydrocarbon group optionally having substituent(s)" represented by $R^{b'}$ is preferably the "lower ($C_{1-6}$)alkyl which may be substituted", the "lower ($C_{2-6}$)alkenyl which may be substituted", the "lower ($C_{2-6}$)alkynyl which may be substituted", the "$C_{3-8}$ cycloalkyl which may be substituted", the "$C_{6-14}$ aryl which may be substituted" and the "$C_{7-16}$ aralkyl which may be substituted" and the like in the above-mentioned substituent group A.

The base used in the present reaction includes inorganic bases such as sodium hydroxide, potassium hydroxide, lithium hydroxide and barium hydroxide, basic salts such as sodium carbonate, potassium carbonate, cesium carbonate, sodium hydrocarbonate, sodium acetate and ammonium acetate, aromatic amines such as pyridine and lutidine, tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine and N-methylmorpholine, alkali metal hydrides such as sodium hydride and potassium hydride, metal amides such as sodium amide, lithium diisopropylamide and lithium hexamethyldisilazide, metal alkoxides such as sodium methoxide, sodium ethoxide, sodium tert-butoxide and potassium tert-butoxide and the like. These bases are used in an amount of about 1 to 10 moles, preferably about 1 to 3 moles to 1 mole of Compound (VIII').

The present reaction is advantageously carried out with use of a solvent inert to a reaction. Such solvent are not particularly limited if the reaction proceeds, and includes preferably, for example, alcohols such as methanol, ethanol, 1-propanol, 2-propanol and tert-butyl alcohol, ethers such as diethyl ether, diisopropyl ether, diphenyl ether, tetrahydrofuran, 1,4-dioxane and 1,2-dimethoxyethane, carbohydrates such as benzene, toluene, cyclohexane and hexane, amides such as N,N-dimethylformamide, N,N-dimethylacetoamide and hexamethylphosphoric triamide, halogenated carbohydrates such as dichloromethane, chloroform, carbon tetrachloride and 1,2-dichloroethane, nitriles such as acetonitrile and propionitrile, esters such as methyl acetate, ethyl acetate and butyl acetate, sulfoxides such as dimethylsulfoxide, water or a mixed solvent thereof and the like.

The reaction time is usually about 10 minutes to about 12 hours, preferably about 20 minutes to about 6 hours. The reaction temperature is usually about −50 to about 150° C., preferably about −20 to about 100° C.

Compound (VIII') can be also produced by condensation of Compound (V') and Compound (VII') under the presence of a dehydrating agent, if desired, when $X^b$ is an oxygen atom or sulfur atom.

The dehydrating agent which may be used in the present reaction includes, for example, an acidic catalyst such as hydrochloric acid, sulfuric acid, phosphoric acid, potassium hydrosulfate, oxalic acid, p-toluenesulfonic acid, 10-camphor sulfonic acid and boron trifluoride ether complex, a basic catalyst such as sodium hydroxide and potassium hydroxide and the like. Furthermore, for example, carbodiimides such as N,N'-dicyclohexylcarbodiimide, alumina, sodium dioxide, phosphorus oxychloride, thionyl chloride, methanesulfonyl chloride and the like may be also used. These acid and base are used in an amount of about 0.1 to 10 moles, preferably about 0.1 to 5.0 moles to 1 mole of Compound (VII').

The present reaction is advantageously carried out without a solvent or with use of a solvent inert to a reaction. Such solvent is not particularly limited if the reaction proceeds, and includes preferably, for example, alcohols such as methanol, ethanol and propanol, ethers such as diethyl ether, tetrahydrofuran, dioxane and 1,2-dimethoxyethane, organic acids such as formic acid and acetic acid, carbohydrates such as benzene, toluene, cyclohexane and hexane, amides such as N,N-dimethylformamide and N,N-dimethylacetoamide, sulfoxides such as dimethylsulfoxide or a mixed solvent thereof and the like.

The reaction time is usually 30 minutes to 24 hours, preferably 30 minutes to 5 hours. The reaction temperature is usually 0 to 200° C., preferably 0 to 150° C.

Compound (VIII') wherein $X^b$ is an oxygen atom can be also produced by condensation of Compound (V') and Compound (VII') with use of Mitsunobu reaction (Synthesis, 1981, 1-27).

The reaction is carried out by reacting Compound (VII') and Compound (V') under the presence of azodicarboxylates such as diethyl azodicarboxylate, diisopropyl azodicarboxylate and 1,1'-(azodicarbonyl)dipiperidine, phosphines such as triphenylphosphine and tributylphosphine and the like.

Compound (V') is used in an amount of about 1 to about 5 moles, preferably about 1 to about 2 moles to 1 mole of Compound (VII').

The "azodicarboxylates" and the "phosphines" are used in an amount of about 1 to about 5 moles, preferably about 1 to about 2 moles, respectively to 1 mole of Compound (VII').

The present reaction is advantageously carried out with use of a solvent inert to a reaction. Such solvent are not particularly limited if the reaction proceeds, and includes preferably, for example, ethers such as diethyl ether, diisopropyl ether, diphenyl ether, tetrahydrofuran, 1,4-dioxane and 1,2-dimethoxyethane, carbohydrates such as benzene, toluene, cyclohexane and hexane, amides such as N,N-dimethylformamide, N,N-dimethylacetoamide and hexamethylphosphoric triamide, halogenated carbohydrates such as dichloromethane, chloroform, carbon tetrachloride and 1,2-dichloroethane, nitriles such as acetonitrile and propionitrile, ketones such as acetone and ethylmethylketone, sulfoxides such as dimethylsulfoxide or a mixed solvent thereof and the like.

The reaction time is usually about 5 minutes to about 48 hours, preferably about 10 minutes to about 24 hours. The reaction temperature is usually about −20 to about 200° C., preferably about 0 to about 100° C.

Compound (III) is produced by hydrolyzing the ester group of Compound (VIII') with use of acid or base. For acidic hydrolysis, there are generally used mineral acids such as hydrochloric acid and sulfuric acid or Lewis acids such as boron trichloride and boron tribromide, combination of Lewis acid and thiol or sulfide, organic acids such as trifluoroacetic acid and p-toluenesulfonic acid. For alkaline hydrolysis, there are used inorganic bases such as sodium hydroxide, potassium hydroxide and barium hydroxide, basic salts such as sodium carbonate and potassium carbonate, metal alkoxides such as sodium methoxide, sodium ethoxide and potassium tertiary butoxide, organic bases such as triethylamine, imidazole and formamidine and the like. These acid and base are used in an amount of about 0.5 to 10 moles, preferably about 0.5 to 6 moles to 1 mole of Compound (VIII').

The present reaction is advantageously carried out without a solvent or with use of a solvent inert to a reaction. Such solvent are not particularly limited if the reaction proceeds, and includes preferably, for example, alcohols such as methanol, ethanol and propanol, aromatic carbohydrates such as benzene and toluene, saturated carbohydrates such as cyclohexane and hexane, organic acids such as formic acid and acetic acid, ethers such as tetrahydrofuran, dioxane and 1,2-dimethoxyethane, amides such as N,N-dimethylformamide and N,N-dimethylacetoamide, halogenated carbohydrates such as dichloromethane, chloroform, carbon tetrachloride and 1,2-dichloroethane, nitriles such as acetonitrile and propionitrile, ketones such as acetone and methylethylketone, sulfoxides such as dimethylsulfoxide, water or a mixed solvent thereof and the like.

The reaction time is usually 10 minutes to 60 hours, preferably 10 minutes to 12 hours. The reaction temperature is usually −10 to 200° C., preferably 0 to 120° C.

Compounds (I) or (VII) can be produced in accordance with the above-mentioned production method.

In each of the above reactions, when a raw material compound have an amino group, a carboxyl group, a hydroxy group as substituent(s), these groups may be protected by ordinary protective groups such as those generally employed in peptide chemistry, and the like. After the reaction, the protective groups may be removed to obtain the objective compound, if necessary.

A protective group for an amino group includes, for example, formyl, or $C_{1-6}$ alkyl-carbonyl (for example, acetyl, propionyl and the like), benzoyl, $C_{1-6}$ alkoxy-carbonyl (for example, methoxycarbonyl, ethoxycarbonyl and the like), phenyloxycarbonyl, $C_{7-10}$ aralkyloxy-carbonyl (for example, benzyloxycarbonyl and the like), trityl and phthaloyl, which optionally have substituent(s) respectively, and the like. These substituents include a halogen atom (for example, fluorine, chlorine, bromine, iodine and the like), $C_{1-6}$ alkyl-carbonyl (for example, acetyl, propionyl, valeryl and the like), nitro and the like, and the number of the substituent is about 1 to 3.

A protective group for a carboxyl group includes, for example, $C_{1-6}$ alkyl (for example, methyl, ethyl, propyl, isopropyl, butyl, tert-butyl and the like), phenyl, trityl, silyl, which optionally have substituent(s) respectively, and the like. These substituents includes a halogen atom (for example, fluorine, chlorine, bromine, iodine and the like), formyl, $C_{1-6}$ alkyl-carbonyl (for example, acetyl, propionyl, butylcarbonyl and the like), nitro, $C_{1-6}$ alkyl (for example, methyl, ethyl, tert-butyl and the like), $C_{1-6}$ aryl (for example, phenyl, naphthyl and the like) and the like, and the number of the substituent is about 1 to 3.

A protective group for a hydroxy group includes, for example, formyl, or $C_{1-6}$ alkyl (for example, methyl, ethyl, propyl, isopropyl, butyl, tert-butyl and the like), phenyl, $C_{7-10}$ aralkyl (for example, benzyl and the like), $C_{1-6}$ alkyl-carbonyl (for example, acetyl, propionyl and the like), phenyloxycarbonyl, $C_{7-10}$ aralkyloxy-carbonyl (for example, benzyloxycarbonyl and the like), tetrahydropyranyl, tetrahydrofuranyl, silyl, which optionally have substituent(s) respectively, and the like. These substituents include a halogen atom (for example, fluorine, chlorine, bromine, iodine and the like), $C_{1-6}$ alkyl (for example, methyl, ethyl, tert-butyl and the like), $C_{7-10}$ aralkyl (for example, benzyl and the like), $C_{6-10}$ aryl (for example, phenyl, naphthyl and the like), nitro and the like, and the number of the substituent is about 1 to 4.

In addition, the protective group may be removed by per se known methods or a method analogous thereto, for example, a method of treating the protective group with an acid, a base, ultraviolet ray, hydrazine, phenylhydrazine, sodium N-methyldithiocarbamate, tetrabutylammonium fluoride, palladium acetate (II), etc., or reduction.

In any case, further if desired, Compound (II) and Compound (III) can be synthesized by using deprotection reactions, acylation reactions, alkylation reactions, hydrogenation reactions, oxidation reactions, reduction reactions, carbon chain extension reactions, substituent exchange reactions, each alone or in combination of two or more of them. As these reactions, for example, methods described in SHIN-JIKKEN KAGAKU KOUZA 14, Vol. 15, 1977 (Maruzen Press), etc. are adopted.

The compounds used in the invention can be produced in accordance with the above-mentioned production method or the method described in JP-A No. 2002-265457, JP-A No. 2002-212171, JP-A No. 2001-226350, JP-A No. 2001-199971, JP-A No. 2000-198772, JP-A No. 2000-80086, JP-A No. 2000-34266, JP-A No. 9-323983, JP-A No. 8-311065 and the like.

When the desired product is obtained in the free form by the above-mentioned reaction, it may be converted into a salt according to an ordinary method, while when obtained in the form of a salt, it can also be converted into a free form or other salt according to an ordinary method. Thus-obtained compound of the invention or a salt thereof can be isolated and purified from a reaction solution by known means, for example, partition, concentration, solvent extraction, fractionation, crystallization, recrystallization, chromatography and the like.

When the compound of the invention is present as a configurational isomer, diastereomer, conformer and the like, it can be separately isolated by a separation or purification means as described above, if desired. When the compound of the invention is present as a racemate, it can be resolved into S form and R form by an ordinary optical resolution method.

When the compound of the invention has its stereoisomers, individual isomers or a mixture thereof may also be encompassed in the invention.

The compound of the invention may be hydrated or non-hydrated.

The compound of the invention may be labeled with an isotope (e.g. $^3H$, $^{14}C$ and $^{35}S$) and the like.

The regulating effect for the 14273 receptor function of the compound of the invention can be measured with use of the method described in Test Example 1 as described below or a method analogous thereto.

The compound of the invention, a salt thereof, and a prodrug thereof (hereinafter, simply referred to as the compound of the invention) has a regulating effect for the 14273 receptor function, especially agonist activity on the 14273 receptor, and further it has low toxicity, and further little side effect, whereby it is useful as a safe 14273 receptor function regulating agent, preferably the 14273 receptor agonist.

Furthermore, the compound of the invention has, for example, an effect for regulating glycerol production from adipocytes, a glycerol in blood regulating effect, a lipolysis regulating effect (preferably, a lipolysis in adipocyte regulating effect), an insulin resistance regulating effect, a stress regulating effect, an adrenocorticotropic hormone (ACTH) secretion regulating effect, a growth hormone secretion regulating effect, a glucagon-like peptide-1 (GLP-1) secretion regulating effect (preferably, an effect for suppressing glycerol production from adipocyte, a glycerol in blood lowering effect, a lipolysis suppressing effect (preferably, an effect for suppressing lipolysis in adipocyte), an insulin resistance suppressing effect, a stress regulating effect, an adrenocorticotropic hormone (ACTH) secretion suppressing effect, a growth hormone secretion suppressing effect and a glucagon-like peptide-1 (GLP-1) secretion promoting effect) and the like, it is useful as a regulator for glycerol production from adipocyte, a glycerol in blood regulating agent, a lipolysis regulating agent (preferably, lipolysis in adipocyte regulating effect), an insulin resistance regulating agent, a stress regulating agent, an adrenocorticotropic hormone (ACTH) secretion regulating agent, a growth hormone secretion regulating agent, a glucagon-like peptide-1 (GLP-1) secretion regulating agent (preferably, a suppressing agent for glycerol production from adipocyte, a glycerol in blood lowering agent, a lipolysis suppressing agent (preferably, a lipolysis in adipocyte suppressing agent), an insulin resistance suppressing agent, a stress regulating agent, an adrenocorticotropic hormone (ACTH) secretion suppressing agent, a growth hormone secretion suppressing agent and a glucagon-like peptide-1 (GLP-1) secretion promoting agent), and the like.

The "stress regulating effect" in the invention refers to, for example, stress improving effect, stress alleviating effect and the like, and the "stress regulating agent" refers to, for example, a stress improving agent, a stress alleviating agent and the like.

A pharmaceutical agent comprising the compound of the invention has excellent the 14273 receptor function regulating effect in mammals (for example, mouse, rat, hamster, rabbit, cat, dog, calf, sheep, monkey, human and the like), whereby it is useful as a regulator for physiological functions which are associated with the 14273 receptor, or a preventing and/or treating agent for clinical conditions or diseases which are associated with the 14273 receptor.

Specifically, based on the effect for regulating glycerol production from adipocyte, the effect for regulating blood-glycerol, the effect for regulating lipolysis, the effect for regulating insulin resistance, the effect for regulating glucagon-like peptide-1 (GLP-1) secretion (preferably, the effect for suppressing glycerol production from adipocyte, blood-glycerol lowering effect, the effect for suppressing lipolysis, the effect for suppressing insulin resistance and the effect for promoting glucagon-like peptide-1 (GLP-1) secretion and the like), the pharmaceutical agent comprising the compound of the invention is useful as an agent for preventing/treating diseases, for example, diabetes mellitus, glucose tolerance disorders, ketosis, acidosis, diabetic neural disorders, diabetic renopathy, diabetic retinopathy, hyperlipidemia, atherosclerosis, angina pectoris, myocardial infarction, sexual dysfunction, overweight, obesity, pituitary dysfunctions (e.g., hypopituitarism, pituitary dwarfism, diabetes insipidus, acromegaly, Cushing's disease (pituitary hyperglucocorticoid), hyperprolactinemia, syndrome of inappropriate secretion of anti-diuretic hormone), cancer (e.g., colorectal cancer), deficits in memory and learning, pancreatic exhaustion, hypoglycemia, insulin allergy, lipotoxicity, fatty atrophy, cancerous cachexia, hyperinsulinemia, hyperglycemia, disorder caused by high FFA flux, hypertriglyceridemia, fatty liver, dysfunction of heat production, cholelithiasis, eating disorder, anorexia, secretion disorders of intestinal hormones (e.g., cholecystokinin (CCK), gastric inhibitory peptide (GIP), gastrin, glucagon-like peptide-1 (GLP-1), somatostatin, gastrin-releasing peptide, secretin, vasoactive intestinal peptide, motilin, substance P, neurotensin, galanin, neuropeptide Y, enkephalins, peptide YY, etc.) or circulatory diseases (preferably, diabetes mellitus, hyperlipemia, overweight, arteriosclerosis, angina pectoris or myocardial infarction), etc.

Furthermore, a pharmaceutical agent comprising the compound of the invention can be used as an agent for preventing/treating diseases, for example, arteriosclerosis, arteriosclerotic diseases and their secondary diseases [e.g., acute coronary syndrome such as atherosclerosis, peripheral arterial disease, acute myocardial infarction, unstable angina, etc., ischemic heart diseases such as restenosis after percutaneous transluminal coronary angioplasty (PTCA), myocardial infarction, angina pectoris, etc., arteriosclerosis including angiocalcinosis, etc., intermittent claudication, apoplexy (cerebral infarction, cerebral embolism, brain hemorrhage, etc.), lacunar infarction, cerebrovascular dementia, gangrene, glomerulosclerosis, nephropathy, Tangier disease, etc.], vascular lesions in atherosclerosis and their secondary diseases [e.g., coronary heart disease (CHD), cerebral ischemia, etc.], lipid dysbolism and its secondary diseases, etc.

Furthermore, based on the effect for regulating adrenocorticotropic hormone (ACTH) secretion (preferably, the effect for suppressing adrenocorticotropic hormone (ACTH) secretion) and the like, a pharmaceutical agent comprising the compound of the invention is useful as an agent for preventing and/or treating, for example, ACTH-producing tumor, Cushing's disease, infectious disease, secondary adrenocortical insufficiency, peptic ulcer, diabetes mellitus, mental disorder (e.g., depression, anxiety), cataract, glaucoma, tuberculous disease, hypertension, Cushing's syndrome (e.g., central obesity, edema, hypertension, menstrual disorder, extensive stretch mark, hirsutism, diabetes mellitus, full moon face, osteoporosis, hemorrhagic diathesis, mental disorder, muscular atrophy, loss of muscle strength, hypokalemia, hypercholesterolemia, impaired glucose resistance, leukocytosis), adrenocortical atrophy, connective tissue diseases (e.g., chronic articular rheumatism, systemic lupus erythematosus, polymyositis, rheumatic fever, scleroderma), kidney diseases (e.g., nephrosis), respiratory diseases (e.g., bronchial asthma, pulmonary tuberculous pleuritis, sarcoidosis, diffuse interstitial pneumonia), alimentary diseases (e.g., ulcerative colitis, cholestatic acute hepatitis, fulminant hepatitis, chronic hepatitis, cirrhosis), neuromuscular diseases (e.g., encephalomyelitis, peripheral neuritis, multiple sclerosis, myasthenia gravis, facial paralysis), blood diseases (e.g., hemolytic anemia, agranulocytosis, purpura, aplastic anemia, leukemia, malignant lymphoma), endocrine-metabolic diseases (e.g., acute or chronic adrenocortical insufficiency, adrenogenital syndrome, malignant exopthalmos due to thyroid gland disease, ACTH isolated deficiency), skin diseases (e.g., urticaria, eczema, dermatitis, herpes zoster, psoriasis, drug allergy) or anaphylactic shock (preferably, ACTH-producing tumor, Cushing's disease, infectious disease, secondary adrenocortical insufficiency, peptic ulcer, diabetes mellitus, mental disorder, cataract, glaucoma, tuberculous disease, hypertension, Cushing's syndrome or adrenocortical atrophy).

Herein, the diabetes mellitus includes insulin-dependent type (Type I) diabetes mellitus, insulin-nondependent type (Type II) diabetes mellitus and pregnant diabetes mellitus. In addition, the hyperlipidemia includes hypertriglyceridemia, hypercholesterolemia, hypoHDL-emia, postprandial hyperlipidemia and the like.

For diagnostic criteria of diabetes, Japan Diabetes Society reported new diagnostic criteria in 1999.

According to this report, diabetes is a condition showing any of the following conditions that the fasting blood glucose level (glucose concentration of intravenous plasma) is not less than 126 mg/dl, the level after 2-hour long of a 75 g oral glucose tolerance test (75 g OGTT) (glucose concentration of intravenous plasma) is not less than 200 mg/dl, and the non-fasting blood glucose level (glucose concentration of intravenous plasma) is not less than 200 mg/dl. A condition not falling under the above-mentioned diabetes and different from "a condition showing the fasting blood glucose level (glucose concentration of intravenous plasma) of less than 110 mg/dl or the level after 2-hour long of a 75 g oral glucose tolerance test (75 g OGTT) (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing the fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and the level after 2-hour long of a 75 g oral glucose tolerance test (glucose concentration of intravenous plasma) of not less than 140 mg/dl and less than 200 mg/dl. According to the report of ADA, a condition showing the fasting blood glucose level (glucose concentration of intravenous plasma) of not less than 110 mg/dl and less than 126 mg/dl is called as IFG (Impaired Fasting Glucose). On the other hand, according to the report of WHO, among the IFG (Impaired Fasting Glucose), a condition showing the level after 2-hour long of a 75 g oral glucose tolerance test (glucose concentration of intravenous plasma) of less than 140 mg/dl is called IFG (Impaired Fasting Glycemia).

The compound of the invention is also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the invention can prevent progress of borderline type, impaired glucose tolerance, IFG (Impaired Fasting Glucose) or IFG (Impaired Fasting Glycemia) into diabetes.

The pharmaceutical comprising the compound of the invention shows low toxicity, and can be safely administered orally or parenterally (e.g., topical, rectal, intravenous administration, etc.) in the form of the compound of the invention as it is or after admixing with a pharmacologically acceptable carrier to give a pharmaceutical preparation such as tablets (including sugar-coated tablets and film-coated tablets), powders, granules, capsules (including soft capsules), liquids, injections, suppositories, sustained-release agents and the like, according to a method known per se generally employed for production methods for pharmaceutical preparations.

The content of the compound of the invention in a pharmaceutical preparation is about 0.01 to about 100% by weight relative to the whole preparation. While the dose varies depending on the administration subject, administration route, diseases, condition and the like, for example, the compound of the invention (as an active ingredient) can be orally administered to a patient with hyperlipidema (about 60 kg of body weight) in about 0.01 to about 30 mg/kg of body weight per day, preferably about 0.1 to about 20 mg/kg of body weight per day, more preferably about 1 to about 20 mg/kg of body weight per day, which may be given at once or in several portions a day.

As the pharmacologically acceptable carrier that may be used for the production of the pharmaceutical agent of the invention, various organic or inorganic carrier substances conventionally used as a preparation material can be mentioned. For example, excipient, lubricant, binder and disintegrant for solid preparations, solvent, dissolution aids, suspending agent, isotonicity agent, buffer and soothing agent for liquid preparations and the like can be mentioned. Furthermore, if necessary, conventional additives such as preservatives, antioxidants, coloring agents, sweetening agents, adsorbing agents, wetting agents and the like can be used as appropriate in suitable amounts.

As the excipient, for example, lactose, sucrose, D-mannitol, starch, corn starch, crystalline cellulose, light anhydrous silicic acid and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium and the like can be mentioned.

As the disintegrant, for example, starch, carboxymethylcellulose, carboxymethylcellulose calcium, carboxymethyl starch sodium, L-hydroxypropylcellulose and the like can be mentioned.

As the solvent, for example, water for injection, alcohol, propylene glycol, macrogol, sesame oil, corn oil, olive oil and the like can be mentioned.

As the dissolution aids, for example, polyethylene glycol, propylene glycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As the isotonicity agent, for example, glucose, D-sorbitol, sodium chloride, glycerin, D-mannitol and the like can be mentioned.

As the buffer, for example, buffers such as phosphate, acetate, carbonate, citrate and the like, and the like can be mentioned.

As the soothing agent, for example, benzyl alcohol and the like can be mentioned.

As the preservative, for example, p-hydroxybenzoic acid esters, chlorobutanol, benzyl alcohol, phenethyl alcohol, dehydroacetic acid, sorbic acid and the like can be mentioned.

As the antioxidant, for example, sulfite, ascorbic acid, α-tocopherol and the like can be mentioned.

Moreover, the compound of the invention can be used in combination with drugs other than the compound of the invention.

As the drugs that can be used in combination with the compound of the invention (hereinafter, it may be abbreviated as a concomitant drug), there can be mentioned, for example, other treating agents for diabetes, treating agents for diabetic complications, treating agents for hyperlipidemia, antihypertensive agents, antiobesity agents, diuretics, chemotreating agents, immunotreating agents, immunomodulators, antiinflammatory agents, antithrombotic agents, treating agents for osteoporosis, antibacterial agents, antifungal agents, antiprotozoal agents, antibiotics, antitussives and expectorant drugs, sedatives, anesthetics, antiulcer agents, tranquilizers, antipsychotic agents, antitumor agents, muscle relaxants, antiepileptics, antidepressants, antiallergic agents, cardiac stimulants, antiarrhythmic agents, vasodilators, vasoconstrictors, narcotic antagonists, vitamins, vitamin derivatives, antiasthmatic agents, antidementia agents, treating agents for pollakiuria or urinary incontinence, treating agents for dysuria, treating agents for atopic dermatitis, treating agents for allergic rhinitis, vasopressors, endotoxin antagonists or antibodies, signal transduction inhibitors, inflammatory mediator effect suppressants, inflammatory mediator effect suppressing antibodies, anti-inflammatory mediator effect suppressants, anti-inflammatory mediator effect suppressing antibodies and the like. Specifically, the following agents can be mentioned.

As other treating agents for diabetes, there can be mentioned insulin preparations (e.g., animal insulin preparations extracted from pancreas of bovine or pig; human insulin preparations genetically synthesized using *Escherichia coli* or yeast; zinc insulin; protamine zinc insulin; fragment or derivative of insulin (e.g., INS-1, etc.), oral insulin preparation and the like), insulin sensitizers (e.g., pioglitazone or a salt thereof (preferably hydrochloride), troglitazone, rosiglitazone or a salt thereof (preferably maleate), Reglixane (JTT-501), Netoglitazone (MCC-555), YM-440, GI-262570, KRP-297, FK-614, CS-011, (γE)-γ-[[[4-[(5-methyl-2-phenyl-4-oxazolyl)methoxy]phenyl]methoxy]imino]benzenebutanoic acid and the like, compounds described in WO 99/58510 (e.g., (E)-4-[4-(5-methyl-2-phenyl-4-oxazolylmethoxy)benzyloxyimino]-4-phenylbutyric acid), compounds described in WO 01/38325, Tesaglitazar (AZ-242), Ragaglitazar (N,N-622), BMS-298585, ONO-5816, BM-13-1258, LM-4156, MBX-102, LY-519818, MX-6054, LY-510929, Balaglitazone (N,N-2344), T-131 or a salt thereof, THR-0921), α-glucosidase inhibitors (e.g., voglibose, acarbose, miglitol, emiglitate, etc.), biguanides (e.g., phenformin, metformin, buformin, etc.), insulin secretagogues [sulfonylurea (e.g., tolbutamide, glibenclamide, gliclazide, chlorpropamide, tolazamide, acetohexamide, glyclopyramide, glimepiride, etc.), repaglinide, senaglinide, mitiglinide or calcium salt hydrate thereof, nateglinide, etc.], GLP-1 receptor agonists [e.g., GLP-1, GLP-1MR agent, N,N-2211, AC-2993 (exendin-4), BIM-51077, Aib(8,35)hGLP-1(7,37)NH$_2$, CJC-1131, etc.], dipeptidyl peptidase IV inhibitors (e.g., NVP-DPP-278, PT-100, P32/98, P93/01, NVP-DPP-728, LAF237, TS-021, etc.), β3 agonists (e.g., CL-316243, SR-58611-A, UL-TG-307, AJ-9677, AZ40140, etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLT (sodium-glucose cotransporter) inhibitors (e.g., T-1095, etc.), 11β-hydroxysteroid dehydrogenase inhibitors (e.g., BVT-3498, etc.), adiponectin or agonists thereof, IKK inhibitors (e.g., AS-2868, etc.), leptin resistance improving drugs, somatostatin receptor agonists (compounds described in WO 01/25228, WO 03/42204, compounds described in WO 98/44921, WO 98/45285, WO 99/22735, etc.), glucokinase activators (e.g., Ro-28-1675) and the like.

Examples of the treating agents for diabetic complications include aldose reductase inhibitors (e.g., Tolrestat, Epalrestat, Zenarestat, Zopolrestat, Fidarestat (SNK-860), Minalrestat (ARI-509), CT-112, etc.), neurotrophic factors and increasing drugs thereof (e.g., NGF, NT-3, BDNF, neurotrophin production-secretion promoters described in WO 01/14372 (e.g., 4-(4-chlorophenyl)-2-(2-methyl-1-imidazolyl)-5-[3-(2-methylphenoxy)propyl]oxazole, etc.) and the like), protein kinase C (PKC) inhibitors (e.g., LY-333531, etc.), AGE inhibitors (e.g., ALT-945, pimagedine, pyratoxanthine, N-phenacylthiazolium bromide (ALT-766), EXO-226, ALT-711, Pyridorin, Pyridoxamine, etc.), active oxygen scavengers (e.g., thioctic acid, etc.), cerebral vasodilators (e.g., tiapuride, etc.), somatostatin receptor agonist (BIM23190), apoptosis signal regulating kinase-1 (ASK-1) inhibitors and the like.

Examples of the treating agents for hyperlipidemia include statin compounds which are cholesterol synthesis inhibitors (e.g., pravastatin, simvastatin, lovastatin, atorvastatin, fluvastatin, cerivastatin or a salt thereof (e.g., sodium salt, etc.), etc.), squalene synthase inhibitors (e.g., compounds described in WO 97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid and the like), fibrate compounds (e.g., bezafibrate, clofibrate, simfibrate, clinofibrate, etc.), antioxidants (e.g., lipoic acid, probucol) and the like.

Examples of the antihypertensive agents include angiotensin converting enzyme inhibitors (e.g., captopril, enalapril, delapril, etc.), angiotensin II antagonists (e.g., losartan, candesartan, cilexetil, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid, etc.), calcium antagonists (e.g., manidipine, nifedipine, amlodipine, efonidipine, nicardipine, etc.), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds encompassed in WO 01/82925 and WO 01/87834, etc.); neuropeptide Y antagonists (e.g., CP-422935, etc.); cannabinoid receptor antagonists (e.g., SR-141716, SR-147778, etc.); ghrelin antagonists; 11β-hydroxysteroid dehydrogenase inhibitors (e.g., BVT-3498, etc.) and the like), pancreatic lipase inhibitors (e.g., orlistat, ATL-962, etc.), β3 agonists (e.g., CL-316243, SR-58611-A, UL-TG-307, AJ-9677, AZ40140, etc.), peptide anorexiants (e.g., leptin, CNTF (Ciliary Neurotropic Factor), etc.), cholecystokinin agonists (e.g., lintitript, FPL-15849, etc.), feeding deterrent (e.g., P-57, etc.) and the like.

Examples of the diuretics include xanthine derivatives (e.g., theobromine sodium salicylate, theobromine calcium salicylate, etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonate dehydratase inhibitors (e.g., acetazolamide and the like), chlorobenzenesulfonamide preparations (e.g., chlorthalidone, mefruside, indapamide, etc.), azosemide, isosorbide, ethacrynic acid, piretanide, bumetanide, furosemide and the like.

Examples of the chemotreating agents include alkylating agents (e.g., cyclophosphamide, ifosfamide, etc.), metabolic antagonists (e.g., methotrexate, 5-fluorouracil, etc.), antitumor antibiotics (e.g., mitomycin, adriamycin, etc.), plant-derived antitumor agent (e.g., vincristine, vindesine, Taxol, etc.), cisplatin, carboplatin, etoposide and the like. Of these, Furtulon or NeoFurtulon, which are 5-fluorouracil derivatives, and the like are preferable.

Examples of the immunotreating agents include microorganism or bacterial components (e.g., muramyl dipeptide derivative, Picibanil, etc.), polysaccharides having immunity potentiating activity (e.g., lentinan, schizophyllan, krestin, etc.), cytokines obtained by genetic engineering techniques (e.g., interferon, interleukin (IL), etc.), colony stimulating factors (e.g., granulocyte colony stimulating factor, erythropoietin, etc.) and the like, with preference given to interleukins such as IL-1, IL-2, IL-12 and the like.

Examples of the antiinflammatory agents include non-steroidal antiinflammatory agents such as aspirin, acetaminophen, indomethacin and the like.

Examples of the antithrombotic agents include heparin (e.g., heparin sodium, heparin calcium, dalteparin sodium, etc.), warfarin (e.g., warfarin potassium, etc.), anti-thrombin drugs (e.g., aragatroban, etc.), thrombolytic agents (e.g., urokinase, tisokinase, alteplase, nateplase, monteplase, pamiteplase, etc.), platelet aggregation suppressors (e.g., ticlopidine hydrochloride, cilostazol, ethyl icosapentate, beraprost sodium, sarpogrelate hydrochloride, etc.) and the like.

Examples of the treating agents for osteoporosis include alfacalcidol, calcitriol, elcatonin, calcitonin salmon, estriol, ipriflavone, pamidronate disodium, alendronate sodium hydrate, incadronate disodium and the like.

Examples of the vitamins include vitamin B1, vitamin B12 and the like.

Examples of the antidementia agents include tacrine, donepezil, rivastigmine, galantamine and the like.

Examples of the treating agents for pollakiuria or urinary incontinence include flavoxate hydrochloride, oxybutynin hydrochloride, propiverine hydrochloride and the like.

Examples of the treating agents for dysuria include acetylcholine esterase inhibitors (e.g., distigmine) and the like.

Furthermore, drugs having a cachexia-improving effect established in animal models and clinical situations, such as cyclooxygenase inhibitors (e.g., indomethacin, etc.) [Cancer Research, Vol. 49, pp. 5935-5939, 1989], progesterone derivatives (e.g., megestrol acetate) [Journal of Clinical Oncology, Vol. 12, pp. 213-225, 1994], glucosteroids (e.g., dexamethasone, etc.), metoclopramide agents, tetrahydrocannabinol agents (publications are all as mentioned above), fat metabolism improving agents (e.g., eicosapentanoic acid, etc.) [British Journal of Cancer, Vol. 68, pp. 314-318, 1993], growth hormones, IGF-1, or antibodies to a cachexia-inducing factor such as TNF-α, LIF, IL-6, oncostatin M and the like, can be used in combination with the compound of the invention.

Furthermore, glycosylation inhibitors (e.g., ALT-711, etc.), nerve regeneration promoting drugs (e.g., Y-128, VX853, prosaptide, etc.), antidepressants (e.g., desipramine, amitriptyline, imipramine, etc.), antiepileptics (e.g., lamotrigine, Trileptal, Keppra, Zonegran, Pregabalin, Harkoseride, carbamazepine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin, gabapentin MR preparations), α2 receptor agonists (e.g., clonidine), local analgesics (e.g., capsaicin), antianxiety drugs (e.g., benzodiazepines), phosphodiesterase inhibitors (e.g., sildenafil), dopamine receptor agonists (e.g., apomorphine) and the like can be also used in combination with the compound of the invention.

By combining the compound of the invention with a concomitant drug, superior effects can be achieved such as (1) possible decreasing dose of the compound of the invention or a concomitant drug as compared to single administration of the compound of the invention or a concomitant drug, (2) possible free choice of the drug to be combined with the compound of the invention according to the conditions of patients (mild condition, severe condition and the like), (3) possible setting of a long treatment period by selecting a concomitant drug having different mechanisms of action from those of the compound of the invention, (4) possible designing of a sustained treatment effect by selecting a concomitant drug having different mechanisms of action from those of the compound of the invention, (5) a synergistic effect afforded by a combined use of the compound of the invention and a concomitant drug, and the like.

In the following, use of the compound of the invention and a concomitant drug in combination is to be referred to as the "concomitant agent of the invention".

For the use of the concomitant agent of the invention, the administration time of the compound of the invention and the concomitant drug is not restricted, and the compound of the invention and the concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

The administration mode of the concomitant agent of the invention is not particularly limited, as long as the compound of the invention and the concomitant drug are combined in administration. Examples of such administration mode include the following methods: (1) The compound of the invention and the concomitant drug are simultaneously formulated to give a single preparation which is administered. (2) The compound of the invention and the concomitant drug are separately formulated to give two kinds of preparations which are administered simultaneously by the same administration route. (3) The compound of the invention and the concomitant drug are separately formulated to give two kinds of preparations which are administered by the same administration route at staggered times. (4) The compound of the invention and the concomitant drug are separately formulated to give two kinds of preparations which are administered simultaneously by the different administration routes. (5) The compound of the invention and the concomitant drug are separately formulated to give two kinds of preparations which are administered by the different administration routes at staggered times (for example, the compound of the invention and the concomitant drug are administered in this order, or in the reverse order), and the like.

A concomitant agent of the invention has low toxicity, and for example, the compound of the invention and/or the above-mentioned concomitant drug can be mixed, according to a method known per se, with a pharmacologically acceptable carrier to give pharmaceutical compositions, for example, tablets (including a sugar-coated tablet, film-coated tablet), powders, granules, capsules (including soft capsules), liquids, injections, suppositories, sustained-release preparations and the like, which can be safely administered orally or parenterally (e.g., topical, rectal, intravenous administration, and the like). An injection can be administered by intravenous, intramuscular, subcutaneous or intraorgan route, or directly to the lesion.

As a pharmacologically acceptable carrier which may be used for preparing the concomitant agent of the invention, those similar to the aforementioned pharmacologically acceptable carriers that can be used for the production of the pharmaceutical agent of the invention can be mentioned. Further, if needed, the aforementioned additives that can be used for the production of the pharmaceutical agent of the invention, such as preservative, antioxidant, coloring agent, sweetening agent, adsorbing agent, wetting agent and the like, can be appropriately used in an appropriate amount.

The compounding ratio of the compound of the invention to the concomitant drug in the concomitant agent of the invention can be appropriately selected depending on an administration subject, administration route, diseases and the like.

For example, the content of the compound of the invention in the concomitant agent of the invention differs depending on the form of a preparation, and usually from about 0.01 to 100% by weight, preferably from about 0.1 to 50% by weight, and further preferably from about 0.5 to 20% by weight, based on the total amount of the preparation.

The content of the concomitant drug in the concomitant agent of the invention differs depending on the form of a preparation, and usually from about 0.01 to 100% by weight, preferably from about 0.1 to 50% by weight, and further preferably from about 0.5 to 20% by weight, based on the total amount of the preparation.

The content of additives such as a carrier in the concomitant agent of the invention differs depending on the form of a preparation, and usually from about 1 to 99.99% by weight, preferably from about 10 to 90% by weight, based on the total amount of the preparation.

In the case when the compound of the invention and the concomitant drug are separately prepared respectively, the same contents may be adopted.

These preparations can be produced by a method known per se usually used in a preparation process.

For example, the compound of the invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH regulator (e.g., hydrochloric acid, sodium hydroxide and the like), a preservative (e.g., ethyl p-hydroxybenzoate, benzoic acid, methylparaben, propylparaben, benzyl alcohol and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or in a dissolution aid such as propylene glycol and formed into an oily injection, to prepare an injection.

In addition, it can be made into a preparation for oral administration by adding, for example, an excipient (e.g., lactose, sucrose, starch and the like), a disintegrant (e.g., starch, calcium carbonate and the like), a binder (e.g., starch, gum Arabic, carboxymethylcellulose, polyvinylpyrrolidone, hydroxypropylcellulose and the like), a lubricant (e.g., talc, magnesium stearate, polyethylene glycol 6000 and the like) and the like, to the compound of the invention or the concomitant drug according to a method known per se, and compression-molding the mixture, and then if desirable, coating the molded product by a method known per se for the purpose of masking of taste, enteric property or sustention. As this coating agent, there can be used, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (methacrylic acid/acrylic acid copolymer, manufactured by Rohm, DE), pigment (e.g., Bengala, titanium dioxide, etc.) and the like. The preparation for oral administration may be any of a quick-release preparation and a sustained-release preparation.

Furthermore, the compound of the invention and the concomitant drug can be made into an oily or aqueous solid, a semisolid or liquid suppository by admixing with an oily base, aqueous base or aqueous gel base according to a method known per se. As the oily base used in the above-mentioned, for example, glycerides of higher fatty acids [e.g., cacao butter, Witepsols (manufactured by Dynamite Nobel, DE), etc.], intermediate grade fatty acids [e.g., Miglyols (manufactured by Dynamite Nobel, DE), etc.], or vegetable oils (e.g., sesame oil, soy bean oil, cotton seed oil and the like), and the like are mentioned. Further, as the aqueous base, for example, polyethylene glycols, propylene glycol and the like are mentioned, and as the aqueous gel base, for example, natural gums, cellulose derivatives, vinyl polymers, acrylic acid polymers and the like are mentioned.

As the above-mentioned sustained-release preparation, sustained-release microcapsules and the like are mentioned. The sustained-release microcapsule can be produced by a method known per se, such as the method shown in the following [2].

The compound of the invention is preferably molded into a preparation for oral administration such as a solid preparation (e.g., powder, granule, tablet, and capsule) and the like, or molded into a preparation for rectal administration such as a suppository. Particularly, a preparation for oral administration is preferable.

The concomitant drug can be made into the above-mentioned preparation form depending on the kind of the drug.

Hereinafter, [1] an injection of the compound of the invention or the concomitant drug, and preparation thereof, [2] a sustained-release preparation or quick-release preparation of the compound of the invention or the concomitant drug, and preparation thereof, [3] a sublingual, buccal or intraoral quick-integrating agent of the compound of the invention or the concomitant drug, and preparation thereof, will be described below specifically.

[1] Injection and Preparation Thereof.

An injection prepared by dissolving the compound of the invention or the concomitant drug into water is preferable. This injection may be allowed to contain a benzoate and/or salicylate.

The injection is obtained by dissolving the compound of the invention or the concomitant drug, and if desirable, a benzoate and/or salicylate, into water.

As the above-mentioned benzoate and salicylate, for example, alkali metal salts such as sodium, potassium and the like, alkaline earth metal salts such as calcium, magnesium and the like, ammonium salts, meglumine salts, organic acid salts such as tromethamol, etc., and the like are mentioned.

The concentration of the compound of the invention or the concomitant drug in the injection is from 0.5 to 50% (w/v), preferably from 3 to 20% (w/v). The concentration of the benzoate or/and salicylate is from 0.5 to 50% (w/v), preferably from 3 to 20% (w/v).

Into the injection of the invention, additives generally used in an injection can be appropriately compounded, for example, a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, and the like), a dispersing agent (e.g., hydroxypropylmethylcellulose, dextrin, and the like), a pH regulator (e.g., hydrochloric acid, sodium hydroxide and the like), a preservative (e.g., ethyl p-hydroxybenzoate, benzoic acid and the like), a dissolving agent (e.g., conc. glycerin, meglumine and the like), a dissolution aid (e.g., propylene glycol, sucrose and the like), a soothing agent (e.g., glucose, benzyl alcohol and the like), and the like. These additives are generally compounded in a proportion usually used in an injection.

It is advantageous that pH of an injection is adjusted to from 2 to 12, preferably from 2.5 to 8.0 by addition of a pH regulator.

An injection is obtained by dissolving the compound of the invention or the concomitant drug and if desirable, a benzoate and/or a salicylate, and if necessary, the above-mentioned additives into water. These dissolutions may be in any order, and can be performed appropriately in the same manner as in a conventional method of producing an injection.

An aqueous solution for injection may be warmed, and alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 minutes.

Further, a preparation endowed with an antibacterial property of a solution may also be produced so that it can be used as a preparation which is divided and administered multiple times.

[2] Sustained Release Preparation or Quick-Release Preparation, and Preparation Thereof A sustained-release preparation is preferable which is obtained, if desirable, by coating a nucleus containing the compound of the invention or the concomitant drug with a film agent such as a water-insoluble substance, a swellable polymer and the like. For example, a sustained-release preparation for oral administration for a single administration per day type is preferable.

As the water-insoluble substance used in a film agent, there are mentioned, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethylmethacrylate/aminoalkyl methacrylate copolymers, polyacrylic acid, polymethacrylic acid, methacrylic acid alkylamide copolymers, poly(methyl ethacrylate), polymethacrylate, polymethacrylamide, aminoalkyl methacrylate copolymers, poly(methacrylic anhydride), glycidyl methacrylate copolymers, particularly, acrylic acid-based polymers such as Eudragits (Rohm Pharma) such as Eudragit RS-100, RL-100, RS-30D, RL-30D, RL-PO, RS-PO (ethyl acrylate/methyl methacrylate/trimethyl chloride methacrylate/ammoniumethyl copolymer), Eudragit NE-30D (methyl methacrylate/ethyl acrylate copolymer), and the like, hardened oils such as hardened castor oil (e.g., Lovery wax (Freund Corporation) and the like), waxes such as carnauba wax, fatty acid glycerin ester, paraffin and the like, polyglycerin fatty acid esters, and the like.

As the swellable polymer, polymers having an acidic dissociating group and showing pH-dependent swelling are preferable, and polymers manifesting slight swelling in acidic regions such as in the stomach and greater swelling in neutral regions such as in the small intestine and the large intestine are preferable.

As such a polymer having an acidic dissociating group and showing pH-dependent swelling, cross-linkable polyacrylic acid polymers such as, for example, Carbomer 934P, 940, 941, 974P, 980, 1342 and the like, polycarbophil and calcium polycarbophil (all are manufactured by BF Goodrich), Hibiswako 103, 104, 105 and 304 (all are manufactured by Wako Pure Chemical Co., Ltd.), and the like, are mentioned.

The film agent used in a sustained-release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl group or carboxyalkyl group such as hydroxypropylcellulose, hydroxypropylmethylcellulose, carboxymethylcellulose sodium and the like, methylcellulose, polyvinylpyrrolidone, polyvinyl alcohol, polyethylene glycol and the like.

The content of a water-insoluble substance in the film agent of a sustained-release preparation is from about 30 to about 90% (w/w), preferably from about 35 to about 80% (w/w), and further preferably from about 40 to 75% (w/w), the content of a swellable polymer is from about 3 to 30% (w/w), preferably from about 3 to about 15% (w/w). The film agent may further contain a hydrophilic substance, and in which case, the content of a hydrophilic substance in the film agent is about 50% (w/w) or less, preferably about 5 to about 40% (w/w), and further preferably from about 5 to about 35% (w/w). This % (w/w) indicates % by weight based on a film agent composition which is obtained by removing a solvent (e.g., water, lower alcohols such as methanol, ethanol and the like) from a film agent solution.

The sustained-release preparation is produced as exemplified below by preparing a nucleus containing a drug, then, coating the resulting nucleus with a film agent solution prepared by heat-dissolving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as the nucleus) is not particularly limited, and preferably, the nucleus is formed into particles such as a granule or fine particle.

When the nucleus is composed of granules or fine particles, the average particle size thereof is preferably from about 150 to 2000 μm, and further preferably, from about 500 to about 1400 μm.

Preparation of the nucleus can be effected by a usual production method. For example, a suitable excipient, binder, disintegrant, lubricant, stabilizer and the like are mixed into a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), and further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose and corn starch are preferable.

As the binder, for example, polyvinyl alcohol, hydroxypropyl cellulose, polyethylene glycol, polyvinyl pyrrolidone, Pluronic F68, gum Arabic, gelatin, starch and the like are used. As the disintegrant, for example, carboxymethylcellulose calcium (ECG505), croscarmellose sodium (Ac-Di-Sol), crosslinked polyvinylpyrrolidone (Crospovidone), low-substituted hydroxypropylcellulose (L-HPC) and the like are used. Among them, hydroxypropylcellulose, polyvinylpyrrolidone, low-substituted hydroxypropylcellulose are preferable. As the lubricant and anticoagulant, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

In addition to the above-mentioned production method, a nucleus can also be prepared by, for example, a rolling granulation method in which a drug or a mixture thereof with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose and waxes can be used, and the average particle size thereof is preferably from about 100 μm to about 1500 μm.

For separating a drug and a film agent contained in a nucleus, the surface of the nucleus may be coated with a protective agent. As the protective agent, for example, the above-mentioned hydrophilic substances, water-insoluble substances and the like are used. The protective agent is preferably polyethylene glycol, and polysaccharides having a hydroxyalkyl group or carboxyalkyl group, and more preferably hydroxypropylmethylcellulose and hydroxypropylcellulose. The protective agent may contain a stabilizer such as acids such as tartaric acid, citric acid, succinic acid, fumaric acid, maleic acid and the like, and a lubricant such as talc and the like. When the protective agent is used, the coating amount is from about 1 to about 15% (w/w), preferably from about 1 to about 10% (w/w), and further preferably from about 2 to about 8% (w/w), based on the nucleus.

The protective agent can be coated by a usual coating method, and specifically, the protective agent can be coated with spray-coating onto a nucleus, for example, by a fluidized bed coating method, pan coating method and the like.

II. Coating of Nucleus with Film Agent

The nucleus obtained in the above-mentioned step I is coated with a film agent solution obtained by heat-dissolving the above-mentioned water-insoluble substance and pH-dependent swellable polymer, and a hydrophilic substance, or by dissolving or dispersing them in a solvent, to give a sustained-release preparation.

As the method for coating a nucleus with the film agent solution, for example, a spray coating method and the like are mentioned.

The composition ratio of the water-insoluble substance, swellable polymer and hydrophilic substance in a film agent solution is appropriately selected so that the contents of these components in a coated film are the same as the above-mentioned contents, respectively.

The coating amount of a film agent is from about 1 to about 90% (w/w), preferably from about 5 to about 50% (w/w), and further preferably from about 5 to about 35% (w/w), based on a nucleus (not including the coating amount of the protective agent).

As the solvent in a film agent solution, water or an organic solvent can be used alone or in admixture thereof. In the case of use in admixture, the mixing ratio of water to an organic solvent (water/organic solvent: by weight ratio) can be varied in the range from 1 to 100%, and preferably from 1 to about 30%. The organic solvent is not particularly limited providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be implemented by spray-coating a film agent solution onto a nucleus, for example, by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hardened castor oil, triethyl citrate, cetyl alcohol, stearyl alcohol and the like may also be added as a plasticizer.

After coating with a film agent, if necessary, an antistatic agent such as talc and the like may be mixed.

The quick-release preparation may be liquid (e.g., solution, suspension, emulsion and the like) or solid (e.g., particle, pill, tablet and the like). As the quick-release preparation, oral preparations and parenteral preparations such as an injection and the like are used, and oral preparations are preferable.

The quick-release preparation may also contain usually carriers, additives and excipients conventionally used in the formulation field (hereinafter, sometimes abbreviated as the excipient), in addition to a drug as an active component. The excipient used is not particularly limited providing it is an excipient ordinarily used as a preparation excipient. For example, as the excipient for an oral solid preparation, lactose, starch, corn starch, crystalline cellulose (Avicel PH101 manufactured by Asahi Kasei Co., Ltd., and the like), powder sugar, granulated sugar, mannitol, light anhydrous silicic acid, magnesium carbonate, calcium carbonate, L-cysteine and the like are mentioned, and preferably, corn starch and mannitol and the like are mentioned. These excipients can be used alone or in combination of two or more. The content of the excipient is, for example, from about 4.5 to about 99.4% (w/w), preferably from about 20 to about 98.5% (w/w), and further preferably from about 30 to about 97% (w/w), based on the total amount of the quick-release preparation.

The content of a drug in the quick-release preparation can be appropriately selected in the range from about 0.5 to about 95% (w/w), preferably from about 1 to about 60% (w/w) based on the total amount of the quick-release preparation.

When the quick-release preparation is an oral solid preparation, it usually contains a disintegrant in addition to the above-mentioned components. As this disintegrant, there are used, for example, carboxymethylcellulose calcium (ECG-505, manufactured by Gotoku Yakuhin), croscarmellose sodium (e.g., Ac-Di-Sol, manufactured by Asahi Kasei Co., Ltd.), Crospovidone (e.g., Kollidon CL, manufactured by BASF), low-substituted hydroxypropylcellulose (manufactured by Shin-Etsu Chemical Co., Ltd.), carboxymethyl starch (manufactured by Matsutani Kagaku K.K.), carboxymethyl starch sodium (Exprotab, manufactured by Kimura Sangyo), partially α-nized starch (PCS, manufactured by Asahi Chemical Industry Co., Ltd.), and the like. For example, those which disintegrate a granule by contact with water causing water-adsorption and swelling, or by making a channel between an active ingredient and an excipient constituting the nucleus, can be used. These disintegrants can be used alone or in combination of two or more. The blending amount of the disintegrant is appropriately selected depending on the kind and blending amount of a drug used, formulation design for releasing property, and the like, and for example, from about 0.05 to about 30% (w/w), preferably from about 0.5 to about 15% (w/w), based on the total amount of the quick-release preparation.

When the quick-release preparation is an oral solid preparation, it may further contain, if desired, additives conventional in solid preparations in addition to the above-mentioned composition. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (e.g., aerosil (Nippon Aerosil)), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like) and a coloring agent (e.g., tar pigment, caramel, iron oxide red, titanium oxide, riboflavins, and the like), and if necessary, an appetizing agent (e.g., sweetening agent, flavor and the like), an adsorbing agent, preservative, wetting agent, antistatic agent and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The quick-release preparation can be prepared based on a usual technology of producing preparations, by mixing the above-mentioned components, and if necessary, further kneading the mixture, and molding it. The above-mentioned mixing is conducted by generally used methods, for example, mixing, kneading and the like. Specifically, when a quick-release preparation is formed, for example, into a particle, it can be prepared, according to the same methods as in the above-mentioned method for preparing a nucleus of a sustained-release preparation, by mixing the components using a vertical granulator, an universal kneader (manufactured by Hata Tekkosho), a fluidized bed granulator FD-5S (manufactured by Powrex), and the like, then, subjecting the mixture to a wet extrusion granulation method, a fluidized bed granulation method and the like.

Thus-obtained quick-release preparation and sustained release preparation may be formulated separately by an ordinary method as they are, or appropriately with preparation excipients and the like, and then administered simultaneously or in combination at any administration interval, or they may be formulated into one oral preparation (e.g., granule, fine particle, tablet, capsule and the like) as they are, or appropriately with preparation excipients and the like. It may also be permissible that they are made into granules or fine particles, and filled in the same capsule to be used as a preparation for oral administration.

[3] Sublingual, Buccal or Intraoral Quick-Disintegrating Agent and Preparation Thereof.

Sublingual, buccal or intraoral quick-disintegrating agents may be a solid preparation such as tablet and the like, or may be an oral mucosa membrane patch (film).

The sublingual, buccal or intraoral quick-disintegrating agent is preferably a preparation containing the compound of the invention or the concomitant drug and an excipient. It may contain also auxiliary agents such as a lubricant, isotonizing agent, hydrophilic carrier, water-dispersible polymer, stabilizer and the like. Further, for easy absorption and increased bioavailability, it may also contain $\beta$-cyclodextrin or $\beta$-cyclodextrin derivatives (e.g., hydroxypropyl-$\beta$-cyclodextrin and the like) and the like.

As the above-mentioned excipient, lactose, sucrose, D-mannitol, starch, crystalline cellulose, light anhydrous silicic acid and the like are mentioned. As the lubricant, magnesium stearate, calcium stearate, talc, colloidal silica and the like are mentioned, and particularly, magnesium stearate and colloidal silica are preferable. As the isotonizing agent, sodium chloride, glucose, fructose, mannitol, sorbitol, lactose, saccharose, glycerin, urea and the like are mentioned, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are mentioned, and particularly, crystalline cellulose (e.g., fine crystalline cellulose and the like) is preferable. As the water-dispersible polymer, gums (e.g., gum tragacanth, gum acacia, guar gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacrylic acid, polyvinyl alcohol, polyethylene glycol, polyvinylpyrrolidone, polycarbophil, ascorbate palmitates and the like are mentioned, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are mentioned, and particularly, citric acid and ascorbic acid are preferable.

The sublingual, buccal or intraoral quick-disintegrating agent can be produced by mixing the compound of the invention or the concomitant drug and an excipient by a method known per se. Further, if desirable, the above-mentioned auxiliary agents such as a lubricant, isotonizing agent, hydrophilic carrier, water-dispersible polymer, stabilizer, coloring agent, sweetening agent, preservative and the like may be mixed. The sublingual, buccal or intraoral quick-disintegrating agent are obtained by mixing the above-mentioned components simultaneously or at a time interval, then subjecting the mixture to tabletting molding under pressure. For obtaining suitable hardness, it may also be permissible that the materials are moistened by using a solvent such as water, alcohol and the like if desired before and after the tabletting process, and after the molding, the materials are dried, to obtain a product.

In the case of molding into a mucosa membrane patch (film), the compound of the invention or the concomitant drug and the above-mentioned water-dispersible polymer (preferably, hydroxypropylcellulose, hydroxypropylmethylcellulose), excipient and the like are dissolved in a solvent such as water and the like, and the resulting solution is cast, to give a film. Further, additives such as a plasticizer, stabilizer, antioxidant, preservative, coloring agent, buffer, sweetening agent and the like may also be added. For imparting suitable elasticity to the film, glycols such as polyethylene glycol, propylene glycol and the like may be contained, or for enhancing adhesion of the film to the mucosa membrane lining in the oral cavity, a bio-adhesive polymer (e.g., polycarbophil, carbopol) may also be contained. In the casting, a solution is poured on the non-adhesive surface, spread to uniform thickness (preferably 10 to 1000 micron) by an application tool such as a doctor blade and the like, then, the solution is dried to form a film. It may be advantageous that thus-formed film is dried at room temperature or under heat, and cut into desired area.

As the preferable intraoral quick-disintegrating agent, there are mentioned solid quick scattering administration agents composed of a network body comprising the compound of the invention or the concomitant drug, and a water-soluble or water-diffusible carrier which is inert to the compound of the invention or the concomitant drug. This network body is obtained by sublimating a solvent from the solid composition constituted of a solution wherein the compound of the invention or the concomitant drug is dissolved in a suitable solvent.

It is preferable that the composition of an intraoral quick-disintegrating agent contains a matrix-forming agent and a secondary component, in addition to the compound of the invention or the concomitant drug.

Examples of the matrix-forming agent include animal proteins or vegetable proteins such as gelatins, dextrins and soybean, wheat and psyllium seed protein and the like; rubber substances such as gum Arabic, cyamoposis gum, agar, xanthane gum and the like; polysaccharides; alginic acids; carboxymethylcelluloses; carrageenans; dextrans; pectins; synthetic polymers such as polyvinylpyrrolidone and the like; substances derived from a gelatin-gum Arabic complex, and the like. Further, they include saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like; and the like.

One or more kinds of the matrix-forming agents can be introduced in a solution or suspension before solidification. Such matrix-forming agent may be present in addition to a surfactant, or may be present while a surfactant being excluded. The matrix-forming agent can help to maintain the diffusion condition of the compound of the invention or the concomitant drug in the solution or suspension, in addition to formation of the matrix.

The composition may contain secondary components such as preservative, antioxidant, surfactant, thickening agent, coloring agent, pH regulator, flavoring agent, sweetening agent, food taste-masking agent and the like. As the suitable coloring agent, red, black and yellow iron oxides, and FD & C dyes such as FD & C Blue 2, FD & C Red 40 and the like manufactured by Ellis and Eberald can be mentioned. Examples of suitable flavoring agents include mint, raspberry, licorice, orange, lemon, grape fruit, caramel, vanilla, cherry, grape flavor and combinations thereof. Examples of suitable pH regulators include citric acid, tartaric acid, phosphoric acid, hydrochloric acid and maleic acid. Examples of suitable sweetening agents include aspartame, acesulfame K and thaumatin and the like. Examples of suitable food taste-masking agents include sodium bicarbonate, ion exchange resin, cyclodextrin-inclusion compounds, adsorbent substances and microcapsulated apomorphine.

The preparation contains the compound of the invention or the concomitant drug generally in an amount of from about 0.1 to about 50% by weight, preferably from about 0.1 to about 30% by weight. Preferred are preparations (such as the above-mentioned sublingual agent, buccal and the like) which can allow 90% or more of the compound of the invention or the concomitant drug to dissolve (in water) within the time range of about 1 to about 60 minutes, preferably about 1 to about 15 minutes, and more preferably about 2 to about 5 minutes, and intraoral quick-disintegrating preparations which are disintegrated within the range of 1 to 60 seconds, preferably 1 to 30 seconds, and further preferably 1 to 10 seconds, after placement in an oral cavity.

The content of the above-mentioned excipient is from about 10 to about 99% by weight, preferably from about 30 to about 90% by weight to the whole preparation. The content of β-cyclodextrin or β-cyclodextrin derivative is from 0 to about 30% by weight to the whole preparation. The content of the lubricant is from about 0.01 to about 10% by weight, preferably from about 1 to about 5% by weight to the whole preparation. The content of the isotonizing agent is from about 0.1 to about 90% by weight, preferably from about 10 to about 70% by weight to the whole preparation. The content of the hydrophilic carrier agent is from about 0.1 to about 50% by weight, preferably from about 10 to about 30% by weight to the whole preparation. The content of the water-dispersible polymer is from about 0.1 to about 30% by weight, preferably from about 10 to about 25% by weight to the whole preparation. The content of the stabilizer is from about 0.1 to about 10% by weight, preferably from about 1 to about 5% by weight to the whole preparation. The above-mentioned preparation may further contain additives such as a coloring agent, sweetening agent, preservative and the like, if necessary.

The dosage of the concomitant agent of the invention varies depending on the kind of the compound of the invention, age, body weight, condition, preparation form, administration method, administration period and the like, and for example, for a diabetic patient (adult, body weight: about 60 kg), it is administered intravenously, at a dose of about 0.01 to about 1000 mg/kg/day, preferably about 0.01 to about 100 mg/kg/day, more preferably about 0.1 to about 100 mg/kg/day, particularly preferably about 0.1 to about 50 mg/kg/day, most preferably about 1.5 to about 30 mg/kg/day, in terms of the compound of the invention or the concomitant drug, respectively, once or divided several times in a day. Of course, since the dosage as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of symptom; age, sex, body weight or sensitivity difference of the subject; administration time or interval; nature, pharmacology or kind of the pharmaceutical preparation; kind of effective ingredient, and the like, and not particularly limited. For example, for oral administration, the amount of a drug is usually from about 0.001 to 2000 mg, preferably from about 0.01 to 500 mg, and further preferably from about 0.1 to 100 mg, per 1 kg body weight of a mammal and this is usually administered once to 4-times divided in a day.

For administration of the concomitant agent of the invention, the compound of the invention may be administered after administration of the concomitant drug or the concomitant drug may be administered after administration of the compound of the invention, though they may be administered simultaneously. When administered at a time interval, the interval varies depending on active ingredients, preparation form and administration method, and for example, when the concomitant drug is administered first, a method is exemplified in which the compound of the invention is administered within time range of from 1 minute to 3 days, preferably from 10 minutes to 1 day, more preferably from 15 minutes to 1 hour, after administration of the concomitant drug. When the compound of the invention is administered first, a method is exemplified in which the concomitant drug is administered within time range of from 1 minute to 1 day, preferably from 10 minutes to 6 hours, more preferably from 15 minutes to 1 hour after administration of the compound of the invention.

In a preferable administration method, for example, the concomitant drug which has been formed into an oral administration preparation is administered orally at a daily dose of about 0.001 to 200 mg/kg, and about 15 minutes after, the compound of the invention which has been formed into an oral administration preparation is administered orally at a daily dose of about 0.005 to 100 mg/kg.

The G protein-coupled receptor protein used in the invention (hereinafter, simply referred to as the 14273 receptor) is a receptor protein comprising the same or substantially identical amino acid sequence as the amino acid sequence represented by SEQ ID NO: 1, SEQ ID NO: 3 or SEQ ID NO: 8.

The 14273 receptor may be any protein derived from any cells (e.g., splenocytes, nerve cells, glial cells, β cells of pancreas, Langerhans' island of pancreas, bone marrow cells, mesangium cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophil, basophil, eosinophil, monocyte), megakaryocyte, synovial cells, chondrocytes, bone cells, osteoblasts, osteoclasts, mammary gland cells, hepatocytes or interstitial cells, the corresponding precursor cells, stem cells or cancer cells of these cells, etc.), or cells in the blood cell systems, or any tissues where such cells are present, e.g., brain or any region of the brain (e.g., olfactory bulb, amygdaloid nucleus, basal ganglia, hippocampus, thalamus, hypothalamus, cerebral cortex, medulla oblongata, cerebellum, occipital lobes, frontal lobe, lateral lobe, putamen, caudate nucleus, corpus callosum, substantia nigra), spinal cord, pituitary, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, peripheral blood cells, prostate, testis, orchis, ovary, placenta, uterus, bone, joint, skeletal muscle, etc. from human and mammals (e.g., guinea pigs, rats, mouse, rabbits, pig, sheep, bovine, monkeys, etc.), or may also be a synthetic protein. Especially, the 14273 receptor is highly expressed in pituitary and adipose tissue.

The amino acid sequence which is substantially identical to the amino acid sequence represented by SEQ ID NO: 1, SEQ ID NO: 3 or SEQ ID NO: 8 is, for example, an amino acid sequence having at least about 85% homology, preferably at least about 90% homology, more preferably at least about 95% homology to the amino acid sequence represented by SEQ ID NO: 1, SEQ ID NO: 3 or SEQ ID NO: 8, and the like.

The protein having substantially identical amino acid sequence as the amino acid sequence of the invention represented by SEQ ID NO: 1, SEQ ID NO: 3 or SEQ ID NO: 8 is preferably, for example, a protein comprising substantially identical amino acid sequence as the amino acid sequence represented by SEQ ID NO: 1, SEQ ID NO: 3 or SEQ ID NO: 8, and has an activity substantially equivalent to that of a protein comprising the amino acid sequence represented by SEQ ID NO: 1, SEQ ID NO: 3 or SEQ ID NO: 8 and the like.

The homology among the amino acid sequences can be calculated using homology search algorithm NCBI BLAST (National Center for Biotechnology Information Basic Local Alignment Search Tool) under the following conditions: expected value=10; gap is allowable; matrix=BLOSUM62; filtering=OFF.

The substantially equivalent activity includes, for example, ligand-binding activity, signal information transduction activity and the like. The term "substantially equivalent" is used to mean that these activities are the same in quality. Therefore, although it is preferred that ligand-binding activity or signal information transduction activity be equivalent (e.g., about 0.01- to 100-fold, preferably about 0.5- to 20-fold, more preferably about 0.5- to 2-fold), quantitative factors such as a level of the activity, a molecular weight of the protein, etc. may differ.

Measurement of the activity such as ligand-binding activity and signal information transduction activity can be carried out in accordance with per se known methods, for example, it can be measured according to the screening method described later.

In addition, examples of the 14273 receptor may be include proteins comprising a) the amino acid sequence represented by SEQ ID NO: 1, SEQ ID NO: 3 or SEQ ID NO: 8 wherein one or at least two amino acids (preferably, about 1 to 30, more preferably about 1 to 10, and further preferably several amino acids (1 to 5)) are deleted, b) the amino acid sequence represented by SEQ ID NO: 1, SEQ ID NO: 3 or SEQ ID NO: 8 wherein one or at least two amino acids (preferably, about 1 to 30, more preferably about 1 to 10, and further preferably several amino acids (1 to 5)) are added, c) the amino acid sequence represented by SEQ ID NO: 1, SEQ ID NO: 3 or SEQ ID NO: 8 wherein one or at least two amino acids (preferably, about 1 to 30, more preferably about 1 to 10, and further preferably several amino acids (1 to 5)) are substituted with other amino acids, or d) an amino acid sequence which contains a combination of these sequences.

The 14273 receptor in the present specification is represented in accordance with the conventional way of describing peptides, that is, the N-terminus (amino terminus) at a left end and the C-terminus (carboxyl terminus) at a right end. In the 14273 receptor which includes the 14273 receptor comprising the amino acid sequence represented by SEQ ID NO: 1, the C-terminus may be any one of a carboxyl group (—COOH), carboxylate (—COO⁻), an amide (—CONH$_2$) or an ester (—COOR).

As R in ester, for example, a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$ alkyl group, e.g., benzyl, phenethyl, etc., or an α-naphthyl-$C_{1-2}$ alkyl group such as α-naphthylmethyl, etc.; as well as a pivaloyloxymethyl group generally used for an oral ester can be used.

When the 14273 receptor has a carboxyl group (or carboxylate) at a position other than the C-terminus, the carboxyl group may be amidated or esterified, and such amidated or esterified form is also included within the 14273 receptor. For the ester group in this case, the same ester group as that described with respect to the above-described C-terminus, and the like can be used.

Further, the 14273 receptor also includes those in which an amino group of an N-terminal methionine residue is protected with a protecting group (e.g., $C_{1-6}$ acyl group such as a formyl group and $C_{1-6}$ alkanoyl group such as an acetyl, etc., and the like), those in which an N-terminal glutamyl group produced by cutting in the living body is converted to pyroglutamate, those in which substituents (e.g., —OH, —SH, an amino group, an imidazole group, an indole group, a guanidino group) on a side chain of an intramolecular amino acid is protected with a suitable protecting group (e.g., $C_{1-6}$ acyl group such as a formyl group and $C_{2-6}$ alkanoyl group such as an acetyl, etc., and the like), and conjugated protein bound with a sugar chain such as so called glycoprotein, etc.

Specific examples of the 14273 receptor include, for example, a 14273 receptor derived from human having the amino acid sequence represented by SEQ ID NO: 1, a 14273 receptor derived from mouse having the amino acid sequence represented by SEQ ID NO: 3 (WO2002/67868, published sequence database: ACCESSION XP_061208, XP_129252), a 14273 receptor derived from rat having the amino acid sequence represented by SEQ ID NO: 8, and the like. The 14273 receptor derived from rat having the amino acid sequence represented by SEQ ID NO: 8 is a novel protein.

As a partial peptide of the 14273 receptor (hereinafter, simply referred to as the partial peptide), any partial peptides of the above-described 14273 receptor can be used. For example, among the protein molecules of the 14273 receptor, the region exposed to outside of the cell membrane having substantially identical receptor-binding activity as those of the 14273 receptor and the like can be used.

Specifically, the partial peptides of the 14273 receptor comprising the amino acid sequence represented by SEQ ID NO: 1, SEQ ID NO: 3 or SEQ ID NO: 8 are peptides containing the regions that were shown to be the extracellular domains (hydrophilic regions) by the hydrophobicity plot analysis. Peptides partially containing hydrophobic region can also be used. Peptides each containing individual domains can be used, but a partial peptide containing a plurality of domains may also be used.

The number of amino acids in the partial peptides of the invention is preferably at least 20 or more, preferably 50 or more, and more preferably 100 or more of the constituent amino acid sequence of the above-described receptor protein of the invention and the like.

The substantially identical amino acid sequence means an amino acid sequence having at least about 85% homology, preferably at least about 90% homology, more preferably at least about 95% homology to these amino acid sequences.

The homology among the amino acid sequences can be calculated using homology search algorithm NCBI BLAST (National Center for Biotechnology Information Basic Local Alignment Search Tool) under the following conditions: expected value=10; gap is allowable; matrix=BLOSUM62; filtering=OFF.

The "substantially equivalent receptor activity" has the same meaning as described above. Measurement of the "substantially equivalent receptor activity" can be carried out similarly to those described above.

In addition, in the partial peptide of the invention, one or at least two amino acids (preferably, about 1 to 10, and further preferably several amino acids (1 to 5)) may be deleted in the above-mentioned amino acid sequence, or one or at least two amino acids (preferably, about 1 to 20, more preferably about 1 to 10, and further preferably several amino acids (1 to 5)) are added to the amino acid sequence, or one or at least two amino acids (preferably, about 1 to 10, more preferably several amino acids (1 to 5), and further preferably about 1 to 3) are optionally substituted with other amino acids in the above-mentioned amino acid sequence.

In addition, in the partial peptide of the invention, the C-terminus may be any one of a carboxyl group (—COOH), carboxylate (—COO⁻), an amide (—CONH$_2$) or an ester (—COOR). When the partial peptide of the invention has a carboxyl group (or carboxylate) at a position other than the C-terminus, the carboxyl group may be amidated or esterified, and such an amidated or esterified form is also included within the partial peptide of the invention. For the ester group in this case, the same ester group as that described with respect to the above-described C-terminus, and the like can be used.

Furthermore, the partial peptides of the invention include peptides in which the amino group of the N-terminal methionine residue is protected by a protecting group, those in which the N-terminal residue is cleaved in the living body and the resulting Gln is converted to pyroglutaminate, those in which substituents on a side chain of an intramolecular amino acid is protected with a suitable protecting group, or conjugated peptides such as so called glycopeptides in which sugar chains are bound, and the like, as in the above-described 14273 receptor.

The salts of the 14273 receptor or partial peptides include physiologically acceptable salts formed with acids or bases, in particular, physiologically acceptable acid addition salts are preferred. For examples, such salts include salts formed with inorganic acids (e.g., hydrochloric acid, phosphoric acid, hydrobromic acid and sulfuric acid) and salts formed with organic acids (e.g., acetic acid, formic acid, propionic acid, fumaric acid, maleic acid, succinic acid, tartaric acid, citric acid, malic acid, oxalic acid, benzoic acid, methanesulfonic acid and benzenesulfonic acid) and the like.

The 14273 receptor and a salt thereof can be manufactured by the methods known per se for purifying receptor protein from the human and mammalian cells or tissues described above. They may also be manufactured by culturing transformants containing the DNA encoding the 14273 receptor described below, and by the protein synthesis method described below or the method analogous thereto.

When the receptor protein is produced from human or mammalian tissues or cells, human or mammalian tissues or cells are homogenized, followed by extraction with acid or the like, and the extract can be subjected to a combination of chromatography such as reverse-phase chromatography and ion-exchange chromatography and the like to isolate and purify the receptor protein.

For the synthesis of the 14273 receptor or a partial peptide thereof or a salt thereof or an amide form thereof, commercially available resins for protein synthesis can be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethyl phenyl acetoamidomethyl resin, polyacrylamide resin, 4-(2',4'-dimethoxyphenyl-hydroxymethyl)phenoxy resin, and 4-(2', 4'-dimethoxyphenyl-Fmoc aminoethyl)phenoxy resin, and the like. Using these resins, amino acids in which the α-amino groups and the side-chain functional groups are appropriately protected are condensed as the sequence of the objective protein on the resin according to the various condensation methods known per se. At the end of the reaction, the protein is excised from the resin and the protecting groups are simultaneously removed. Then, intramolecular disulfide bond-forming reaction is performed in a highly-diluted solution to obtain the objective protein or its amide form.

For condensation of the protected amino acids described above, various activation reagents for protein synthesis can be used, but carbodiimides are particularly good. For carbodiimides, DCC, N,N'-diisopropylcarbodiimide, and N-ethyl-N'-(3-dimethylaminoprolyl)carbodiimide can be used. For activation by these reagents, the protected amino acids added with an additive for suppressing racemization (e.g., HOBt, HOOBt) directly to the resin, or the protected amino acids can be previously activated as symmetric acid anhydrides, HOBt esters or HOOBt esters, and then added to the resin.

The solvent used for activation of the protected amino acids and condensation with the resin can be appropriately selected from solvents known to be used in protein condensation reaction. For example, acid amides such as N,N-dimethylformamide, N,N-dimethylacetoamide, N-methylpyrrolidone, etc.; halogenated hydrocarbons such as methylene chloride chloroform, etc.; alcohols such as trifluoroethanol, etc.; sulfoxide such as dimethylsulfoxide, etc.; pyridine; ethers such as dioxane, tetrahydrofuran, etc.; nitrites such as acetonitrile propionitrile, etc.; esters such as methyl acetate, ethyl acetate, etc.; or appropriate mixtures of these solvents, and the like can be used. The reaction temperature is appropriately selected from the range known to be used in protein bonding reaction, and usually appropriately selected from the range from about −20° C. to 50° C. The activated amino acid derivatives are usually used in 1.5 to 4-fold excessive amount. When condensation is insufficient as a result of a test using a ninhydrin reaction, sufficient condensation can be performed by repeating a condensation reaction without leaving a protecting group. When insufficient condensation can be obtained by repeating a reaction even if a reaction is repeated, an unreacted amino acid can be acetylated by using acetic anhydride or acetylimidazole.

For the protecting groups for a raw material amino group, for examples, Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc, and the like can be used.

A carboxyl group can be protected by, for example, alkyl esterification (straight, branched or cyclic alkyl esterification such as methyl, ethyl, propyl, butyl, t-butyl, cyclopentyl, cyclohexyl, cycloheptyl, cyclooctyl and 2-adamantyl, etc.), aralkyl esterification (e.g. benzyl esterification, 4-nitrobenzyl esterification, 4-methoxybenzyl esterification, 4-chlorobenzyl esterification and benzhydryl esterification), phenacyl esterification, benzyloxycarbonyl hydrazidation, t-butoxycarbonyl hydrazidation, trityl hydrazidation, and the like.

A hydroxy group of serine can be protected, for example, by esterification or etherification. As a group suitable for this esterification, for example, lower alkanoyl groups such as acetyl group, etc., aroyl groups such as benzoyl group, etc., and groups derived from carbonic acid such as benzyloxycarbonyl group, ethoxycarbonyl group, etc., and the like can be used. In addition, examples of a group suitable for etherification include benzyl group, tetrahydropyranyl group, and t-butyl group.

As a protecting group of the phenolic hydroxy group of tyrosine, for example, Bzl, $Cl_2$-Bzl, 2-nitrobenzyl, Br-Z, t-butyl, and the like can be used.

As a protecting group of the imidazole of histidine, for example, Tos, 4-methoxy-2,3,6-trimethylbenzenesulfonyl, DNP, benzyloxymethyl, Bum, Boc, Trt, and Fmoc can be used.

As an activated carboxyl groups in a raw material, for example, corresponding acid anhydride, azide, active ester [ester formed with alcohol (e.g., pentachlorophenol, 2,4,5-trichlorophenol, 2,4-dinitrophenol, cyanomethyl alcohol, paranitrophenol, HONB, N-hydroxysuccinimide, N-hydroxyphthalimide and HOBt)], and the like can be used. As an activated amino group of a raw material, for example, corresponding phosphoric amide can be used.

For the method for removing (eliminating) the protecting groups, for example, catalytic reduction in a hydrogen stream in the presence of a catalyst such as Pd-black, Pd-carbon, etc., acid treatment with anhydrous hydrogen fluoride, methanesulfonic acid, trifluoromethanesulfonic acid or trifluoroacetic acid, or mixture of these acids, etc., basic treatment with diisopropylethylamine, triethylamine, piperidine piperazine, etc., reduction by sodium in liquid ammonia and the like can be used. The elimination reaction by the acid treatment described above is generally performed at a temperature ranging from about −20° C. to 40° C. In acid treatment, addition of a cation scavenger such as anisole, phenol, thioanisole, m-cresol, p-cresol, dimethylsulfide, 1,4-butanedithiol, and 1,2-ethanedithiol and the like is effective. Further, 2,4-dinitrophenyl group used as the protecting group of imidazole of histidine is removed by treatment with thiophenol. A formyl group used as a protecting group for indole of tryptophan is also removed by alkali treatment with a dilute sodium hydroxide solution, dilute ammonia, etc. in addition to deprotection with acid treatment in the presence of the above 1,2-ethanedithiol, 1,4-buthanedithiol, etc.

Protection of functional groups that should not be involved in the reaction for the raw materials, protecting groups, elimination of the protecting groups, activation of functional groups involved in the reaction, and the like may be appropriately selected from known per se groups or means.

In another method for obtaining an amide form of the protein, for example, first, the α-carboxyl group of the carboxy terminal amino acid is protected by amidation, and the peptide (protein) chain is extended for a desired length from the amino group side. Then, a protein in which only the protecting group of the N-terminal α-amino group was removed from the peptide chain and a protein in which only the protecting group of the C-terminal carboxyl group is removed are produced. These two proteins are condensed in the mixed solvent as described above. The details of the condensation reaction are the same as described above. After the protected protein obtained by condensation is purified, all protecting groups are removed by the method described above, to give the desired crude protein. The desired protein in amide form can be obtained by purifying this crude protein using various known means for purification and by lyophilizing the major fraction.

To obtain an ester form of protein, for example, the α-carboxyl group of the carboxy terminal amino acid is condensed with desired alcohols to prepare amino acid ester, and the desired ester form of protein can be obtained by the same procedure as in the preparation of the amide form of the protein.

The partial peptide of the 14273 receptor or a salt thereof can be manufactured by a method for peptide synthesis known per se or by cleaving the 14273 receptor with appropriate peptidase. For the method for peptide synthesis, for example, either solid phase synthesis or liquid phase synthesis may be used. The objective peptide can be produced by condensing the partial peptide or amino acid, which may compose the 14273 receptor, with the residual portion to obtain a product and by eliminating the protecting groups in the case that the product has protecting group. An example of the condensing method and elimination of protecting groups known per se are those methods described in the following a) to e).

a) M. Bodanszky and M. A. Ondetti: Peptide Synthesis, Interscience Publishers, New York (1966)
b) Schroeder and Luebke: The Peptide, Academic Press, New York (1965)
c) N. Izumiya, et al.: Fundamentals and Experiment for Peptide Synthesis, Maruzen (K.K.) (1975)
d) H. Yajima and S. Sakakibara: Biochemical Experimental Course 1, Protein Chemistry IV, 205, (1977)
e) H. Yajima ed.: Development of medicines, a second series, vol. 14, Peptide Synthesis, Hirokawashoten After the reaction, the partial peptide of the invention is purified by a combination of conventional purification methods, for example, solvent extraction, distillation, column chromatography, liquid chromatography, recrystallization and the like. When the partial peptide obtained by the above methods is free form, it can be converted to an appropriate salt form by known methods. On the other hand, when a salt form is obtained, it can be converted to the free form by known methods.

The polynucleotide encoding the 14273 receptor may be any polynucleotide containing the base sequence (DNA or RNA, preferably DNA) encoding the 14273 receptor described above. The polynucleotide may be DNA and RNA including mRNA encoding the 14273 receptor, which may be double-stranded or single-stranded. When the polynucleotide is double-stranded, it may be double-stranded DNA, double-stranded RNA, or DNA:RNA hybrid. When the polynucleotide is single-stranded, it may be sense strand (i.e., coding strand) or antisense strand (i.e., non-coding strand).

Using the polynucleotide encoding the 14273 receptor, mRNA of the 14273 receptor can be quantified by, for example, the known method described in extra edition of Jikken Igaku 15 (7) 'New PCR and its application' (1997) or methods analogous thereto.

The DNA encoding the 14273 receptor may be any DNA of genomic DNA, genomic DNA library, cDNA derived from the above-described cells and tissues and cDNA library derived from the above-described cells and tissues, and synthetic DNA. A vector used for a library may be any of bacteriophage, plasmid, cosmid and phargemide. The DNA may be directly amplified by Reverse Transcriptase Polymerase Chain Reaction (hereinafter, abbreviated as RT-PCR method) using total RNA or mRNA fraction prepared from the above-described cells and tissues.

Specifically, DNA encoding the 14273 receptor may be any DNA as long as they are, for example, DNA comprising the base sequence represented by SEQ ID NO: 2, SEQ ID NO: 4 or SEQ ID NO: 9, or DNA having a base sequence which hybridizes to the base sequence represented by SEQ ID NO: 2, SEQ ID NO: 4 or SEQ ID NO: 9 under highly stringent condition, and which encodes a receptor protein having substantially equivalent activity (for example, ligand-binding activity, signal transduction activity and the like) to the 14273 receptor having the amino acid sequence represented by SEQ ID NO: 1, SEQ ID NO: 3 or SEQ ID NO: 8.

As DNA which can hybridize to the base sequence represented by SEQ ID NO: 2, SEQ ID NO: 4 or SEQ ID NO: 9, for example, DNA comprising a base sequence which has at least about 85% homology, preferably at least about 90% homology, more preferably at least about 95% homology to the base sequence represented by SEQ ID NO: 2, SEQ ID NO: 4 or SEQ ID NO: 9 and the like can be used.

The homology among the base sequences can be calculated using homology search algorithm NCBI BLAST (National Center for Biotechnology Information Basic Local Alignment Search Tool) under the following conditions: expected value=10; gap is allowable; filtering=ON; match score=1; mismatch score=−3.

The hybridization can be carried out by the per se known method or analogous thereto, for example, according to the method described in Molecular Cloning, 2nd (J. Sambrook et al., Cold Spring Harbor Lab. Press, 1989), and the like. When a commercially available library is used, hybridization can be performed according to a method described in the attached instruction. More preferably, hybridization can be carried out under highly stringent conditions.

Highly stringent conditions denote, for example, the conditions of the sodium concentration of about 19 to 40 mM, preferably about 19 to 20 mM, and a temperature of about 50 to 70° C., preferably about 60 to 65° C. In particular, hybridization conditions of the sodium concentration of about 19 mM and a temperature of about 65° C. are most preferable.

More specifically, DNA having the base sequence represented by SEQ ID NO: 2 and the like can be used as DNA which encodes the human 14273 receptor having the amino acid sequence represented by SEQ ID NO: 1.

DNA having the base sequence represented by SEQ ID NO: 4 and the like can be used as DNA which encodes the mouse 14273 receptor having the amino acid sequence represented by SEQ ID NO: 3.

DNA having the base sequence represented by SEQ ID NO: 9 and the like can be used as DNA which encodes the rat 14273 receptor having the amino acid sequence represented by SEQ ID NO: 8.

The polynucleotide encoding the partial peptide of the invention may be any polynucleotide so long as it comprises a base sequence (DNA or RNA, preferably DNA) encoding the partial peptide of the invention described above. The DNA may also be any DNA of genomic DNA, genomic DNA library, cDNA derived from the above-described cells and tissues, cDNA library derived from the above-described cells and tissues and synthetic DNA. The vector to be used for the library may be any of bacteriophage, plasmid, cosmid, phagemid and the like. In addition, the DNA can be amplified by reverse transcriptase polymerase chain reaction (hereinafter, abbreviated as RT-PCR method) with mRNA fraction prepared from the above-described cells or tissues.

Specifically, as DNA encoding the partial peptide of the invention, any DNAs can be used as long as they are, for example, (1) DNA comprising partial base sequence of the DNA comprising the base sequence represented by SEQ ID NO: 2, SEQ ID NO: 4 or SEQ ID NO: 9, or (2) DNA having a base sequence which hybridizes to the base sequence represented by SEQ ID NO: 2, SEQ ID NO: 4 or SEQ ID NO: 9 under high stringent condition, and which encodes a receptor protein having substantially equivalent activity (for example, ligand-binding activity, signal transduction activity and the like) to the 14273 receptor having the amino acid sequence represented by SEQ ID NO: 1, SEQ ID NO: 3 or SEQ ID NO: 8.

As DNA which can hybridize to the base sequence represented by SEQ ID NO: 1, SEQ ID NO: 3 or SEQ ID NO: 8, for example, DNA comprising a base sequence which has at least about 85% homology, preferably at least about 90% homology, more preferably at least about 95% homology to the base sequence represented by SEQ ID NO: 1, SEQ ID NO: 3 or SEQ ID NO: 8 and the like can be used.

The homology among the base sequences can be calculated using homology search algorithm NCBI BLAST (National Center for Biotechnology Information Basic Local Alignment Search Tool) under the following conditions: expected value=10; gap is allowable; filtering=ON; match score=1; mismatch score=−3.

The hybridization can be carried out by the per se known method or analogous thereto, for example, according to the method described in Molecular Cloning, 2nd (J. Sambrook et al., Cold Spring Harbor Lab. Press, 1989), and the like. When a commercially available library is used, hybridization can be performed according to a method described in the attached instruction. More preferably, the hybridization can be carried out under highly stringent conditions.

Highly stringent conditions denote, for example, the conditions of the sodium concentration of about 19 to 40 mM, preferably about 19 to 20 mM, and a temperature of about 50 to 70° C., preferably about 60 to 65° C. In particular, hybridization conditions of the sodium concentration of about 19 mM and a temperature of about 65° C. are most preferable.

For the means for cloning the DNA completely encoding the 14273 receptor or partial peptides thereof (hereinafter, comprehensively abbreviated as the 14273 receptor), the DNA is amplified by PCR using synthetic DNA primers having a partial base sequence of the 14273 receptor, or the DNA inserted in an appropriate vector can be selected by hybridization with the labeled DNA fragment encoding a part or entire region of the 14273 receptor or synthetic DNA. Hybridization can be performed, for example, by the method described in Molecular Cloning, 2nd (J. Sambrook et al., Cold Spring Harbor Lab. Press, 1989) and the like. When a commercially available library is used, hybridization can be performed according to a method described in the attached instruction.

Conversion of the DNA base sequences can be performed by PCR or methods known per se such as ODA-LA PCR, Gapped duplex method and Kunkel method or methods analogous thereto using a known kit such as Mutan™-super Express Km (TAKARA BIO K.K.), Mutan™-K (TAKARA BIO K.K.) and the like.

The cloned DNAs encoding the 14273 receptor can be used depending on the object without treatment or used after digestion with restriction enzymes or addition of linkers, if desired. The DNA may have ATG as a translation initiation codon at its 5'-terminal end or may have TAA, TGA or TAG as a translation termination codon at its 3'-terminal end. These translation initiation codon and translation termination codon may be added using a suitable synthetic DNA adaptor.

Expression vectors for the 14273 receptor can be manufactured, for example, as follows: (i) the objective DNA fragment is excised from the DNA encoding the 14273 receptor, and (ii) the DNA fragment is ligated to downstream of the promoter in an appropriate vector.

As a vector, a plasmid derived from *Escherichia coli* (e.g., pBR322, pBR325, pUC12 and pUC13), a plasmid derived from *Bacillus subtilis* (e.g., pUB110, pTP5 and pC194), a plasmid derived from yeast (e.g., pSH19 and pSH15), a bacteriophage such as λ phage, etc., an animal virus such as retrovirus, vacciniavirus, baculovirus, etc., as well as pA1-11, pXT1, pRc/CMV, pRc/RSV, pcDNAI/Neo and the like can be used.

As a promoter used in the present invention, any promoters may be used as long as they are suitable depending upon hosts used for expressing a gene. Examples thereof include a SR α promoter, a SV40 promoter, a LTR promoter, a CMV promoter, a HSV-TK promoter and the like when an animal cell is used as a host.

Among them, a CMV promoter, a SR α promoter and the like can be preferably used. When a host is a bacterium belonging to genus *Escherichia*, a trp promoter, a lac promoter, a recA promoter, a λ $P_L$ promoter, an lpp promoter and the like are preferred. When a host is a bacterium belonging to genus *Bacillus*, a SPO1 promoter, a SPO2 promoter, a penP promoter and the like are preferred. When a host is yeast, a PHO5 promoter, a PGK promoter, a GAP promoter, an ADH promoter and the like are preferred. When a host is an insect cell, a polyhedrin promoter, a P10 promoter and the like are preferred.

In addition to the above-described vectors, expression vectors containing an enhancer, a splicing signal, a polyA addition signal, a selection marker, and a SV40 replication origin (hereinafter, sometimes abbreviated as SV40ori) can be used, if desired. Examples of the selection marker include dihydrofolate reductase (hereinafter, sometimes abbreviated as dhfr) gene [methotrexate (MTX)-resistant], ampicillin resistant gene (hereinafter, abbreviated as Amp$^r$), neomycin resistant gene (hereinafter, sometimes abbreviated as Neo$^r$, G418 resistant) and the like. In particular, when dhfr gene is used as a selection marker using CHO (dhfr$^-$) cells, the objective gene can be selected by using a thymidine free medium.

In addition, if necessary, a signal sequence suitable for the host is added to an N-terminal end of the receptor protein of the invention. When a host is a bacterium belonging to genus *Escherichia*, a PhoA signal sequence, an OmpA signal sequence and the like can be used. When a host is a bacterium belonging to genus *Bacillus*, an α-amylase signal sequence, a subtilisin signal sequence and the like can be used. When a host is yeast, a MF α signal sequence, a SUC2 signal sequence and the like can be used. When a host is an animal cell, an insulin signal sequence, an α-interferon signal sequence, an antibody signal sequence and the like can be used.

Using thus constructed vector containing the DNA encoding the 14273 receptor, transformants can be prepared.

For the host, for example, a bacterium belonging to genus *Escherichia*, a bacterium belonging to genus *Bacillus*, yeast, an insect cell, an insect, an animal cell and the like can be used.

As the specific examples of the bacterium belonging to genus *Escherichia, Escherichia coli* K12 DH1 [Proceedings of the National Academy of Sciences of the USA (Proc. Natl. Acad. Sci. USA), Vol. 60, 160 (1968)], JM103 [Nucleic Acids Research, Vol. 9, 309 (1981)], JA221 [Journal of Molecular Biology, Vol. 120, 517 (1978)], HB101 [Journal of Molecular Biology, Vol. 41, 459 (1969)], C600 [Genetics, Vol. 39, 440 (1954)] and the like can be used.

As the bacterium belonging to genus *Bacillus*, for example, *Bacillus subtilis* MI114 [Gene, Vol. 24, 255 (1983)] 207-21 [Journal of Biochemistry, Vol. 95, 87 (1984)] and the like can be used.

As the yeast, for example, *Saccharomyces cerevisiae* AH22, AH22R$^-$, NA87-11A, DKD-5D, 20B-12, *Schizosaccharomyces pombe* NCYC1913, NCYC2036, *Pichia pastoris* and the like can be used.

As the insect cell, for example, when a virus is AcNPV, an established cell derived from a larva of Barathra (*Spodoptera frugiperda* cell; Sf cell), MG1 cells derived from a midgut of *Trichoplusia ni*, High Five™ cell derived from an egg of *Trichoplusia ni*, a cell derived from *Mamesira brassicae*, a cell derived from *Estigmena acrea* and the like can be used. When a virus is BmNPV, an established cell derived from a silkworm (*Bombyx mori* N; BmN cell) is used. For the Sf cells, for example, a Sf9 cell (ATCC CRL1711), a Sf21 cell (Vaughn, J. L. et al., In Vivo, Vol. 13, 213-217 (1977)) and the like can be used.

As the insect, for example, a larva of a silkworm and the like can be used [Maeda et al., Nature, Vol. 315, 592 (1985)].

As the animal cell, for example, a monkey cell COS-7, Vero, a Chinese hamster cell CHO (hereinafter, abbreviated as CHO cells), a dhfr gene-deficient Chinese hamster cell CHO (hereinafter, abbreviated as CHO (dhfr$^-$) cells), a mouse L cell, a mouse AtT-20 cell, a mouse myeloma cell, rat GH3, a human FL cell, a human HEK 293 cell and the like can be used.

A bacterium belonging to genus *Escherichia* can be transformed according to, for example, the methods described in Proc. Natl. Acad. Sci. USA, Vol. 69, 2110 (1972) and Gene, Vol. 17, 107 (1982) and the like.

A bacterium belonging to genus *Bacillus* can be transformed according to, for example, the method described in Molecular & General Genetics, Vol. 168, 111 (1979) and the like.

Yeast can be transformed according to, for example, the methods described in Methods in Enzymology, Vol. 194, 182-187 (1991) and Proc. Natl. Acad. Sci. USA, Vol. 75, 1929 (1978) and the like.

An insect cell or an insect can be transformed according to, for example, the method described in Bio/Technology, Vol. 6, 47-55 (1988) and the like.

An animal cell can be transformed by, for example, the methods described in Cell Technology (Saibo Kogaku), a separate volume 8, New Cell Technology Experimental Protocol, 263-267 (1995) (published by Shujunsha) and Virology, Vol. 52, 456 (1973).

As described above, the transformants transformed by the expression vector containing the DNA encoding the 14273 receptor can be obtained.

For the medium for culturing the transformants wherein the host is the bacterium belonging to *Escherichia* or *Bacillus*, liquid medium is suitable, in which a carbon source, a nitrogen source, inorganic substances and others necessary for growth of a transformant are contained therein. Examples of the carbon source include glucose, dextrin, soluble starch and sucrose, examples of the nitrogen sucrose include inorganic or organic substances such as ammonium salts, nitrates, corn steep liquor, peptone, casein, broth extract, soy bean cake and potato extract, and examples of inorganic substances include calcium chloride, sodium dihydrogen phosphate and magnesium chloride. In addition, yeast extract, vitamins, growth promoting factors and the like can be added. The pH of the medium is desirably about 5 to 8.

As a medium upon culturing for the bacterium belonging to genus *Escherichia*, for example, a M9 medium containing glucose and casamino acids (Miller, Journal of Experiments in Molecular Genetics, 431-433, Cold Spring Harbor Laboratory, New York, 1972) is preferred. Here, in order to allow a promoter to work effectively, a medicine such as 3β-indolylacrylic acid can be added.

When the host is the bacterium belonging to genus *Escherichia*, the culturing is usually performed at about 15 to 43° C. for about 3 to 24 hours and, if necessary, aeration and stirring can be added.

When the host is the bacterium belonging to genus *Bacillus*, the culturing is usually performed at about 30 to 40° C. for about 6 to 24 hours and, if necessary, aeration and stirring can be added.

When a transformant for which a host is yeast is cultured, examples of a medium include a Burkholder minimum medium [Bostian, K. L. et al., Proc. Natl. Acad. Sci. USA, Vol. 77, 4505 (1980)] and a SD medium containing 0.5% casamino acid [Bitter, G. A. et al., Proc. Natl. Acad. Sci. USA, Vol. 81, 5330 (1984)]. The pH of the medium is preferably adjusted to about 5 to 8. The culturing is usually performed at about 20 to 35° C. for about 24 to 72 hours and, if necessary, aeration and stirring are added.

When a transformant for which a host is an insect cell or an insect is cultured, a Grace's insect medium (Grace, T. C. C., Nature, Vol. 195, 788 (1962)), to which additives such as 10% immobilized bovine serum are appropriately added, and the like can be used. The pH of the medium is preferably adjusted to about 6.2 to 6.4. Usually, the culturing is performed at about 27° C. for about 3 to 5 days and, if necessary, aeration and stirring are added.

When a transformant for which a host is an animal cell is cultured, a MEM medium containing about 5 to 20% fetal bovine serum [(Science, Vol. 122, 501 (1952)), a DMEM medium [Virology, Vol. 8, 396 (1959)], a RPMI 1640 medium [The Journal of the American Medical Association, Vol. 199, 519 (1967)], a 199 medium [Proceeding of the Society for the Biological Medicine, Vol. 73, 1 (1950)] and the like can be used. The pH is preferably about 6 to 8. Usually, the culturing is performed at about 30 to 40° C. for about 15 to 60 hours and, if necessary, aeration and stirring are added.

As described above, the 14273 receptor can be produced intracellularly, on cell membrane or extracellularly of the transformants.

The 14273 receptor can be separated and purified from the culture described above by, for example, the methods described below.

When the 14273 receptor is extracted from the cultured bacterial cells or cells, the bacterial cells or cells are collected after culture by a known method, and suspended in appropriate buffer. The bacterial cells or cells are then disrupted using ultrasonication, lysozymes, and/or by freezing-melting and the like, and the crude extract of the 14273 receptor is obtained by centrifugation or filtration. The buffer may contain a protein denaturing agent such as urea and guanidine hydrochloride and a surfactant such as Triton X-100™. When the 14273 receptor is secreted into the culture solution, after the culturing is complete, the bacterial cells or cells and the supernatant are separated by the per se known method and the supernatant is collected.

Purification of the thus obtained culture supernatant or a 14273 receptor contained in the extract can be performed by appropriately combining the per se known separating and purifying methods. Examples of these known separating and purifying methods include a method utilizing the solubility such as salting out and solvent precipitating method, a method utilizing a difference mainly in a molecular weight such as a dialysis method, an ultra filtration method, a gel filtration method, and a SDS-polyacrylamide gel electrophoresis method, a method utilizing difference in charge such as ion exchange chromatography, a method utilizing specific affinity such affinity chromatography, a method utilizing a difference in hydrophobicity such as reverse-phase high performance liquid chromatography, a method utilizing a difference in an isoelectric point such as an isoelectric focusing method and the like.

When the thus obtained 14273 receptor is in a free form, the free form can be converted to a salt form by methods known per se or methods analogous thereto. Conversely, when the 14273 receptor is obtained in a salt form, the salt form can be converted to the free form or other salts by methods known per se or methods analogous thereto.

In addition, the 14273 receptor produced by recombinants can be optionally modified or a polypeptide can be partially removed from the 14273 receptor by treating the 14273 receptor with an appropriate protein-modifying enzyme before or after purification. For the protein-modifying enzyme, for example, trypsin, chymotrypsin, arginylendopeptidase, protein kinase, glycosidase and the like can be used.

The activity of the 14273 receptor thus produced can be measured by binding assay using labeled ligands and by enzyme immunoassay using specific antibody and the like.

Hereinafter, a screening method for a compound that changes the bindability between the 14273 receptor and a fatty acid, which is a physiological ligand thereof, or a salt thereof (i.e., other ligands to the 14273 receptor, the 14273 receptor agonist, the 14273 receptor antagonist and the like) is described in detail.

One of the ligands for the 14273 receptor is a fatty acid or a salt thereof. As the fatty acids, oleic acid, palmitoleic acid, linoleic acid, γ-linolenic acid, arachidonic acid, docosahexaenoic acid (DHA) and the like can be used. Among them, palmitoleic acid, linoleic acid, γ-linolenic acid, and the like are preferred.

As salts of the fatty acids, salts with acids (e.g., inorganic acids, organic acids, etc.), salts with bases (e.g., alkali metals such as sodium, potassium, etc.; alkaline earth metals such as calcium, etc.) and the like can be used, and particularly bases are preferred.

Hereinafter, the fatty acids or salts thereof are simply referred to as the "fatty acid".

As described above, since the compound of the invention has agonist activity for the 14273 receptor, it is possible to screen the 14273 receptor ligand, agonist or antagonist in good efficiency from the test compound by using a binding assay system with use of the 14273 receptor (including cells which expresses recombinant or endogenous 14273 receptor and its cell membrane fraction and the like) and the compound of the invention as a surrogate ligand.

The 14273 receptor ligand and agonist are physiological and non-physiological compounds which show cell-stimulating activity by binding to the 14273 receptor (hereinafter, comprehensively referred to as the "14273 receptor agonist").

Examples of the cell-stimulating activities include the activities that promote or suppress arachidonic acid release, acetylcholine release, intracellular $Ca^{2+}$ release, intracellular cAMP production, intracellular cGMP production, inositol phosphate production, changes in cell membrane potential, phosphorylation or activation of intracellular proteins (e.g., MAP kinase), activation of c-fos, pH reduction, etc., activity of suppressing adrenocorticotropic hormone (ACTH) secretion, etc. Among those the activity of increasing intracellular $Ca^{2+}$ level, activity of suppressing the intracellular cAMP production, phosphorylation or activation of MAP kinase, the activity of suppressing adrenocorticotropic hormone (ACTH) secretion, etc. are preferred.

The 14273 receptor antagonist is a compound which binds to the 14273 receptor, but shows no cell-stimulating activity, or shows inverse effect to the cell-stimulating activity (inverse agonistic activity). That is, the "14273 receptor antagonist" in the present specification is used as a concept to comprise not only so-called neutral antagonist, but also inverse agonist.

In addition, by using the screening method of the invention, it is possible to screen a compound which potentiates the binding affinity of a fatty acid to the 14273 receptor, or a compound which decreases the binding affinity of a fatty acid to the 14273 receptor, and the like.

In other words, the invention provides a method for screening a compound or a salt thereof that changes the binding property of the 14273 receptor to a fatty acid, which comprises comparing (i) the case where the 14273 receptor is brought into contact with the compound of the invention; and (ii) the case where the 14273 receptor is brought into contact with the compound of the invention and the test compound.

The screening method of the invention is characterized by assaying and comparing, e.g., the binding amounts of a fatty acid to the 14273 receptor, the cell-stimulating activities, etc. in the cases (i) and (ii).

Examples of the cell-stimulating activities include the activities that promote or suppress arachidonic acid release, acetylcholine release, intracellular $Ca^{2+}$ release, intracellular cAMP production, intracellular cGMP production, inositol phosphate production, changes in cell membrane potential, phosphorylation or activation of intracellular proteins (e.g., MAP kinase), activation of c-fos, pH reduction, etc., activity of suppressing glycerol production from adipocyte, activity of lowering blood-glycerol, activity of suppressing lipolysis (preferably, activity of suppressing lipolysis in adipocytes), activity of suppressing insulin resistance, activity of regulating stress, activity of suppressing adrenocorticotropic hormone (ACTH) secretion, activity of suppressing growth hormone secretion, activity of promoting glucagon-like peptide-1 (GLP-1) secretion and the like. Among those preferred are activity of increasing the intracellular $Ca^{2+}$ level, activity of suppressing the intracellular cAMP production, phosphorylation or activation of MAP kinase, activity of suppressing glycerol production from adipocyte, activity of lowering blood-glycerol, activity of suppressing lipolysis (preferably, activity of suppressing lipolysis in adipocytes), activity of suppressing insulin resistance, activity of regulating stress, activity of suppressing adrenocorticotropic hormone (ACTH) secretion, activity of suppressing growth hormone secretion, activity of promoting glucagon-like peptide-1 (GLP-1) secretion and the like.

More specifically, the invention provides the following methods.

a) A method of screening a compound or a salt thereof that changes the binding property of a fatty acid to the 14273 receptor, characterized in that binding amounts of a labeled compound of the invention to the 14273 receptor are determined and compared in the cases of when the labeled compound of the invention is brought into contact with the 14273 receptor, and when the labeled compound of the invention and the test compound are brought into contact with the 14273 receptor, b) A method of screening a compound or a salt thereof that changes the binding property of a fatty acid to the 14273 receptor, characterized in that binding amounts of the labeled compound of the invention to cells or a membrane fraction for the cells are determined and compared in the cases of when the labeled compound of the invention is contacted with the cells-containing the 14273 receptor or the cell membrane fraction, and when the labeled compound of the invention and the test compound are contacted with the cells containing the 14273 receptor or the cell membrane fraction, c) A method of screening a compound or a salt thereof that changes the binding property of a fatty acid to the 14273 receptor, characterized in that binding amounts of a labeled compound of the invention to the 14273 receptor are determined and compared in the cases of when the labeled compound of the invention is brought into contact with the 14273 receptor expressed on a cell membrane by culturing transformants containing the DNA of the invention, and when the labeled compound of the invention and a test compound are brought into contact with the 14273 receptor expressed on the cell membrane by culturing transformants containing the DNA of the invention, d) A method of screening a compound or a salt thereof that changes the binding property of a ligand to the 14273 receptor, characterized in that the 14273 receptor-mediated cell stimulating activities are determined and compared in the cases of when a compound capable of activating the 14273 receptor (e.g., the compound of the invention, etc.) is brought into contact with cells (e.g., CHO cells and AtT-20 cells) containing the 14273 receptor, and when a compound capable of activating the 14273 receptor and a test compound are brought into contact with the cells containing the 14273 receptor, and e) A method of screening a compound or a salt thereof that changes the binding property of a fatty acid to the 14273 receptor, characterized in that the receptor-mediated cell stimulating activities are determined and compared in the cases of when a compound capable of activating the 14273 receptor (e.g., the compound of the invention, etc.) is brought into contact with the 14273 receptor expressed on a cell membrane by culturing transformants containing the DNA of the invention, and when a compound capable of activating the 14273 receptor and a test compound are brought into contact with the 14273 receptor expressed on a cell membrane by culturing transformants containing the DNA of the invention.

The compound of the invention is easily labeled as compared to a fatty acid, which is a natural ligand, and thus, suitable for screening.

The screening method of the invention will be specifically explained below.

First, the 14273 receptor, which is used for the screening method of the invention, may be any one so long as it contains the 14273 receptor described above, though cell membrane fractions from mammalian organs containing the 14273 receptor are preferably employed. Since it is very difficult to acquire human-derived organs especially, human-derived 14273 receptor, etc. expressed abundantly with use of recombinants are suitable for use in the screening.

In producing the 14273 receptor, the methods described above can be used, and the DNA of the invention is preferably expressed on mammalian cells or insect cells. As the DNA fragment encoding the target protein region, a complementary DNA can be used, but it is not limited thereto. For example, gene fragments or a synthetic DNA may also be used. In order to introduce the DNA fragment encoding the 14273 receptor into host animal cells and express the same efficiently, the DNA fragment is preferably incorporated into the downstream of a polyhedron promoter of nuclear polyhedrosis virus (NPV) belonging to the Baculovirus, in which the host is insects, a SV40-derived promoter, a promoter of retrovirus, a metallothionein promoter, a human heat shock promoter, a cytomegalovirus promoter, a SR α promoter, etc. The quantity and quality of the thus-expressed receptors can be examined by a method known per se, for example, by the method described in the literature [Nambi, P. et al., The Journal of Biological Chemistry, Vol. 267, pp. 19555-19559, 1992].

Accordingly, in the screening method of the invention, the substance containing the 14273 receptor may be any of the 14273 receptor purified by the method known per se, or cells containing the 14273 receptor or a membrane fraction for cells containing the 14273 receptor.

When the cells containing the 14273 receptor are used in the screening method of the invention, the cells may be fixed with glutaraldehyde, formalin, etc. The fixation may be carried out by a method known per se.

The cells containing the 14273 receptor refer to host cells which express the 14273 receptor. Preferred examples of such host cells include *Escherichia coli, Bacillus subtilis*, yeast, insect cells, animal cells, etc.

The membrane fraction for the cells means a fraction abundant in cell membranes obtained by cell disruption and subsequent fractionation by a method known per se. Examples of cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, and the like. Cell membrane fractionation is implemented mainly by fractionation using a centrifugal force such as centrifugation for fractionation and density gradient centrifugation. For example, cell disruption fluid is centrifuged at a low speed (500 rpm to 3,000 rpm) for a short period of time (usually about 1 to 10 minutes), and the resulting supernatant is further centrifuged at a higher speed (15,000 rpm to 30,000 rpm) usually for 30 minutes to 2 hours. The precipitate thus obtained is used as the membrane fraction. The membrane fraction is rich in the expressed 14273 receptor and membrane components such as cell-derived phospholipids, membrane proteins, etc.

The amount of the 14273 receptor in the cells containing the 14273 receptor or the membrane fraction is preferably $10^3$ to $10^8$ molecules per cell, and more preferably $10^5$ to $10^7$ molecules per cell. As the level of expression increases, the ligand-binding activity per unit of membrane fraction (specific activity) increases so that not only the highly sensitive screening system can be constructed but also large quantities of samples can be assayed with the same lot.

To perform a) through c) above for screening the compound that changes the binding property of the compound of the invention to the 14273 receptor, for example, an appropriate fraction for the 14273 receptor and a labeled compound of the invention are required.

AS the 14273 receptor fraction, preferred are a natural type 14273 receptor fraction or a recombinant type 14273 receptor fraction having an activity equivalent thereto. Herein, the equivalent activity is intended to mean equivalent ligand-binding activity or signal transduction activity.

As the labeled compound of the invention, a labeled compound of the invention, a labeled β-alanine analogue or labeled L-carnosine and the like are used. For example, the compounds of the invention labeled with [$^3$H], [$^{125}$I], [$^{14}$C], [$^{35}$S], etc. can be used.

Specifically, the compound that changes the binding property of the compound of the invention to the 14273 receptor is screened by the following procedures. First, a sample of the 14273 receptor is prepared by suspending a cell containing the 14273 receptor or a membrane fraction for the cell in a buffer suitable for use in the screening method. Any buffer can be used so long as it does not interfere the binding affinity of the compound of the invention to the 14273 receptor, including a phosphate buffer or a Tris-HCl buffer, having pH of 4 to 10 (preferably pH of 6 to 8), etc. For the purpose of reducing non-specific binding, a surfactant such as CHAPS, Tween-80™ (Kao-Atlas Inc.), digitonin, deoxycholate, etc., may be added to the buffer. Further, for the purpose of suppressing the degradation of the receptor or ligand by a protease, a protease inhibitor such as PMSF, leupeptin, E-64 (manufactured by Peptide Institute, Inc.), pepstatin, etc. may also be added. A given amount (5,000 cpm to 500,000 cpm) of the labeled compound of the invention is added to 0.01 ml to 10 ml of the receptor protein solution, in which $10^{-4}$ M to $10^{-10}$ M of a test compound is co-present. To determine the amount of non-specific binding (NSB), a reaction tube containing an unlabeled compound of the invention in a large excess is also prepared. The reaction is carried out at about 0 C to 50° C., preferably about 4° C. to 37° C. for about 20 minutes to 24 hours, preferably about 30 minutes to 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. When the amount of nonspecific binding (NSB) is subtracted from the count ($B_0$) where any competitive substance is absent and the resulting count ($B_0$ minus NSB) is made 100%, the test compound showing the specific binding amount (B−NSB) of, e.g., 50% or less may be selected as a candidate compound capable of competitive inhibition.

The methods d) and e) described above for screening the compound that changes the binding property of the compound of the invention to the 14273 receptor can be performed as follows. For example, the cell-stimulating activities mediated by the 14273 receptor can be determined by a method known per se, or using an assay kit commercially available.

Specifically, the cells containing the 14273 receptor are first cultured in a multiwell plate, etc. Prior to screening, the medium is replaced with fresh medium or with an appropriate non-cytotoxic buffer, followed by culturing for a given period of time in the presence of a test compound, etc. Subsequently, the cells are extracted or the supernatant is recovered and the resulting product is quantified by appropriate procedures. When it is difficult to detect the production of the cell-stimulating activity indicator (e.g., $Ca^{2+}$, cAMP, arachidonic acid, etc.) due to a degrading enzyme contained in the cells, an inhibitor against a degrading enzyme may be added to perform the assay. For the activities such as the cAMP production suppression activity, it can be detected in terms of the suppressing effect on the cells in which the baseline production is increased by forskolin and the like.

For screening through the assay for the cell stimulating activities, cells where an appropriate 14273 receptor has been expressed are necessary. Preferred are cell lines containing a natural type 14273 receptor and cell lines wherein the above recombinant type 14273 receptor has been expressed.

Examples of the test compounds include peptides, proteins, non-peptide compounds, synthetic compounds, fermentation products, cell extracts, plant extracts, animal tissue extracts, etc. These compounds may be either a novel compound or a known compound.

The test compound may form salts and may be used in the form of salts with physiologically acceptable acids (e.g., inorganic acids, etc.) or bases (e.g., organic acids, etc.), and particularly preferably in the form of physiologically acceptable acid addition salts. Examples of such salts include salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

As the test compound, a compound designed to bind to the ligand-binding pocket, based on the atomic coordinate and the position of the ligand-binding pocket in the active site of the 14273 receptor, is preferably used. The atomic coordinate and the position of the ligand-binding pocket in the active site of the 14273 receptor can be determined by methods known per se or methods analogous thereto.

Using the method of screening the agonist to the 14273 receptor described above, it can be confirmed whether the compound that changes the binding property of the compound of the invention to the 14273 receptor is either an agonist or an antagonist.

The kit for screening the compound or salts thereof that changes the binding property of the fatty acid to the 14273 receptor is a kit comprising the 14273 receptor, cells containing the 14273 receptor, or a membrane fraction for cells containing the 14273 receptor, and the like.

Examples of the screening kit of the invention include the following.

1. Reagent for screening a) Assay buffer and wash buffer

Hanks' balanced salt solution (manufactured by Gibco Co., Ltd.) supplemented with 0.05% bovine serum albumin (manufactured by Sigma Chemical Co.).

The solution is sterilized by filtration through a filter having a bore diameter of 0.45 µm, and stored at 4° C. or may be prepared at use.

b) Sample for 14273 receptor

CHO cells wherein the 14273 receptor has been expressed are passaged in a 12-well plate at a density of $5 \times 10^5$ cells/well followed by culturing at 37° C. under 5% $CO_2$ and 95% air for 2 days.

c) Labeled compound of the invention

The compound of the invention labeled with [$^3$H], [$^{125}$I], [$^{14}$C], [$^{35}$S], etc., commercially available The labeled compound of the invention is stored at 4° C. or −20° C. in the state of an aqueous solution and diluted to 1 µM with the assay buffer upon at use.

d) Standard solution of compound of the invention

The compound of the invention is dissolved in and adjusted to 1 mM with PBS containing 0.1% bovine serum albumin (manufactured by Sigma Chemical Co.) and stored at −20° C.

2. Assay method a) 14273 receptor expressing CHO cells, cultured in a 12-well culture plate, are washed twice with 1 ml of the assay buffer, and 490 µl of the assay buffer is added to each well.

b) After adding 5 µl of a $10^{-3}$-$10^{-10}$ M solution of a test compound, 5 µl of the labeled compound of the invention is added to the mixture, and the cells are incubated at room temperature for 1 hour. To determine the amount of the non-specific binding, 5 µl of $10^{-3}$ M compound of the invention is added instead of the test compound.

c) The reaction solution is removed, and the wells are washed 3 times with 1 ml of the wash buffer. The labeled ligand bound to the cells is dissolved in 0.2N NaOH-1% SDS, and mixed with 4 ml of liquid scintillator A (manufactured by Wako Pure Chemical Industries, Ltd.).

d) The radioactivity is measured using a liquid scintillation counter (manufactured by Beckman Co.), and the percent Maximum Binding (PMB) is calculated by the equation as below.

$$PMB = [(B-NSB)/(B_0-NSB)] \times 100$$

PMB: Percent Maximum Binding
B: Value obtained in the case of adding a test substance
NSB: Non-specific binding
$B_0$: Maximum binding The compound or the salt thereof, which can be obtained by using the screening methods or the screening kits of the invention, is a compound or a salt thereof that changes the binding property of a fatty acid to the 14273 receptor. Specifically, the compound is: (a) a compound or a salt thereof having the cell-stimulating activities mediated by the G protein-coupled receptor (so-called agonist to the 14273 receptor); (b) a compound or a salt thereof having no cell stimulating activity (so-called antagonist to the 14273 receptor); (c) a compound or a salt thereof that potentiates the binding affinity of the fatty acid to the 14273 receptor; or (d) a compound or a salt thereof that reduces the binding affinity of the fatty acid to the 14273 receptor.

Examples of these compounds obtained by using the screening methods or the screening kits of the invention may be include peptides, proteins, non-peptide compounds, synthetic compounds, fermentation products, and the like, and those may be a novel compound or a known compound.

As salts of the compounds obtained by using the screening methods or the screening kits of the invention, there are employed salts with physiologically acceptable acids (e.g., inorganic acids, etc.) or bases (e.g., organic acids, etc.), and in particular, physiologically acceptable acid addition salts are preferred. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

Since the agonists to the 14273 receptor have the same physiological activities as the fatty acid, which is a ligand to the 14273 receptor, the agonists are useful as safe and low toxic pharmaceuticals, correspondingly to the physiological activities possessed by the fatty acid.

Since the antagonists to the 14273 receptor can suppress the physiological activities possessed by the fatty acid, which is a ligand to the 14273 receptor, the antagonists are useful as safe and low toxic pharmaceuticals to suppress the physiological activities of the fatty acid.

The compound or the salt thereof that potentiates the binding affinity of the fatty acid to the 14273 receptor can potentiate the physiological activities possessed by the fatty acid as a ligand to the 14273 receptor, and it is thus useful as a safe and low toxic pharmaceutical correspondingly to the physiological activities possessed by the fatty acid.

The compound or the salt thereof that reduces the binding affinity of the fatty acid to the 14273 receptor can reduce the physiological activities possessed by the fatty acid as a ligand to the 14273 receptor, and it is thus useful as a safe and low toxic pharmaceutical to suppress the physiological activities of the fatty acid.

Specifically, (i) the agonist to the 14273 receptor or (ii) the compound or the salt thereof that potentiates the binding affinity of the fatty acid to the 14273 receptor, which is obtained by using the screening methods or screening kits of the invention is useful as an agent for regulating glycerol production from adipocytes, an agent for regulating blood glycerol, an agent for regulating lipolysis, an insulin resistance regulating agent, a stress regulating agent, an agent for regulating adrenocorticotropic hormone (ACTH) secretion, an agent for regulating growth hormone secretion, an agent for regulating glucagon-like peptide-1 (GLP-1) secretion (preferably, an agent for suppressing glycerol production from adipocytes, an agent for lowering blood glycerol, an agent for suppressing lipolysis, an agent for suppressing insulin resistance and a stress regulating agent, an adrenocorticotropic hormone (ACTH) secretion suppressing agent, a growth hormone secretion suppressing agent and a glucagon-like peptide-1 (GLP-1) secretion promoting agent).

In addition, (i) the agonist to the 14273 receptor or (ii) the compound or the salt thereof that potentiates the binding affinity of the fatty acid to the 14273 receptor, which is obtained by using the screening methods or screening kits of the invention, is useful as an agent for preventing/treating, for example, diabetes mellitus, impaired glucose tolerance, ketosis, acidosis, diabetic neuropathy, diabetic nephropathy, diabetic retinopathy, hyperlipemia, arteriosclerosis, angina pectoris, myocardial infarction, sexual dysfunction, obesity, pituitary dysfunctions (e.g., hypopituitarism, pituitary dwarfism, diabetes insipidus, acromegaly, Cushing's disease, hyperprolactinemia, syndrome of inappropriate secretion of anti-diuretic hormone), cancer (e.g., colorectal cancer), deficits in memory and learning, pancreatic exhaustion, hypoglycemia, insulin allergy, lipotoxicity, fatty atrophy, cancerous cachexia, hyperinsulinemia, hyperglycemia, disorder caused by high FFA flux, hypertriglyceridemia, fatty liver, dysfunction of heat production, cholelithiasis, eating disorder, anorexia, secretion disorders of intestinal hormones (e.g., cholecystokinin (CCK), gastric inhibitory peptide (GIP), gastrin, glucagon-like peptide-1 (GLP-1), somatostatin, gastrin-releasing peptide, secretin, vasoactive intestinal peptide, motilin, substance P, neurotensin, galanin, neuropeptide Y, enkephalins, peptide YY, etc.) or circulatory diseases (especially, diabetes mellitus, hyperlipemia, overweight, arteriosclerosis, angina pectoris or myocardial infarction).

Moreover, (i) the agonist to the 14273 receptor or (ii) the compound or the salt thereof that potentiates the binding affinity of the fatty acid to the 14273 receptor, which is obtained by using the screening methods or screening kits of the invention, can be used as an agent for preventing/treating diseases, for example, arteriosclerosis, arteriosclerotic diseases and their secondary diseases [e.g., acute coronary syndrome such as atherosclerosis, peripheral arterial disease, acute myocardial infarction, unstable angina, etc., ischemic heart diseases such as restenosis after percutaneous transluminal coronary angioplasty (PTCA), myocardial infarction, angina pectoris, etc., arteriosclerosis including angiocalcinosis, etc., intermittent claudication, apoplexy (cerebral infarction, cerebral embolism, brain hemorrhage, etc.), lacunar infarction, cerebrovascular dementia, gangrene, glomerulosclerosis, nephropathy, Tangier disease, etc.], vascular lesions in atherosclerosis and their secondary diseases [e.g., coronary heart disease (CHD), cerebral ischemia, etc.], lipid dysbolism and its secondary diseases, etc.

Furthermore, (i) the agonist to the 14273 receptor or (ii) the compound or the salt thereof that potentiates the binding affinity of the fatty acid to the 14273 receptor, which is obtained by using the screening methods or screening kits of the invention, acts as an adrenocorticotropic hormone (ACTH) secretion suppressing agent and can be used as an agent for preventing/treating diseases, for example, ACTH-producing tumor, Cushing's disease, infectious disease, secondary adrenocortical insufficiency, peptic ulcer, diabetes mellitus, mental disorder, cataract, glaucoma, tuberculous disease, hypertension, Cushing's syndrome (e.g., central obesity, edema, hypertension, menstrual disorder, extensive stretch mark, hirsutism, diabetes mellitus, full moon face, osteoporosis, hemorrhagic diathesis, mental disorder (e.g., depression, anxiety), muscular atrophy, loss of muscle strength, hypokalemia, hypercholesterolemia, impaired glucose resistance, leukocytosis), adrenocortical atrophy, etc.

(i) The antagonist to the 14273 receptor or (ii) the compound or the salt thereof that reduces the binding affinity of the fatty acid to the 14273 receptor, which is obtained by using the screening methods or screening kits of the invention is useful as an agent for regulating glycerol production from adipocytes, an agent for regulating blood glycerol, an agent for regulating lipolysis, an insulin resistance regulating agent, a stress regulating agent, an agent for regulating adrenocorticotropic hormone (ACTH) secretion, an agent for regulating growth hormone secretion, an agent for regulating glucagon-like peptide-1 (GLP-1) secretion (preferably, an agent for promoting glycerol production from adipocytes, an agent for increasing blood glycerol, an agent for promoting lipolysis, an agent for promoting insulin resistance, a stress regulating agent and an agent for promoting adrenocorticotropic hormone (ACTH) secretion, an agent for promoting growth hormone secretion and an agent for suppressing glucagon-like peptide-1 (GLP-1) secretion).

Further, (i) the antagonist to the 14273 receptor or (ii) the compound or the salt thereof that reduces the binding affinity of the fatty acid to the 14273 receptor, which is obtained by using the screening methods or screening kits of the invention, is useful as an agent for preventing/treating, for example, diabetes mellitus, impaired glucose tolerance, ketosis, acidosis, diabetic neuropathy, diabetic nephropathy, diabetic retinopathy, hyperlipemia, arteriosclerosis, angina pectoris, myocardial infarction, sexual dysfunction, obesity, pituitary dysfunction (e.g., hypopituitarism, pituitary dwarfism, diabetes insipidus, acromegaly, Cushing's disease, hyperprolactinemia, syndrome of inappropriate secretion of anti-diuretic hormone), cancer (e.g., colorectal cancer), deficits in memory and learning, pancreatic exhaustion, hypoglycemia, insulin allergy, lipotoxicity, fatty atrophy, cancerous cachexia, hyperinsulinemia, hyperglycemia, disorder caused by high FFA flux, hypertriglyceridemia, fatty liver, dysfunction of heat production, cholelithiasis, eating disorder, anorexia, secretion disorders of intestinal hormones (e.g., cholecystokinin (CCK), gastric inhibitory peptide (GIP), gastrin, glucagon-like peptide-1 (GLP-1), somatostatin, gastrin-releasing peptide, secretin, vasoactive intestinal peptide, motilin, substance P, neurotensin, galanin, neuropeptide Y, enkephalins, peptide YY, etc.), circulatory diseases, etc. (especially, anorexia and obesity, among others, obesity with visceral fat accumulation), etc., or as a stress regulating agent.

Also, (i) the antagonist to the 14273 receptor or (ii) the compound or the salt thereof that reduces the binding affinity of the fatty acid to the 14273 receptor, which is obtained by using the screening methods or screening kits of the invention, can be used as an agent for preventing/treating diseases, for example, arteriosclerosis, arteriosclerotic diseases and their secondary diseases [e.g., acute coronary syndrome such as atherosclerosis, peripheral arterial disease, acute myocardial infarction, unstable angina, etc., ischemic heart diseases such as restenosis after percutaneous transluminal coronary angioplasty (PTCA), myocardial infarction, angina pectoris, etc., arteriosclerosis including angiocalcinosis, etc., intermittent claudication, apoplexy (cerebral infarction, cerebral embolism, brain hemorrhage, etc.), lacunar infarction, cerebrovascular dementia, gangrene, glomerulosclerosis, nephropathy, Tangier disease, etc.], vascular lesions in atherosclerosis and their secondary diseases [e.g., coronary heart disease (CHD), cerebral ischemia, etc.], lipid dysbolism and its secondary diseases, etc.

In addition, (i) the antagonist to the 14273 receptor or (ii) the compound or the salt thereof that reduces the binding affinity of the fatty acid to the 14273 receptor, which is obtained by using the screening methods or screening kits of the invention, acts as an agent for promoting adrenocorticotropic hormone (ACTH) secretion and is useful as a pharmaceutical such as an agent for preventing/treating, e.g., connective tissue diseases (e.g., chronic articular rheumatism, systemic lupus erythematosus, polymyositis, rheumatic fever, scleroderma), kidney diseases (e.g., nephrosis), respiratory diseases (e.g., bronchial asthma, pulmonary tuberculous pleuritis, sarcoidosis, diffuse interstitial pneumonia), alimentary diseases (e.g., ulcerative colitis, cholestatic acute hepatitis, fulminant hepatitis, chronic hepatitis, cirrhosis), neuromuscular diseases (e.g., encephalomyelitis, peripheral neuritis, multiple sclerosis, myasthenia gravis, facial paralysis), blood diseases (e.g., hemolytic anemia, agranulocytosis, purpura, aplastic anemia, leukemia, malignant lymphoma), endocrine-metabolic diseases (e.g., acute or chronic adrenocortical insufficiency, adrenogenital syndrome, malignant exopthalmos due to thyroid gland disease, ACTH isolated deficiency), skin diseases (e.g., urticaria, eczema, dermatitis, herpes zoster, psoriasis, drug allergy) or anaphylactic shock, etc.

A compound or a salt thereof derived from the above-described compound or salt thereof obtained by the screening can also be used as well.

The compound or the salt thereof obtained by using the screening methods or screening kits of the invention can be used in combination with the above-described concomitant drug. In this case, the time of administration of the compound or the salt thereof obtained using the screening methods or screening kits of the invention and that of above-described the concomitant drug are not limited, and they may be administered simultaneously or with time intervals to the subject to be administered. The dose of the concomitant drug can be appropriately chosen, based on the dose clinically employed. The ratio of the compound or the salt thereof obtained using the screening methods or screening kits of the invention to the concomitant drug can be appropriately chosen according to the subject to be administered, administration route, target disease, clinical conditions, and combination thereof. In the case where the subject to be administered is human, for example, the concomitant drug may be used in an amount of 0.01 to 100 parts by weight per 1 part by weight of, e.g., the agonist.

Where the compound or the salt thereof, which is obtained by using the screening methods or screening kits of the invention, is used as the above-described pharmaceutical composition, the compound or the salt thereof can be prepared into a preparation according to a common manner.

For example, the compound or the salt thereof can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound or the salt, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in these preparations is controlled in such an amount that an appropriate dose is obtained within the specified range given.

As additives miscible with tablets, capsules, etc., a binder such as gelatin, corn starch, tragacanth or gum Arabic, an excipient such as crystalline cellulose, a swelling agent such as corn starch, gelatin, alginic acid, etc., a lubricant such as magnesium stearate, a sweetening agent such as sucrose, lactose or saccharin, a flavoring agent such as peppermint, akamono oil or cherry, and the like, are used. When the dosage unit is in the form of capsules, liquid carriers such as oils and fats may further be contained together with materials of the above-described types. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc., to prepare the pharmaceutical composition. Examples of aqueous liquid for injection include physiological saline, an isotonic solution containing glucose and other auxiliary agents (e.g., D-sorbitol, D-mannitol, sodium chloride, etc.) and the like, which may be used in combination with an appropriate dissolution aid such as an alcohol (e.g., ethanol), a polyalcohol (e.g., propylene glycol, polyethylene glycol), a nonionic surfactant (e.g., polysorbate 80™ and HCO-50), etc. As oily liquid, sesame oil, soybean oil and the like may be used, and it may be used in combination with a dissolution aid such as benzyl benzoate, benzyl alcohol, etc.

Furthermore, the drugs as described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is generally filled in an appropriate ampoule.

Since the thus-obtained pharmaceutical preparation is safe and low toxic, the preparation can be administered to human or mammals (e.g., rats, mouse, rabbits, sheep, pig, bovine, cats, dogs, monkeys, etc.).

The dose of the agonist to the 14273 receptor may vary depending on the subject to be administered, target organ, conditions, methods for administration, etc.; in oral administration, the dose for the patient with diabetes mellitus (as 60 kg of body weight) is generally about 0.1 mg to 100 mg, preferably about 1.0 to 50 mg, and more preferably about 1.0 to 20 mg per day. In parenteral administration, the single dose may vary depending on subject to be administered, target organ, conditions, methods for administration, etc., but it is advantageous to administer the active ingredient intravenously to the patient with diabetes mellitus (as 60 kg of body weight) in a daily dose of about 0.01 to 30 mg, preferably about 0.1 to 20 mg, and more preferably about 0.1 to 10 mg. In the case of other animals, an amount calculated per 60 kg can be administered.

EXAMPLES

The present invention will be further explained in detail below by way of Reference Examples, Examples, Preparation Examples and Test Examples. However, these Examples are mere illustrative examples and do not limit the invention. Further, variations thereof are possible without departing from the scope of the present invention.

"Room temperature" in the following Reference Examples and Examples indicates normally about 10° C. to about 35° C. With respect to %, the same term describing yield indicates mol/mol %, and the same term describing the solvent used in chromatography indicates % by volume, while others indicates % by weight. In proton NMR spectra, those which cannot be identified to be broad, such as OH or NH protons, are not described as data.

Other symbols used in the present text indicate the following meanings.
s: singlet
d: doublet
t: triplet
q: quartet
m: multiplet
br: broad
J: coupling constant
Hz: Hertz
CDCl$_3$: deuterated chloroform
DMSO-d$_6$: deuterated dimethylsulfoxide
$^1$H NMR: proton nuclear magnetic resonance In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.
DNA: deoxyribonucleic acid
cDNA: complementary deoxyribonucleic acid
A: adenine
T: thymine
G: guanine
C: cytosine
U: uracil
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid
*: corresponds to a termination codon
Me: methyl group
Et: ethyl group
Bu: butyl group
Ph: phenyl group
TC: thiazolidine-4(R)-carboxamide group Further, substituents, protective groups, reagents and solvents, which are frequently used throughout the present specification, are shown by the following abbreviations.
Tos: p-toluenesulfonyl
CHO: formyl
Bzl: benzyl
Cl$_2$Bzl: 2,6-dichlorobenzyl
Bom: benzyloxymethyl
Z: benzyloxycarbonyl
Cl-Z: 2-chlorobenzyloxycarbonyl
Br-Z: 2-bromobenzyloxycarbonyl
Boc: t-butoxycarbonyl
DNP: dinitrophenol
Trt: trityl
Bum: t-butoxymethyl
Fmoc: N-9-fluorenylmethoxycarbonyl
HOBt: 1-hydroxybenzotriazole
HOOBt: 3,4-dihydro-3-hydroxy-4-oxo-1,2,3-benzotriazine
HONB: 1-hydroxy-5-norbornene-2,3-dicarboximide
DCC: N,N'-dicyclohexylcarbodiimide
DMF: N,N-dimethylformamide
THF: tetrahydrofuran The sequence identification numbers in the sequence listing of the specification indicates the following sequence.
SEQ ID NO:1
    This shows the amino acid sequence of the human-derived 14273 receptor.
SEQ ID NO:2
    This shows the base sequence of cDNA encoding the human-derived 14273 receptor.
SEQ ID NO:3
    This shows the amino acid sequence of the mouse-derived 14273 receptor.
SEQ ID NO:4
    This shows the base sequence of cDNA encoding the mouse-derived 14273 receptor.
SEQ ID NO:5
    This shows the base sequence of the primer used for the PCR reaction in Reference Example A3.
SEQ ID NO:6
    This shows the base sequence of the primer used for the PCR reaction in Reference Example A3.
SEQ ID NO:7
    This shows the base sequence of the probe used for the PCR reaction in Reference Example A3.
SEQ ID NO:8
    This shows the amino acid sequence of the rat-derived 14273 receptor.
SEQ ID NO:9
    This shows the base sequence of cDNA encoding the rat-derived 14273 receptor.
SEQ ID NO:10
    This shows the base sequence of the primer used for the PCR reaction in Reference Example A4.
SEQ ID NO:11
    This shows the base sequence of the primer used for the PCR reaction in Reference Example A4.
SEQ ID NO:12
    This shows the base sequence of the probe used for the PCR reaction in Reference Example A4.
SEQ ID NO:13
    This shows the base sequence of the primer 1 used for the PCR reaction in Reference Example A5.
SEQ ID NO:14
    This shows the base sequence of the primer 2 used for the PCR reaction in Reference Example A5.

SEQ ID NO:15
This shows the base sequence of the primer used for the PCR reaction in Reference Example A8.
SEQ ID NO:16
This shows the base sequence of the primer used for the PCR reaction in Reference Example A9.
SEQ ID NO:17
This shows the base sequence of the probe used for the PCR reaction in Reference Example A9.
SEQ ID NO:18
This shows the base sequence of the primer used for the PCR reaction in Reference Example A9.
SEQ ID NO:19
This shows the base sequence of the primer used for the PCR reaction in Reference Example A9.
SEQ ID NO:20
This shows the base sequence of the probe used for the PCR reaction in Reference Example A9.

A transformant *Escherichia coli* JM109/pTArat14273 obtained in Reference Example A5 later described has been deposited in International Patent Organism Depositary of National Institute of Advanced Industrial Science and Technology (AIST) of Central 6, 1-1-1 Higashi, Tsukuba, Ibaraki, 305-8566, Japan, since Apr. 18, 2003 under the accession number FERM BP-8361.

Reference Example A1

Construction of Expression Vectors of Human and Mouse 14273 Receptors

The DNA fragments encoding human and mouse 14273 receptors were cloned from MTC Panel (Clontech) by PCR in accordance with the sequence described in WO 2002/67868 and WO 2000/00611, respectively. The resulting DNA fragments were introduced into SalI and SpeI sites of a pAKKO-111 vector to construct each expression plasmid. Continuously, using a known method per se, these expression plasmids were transfected into CHO (dhfr−) cells, the cells into which the expression plasmids were introduced were selected by a medium without containing thymidine to give a stably expressing cells of each receptor.

Reference Example A2

Verification of Reactivity of Fatty Acid to Human and Mouse 14273 Receptors

Figure 2:
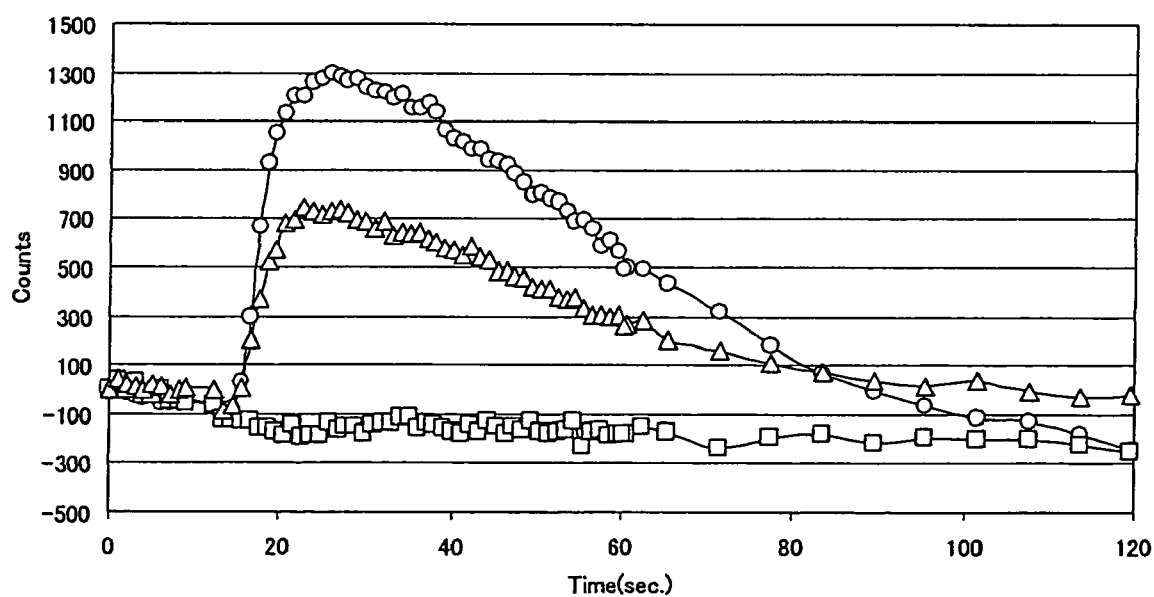
FIG. 2 shows the results of investigation on the change in the intracellular $Ca^{2+}$ concentration when 30 μM of linoleic acid was added. The term Counts on the ordinate indicates the fluorescence intensity indicating the intracellular $Ca^{2+}$ concentration, while the term Time (sec.) on the abscissa indicates the time passage (seconds) after sample addition. Symbol ○ indicates CHO-K1 cells expressing human 14273, symbol Δ indicates CHO-K1 cells expressing mouse 14273, and symbol □ indicates control CHO-K1 cells which do not express 14273.
Figure 3:
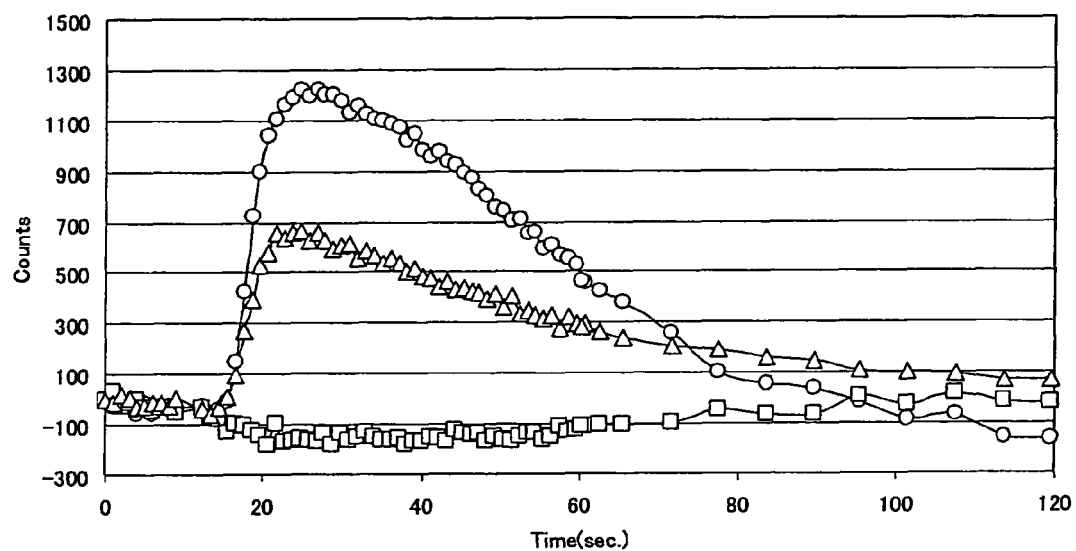
FIG. 3 shows the results of investigation on the change in the intracellular $Ca^{2+}$ concentration when 30 μM of γ-linolenic acid was added. The term Counts on the ordinate indicates the fluorescence intensity indicating the intracellular $Ca^{2+}$ concentration, while the term Time (sec.) on the abscissa indicates the time passage (seconds) after sample addition. Symbol ○ indicates CHO-K1 cells expressing human 14273, symbol Δ indicates CHO-K1 cells expressing mouse 14273, and symbol □ indicates control CHO-K1 cells which do not express 14273.
Figure 4:
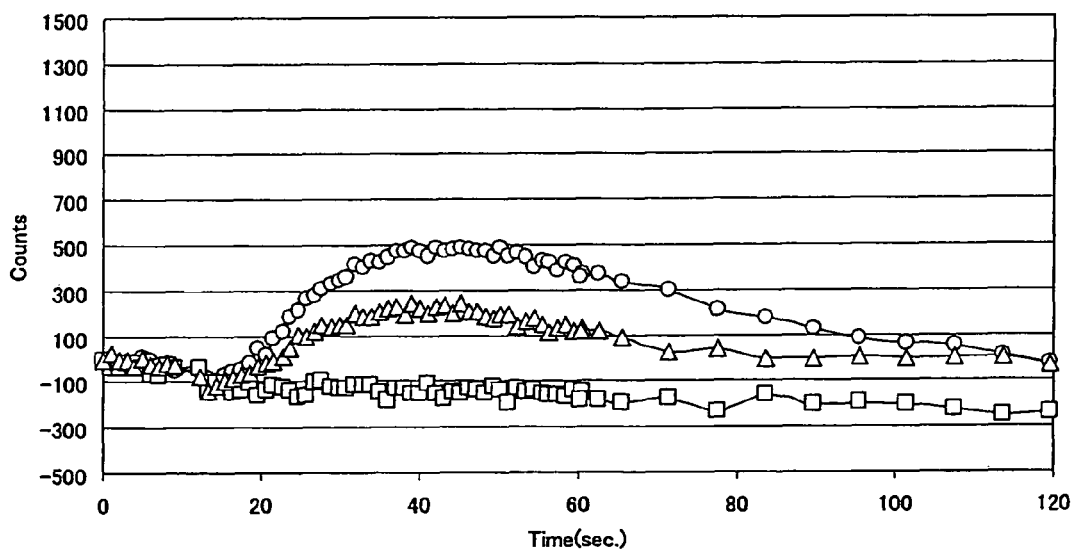
FIG. 4 shows the results of investigation on the change in the intracellular $Ca^{2+}$ concentration when 30 μM of arachidonic acid was added. The term Counts on the ordinate indicates the fluorescence intensity indicating the intracellular $Ca^{2+}$ concentration, while the term Time (sec.) on the abscissa indicates the time passage (seconds) after sample addition. Symbol ○ indicates CHO-K1 cells expressing human 14273, symbol Δ indicates CHO-K1 cells expressing mouse 14273, and symbol □ indicates control CHO-K1 cells which do not express 14273.
Figure 5:
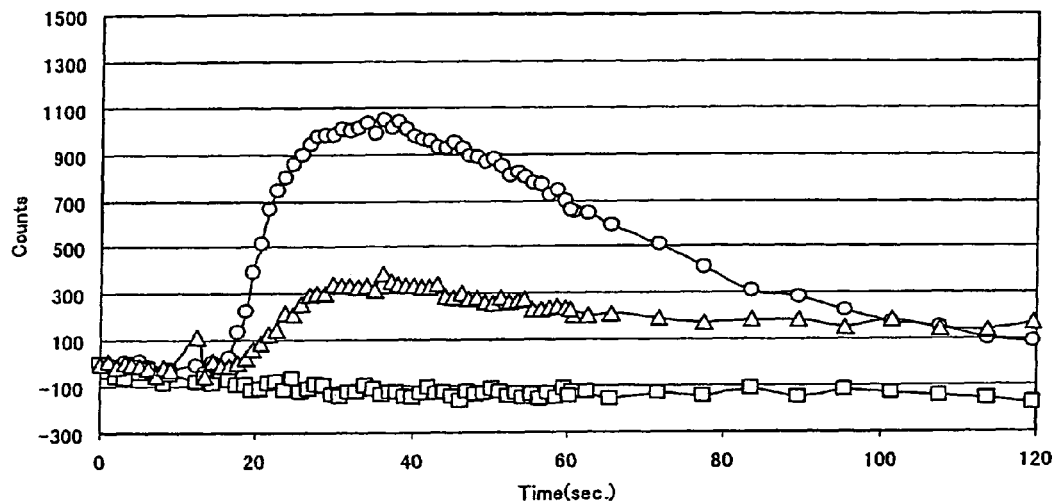
FIG. 5 shows the results of investigation on the change in the intracellular $Ca^{2+}$ concentration when 30 μM of docosahexaenoic acid (DHA) was added. The term Counts on the ordinate indicates the fluorescence intensity indicating the intracellular $Ca^{2+}$ concentration, while the term Time (sec.) on the abscissa indicates the time passage (seconds) after sample addition. Symbol ○ indicates CHO-K1 cells expressing human 14273, symbol Δ indicates CHO-K1 cells expressing mouse 14273, and symbol □ indicates control CHO-K1 cells which do not express 14273.

CHO-K1 cell line was cultured using Ham's F-12 medium (Invitrogen) containing 10% fetal bovine serum (Invitrogen), unless otherwise described. On the day before transfection was conducted, $4.5 \times 10^5$ cells were dispersed per 10 cm$^2$, and cultured at 37° C. for 15 hours by a $CO_2$ incubator adjusted to a $CO_2$ concentration of 5%. Transfection was carried out using a Lipofectamine reagent (Invitrogen) in accordance with the instruction accompanying the reagent. In the case of using a 6-well plate as culture dish, the following steps were performed. First of all, two tubes having a volume of 1.5 ml each were provided, and 100 μl of an Opti-MEM-I medium (Invitrogen) was dispensed to each of the tubes. Next, after adding 1 μg of an expression vector to one tube and adding 6 μl of the Lipofectamine reagent to the other tube, both of them were mixed, and left at rest at room temperature for 20 minutes. A mixture for transfection, in which 800 μl of the Opti-MEM-I medium was added to this solution, was added to the CHO-K1 cells previously washed using the Opti-MEM-I medium, and then the cells were cultured in the $CO_2$ incubator for 6 hours. The cells after culturing were rinsed using PBS (Invitrogen), then detached using a 0.05% trypsin/EDTA solution (Invitrogen), and recovered through centrifugation. The number of the obtained cells was measured, and the cells were diluted to a concentration of $5 \times 10^4$ cells per 100 μl of the medium. This dilution was separately injected to a Black-walled 96-well plate (Costar) in an amount of 100 μl per well, and then the cells were incubated overnight in a $CO_2$ incubator. To the CHO-K1 cells which transiently expressed the receptor during the transfection operation, various test samples were added, and the change in the intracellular calcium concentration during this operation was measured using FLIPR (Molecular Device). In order to measure the change in the intracellular calcium concentration with FLIPR, the following pretreatment was performed. First, Assay Buffer for washing cells was prepared in order to add a fluorescent dye Fluo3-AM (DOJIN) to the cells, or to wash cells immediately before performing the FLIPR assay. To a solution prepared by adding 20 ml of 1 M HEPES (pH 7.4) (DOJIN) to 1000 ml of HBSS (Invitrogen) (hereinafter, HBSS/HEPES solution), 10 ml of a solution prepared by dissolving 710 mg of probenecid (Sigma) in 5 ml of a 1 N NaOH solution, and then further added 5 ml of the HBSS/HEPES solution thereto was added, and this solution was used as the Assay Buffer. Subsequently, 50 μg of Fluo3-AM was dissolved in 21 μl of DMSO (DOJIN), an equivalent of 20% pluronic acid (Molecular Probes) was added, and after mixing, the mixture was added to 10.6 ml of the Assay Buffer containing 105 μl of fetal bovine serum to prepare a fluorescent dye solution. The medium of the transfected CHO-K1 cells was removed, and immediately 100 μl of the fluorescent dye solution was separately injected to each well. The cells were incubated in a $CO_2$ incubator for 1 hour to allow the cells to take up the fluorescent dye. The cells after incubation were washed using the Assay Buffer, and then placed in the FLIPR. The test sample to be added to the receptor expressing CHO-K1 cells was prepared using the Assay Buffer and simultaneously placed in the FLIPR. After performing the pretreatment as described above, the changes in the intracellular calcium concentration after addition of various test samples were measured using FLIPR. As a result, when palmitoleic acid (FIG. 1), linoleic acid (FIG. 2), γ-linolenic acid (FIG. 3), arachidonic acid (FIG. 4) and docosahexaenoic acid (DHA, FIG. 5) were added thereto, it was found that the CHO-K1 cells expressing the human and mouse 14273 receptors specifically responsed (increase in the intracellular calcium concentration). In the CHO-K1 cells into which only the control expression vector was introduced, the above response was not found. That is, it became clear that an endogenous ligand of the human and mouse 14273 receptors is a fatty acid.

Reference Example A3

Distribution of Human 14273 Receptor mRNA Expression

Figure 6:
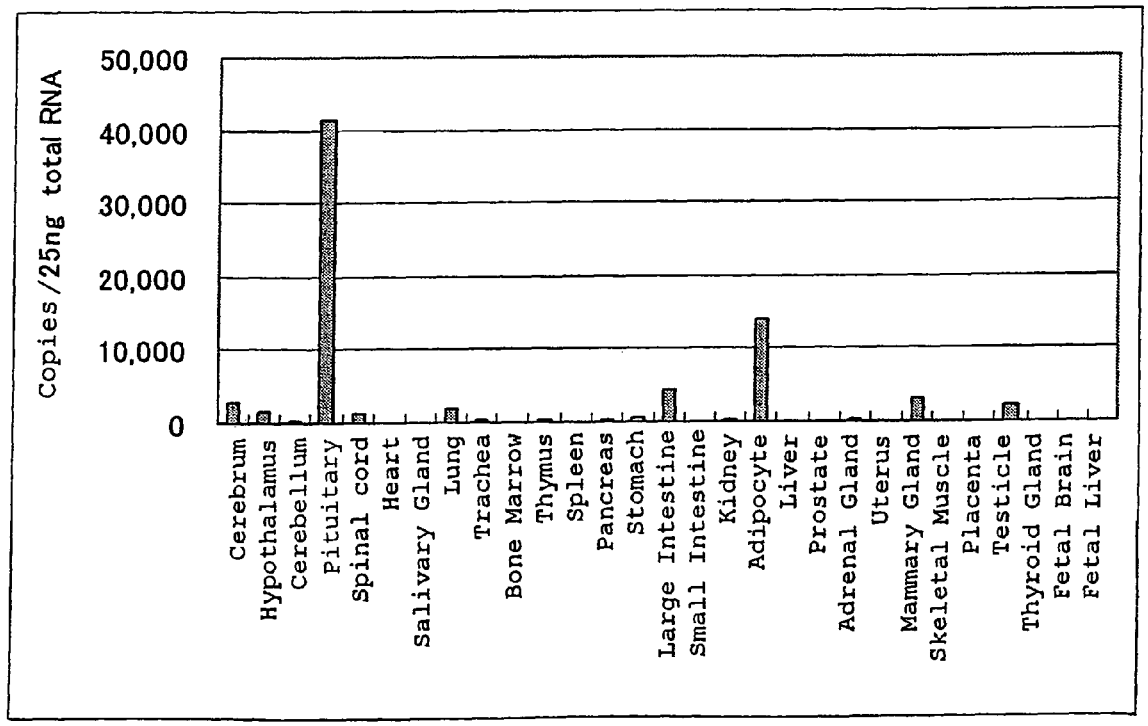
FIG. 6 shows a tissue distribution of 14273 mRNA expression in various human tissues. The term Copies/25 ng total RNA refers to the number of copies per 25 ng of total RNA.

For quantification of the expression level of mRNA, an ABI PRISM 7700 Sequence Detector (Applied Biosystems) was used. For the quantification of the expression level, [5'-GCT-GTGGCATGCTTTTAAAC-3' (SEQ ID NO:5) and 5'-CGCTGTGGATGTCTATTTGC-3' (SEQ ID NO:6)] were used as a primer, and [5'-AGTTCATTTCCAGTACCCTC-CATCAGTGGC-3' (SEQ ID NO:7)] was used as a probe. Based on the base sequence (SEQ ID NO:2) of the human type 14273 receptor, the primers and probe were designed using Primer Express (Applied Biosystems), which is a software exclusive for the ABI PRISM Sequence Detector. For the template cDNA, one obtained by synthesizing through a reverse transcription reaction using, as the random primer, 1 μg of total RNA (Clontech) derived from various human tissues was used. In the reverse transcription reaction, Super Script II (Gibco BRL Life Technologies Inc.) was used as the reverse transcriptase, and the reaction was carried out according to the attached protocols. A reaction solution for the ABI PRISM 7700 Sequence Detector was prepared by mixing 12.5 μl of TaqMan Universal PCR Master Mix (Applied Biosystems), 0.9 μM of each primer, 0.25 μM of the probe and the cDNA solution in 25 μl of distillated water. The reaction of the ABI PRISM 7700 Sequence Detector was repeatedly carried out in 40 cycles of 95° C. for 15 seconds and 60° C. for 1 minute, after 50° C. for 2 minutes and 95° C. for 10 minutes. FIG. 6 shows a distribution of mRNA expression in various human tissues. High expression levels were found in the pituitary, adipose tissues and large intestine.

Reference Example A4

Distribution of Rat 14273 Receptor mRNA Expression

Figure 7:
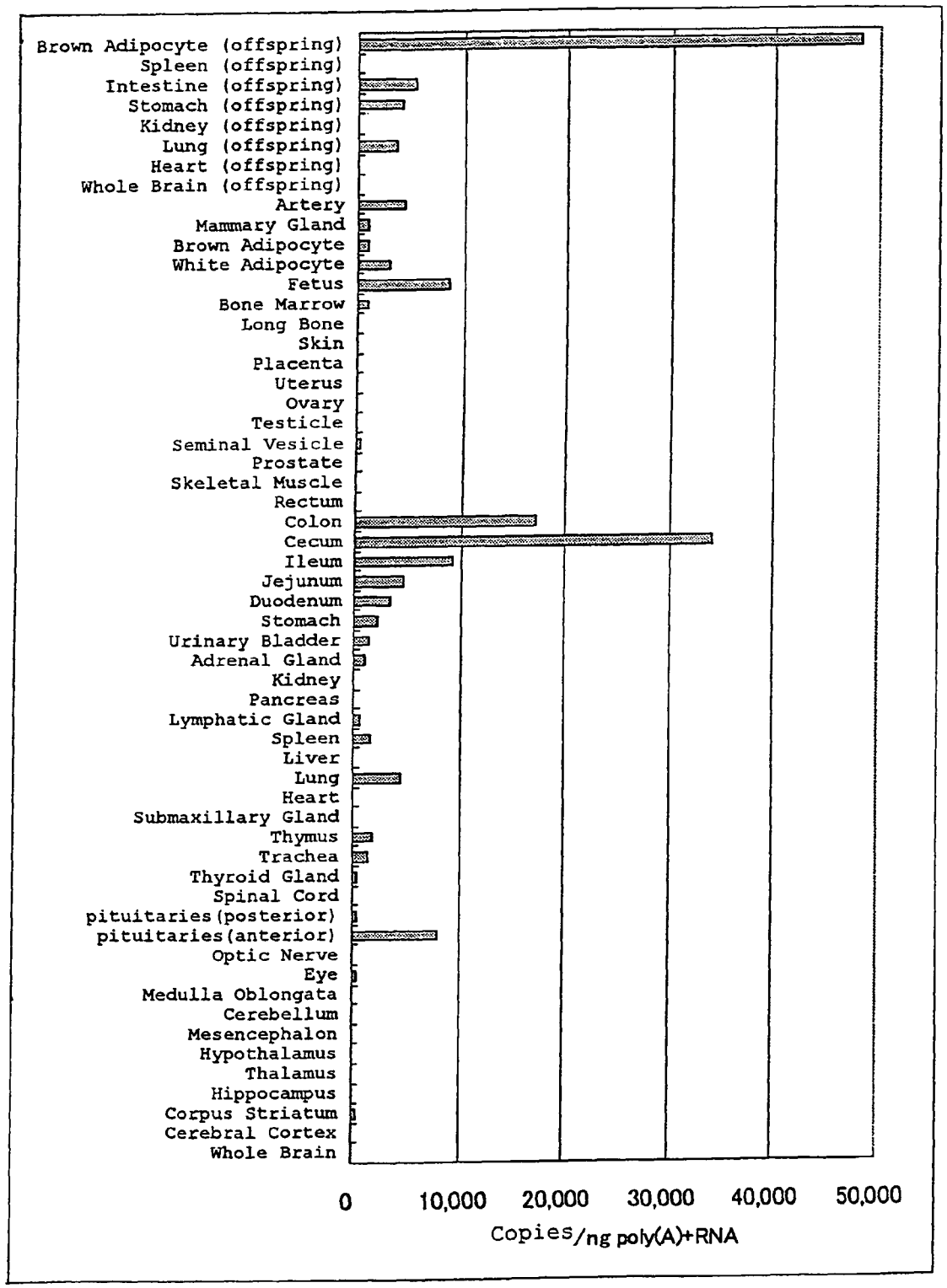
FIG. 7 shows a tissue distribution of 14273 mRNA expression in various rat tissues. The term Copies/ng poly(A)+ RNA refers to the number of copies per ng of poly(A)+ RNA.
Figure 8:
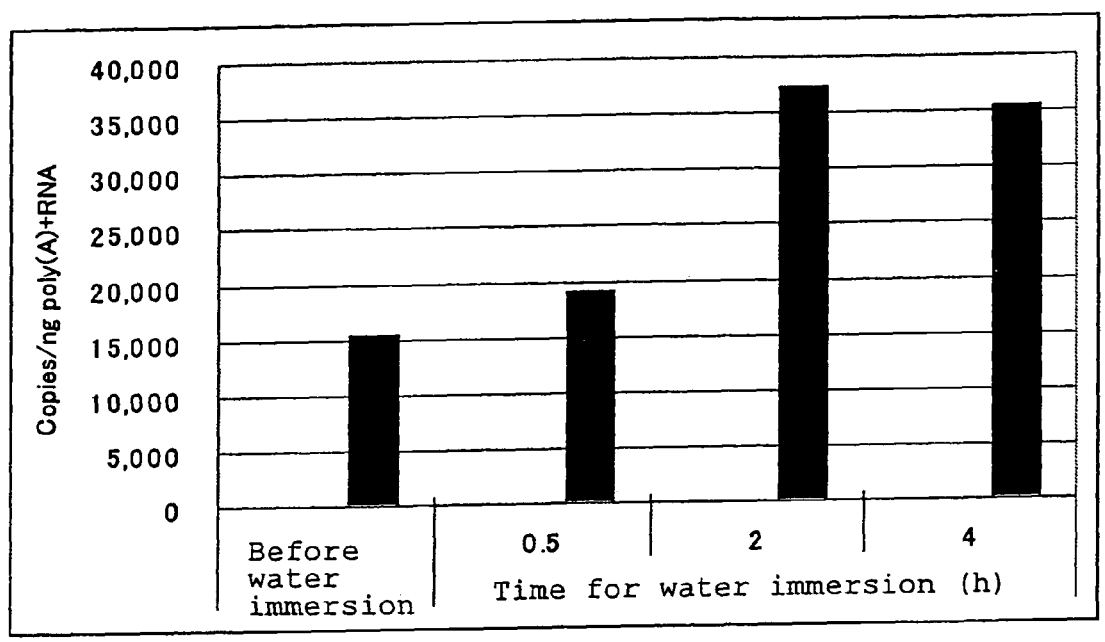
FIG. 8 shows the results of investigation on the increase in 14273 mRNA expression in water immersion restraint stress-induced rat pituitaries. The abscissa indicates the time of water immersion (h). The term Copies/ng poly(A)+ RNA on the ordinate refers to the number of copies per ng of poly(A)+ RNA.

For quantification of the expression level of mRNA, an ABI PRISM 7700 Sequence Detector (Applied Biosystems) was used. For the quantification of the expression level, [5'-GTG-GTGGCCTTCACGTTTG-3' (SEQ ID NO:10), 5'-CGCTC-CTGAACAGCGACAT-3' (SEQ ID NO:11)] were used as a primer, and [5'-CAACTCCGCCCTAAACCCCATTCTGT-3' (SEQ ID NO:12)] was used as a probe. Based on the base sequence (SEQ ID NO:9) of the rat type 14273 receptor, the primers and probe were designed using software program Primer Express (Applied Biosystems) exclusively for the ABI PRISM Sequence Detector. For the template cDNA, various organs were removed from normal rats and rats under water immersion restraint stress, and total RNA was prepared using Isogen (Nippon Gene), and poly(A)$^+$ RNA was prepared by an mRNA purification kit (Pharmacia), according to the respective manuals. 1 μg of the resulting poly(A)$^+$ RNA was treated with DnaseI (Amplification Grade, Gibco BRL Life Technologies Inc.), and then cDNA was synthesized at 42° C. from a fraction of 160 ng thereof using a RNA PCR Kit (Takara) according to the manual. A reaction solution of the ABI PRISM 7700 Sequence Detector was prepared by mixing 12.5 μl of TaqMan Universal PCR Master Mix (Applied Biosystems), 0.9 μM of each primer, 0.25 μM of the probe and the cDNA solution in 25 μl of distillated water. The reaction of the ABI PRISM 7700 Sequence Detector was repeatedly carried out in 40 cycles of 95° C. for 15 seconds and 60° C. for 1 minute, after 50° C. for 2 minutes and 95° C. for 10 minutes. FIG. 7 shows a distribution of mRNA expression in various tissues. High expression levels were found in the pituitary, lung, adipose tissues and intestine. It was cleared that increase in the expression level of 14273 receptor. mRNA was detected in the pituitary of the rat under water immersion restraint stress, and thus, the 14273 receptor was involved with the regulation of the stress (FIG. 8).

Reference Example A5

Cloning of cDNA Encoding Rat-Derived 14273 Receptor and Determination of Base Sequence Thereof PCR was carried out using rat brain DNA as a template, primer 1 (SEQ ID NO: 13) and primer 2 (SEQ ID NO:14). The PCR was carried out using Klentaq DNA Polymerase (Clontech) by cycles of (i) 95° C. for 2 minutes, (ii) 98° C. for 10 seconds, 63° C. for 20 seconds and 72° C. for 1 minute, which was repeated 35 times, and finally, extension reaction at 72° C. for 7 minutes. After the reaction, the amplified product was cloned into a plasmid vector pCR2.1 TOPO (Invitrogen) according to the prescription of a TOPO TA Clonig Kit (Invitrogen). The cloned product was introduced into *Escherichia coli* JM109 (Takara Bio), and the clones having the plasmid were selected in a LB agar medium containing ampicillin. The base sequence of each clone was analysed, and as a result, the cDNA sequence (SEQ ID NO:9) encoding a novel G protein-coupled receptor protein was obtained. The novel receptor protein containing the amino acid sequence (SEQ ID NO:8) derived from the cDNA was designated as rat14273. Further, a transformant was designated as *Escherichia coli* JM109/pTArat14273.

Reference Example A6

Figure 9:
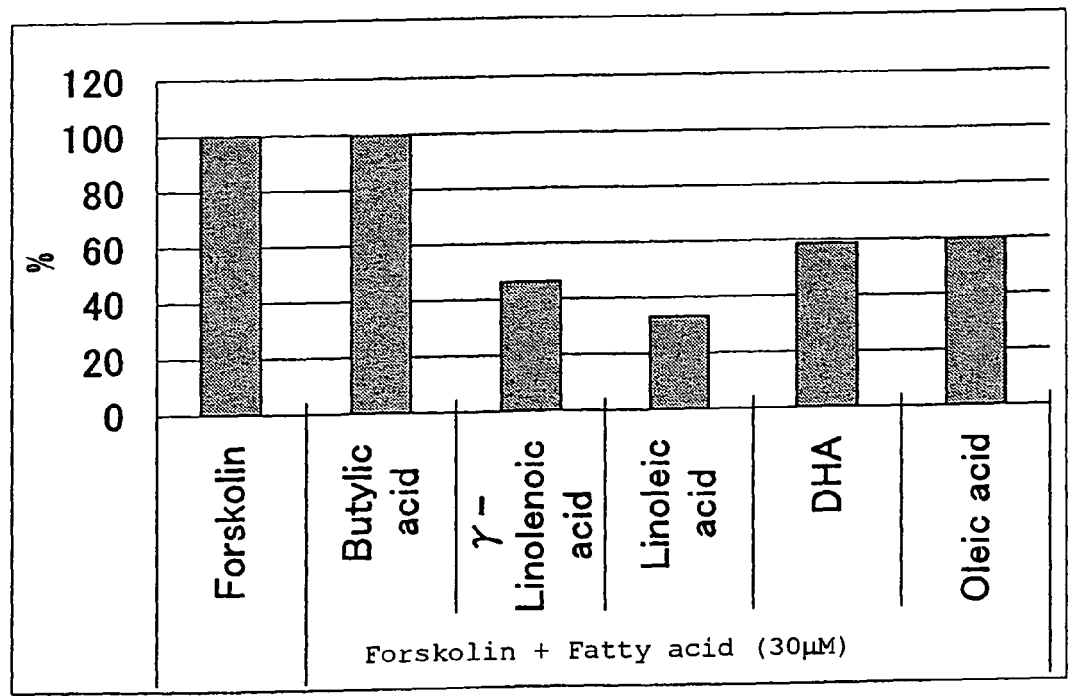
FIG. 9 shows the results of investigation on the effect of fatty acids on the cAMP production by CHO cells expressing human 14273. The term Forskolin indicates no addition of fatty acids in the presence of forskolin, the term Butyric acid indicates the addition of butyric acid (30 μM) in the presence of forskolin, the term γ-Linolenic acid indicates the addition of γ-linolenic acid (30 μM) in the presence of forskolin, the term Linoleic acid indicates the addition of linoleic acid (30 μM) in the presence of forskolin, the term DHA indicates the addition of DHA (30 μM) in the presence of forskolin, and the term Oleic acid indicates the addition of oleic acid (30 μM) in the presence of forskolin. The percentage % on the ordinate indicates the relative values of cAMP production on addition of each fatty acid, as 100% indicates the forskolin-induced cAMP production subtracted with a basal value.

Influence of Fatty Acid on cAMP Production in Human 14273 Receptor Expressing CHO Cells Human 14273 receptor expressing CHO cells were cultured on a 96-well plate for 20 hours in a concentration of 1×10$^5$/well. The cells were washed twice with 100 μl of Assay Buffer (DMEM (Invitrogen) containing 0.1 mM of IBMX (Wako Pure Chemical Industries, Ltd.) and 0.1 mM of Ro-20-1724 (Biomol)). Then, butyric acid, γ-linolenic acid, linoleic acid, DHA and oleic acid (all from SIGMA), which were dissolved in Assay Buffer containing or not containing a 2 μM of Forskolin (Wako Pure Chemical Industries, Ltd.), were added thereto, and the mixture was reacted at 37° C. for 10 minutes. After the reaction, the cells were dissolved according to the prescription of cAMP Screen (ABI), to measure a cAMP level in the cells. As a result, in the case of not containing Forskolin, activity of cAMP production in human 14273 receptor expressing CHO cells was not shown in each fatty acid. On the contrary, in the presence of Forskolin (2 μM), a cAMP production suppressing activity in the human 14273 receptor expressing CHO cells was shown with γ-linolenic acid, linoleic acid, DHA and oleic acid, but the suppressing activity was not shown with butyric acid (FIG. 9). In the control CHO cells which do not express human 14273 receptor, the cAMP production suppressing activity was not found.

Reference Example A7

Figure 10:
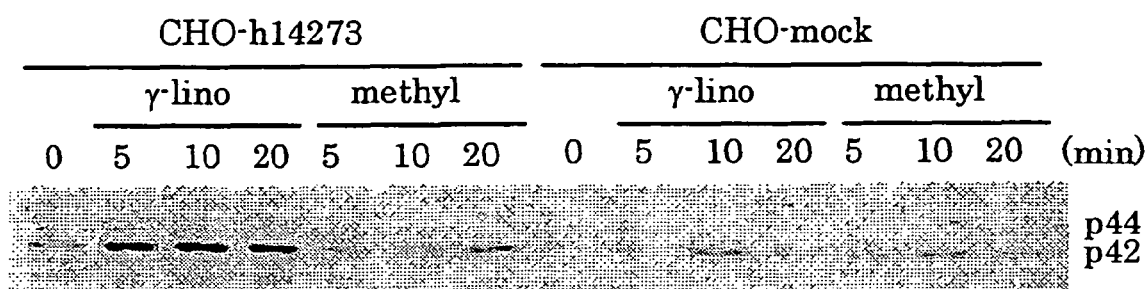
FIG. 10 shows the results of detection of MPA kinase activation in CHO cells expressing human 14273 induced by addition of fatty acids. The term CHO-h14273 indicates the use of CHO cells expressing human 14273, while the term CHO-mock indicates the use of CHO cells not expressing human 14273. The term γ-lino indicates the addition of γ-linolenic acid, while the term methyl indicates the addition of methyl linolate. The Number (min) indicates the time passage (min) after sample addition. The term p44 indicates the band of phosphorylated and activated ERK1. The term p42 indicates the band of phosphorylated and activated ERK2.

Activation of Map Kinase in Human 14273 Receptor Expressing CHO Cells by Adding Fatty Acids Using the expression vector of human 14273 receptor produced in Reference Example A1, the human 14273 receptor expressing CHO cells (CHO-h14273) produced by a known method per se or CHO-mock cells were dispersed at a 6-well plate in a concentration of 3×10$^5$/well. The cells were incubated overnight in a low serum concentration medium (0.5% dialyzed fetal bovine serum was added to a MEM α medium without containing nucleic acid), the medium was changed to a serum-free medium (MEM α medium without containing nucleic acid), and the cells were further incubated overnight. After changing for a new serum-free medium and culturing for 4 hours, 30 μM of various fatty acids were added thereto. After conducting the incubation for 10 minutes, the cells were dissolved and extracted with a sample buffer (TEFCO), and separation was carried out by SDS-PAGE. Next, western blotting was conducted using PhosphoPlus p44/42 MAP kinase (Thr202/Tyr204) Antibody Kit (Cell Signaling Technology, Inc.). As a result, activation of the above protein by phosphorylation of MAP kinase after adding fatty acids was generated only in the human 14273 receptor expressing CHO cells, as shown in FIG. 10.

Reference Example A8

Change in 14273 Receptor Expression in 3T3-L1 Cells During Differentiation to Adipocytes Changes in the 14273 receptor expression in 3T3-L1 cells, a mouse fibroblast-like cell line, during differentiation to adipocytes were analyzed by the following means.

The medium used was Dulbecco's Modified Eagle Medium (DMEM, Invitrogen) containing 4.5 g/l of glucose and 1.5 g/l of $Na_2HCO_3$, to which 10% fetal bovine serum (ThermoTrace), 100 U/ml of penicillin, and 100 µg/ml of streptomycin were added. 3T3-L1 cells cultured to a confluent state in a 75-cm² flask were given stimulation for differentiation induction for 2 days using the aforementioned medium containing 2.5 µM of dexamethazone, 0.5 mM of 3-isobutyl-1-methylxanthine and 10 µg/ml of insulin, and then were cultured in the above-mentioned medium containing 10 µg/ml of insulin. At each culturing phase, the cells were washed two times with PBS(−) and preserved at −80° C. until the time of RNA extraction.

Figure 11:
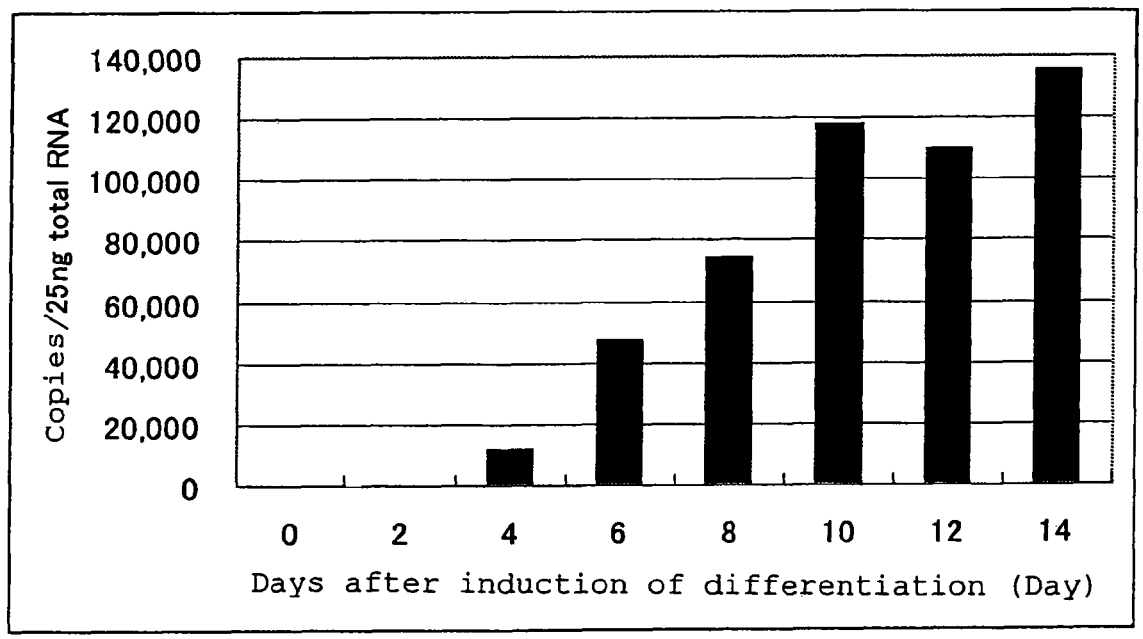
FIG. 11 shows the results of the change of 14273 receptor expression during differentiation of 3T3-L1 cells into adipocytes. The abscissa indicates the number of days (day) after the start of adipocyte differentiation of 3T3-L1 cells. The term Copies/25 ng total RNA on the ordinate indicates the amount of 14273 receptor mRNA expressions in the obtained 3T3-L1 cells, calculated as the number of copies per 25 ng of total RNA.

Total RNA was extracted using Isogen (Nippon Gene). The cDNA was obtained by performing a reaction at 42° C. using 1 µg of RNA, the random primer, and SuperScriptII reverse transcriptase (GIBCO BRL Life Technologies, Inc.) as the reverse transcriptase, according to the accompanied manual, and after the completion of the reaction, the products were precipitated using ethanol and dissolved in 100 µl therein. RT-PCR was carried out using Sequence Detection System Prism 7700 (PE Biosystems), and 5'-TCCGAGTGTC-CCAACAAGACTAC-3' (SEQ ID NO:15) and 5'-GACTC-CACATGATGAAGAAGGAAA-3' (SEQ ID NO:16) were used as the primers for amplification and detection, while 5'-(Fam)CCGCACGCTCTTCCTGCTCATG-(Tamra)-3' (SEQ ID NO:17) was used as the TaqMan probe. The RT-PCR reaction solution was prepared by adding 0.05 µl each of the 100 µM primer solutions, 0.5 µl of 5 µM TaqMan probe, and 0.5 µl of the above-prepared cDNA solution to 12.5 µl of TaqMan Universal PCR Master Mix (PE Biosystems), and then adding distilled water to adjust the total volume of the reaction solution to 25 µl. PCR reaction was carried out by repeating 40 cycles of 95° C. for 15 sec and 60° C. for 1 min, after 50° C. for 2 min, 95° C. for 10 min. The amount of 14273 receptor mRNA expression in the resulting 3T3-L1 cells was calculated as the number of copies per 25 ng of total RNA (FIG. 11).

As a result, the 14273 receptor was expressed only in small amounts before the differentiation induction of 3T3-L1 cells to adipocytes; however, after the differentiation induction, the amount of expression was confirmed to be significantly increased, such that 136027 copies/25 ng total RNA was obtained on the 14$^{th}$ day. From this, it was believed that the 14273 receptor takes an important role in adipocytes.

Reference Example A9

Change in 14273 Receptor Expression Associated with Induction of Adipocyte Differentiation of Rat Primary Cultured Preadipocyte For S.D. rat subcutaneous adipose-derived white preadipocyte, and scapular brown adipose-derived brown preadipocyte (Hokudo), changes in the 14273 receptor expression associated with induction of adipocyte differentiation of the respective primary cultured preadipocytes, were analyzed by the following means.

Figure 12:
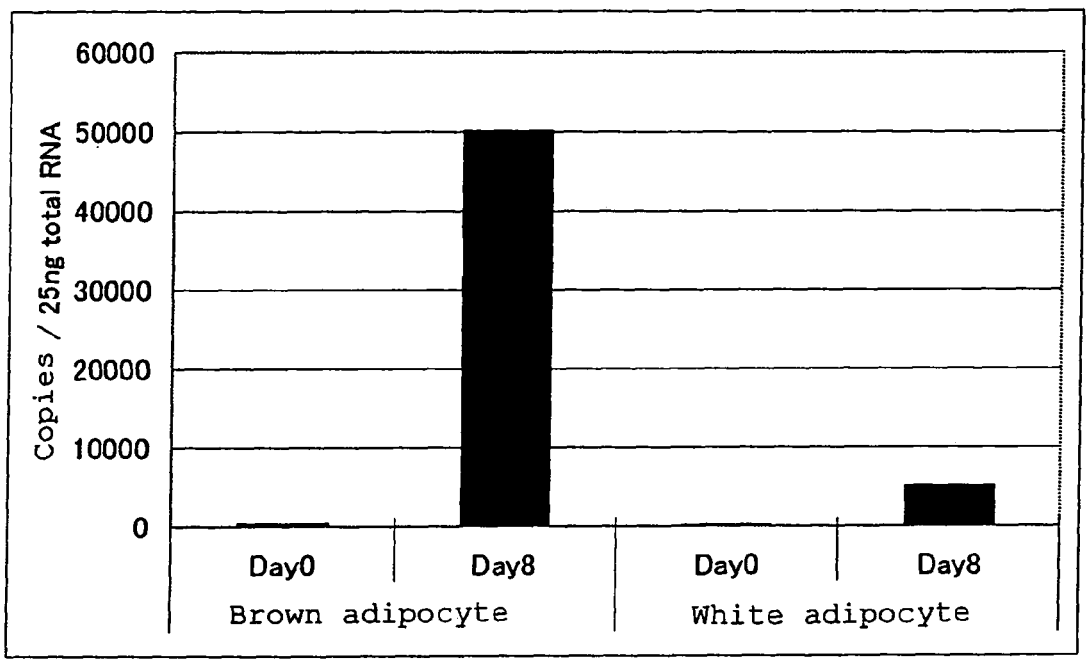
FIG. 12 shows the results of the change of 14273 receptor expression during differentiation of primary cultured rat preadipocytes into adipocytes. The term Day 0 indicates the use of cells before differentiation, while the term Day 8 indicates the use of cells after 8 days of the induction of differentiation. The term Copies/25 ng total RNA on the ordinate indicates the copy number of 14273 receptor mRNA expression in the obtained primary cultured adipocytes per 25 ng of total RNA.

The medium used was Dulbecco's Modified Eagle Medium (DMEM, Invitrogen) containing 4.5 g/l of glucose and 1.5 g/l of $Na_2HCO_3$, to which 10% fetal bovine serum (Hyclone), 100 U/ml of penicillin, and 100 µg/ml of streptomycin were added. each cells cultured to a confluent state in a 25-cm² flask were given stimulation for differentiation induction for 2 days using the aforementioned medium containing 2.5 µM of dexamethazone, 0.5 mM of 3-isobutyl-1-methylxanthine and 10 µg/ml of insulin, and then were cultured for 8 days in the above-mentioned medium containing 10 µg/ml of insulin. Total RNA was extracted from the cells before differentiation induction and the cells after culturing of 8 days after the differentiation induction, using Isogen (Nippon Gene). The cDNA was prepared by reacting 1 µg of total RNA at 42° C. using random primer and SuperScript™ II reverse transcriptase (Invitrogen) as the reverse transcriptase, according to the accompanied manual. After the completion of the reaction, the product was immersed in ethanol and dissolved in 40 µl of Tris-EDTA buffer. RT-PCR was carried out using Sequence Detection System Prism 7700 (PE Biosystems), and 5'-GTGGTGGCCTTCACGTTTG-3' (SEQ ID NO:18) and 5'-CGCTCCTGAACAGCGACAT-3' (SEQ ID NO:19) were used as the primers for amplification and detection, while 5'-(Fam)CAACTCCGCCCTAAACCCCAT-TCTGT-(Tamra)-3' (SEQ ID NO:20) was used as the TaqMan probe. The RT-PCR reaction solution was prepared by adding 0.225 µl each of the 100 µM primer solutions, 1.25 µl of 5 µM TaqMan probe, and 1 µl of the above-prepared cDNA solution to 12.5 µl of TaqMan Universal PCR Master Mix (Applied Biosystems), and then adding distilled water to adjust the total volume of the reaction solution to 25 µl. PCR reaction was carried out by repeating 40 cycles of 95° C. for 15 sec and 60° C. for 1 min, after 50° C. for 2 min and 95° C. for 10 min. The amount of 14273 receptor mRNA expression in the resulting primary cultured adipocytes was calculated as the number of copies per 25 ng of total RNA (FIG. 12).

As a result, the 14273 receptor was expressed only in small amounts before the differentiation in the primary cultured white preadipocyte and primary cultured brown preadipocyte; however, after the differentiation induction, the amount of expression was confirmed to be significantly increased. From this, it was believed that the 14273 receptor takes an important role in adipocytes.

Reference Example A10

Inhibitory Activity of Fatty Acids Against Adrenocorticotrophic Hormone (ACTH) Secretion from AtT-20 Cells The effect of free fatty acid on ACTH secretion in AtT-20 cells, a mouse pituitary corticotroph cell line, was analyzed by the following means.

First, an adhesive substrain from AtT/20 cell line (floatability) was cloned by the contact selection method using a poly-D-Lysine-coated flask. The medium used was Dulbecco's Modified Eagle Medium (DMEM, Invitrogen) containing 4.5 g/l of glucose, to which 10% fetal bovine serum (ThermoTrace), 100 U/ml of penicillin, and 100 µg/ml of streptomycin were added. This adhesive AtT/20 substrain cells were dispersed on a poly-D-Lysine-coated 96-well plate at a concentration of $4 \times 10^4$ cells/well/100 µl, and cultured for two nights to provide for the assay. The buffer to be used for the assay was Dulbecco's Modified Eagle Medium (DMEM, Invitrogen) containing 25 mM of HEPES (pH 7.1) and 1 g/l of glucose. The cells were washed twice with this buffer, and 100 ml of a buffer containing a predetermined concentration of aliphatic acid was added thereto. Then cells were preincubated in a $CO_2$ incubator at 37° C. for 1 hour. Next, the medium was exchanged with a buffer containing fatty acids in the co-presence of 10 nM of corticotrophic hormone releasing factor (CRF), and the cells were incubated in the $CO_2$ incubator at 37° C. for 90 minutes. After 90 minutes, the plate was mildly agitated and then centrifuged at room temperature at 1200 rpm for 5 minutes, thus recovering 50 ml of a sample from the middle layer. During the above-described experimental process, the fatty acids were conjugated with bovine serum albumin (BSA, Sigma) at a molar ratio of BSA:FFA=4:1 throughout the process. The same amount of BSA was also added to the medium as treated only with the buffer or only with CRF. The recovered samples were used to measure the ACTH concentrations using an ACTH measuring kit (Mitsubishi Medical ACTH IRMA "Yuka").

Figure 13:
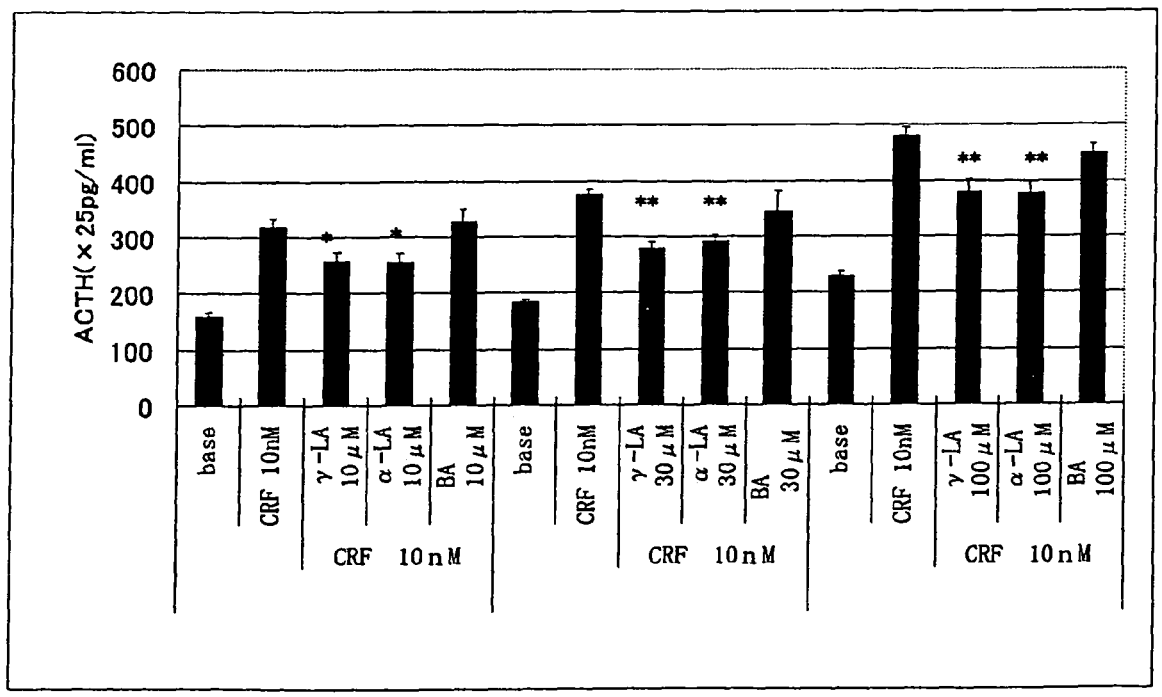
FIG. 13 shows the results of the effect of fatty acids on the inhibition of the corticotrophin releasing factor (CRF)-induced ACTH secretion from AtT-20 cells. The term base indicates no addition of fatty acids in the absence of CRF. The term CRF indicates no addition of fatty acids in the presence of CRF (10 nM). The terms γ-LA, α-LA and BA indicate addition of γ-linolenic acid, α-linolenic acid and butyric acid, respectively, in the presence of CRF (10 nM). The term ACTH (×25 pg/ml) indicates the amount of ACTH secretion. Average+standard deviation (n=8). **, p<0.01; *, p<0.05 (Student's t test).

As a result, significant suppression of CRF-induced ACTH secretion by γ-linolenic acid (γ-LA) and α-linolenic acid (α-LA) was verified, as shown in FIG. 13. On the other hand, butyric acid (BA) which does not exhibit an agonistic activity against 14273 receptor did not exhibit significant inhibition of CRF-induced ACTH secretion.

Reference Example 1

Methyl 4-(phenylmethoxy)benzenepropanoate

To a solution of ice-cooled methyl 4-hydroxybenzenepropanoate (0.70 g, 3.9 mmol), benzyl alcohol (0.48 mL, 4.7 mmol) and triphenylphosphine (1.2 g, 4.7 mmol) in tetrahydrofuran (5 mL) was added dropwise diethyl azodicarboxylate (0.73 mL, 4.7 mmol), and the mixture was stirred for 2 hours with ice cooling. To the reaction solution was added water, and the reaction mixture was extracted with ethyl acetate. The extract was washed with water, and then concentrated under reduced pressure. The residue was purified with silica gel column chromatography (hexane/ethyl acetate=17:3) to give the title compound (0.62 g, yield 59%) as powders.

1H NMR (CDCl3) δ 2.59 (2H, t, J=7.5 Hz), 2.89 (2H, t, J=7.5 Hz), 3.66 (3H, s), 5.04 (2H, s), 6.90 (2H, d, J=8.6 Hz), 7.11 (2H, d, J=8.6 Hz), 7.29-7.44 (5H, m).

Reference Example 2

Methyl 4-[(3-bromophenyl)methoxy]benzenepropanoate

In the same manner as in Reference Example 1, the title compound as white powders was obtained from methyl 4-hydroxybenzenepropanoate and 3-bromobenzyl alcohol. Yield 68%.

$^1$H NMR (CDCl$_3$) δ 2.60 (2H, t, J=8.0 Hz), 2.90 (2H, t, J=8.0 Hz), 3.66 (3H, s), 5.00 (2H, s), 6.88 (2H, d, J=8.6 Hz), 7.12 (2H, d, J=8.6 Hz), 7.21-7.27 (1H, m), 7.34 (1H, d, J=7.5 Hz), 7.45 (1H, d, J=7.8 Hz), 7.59 (1H, s).

Reference Example 3

Methyl 4-([1,1'-biphenyl]-3-ylmethoxy)benzenepropanoate

Methyl 4-[(3-bromophenyl)methoxy]benzenepropanoate (0.60 g, 1.7 mmol), phenyl boronate (0.25 g, 2.1 mmol) and sodium carbonate (0.55 g, 5.2 mmol) were dissolved in toluene-methanol-water (5:1:1, 35 mL), the mixture was purged with argon, and then tetrakistriphenylphosphine palladium (99 mg, 0.086 mmol) was added thereto. The reaction solution was heated under reflux overnight under argon atmosphere. The reaction solution was cooled, and then water was added to the reaction solution, followed by extraction with ethyl acetate. The extract was washed with water, dried and then concentrated. The residue was purified with silica gel column chromatography (hexane/ethyl acetate=18:1) to give the title compound (0.55 g, yield 92%) as white powders.

$^1$H NMR (CDCl$_3$) δ 2.60 (2H, t, J=8.0 Hz), 2.90 (2H, t, J=8.0 Hz), 3.66 (3H, s), 5.10 (2H, s), 6.92 (2H, d, J=8.5 Hz), 7.12 (2H, d, J=8.5 Hz), 7.35-7.47 (5H, m), 7.54-7.65 (4H, m).

Reference Example 4

Methyl 4-(2-phenylethoxy)benzenepropanoate

In the same manner as in Reference Example 1, the title compound was obtained from methyl 4-hydroxybenzenepropanoate and phenethyl alcohol. Yield 89%.

Oil.

$^1$H NMR (CDCl$_3$) δ 2.58 (2H, t, J=7.5 Hz), 2.88 (2H, t, J=7.5 Hz), 3.08 (2H, t, J=7.1 Hz), 4.14 (2H, t, J=7.1 Hz), 6.81 (2H, d, J=8.6 Hz), 7.09 (2H, d, J=8.6 Hz), 7.20-7.34 (5H, m).

Reference Example 5

4-(2-Phenylethoxy)benzenepropanoic acid

To a solution of methyl 4-(2-phenylethoxy)benzenepropanoate (0.65 g, 2.3 mmol) in methanol (3 mL) was added a 2 N aqueous sodium hydroxide solution (3 mL), and the mixture was stirred at 50° C. for 1 hour. To the reaction solution was added 2 N hydrochloric acid (2.5 mL), and extracted with ethyl acetate. The extract was washed with water, and then concentrated under reduced pressure. The residue was recrystallized from ethyl acetate-hexane to give the title compound (0.50 g, yield 81%).

Melting point 91-92° C.

$^1$H NMR (CDCl$_3$) δ 2.63 (2H, t, J=7.5 Hz), 2.89 (2H, t, J=7.5 Hz), 3.08 (2H, t, J=7.2 Hz), 4.15 (2H, t, J=7.2 Hz), 6.82 (2H, d, J=8.6 Hz), 7.10 (2H, d, J=8.6 Hz), 7.20-7.34 (5H, m).

Reference Example 6

4-([1,1'-Biphenyl]-3-ylmethoxy)benzenepropanoic acid

In the same manner as in Reference Example 5, the title compound was obtained from methyl 4-([1,1'-biphenyl]-3-ylmethoxy)benzenepropanoate. Yield 48%.

Melting point 125-126° C. (recrystallization from ethyl acetate-hexane).

$^1$H NMR (CDCl$_3$) δ 2.65 (2H, t, J=7.9 Hz), 2.91 (2H, t, J=7.9 Hz), 5.10 (2H, s), 6.93 (2H, d, J=8.6 Hz), 7.13 (2H, d, J=8.6 Hz), 7.30-7.47 (5H, m), 7.50-7.61 (3H, m), 7.65 (1H, s).

Reference Example 7

Methyl 4-[(3-phenoxyphenyl)methoxy]benzenepropanoate

In the same manner as in Reference Example 1, the title compound was obtained from methyl 4-hydroxybenzenepropanoate and 3-phenoxybenzyl alcohol. Yield 66%.

Oil.

$^1$H NMR (CDCl$_3$) δ 2.59 (2H, t, J=8.1 Hz), 2.89 (2H, t, J=8.1 Hz), 3.66 (3H, s), 5.01 (2H, s), 6.90-7.20 (9H, m), 7.20-7.36 (4H, m).

Reference Example 8

4-[(3-Phenoxyphenyl)methoxy]benzenepropanoic acid

In the same manner as in Reference Example 5, the title compound was obtained from methyl 4-[(3-phenoxyphenyl)methoxy]benzenepropanoate. Yield 50%.

Melting point 94-95° C. (recrystallization from ethyl acetate-hexane).

$^1$H NMR (CDCl$_3$) δ 2.64 (2H, t, J=7.9 Hz), 2.90 (2H, t, J=7.9 Hz), 5.01 (2H, s), 6.86-6.90 (2H, m), 6.88-6.98 (1H, m), 7.00-7.03 (2H, m), 7.08-7.17 (5H, m), 7.30-7.36 (3H, m).

Reference Example 9

2-(4-Bromophenoxy)-2,3-dihydro-1H-indene

In the same manner as in Reference Example 1, the title compound was obtained from 2-indanol and 4-bromophenol. Yield 59%.

Melting point 83-84° C. (recrystallization from ethyl acetate-diisopropyl ether).

$^1$H NMR (CDCl$_3$) δ 3.13 (1H, d, J=3.0 Hz), 3.18 (1H, d, J=3.0 Hz), 3.33 (1H, d, J=6.2 Hz), 3.39 (1H, d, J=6.2 Hz), 5.09-5.15 (1H, m), 6.78 (2H, d, J=9.0 Hz), 7.16-7.26 (4H, m), 7.37 (2H, d, J=9.0 Hz).

Reference Example 10

Methyl (E)-3-[4-[(2,3-dihydro-1H-inden-2-yl)oxy]phenyl]-2-propenoate

To a solution of 2-(4-bromophenoxy)-2,3-dihydro-1H-indene (1.4 g, 4.7 mmol) in N,N-dimethylformamide (4.7 mL) were added sodium hydrogen carbonate (1.0 g, 12 mmol), methyl acrylate (0.86 mL, 9.5 mmol), tetrabutylammonium chloride (2.0 g, 7.1 mmol) and palladium acetate (31 mg, 0.14 mmol), and the mixture was stirred at 100° C. for 24 hours. The reaction solution was returned to room temperature and then filtered. Water was added thereto, and the reaction mixture was extracted with ethyl acetate. The extract was washed with saturated brine, then dried over anhydrous magnesium sulfate and concentrated. The residue was recrystallized from ethyl acetate-hexane to give the title compound (0.96 g, yield 69%).

Melting point 115-116° C.

$^1$H NMR (CDCl$_3$) δ 3.16 (1H, d, J=2.9 Hz), 3.21 (1H, d, J=2.9 Hz), 3.37 (1H, d, J=6.4 Hz), 3.43 (1H, d, J=6.4 Hz), 3.80 (3H, s), 5.17-5.23 (1H, m), 6.31 (1H, d, J=16 Hz), 6.91 (2H, d, J=9.0 Hz), 7.17-7.27 (4H, m), 7.47 (2H, d, J=9.0 Hz), 7.65 (1H, d, J=16 Hz).

Reference Example 11

1-[(4-Bromo-2,6-difluorophenyl)oxy]-2,3-dihydro-1H-indene

In the same manner as in Reference Example 1, the title compound was obtained from 1-indanol and 4-bromo-2,6-difluorophenol. Yield 74%.

Melting point 46-46° C. (recrystallization from ethyl acetate).

$^1$H NMR (CDCl$_3$) δ 2.34-2.40 (2H, m), 2.83-2.92 (1H, m), 3.20-3.31 (1H, m), 5.64 (1H, t, J=4.4 Hz), 7.04-7.13 (2H, m), 7.17-7.22 (1H, m), 7.28-7.32 (3H, m).

Reference Example 12

Methyl (E)-3-[4-[(2,3-dihydro-1H-inden-1-yl)oxy]-3,5-difluorophenyl]-2-propenoate In the same manner as in Reference Example 10, the title compound was obtained from 1-[(4-bromo-2,6-difluorophenyl)oxy]-2,3-dihydro-1H-indene. Yield 40%.

Melting point 74-75° C. (recrystallization from ethyl acetate-diisopropyl ether).

$^1$H NMR (CDCl$_3$) δ 2.37-2.43 (2H, m), 2.84-2.93 (1H, m), 2.32-3.32 (1H, m), 3.81 (3H, s), 5.74 (1H, t, J=4.5 Hz), 6.34 (1H, d, J=16 Hz), 7.03-7.12 (2H, m), 7.16-7.23 (1H, m), 7.28-7.35 (2H, m), 7.53 (1H, d, J=16 Hz).

Reference Example 13

Methyl 4-[(2,3-dihydro-1H-inden-1-yl)oxy]-3,5-difluorobenzenepropanoate

To a mixture of methyl (E)-3-[4-[(2,3-dihydro-1H-inden-1-yl)oxy]-3,5-difluorophenyl]-2-propenoate (0.52 g, 1.6 mmol), samarium (1.2 g, 7.9 mmol), tetrahydrofuran (3 mL) and methanol (7 mL) was added iodine (0.80 g, 3.2 mmol), and the reaction mixture was stirred at room temperature overnight. 1 N Hydrochloric acid (20 mL) was added thereto, and the mixture was stirred for 20 minutes, then diluted with water and extracted with ethyl acetate. The extract was washed with water, dried over anhydrous sodium sulfate and concentrated. The residue was purified with silica gel column chromatography (hexane/ethyl acetate=10:1) to give the title compound. Yield 60%.

Oil.

$^1$H NMR (CDCl$_3$) δ 2.34-2.40 (2H, m), 2.61 (2H, t, J=7.5 Hz), 2.81-2.91 (3H, m), 3.20-3.30 (1H, m), 5.61 (1H, t, J=4.4 Hz), 6.72-6.78 (2H, m), 7.16-7.22 (1H, m), 7.29-7.31 (2H, m), 7.34 (1H, d, J=7.4 Hz).

Reference Example 14

3,5-Difluoro-4-[(2,3-dihydro-1H-inden-1-yl)oxy]benzenepropanoic acid

In the same manner as in Reference Example 5, the title compound was obtained from methyl 3,5-difluoro-4-[(2,3-dihydro-1H-inden-1-yl)oxy]benzenepropanoate. Yield 75%.

Melting point 88-89° C. (recrystallization from ethyl acetate-hexane).

$^1$H NMR (CDCl$_3$) δ 2.34-2.40 (2H, m), 2.67 (2H, t, J=7.5 Hz), 2.81-2.92 (3H, m), 3.20-3.30 (1H, m), 5.62 (1H, t, J=4.4 Hz), 6.72-6.80 (2H, m), 7.17-7.23 (1H, m), 7.29-7.36 (3H, m).

Reference Example 15

Methyl 3-chloro-4-[(2,3-dihydro-1H-inden-1-yl)oxy]benzenepropanoate

In the same manner as in Reference Example 1, the title compound was obtained from methyl 3-chloro-4-hydroxybenzenepropanoate and 2,3-dihydro-1H-indan-1-ol. Yield 91%.

Oil.

¹H NMR (CDCl₃) δ 2.20-2.31 (1H, m), 2.50-2.60 (1H, m), 2.61 (2H, t, J=7.9 Hz), 2.87-2.97 (3H, m), 3.13-3.23 (1H, m), 3.68 (3H, s), 5.71 (1H, dd, J=4.9 Hz, 6.6 Hz), 7.01-7.08 (2H, m), 7.22-7.31 (4H, m), 7.43 (1H, d, J=7.3 Hz).

Reference Example 16

3-Chloro-4-[(2,3-dihydro-1H-inden-1-yl)oxy]benzenepropanoic acid

In the same manner as in Reference Example 5, the title compound was obtained from methyl 3-chloro-4-[(2,3-dihydro-1H-inden-1-yl)oxy]benzenepropanoate. Yield 56%.

¹H NMR (CDCl₃) δ 2.20-2.31 (1H, m), 2.50-2.61 (1H, m), 2.67 (2H, t, J=7.7 Hz), 2.86-2.99 (3H, m), 3.12-3.22 (1H, m), 5.71 (1H, dd, J=5.0 Hz, 6.5 Hz), 7.01-7.09 (2H, m), 7.20-7.31 (4H, m), 7.43 (1H, d, J=7.3 Hz).

Reference Example 17

Methyl 4-([1,1'-biphenyl]-3-ylmethoxy)-3-chlorobenzenepropanoate

In the same manner as in Reference Example 3, the title compound was obtained from methyl 4-[(3-bromophenyl)methoxy]-3-chlorobenzenepropanoate and phenyl boronate. Yield 44%.

Oil.

¹H NMR (CDCl₃) δ 2.59 (2H, t, J=7.8 Hz), 2.87 (2H, t, J=7.8 Hz), 3.66 (3H, s), 5.19 (2H, s), 6.91 (1H, d, J=8.4 Hz), 7.02 (1H, dd, J=8.4 Hz, 2.1 Hz), 7.24 (1H, d, J=2.1 Hz), 7.33-7.38 (1H, m), 7.42-7.49 (4H, m), 7.54-7.62 (3H, m), 7.68 (1H, m).

Reference Example 18

4-([1,1'-Biphenyl]-3-ylmethoxy)-3-chlorobenzenepropanoic acid

In the same manner as in Reference Example 5, the title compound was obtained from methyl 4-([1,1'-biphenyl]-3-ylmethoxy)-3-chlorobenzenepropanoate. Yield 54%.

Melting point 77.0-77.5° C. (recrystallization from diisopropyl ether-hexane).

¹H NMR (CDCl₃) δ 2.64 (2H, t, J=7.8 Hz), 2.88 (2H, t, J=7.8 Hz), 5.19 (2H, s), 6.92 (1H, d, J=8.4 Hz), 7.03 (1H, dd, J=8.4 Hz, 2.1 Hz), 7.25-7.26 (1H, m), 7.32-7.38 (1H, m), 7.42-7.48 (4H, m), 7.53-7.62 (3H, m), 7.68 (1H, m).

Reference Example 19

Methyl 4-[(1,2,3,4-tetrahydronaphthalen-1-yl)oxy]benzenepropanoate

In the same manner as in Reference Example 1, the title compound as white powders was obtained from methyl 4-hydroxybenzenepropanoate and 1,2,3,4-tetrahydro-1-naphthol. Yield 63%.

¹H NMR (CDCl₃) δ 1.70-1.75 (1H, m), 1.98-2.16 (3H, m), 2.62 (2H, t, J=8.2 Hz), 2.77-2.87 (2H, m), 2.92 (2H, t, J=8.2 Hz), 3.68 (3H, s), 5.23 (1H, t, J=4.2 Hz), 6.95 (2H, d, J=8.6 Hz), 7.11-7.16 (3H, m), 7.21 (2H, dt, J=2.2 Hz, 6.8 Hz) 7.38-7.36 (1H, m).

Reference Example 20

4-[(1,2,3,4-Tetrahydronaphthalen-1-yl)oxy]benzenepropanoic acid

In the same manner as in Reference Example 5, the title compound was obtained from methyl 4-[(1,2,3,4-tetrahydronaphthalen-1-yl)oxy]benzenepropanoate. Yield 51%.

Melting point 69-70° C. (recrystallization from diisopropyl ether-hexane).

¹H NMR (CDCl₃) δ 1.70-1.85 (1H, m), 1.98-2.16 (3H, m), 2.74-2.89 (2H, m), 2.67 (2H, t, J=7.4 Hz), 2.93 (2H, t, J=7.4 Hz), 5.33 (1H, t, J=4.1 Hz), 6.96 (2H, d, J=8.6 Hz), 7.14-7.24 (5H, m), 7.36-7.39 (1H, m).

Reference Example 21

2,3-Dihydro-2,2-dimethyl-1H-inden-1-one

To a 60% solution of sodium hydride (2.7 g, 68 mmol) in 1,2-dimethoxyethane (30 mL) was slowly added 2,3-dihydro-1H-inden-1-one (3.0 g, 23 mmol). The mixture was stirred at room temperature for 10 minutes, and then methyl iodide (5.7 ml, 91 mmol) was added thereto and the reaction mixture was stirred at room temperature for 1 hour. To the reaction solution was added water, and the reaction mixture was extracted with ethyl acetate. The extract was washed with water, and then concentrated under reduced pressure. The residue was purified with silica gel column chromatography (hexane) to give the title compound (4.0 g, yield 99%).

¹H NMR (CDCl₃) δ 1.24 (6H, s), 3.01 (2H, s), 7.35-7.44 (2H, m), 7.59 (1H, dt, J=1.2 Hz, 7.6 Hz), 7.76 (1H, d, J=7.8 Hz).

Reference Example 22

2,3-Dihydro-5-(phenylmethoxy)-1H-inden-1-one

To a solution of 2,3-dihydro-5-hydroxy-1H-inden-1-one (1.0 g, 6.2 mmol), benzyl alcohol (0.65 g, 5.6 mol) and tributylphosphine (1.7 g, 8.4 mmol) in tetrahydrofuran (30 mL) was added 1,1'-(azocarbonyl)dipiperidine (2.1 g, 8.4 mmol), and the mixture was stirred at room temperature for 16 hours. Insolubles were filtered off, and then the filtrate was concentrated. The residue was purified with silica gel column chromatography (hexane/ethyl acetate=10:1) to give the title compound (1.3 g, yield 97%) as powders.

¹H NMR (CDCl₃) δ 2.67 (2H, t, J=6.1 Hz), 3.08 (2H, t, J=6.1 Hz), 5.15 (2H, s), 6.97 (2H, s), 7.30-7.45 (5H, m), 7.70 (1H, d, J=9.1 Hz).

Reference Example 23

2,3-Dihydro-5-(phenylmethoxy)-1H-inden-1-ol 2,3-Dihydro-5-(phenylmethoxy)-1H-inden-1-one (1.3 g, 5.46 mmol) was dissolved in a mixed solution of tetrahydrofuran (20 mL) and methanol (10 mL). Sodium borohydride (0.41 g, 11 mmol) was added thereto, and then the mixture was stirred at room temperature for 2 hours. To the reaction solution was added water, and the reaction mixture was extracted with ethyl acetate. The extract was dried, and then concentrated under reduced pressure. The residue was purified with silica gel column chromatography (hexane/ethyl acetate=3:1) to give the title compound (1.16 g, yield 89%) as white powders.

$^1$H NMR (CDCl$_3$) δ 1.70 (1H, d, J=5.0 Hz), 1.85-2.05 (1H, m) 2.40-2.55 (1H, m), 2.70-2.85 (1H, m), 2.95-3.10 (1H, m), 5.05 (2H, s), 5.10-5.20 (1H, m), 6.85-6.87 (1H, m), 7.25-7.45 (6H, m).

Reference Example 24

Methyl 4-[(2,3-dihydro-2,2-dimethyl-1H-inden-1-yl)oxy]benzenepropanoate

In the same manner as in Reference Example 23, 2,3-dihydro-2,2-dimethyl-1H-inden-1-ol was obtained from 2,3-dihydro-2,2-dimethyl-1H-inden-1-one. The resulting compound was condensed with methyl 4-hydroxybenzenepropanoate in the same manner as in Reference Example 1 to give the title compound. Yield from 2,3-dihydro-2,2-dimethyl-1H-inden-1-one is 60%.

Oil.
$^1$H NMR (CDCl$_3$) δ 1.13 (3H, s), 1.23, (3H, s), 2.62 (2H, t, J=7.5 Hz), 2.73 (1H, d, J=15.4 Hz), 2.86 (1H, d, J=15.4 Hz), 2.93 (2H, t, J=7.5 Hz), 3.86 (3H, s), 5.28 (1H, s), 6.98 (2H, d, J=8.6 Hz), 7.11-7.27 (6H, m).

Reference Example 25

4-[(2,3-Dihydro-2,2-dimethyl-1H-inden-1-yl)oxy]benzenepropanoic acid

In the same manner as in Reference Example 5, the title compound was obtained from methyl 4-[(2,3-dihydro-2,2-dimethyl-1H-inden-1-yl)oxy]benzenepropanoate. Yield 46%.

Oil.
$^1$H NMR (CDCl$_3$) δ 1.13 (3H, s), 1.23, (3H, s), 2.68 (2H, t, J=7.3 Hz), 2.73 (1H, d, J=18.9 Hz), 2.87 (1H, d, J=18.9 Hz), 2.93 (2H, t, J=7.3 Hz), 5.28 (1H, s), 6.98 (2H, d, J=8.6 Hz), 7.00-7.27 (6H, m).

Reference Example 26

Ethyl 4-(3-phenylpropoxy)benzenepropanoate

To a solution of ice-cooled ethyl 4-hydroxybenzenepropanoate (0.40 g, 2.1 mmol) in N,N-dimethylformamide (15 mL) was added 60% sodium hydride (0.11 g, 2.7 mmol), and the mixture was stirred for 30 minutes. Then, 1-bromo-3-phenylpropane (0.53 g, 2.7 mmol) was added thereto, and the mixture was stirred at room temperature for 3 hours. To the reaction solution was added water, and the reaction mixture was extracted with ethyl acetate. The extract was washed with water, dried, and then concentrated. The residue was purified with silica gel column chromatography (hexane/ethyl acetate=18:1) to give the title compound (0.29 g, yield 46%).

Oil.
$^1$H NMR (CDCl$_3$) δ 1.23 (3H, t, J=7.1 Hz), 2.04-2.13 (2H, m), 2.58 (2H, t, J=8.1 Hz), 2.88 (2H, t, J=8.1 Hz), 3.94 (2H, t, J=6.3 Hz), 4.12 (2H, q, J=7.1 Hz), 6.81 (2H, d, J=8.6 Hz), 7.10 (2H, d, J=8.6 Hz), 7.19-7.31 (5H, m).

Reference Example 27

Methyl 4-([1,1'-biphenyl]-2-ylmethoxy)benzenepropanoate

In the same manner as in Reference Example 26, the title compound was obtained from methyl 4-hydroxybenzenepropanoate and 2-phenylbenzyl bromide. Yield 52%.

Oil.
$^1$H NMR (CDCl$_3$) δ 2.58 (2H, t, J=8.1 Hz), 2.87 (2H, t, J=8.1 Hz), 3.66 (3H, s), 4.91 (2H, s), 6.78 (2H, d, J=8.6 Hz), 7.06 (2H, d, J=8.6 Hz), 7.33-7.40 (8H, m), 7.50-7.70 (1H, m).

Reference Example 28

4-([1,1'-Biphenyl]-2-ylmethoxy)benzenepropanoic acid

In the same manner as in Reference Example 5, the title compound was obtained from methyl 4-([1,1'-biphenyl]-2-ylmethoxy)benzenepropanoate. Yield 45%.

Melting point 103-104° C. (recrystallization from ethyl acetate-hexane).
$^1$H NMR (CDCl$_3$) δ 2.63 (2H, t, J=7.9 Hz), 2.88 (2H, t, J=7.9 Hz), 4.91 (2H, s), 6.79 (2H, d, J=8.6 Hz), 7.08 (2H, d, J=8.6 Hz), 7.33-7.50 (8H, m), 7.60-7.70 (1H, m).

Reference Example 29

Methyl 4-[(2-phenoxyphenyl)methoxy]benzenepropanoate

In the same manner as in Reference Example 1, the title compound as white powders was obtained from methyl 4-hydroxybenzenepropanoate and 2-phenoxybenzyl alcohol. Yield 93%.

$^1$H NMR (CDCl$_3$) δ 2.59 (2H, t, J=8.1 Hz), 2.88 (2H, t, J=8.1 Hz), 3.66 (3H, s), 5.13 (2H, s), 6.89 (3H, t, J=8.6 Hz), 6.98 (2H, d, J=8.1 Hz), 7.07-7.20 (4H, m), 7.25-7.40 (3H, m), 7.50-7.60 (1H, m).

Reference Example 30

4-[(2-Phenoxyphenyl)methoxy]benzenepropanoic acid

In the same manner as in Reference Example 5, the title compound was obtained from methyl 4-[(2-phenoxyphenyl)methoxy]benzenepropanoate. Yield 45%.

Melting point 114-115° C. (recrystallization from ethyl acetate-hexane).
$^1$H NMR (CDCl$_3$) δ 2.63 (2H, t, J=7.9 Hz), 2.89 (2H, t, J=7.9 Hz), 5.13 (2H, s), 6.86-6.92 (3H, m), 6.95-7.00 (2H, m), 7.06-7.12 (3H, m), 7.16 (1H, dd, J=7.5 Hz, 1.0 Hz), 7.24-7.36 (3H, m), 7.58 (1H, dd, J=7.5 Hz, 1.4 Hz).

Reference Example 31

5-Bromo-1,3-difluoro-2-(methoxymethoxy)benzene

In the same manner as in Reference Example 26, the title compound was obtained from 4-bromo-2,6-difluorophenol and chloromethylmethyl ether. Yield 88%.

Oil.
$^1$H NMR (CDCl$_3$) δ 3.58 (3H, s), 5.13 (2H, s), 7.04-7.13 (2H, m).

Reference Example 32

Ethyl 3,5-difluoro-4-(methoxymethoxy)benzenepropanoate

To a solution of 5-bromo-1,3-difluoro-2-(methoxymethoxy)benzene (4.4 g, 21 mmol), acrolein diethyl acetal (9.4 mL, 62 mmol), tetrabutylammonium chloride (5.7 g, 21 mmol) and diisopropylethylamine (18 mL, 0.10 mol) in N,N-dimethylformamide (40 mL) was added palladium acetate (0.14 g, 0.62 mmol), and the mixture was stirred under argon atmosphere at 90° C. for 18 hours. After the reaction solution was returned to room temperature, water was added thereto, and the reaction mixture was extracted with ethyl acetate. The extract was washed with water, and then concentrated under reduced pressure. The residue was purified with silica gel column chromatography (hexane/ethyl acetate=49:1 to 4:1) to give the title compound (2.4 g, yield 42%).
Oil.
NMR (CDCl$_3$) δ 1.24 (3H, t, J=7.1 Hz), 2.58 (2H, t, J=7.5 Hz), 2.88 (2H, t, J=7.5 Hz), 3.59 (3H, s), 4.13 (2H, q, J=7.1 Hz), 5.12 (2H, s), 6.70-6.84 (2H, m).

Reference Example 33

Ethyl 3,5-difluoro-4-hydroxybenzenepropanoate

To a solution of ethyl 3,5-difluoro-4-(methoxymethoxy) benzenepropanoate (2.3 g, 8.4 mmol) in ethanol (12 mL) was added hydrochloric acid (0.5 mL), and the mixture was stirred at 50° C. for 1 hour. After the reaction solution was returned to room temperature, water was added thereto, and the reaction mixture was extracted with ethyl acetate. The extract was washed with water, and then concentrated under reduced pressure. The residue was purified with silica gel column chromatography (hexane/ethyl acetate=9:1 to 1:1) to give the title compound (1.7 g, yield 88%).
Oil.
NMR (CDCl$_3$) δ 1.24 (3H, t, J=7.1 Hz), 2.57 (2H, t, J=7.4 Hz), 2.85 (2H, t, J=7.4 Hz), 4.13 (2H, q, J=7.1 Hz), 5.16 (1H, br s), 6.68-6.82 (2H, m).

Reference Example 34

5-Bromo-1,3-difluoro-2-[(3-methoxyphenyl)methoxy]benzene

In the same manner as in Reference Example 1, the title compound was obtained from 4-bromo-2,6-difluorophenol and 3-methoxybenzyl alcohol. Yield 32%.
Oil.
NMR (CDCl$_3$) δ 3.81 (3H, s), 5.13 (2H, s), 6.85-6.89 (1H, m), 6.96-6.99 (2H, m), 7.01-7.11 (2H, m), 7.23-7.29 (1H, m).

Reference Example 35

5-Bromo-2-[(3-ethoxyphenyl)methoxy]-1,3-difluorobenzene

In the same manner as in Reference Example 1, the title compound was obtained from 4-bromo-2,6-difluorophenol and 3-ethoxybenzyl alcohol. Yield 60%.
Oil.
NMR (CDCl$_3$) δ 1.41 (3H, t, J=7.1 Hz), 4.03 (2H, q, J=7.1 Hz), 5.11 (2H, s), 6.83-6.88 (1H, m), 6.94-6.97 (2H, m), 7.01-7.10 (2H, m), 7.22-7.28 (1H, m).

Reference Example 36

5-Bromo-1,3-difluoro-2-[[3-(1-methylethoxy)phenyl]methoxy]benzene

In the same manner as in Reference Example 1, the title compound was obtained from 4-bromo-2,6-difluorophenol and 3-isopropoxybenzyl alcohol. Yield 54%.
Oil.
NMR (CDCl$_3$) δ 1.32 (6H, d, J=6.0 Hz), 4.55 (1H, septet, J=6.0 Hz), 5.11 (2H, s), 6.83-6.87 (1H, m), 6.93-6.96 (2H, m), 7.00-7.09 (2H, m), 7.22-7.27 (1H, m).

Reference Example 37

4-Bromo-2-fluoro-1-(methoxymethoxy)benzene

In the same manner as in Reference Example 26, the title compound was obtained from 4-bromo-2-fluorophenol and chloromethylmethyl ether. Yield 96%.
Oil.
$^1$H NMR (CDCl$_3$) δ 3.51 (3H, s), 5.19 (2H, s), 7.08 (1H, t, J=8.6 Hz), 7.16-7.20 (1H, m), 7.23-7.27 (1H, m).

Reference Example 38

Ethyl 3-fluoro-4-(methoxymethoxy)benzenepropanoate

In the same manner as in Reference Example 32, the title compound was obtained from 4-bromo-2-fluoro-1-(methoxymethoxy)benzene and acrolein diethyl acetal. Yield 31%.
Oil.
$^1$H NMR (CDCl$_3$) δ 1.24 (3H, t, J=7.1 Hz), 2.58 (2H, t, J=7.4 Hz), 2.89 (2H, t, J=7.4 Hz), 3.52 (3H, s), 4.13 (2H, q, J=7.1 Hz), 5.18 (2H, s), 6.87-6.97 (2H, m), 7.09 (1H, t, J=8.4 Hz).

Reference Example 39

Ethyl 3-fluoro-4-hydroxybenzenepropanoate

In the same manner as in Reference Example 33, the title compound was obtained from ethyl 3-fluoro-4-(methoxymethoxy)benzenepropanoate. Yield 94%.
Oil.
$^1$H NMR (CDCl$_3$) δ 1.23 (3H, t, J=7.2 Hz), 2.57 (2H, t, J=7.4 Hz), 2.87 (2H, t, J=7.4 Hz), 4.12 (2H, q, J=7.2 Hz), 5.18 (1H, br s), 6.83-6.94 (3H, m).

Reference Example 40

Methyl (E)-3-(4-hydroxy-3-methoxyphenyl)-2-propenoate

To a solution of (E)-3-(4-hydroxy-3-methoxyphenyl)-2-propenoic acid (3.0 g, 15 mmol) in methanol (30 mL) was added sulfuric acid (0.5 mL), and the mixture was heated under reflux for 12 hours. After the reaction solution was returned to room temperature, water was added thereto, and the reaction mixture was extracted with ethyl acetate. The extract was washed with water, and then concentrated under reduced pressure to give the title compound (3.1 g, yield 97%) as an oily matter. The obtained compound was used in the next reaction without purification.
$^1$H NMR (CDCl$_3$) δ 3.80 (3H, s), 3.90 (3H, s), 5.95 (1H, br s), 6.29 (1H, d, J=15.9 Hz), 6.91 (1H, d, J=8.1 Hz), 7.02 (1H, d, J=1.8 Hz), 7.07 (1H, dd, J=1.8 Hz, 8.1 Hz), 7.62 (1H, d, J=15.9 Hz).

Reference Example 41

Methyl 4-hydroxy-3-methoxybenzenepropanoate

To a solution of methyl (E)-3-(4-hydroxy-3-methoxyphenyl)-2-propenoate (3.0 g, 14 mmol) in methanol (30 mL) was added 10% palladium carbon (50% water content, 0.20 g), and the mixture was stirred at room temperature for 4 hours under hydrogen atmosphere. The reaction solution was filtered, and then the filtrate was concentrated under reduced pressure to give the title compound (3.0 g, yield 97%) as an oily matter. The obtained compound was used in the next reaction without purification.

$^1$H NMR (CDCl$_3$) δ 2.60 (2H, t, J=8.1 Hz), 2.88 (2H, t, J=8.1 Hz), 3.67 (3H, s), 3.87 (3H, s), 5.50 (1H, br s), 6.66-6.70 (2H, m), 6.82 (1H, d, J=7.8 Hz).

Reference Example 42

2,3-Dihydro-6-methoxy-2,2-dimethyl-1H-inden-1-one

In the same manner as in Reference Example 21, the title compound was obtained from 2,3-dihydro-6-methoxy-1H-inden-1-one. Yield 85%.

Oil.

$^1$H NMR (CDCl$_3$) 1.23 (6H, s), 2.92 (2H, s), 3.84 (3H, s), 7.17-7.20 (2H, m), 7.31 (1H, d, J=9.1 Hz).

Reference Example 43

Methyl 4-[(2,3-dihydro-6-methoxy-2,2-dimethyl-1H-inden-1-yl)oxy]benzenepropanoate In the same manner as in Reference Example 23, 2,3-dihydro-6-methoxy-2,2-dimethyl-1H-inden-1-ol was obtained from 2,3-dihydro-6-methoxy-2,2-dimethyl-1H-inden-1-one. The resulting compound was condensed with methyl 4-hydroxybenzenepropanoate in the same manner as in Reference Example 1, to give the title compound. Yield from 2,3-dihydro-6-methoxy-2,2-dimethyl-1H-inden-1-one is 54%.

Oil.

$^1$H NMR (CDCl$_3$) 1.11 (3H, s), 1.22 (3H, s), 2.60-2.69 (3H, m), 2.88 (1H, d, J=15.1 Hz), 2.91 (2H, t, J=7.5 Hz), 3.68 (3H, s), 3.73 (3H, s), 5.25 (1H, s), 6.78-6.80 (2H, m), 6.98 (2H, d, J=8.6 Hz), 7.09-7.14 (3H, m).

Reference Example 44

4-[(2,3-Dihydro-6-methoxy-2,2-dimethyl-1H-inden-1-yl)oxy]benzenepropanoic acid

In the same manner as in Reference Example 5, the title compound was obtained from methyl 4-[(2,3-dihydro-6-methoxy-2,2-dimethyl-1H-inden-1-yl)oxy]benzenepropanoate. Yield 99%.

Oil.

$^1$H NMR (CDCl$_3$) 1.12 (3H, s), 1.22 (3H, s), 2.64-2.70 (3H, m), 2.78 (1H, d, J=15.1 Hz), 2.93 (2H, t, J=7.5 Hz), 3.73 (3H, s), 5.25 (1H, s), 6.76-6.80 (2H, m), 6.99 (2H, d, J=8.6 Hz), 7.09-7.16 (3H, m).

Reference Example 45

6-Chloro-2,3-dihydro-2,2-dimethyl-1H-inden-1-one

In the same manner as in Reference Example 21, the title compound was obtained from 6-chloro-2,3-dihydro-1H-inden-1-one. Yield 55%.

Oil.

$^1$H NMR (CDCl$_3$) 1.24 (6H, s), 2.96 (2H, s), 7.37 (1H, d, J=8.0 Hz), 7.55 (1H, dd, J=1.8 Hz, 8.0 Hz), 7.72 (1H, d, J=1.8 Hz).

Reference Example 46

Methyl 4-[(6-chloro-2,3-dihydro-2,2-dimethyl-1H-inden-1-yl)oxy]benzenepropanoate In the same manner as in Reference Example 23, 6-chloro-2,3-dihydro-2,2-dimethyl-1H-inden-1-ol was obtained from 6-chloro-2,3-dihydro-2,2-dimethyl-1H-inden-1-one. The resulting compound was condensed with methyl 4-hydroxybenzenepropanoate in the same manner as in Reference Example 1 to give the title compound. Yield from 6-chloro-2,3-dihydro-2,2-dimethyl-1H-inden-1-one is 26%.

Oil.

$^1$H NMR (CDCl$_3$) 1.11 (3H, s), 1.22 (3H, s), 2.60-2.71 (3H, m), 2.80 (1H, d, J=15.5 Hz), 2.92 (2H, t, J=7.5 Hz), 3.68 (3H, s), 5.23 (1H, s), 6.96 (2H, d, J=8.6 Hz), 7.11-7.22 (5H, m).

Reference Example 47

4-[(6-Chloro-2,3-dihydro-2,2-dimethyl-1H-inden-1-yl)oxy]benzenepropanoic acid

In the same manner as in Reference Example 5, the title compound was obtained from methyl 4-[(6-chloro-2,3-dihydro-2,2-dimethyl-1H-inden-1-yl)oxy]benzenepropanoate. Yield 99%.

Oil.

$^1$H NMR (CDCl$_3$) 1.11 (3H, s), 1.23 (3H, s), 2.66-2.71 (3H, m), 2.80 (1H, d, J=15.5 Hz), 2.94 (2H, t, J=7.5 Hz), 5.24 (1H, s), 6.96 (2H, d, J=8.6 Hz), 7.11-7.22 (5H, m).

Reference Example 48

2,3-Dihydro-2,2,6-trimethyl-1H-inden-1-one

In the same manner as in Reference Example 21, the title compound was obtained from 2,3-dihydro-6-methyl-1H-inden-1-one. Yield 49%.

Oil.

$^1$H NMR (CDCl$_3$) 1.23 (6H, s), 2.40 (3H, s), 2.95 (2H, s), 7.31 (1H, d, J=7.8 Hz), 7.41 (1H, dd, J=1.0 Hz, 7.8 Hz), 7.56 (1H, s).

Reference Example 49

Methyl 4-[(2,3-dihydro-2,2,6-trimethyl-1H-inden-1-yl)oxy]benzenepropanoate

In the same manner as in Reference Example 23, 2,3-dihydro-2,2,6-trimethyl-1H-inden-1-ol was obtained from 2,3-dihydro-2,2,6-trimethyl-1H-inden-1-one. The resulting compound was condensed with methyl 4-hydroxybenzenepropanoate in the same manner as in Reference Example 1 to give the title compound. Yield from 2,3-dihydro-2,2,6-trimethyl-1H-inden-1-one is 44%.

Oil.

$^1$H NMR (CDCl$_3$) 1.11 (3H, s), 1.22 (3H, s), 2.29 (3H, s), 2.63 (2H, d, J=7.4 Hz), 2.68 (1H, d, J=15.3 Hz), 2.81 (1H, d, J=15.3 Hz), 2.92 (2H, t, J=7.4 Hz), 3.68 (3H, s), 5.25 (1H, s), 6.98 (2H, d, J=8.6 Hz), 7.03-7.15 (5H, m).

Reference Example 50

4-[(2,3-Dihydro-2,2,6-trimethyl-1H-inden-1-yl)oxy]benzenepropanoic acid

In the same manner as in Reference Example 5, the title compound was obtained from methyl 4-[(2,3-dihydro-2,2,6-trimethyl-1H-inden-1-yl)oxy]benzenepropanoate. Yield 78%.

Oil.

$^1$H NMR (CDCl$_3$) 1.11 (3H, s), 1.22 (3H, s), 2.29 (3H, s), 2.66-2.71 (3H, m), 2.81 (1H, d, J=15.3 Hz), 2.93 (2H, t, J=7.5 Hz), 5.25 (1H, s), 6.99 (2H, d, J=8.6 Hz), 7.06-7.16 (5H, m).

Reference Examples 51 to 136 are shown as below. Unless specifically described, $^1$H NMR is measured using deuterated chloroform as a solvent. Further, chemical shift is a δ value (ppm), and the unit of coupling constants is Hz.

Reference Example 51

(2-Morpholin-4-ylphenyl)methanol

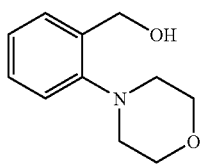

2-Fluorobenzaldehyde (1.0 g, 8.1 mmol) was dissolved in DMF (20 mL), morpholine (2.0 mL) and potassium carbonate (1.1 g, 8.1 mmol) were added thereto, and then the mixture was stirred at 80° C. for 2 days. To the reaction solution was added water, and the reaction mixture was extracted with ethyl acetate. The extract was dried, and then concentrated under reduced pressure. The residue was purified with silica gel column chromatography (hexane/ethyl acetate=98:2 to 60:40) to give an oily matter. The resulting oily matter was dissolved in methanol (20 mL), sodium borohydride (613 mg, 16.2 mmol) was added thereto, and the mixture was stirred at room temperature for 3 hours. To the reaction solution was added water, and the reaction mixture was extracted with ethyl acetate. The extract was dried, and then concentrated under reduced pressure to give the title compound (474 mg, yield 30%).

Oil.

$^1$H NMR: 3.00 (4H, t, J=4.6), 3.98 (2H, t, J=4.6), 2.83 (2H, t, J=7.8), 4.81 (2H, s), 4.97 (1H, s), 7.14-7.30 (4H, m).

Reference Example 52

[2-(Cyclopentyloxy)phenyl]methanol

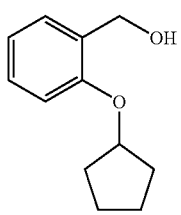

Salicylaldehyde (1.0 g, 8.2 mmol) was dissolved in DMF (10 mL), cyclopentyl bromide (1.76 mL, 16.4 mmol) and sodium hydride (394 mg, 9.8 mmol) were added thereto, and then the mixture was stirred at room temperature for 2 hours. To the reaction solution was added water, and the reaction mixture was extracted with ethyl acetate. The extract was dried, and then concentrated under reduced pressure. The residue was purified with silica gel column chromatography (hexane/ethyl acetate=100:0 to 90:10) to give an oily matter. The resulting oily matter was dissolved in methanol (10 mL), sodium borohydride (620 mg, 16.4 mmol) was added thereto, and then the mixture was stirred at room temperature for 2 hours. The residue was purified with silica gel column chromatography (hexane/ethyl acetate=100:0 to 70:30) to give the title compound (349 mg, yield 25%).

Oil.

$^1$H NMR: 1.61-1.93 (8H, m), 2.46 (1H, t, J=6.5), 4.65 (2H, d, J=6.5), 4.83-4.87 (1H, m), 6.86-6.93 (2H, m), 7.20-7.26 (2H, m).

Reference Example 53

(2-Methoxyphenyl)methanol

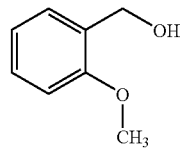

In the same manner as in Reference Example 52, the title compound was obtained from salicylaldehyde and methyl iodide. Yield 79%.

Oil.

$^1$H NMR: 2.29 (1H, t, J=6.6), 3.87 (3H, s), 4.69 (2H, d, J=6.6), 6.88-6.97 (2H, m), 7.26-7.31 (2H, m).

Reference Example 54

(2-Isobutoxyphenyl)methanol

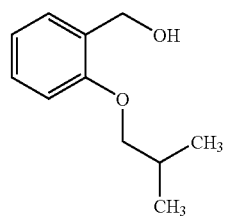

In the same manner as in Reference Example 52, the title compound was obtained from salicylaldehyde and isobutyl bromide. Yield 61%.

Oil.

$^1$H NMR: 1.05 (6H, d, J=6.7), 2.04-2.18 (1H, m), 2.36 (1H, t, J=6.5), 3.79 (2H, d, J=6.4), 4.71 (2H, d, J=6.5), 6.85-6.96 (2H, m), 7.22-7.28 (2H, m).

Reference Example 55

[2-(Cyclohexyloxy)phenyl]methanol

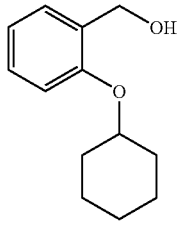

In the same manner as in Reference Example 52, the title compound was obtained from salicylaldehyde and cyclohexyl bromide. Yield 4%.

Oil.

$^1$H NMR: 1.36-1.45 (3H, m), 1.54-1.61 (3H, m), 1.75-1.82 (2H, m), 1.96-2.01 (2H, m), 2.53 (1H, t, J=6.6), 4.34-4.39 (1H, m), 4.68 (2H, d, J=6.6), 6.88-6.93 (2H, m), 7.21-7.24 (2H, m).

Reference Example 56

(2-Isopropoxyphenyl)methanol

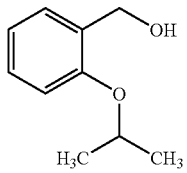

In the same manner as in Reference Example 52, the title compound was obtained from salicylaldehyde and isopropyl bromide. Yield 73%.

Oil.

$^1$H NMR: 1.37 (6H, d, J=6.0), 2.48 (1H, t, J=6.6), 4.61-4.68 (3H, m), 6.87-6.94 (2H, m), 7.22-7.26 (2H, m).

Reference Example 57

[2-(Tetrahydrofuran-2-ylmethoxy)phenyl]methanol

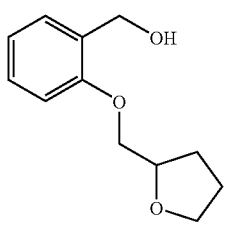

In the same manner as in Reference Example 52, the title compound was obtained from salicylaldehyde and 2-(bromomethyl)tetrahydrofuran. Yield 37%.

Oil.

$^1$H NMR: 1.70-2.15 (4H, m), 3.24 (1H, brt), 3.82-3.98 (3H, m), 4.11-4.16 (1H, m), 4.25-4.35 (1H, m), 4.55-4.77 (2H, m), 6.87-6.97 (2H, m), 7.23-7.28 (2H, m).

Reference Example 58

[3-(Methoxymethoxy)phenyl]methanol

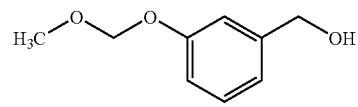

In the same manner as in Reference Example 52, the title compound was obtained from salicylaldehyde and chloromethylmethyl ether. Yield 50%.

Oil.

$^1$H NMR: 1.68 (1H, brt), 3.48 (3H, s), 4.68 (2H, s), 5.19 (2H, s), 6.95-7.06 (3H, m), 7.26-7.31 (1H, m).

Reference Example 59

(2-Piperidin-1-ylphenyl)methanol

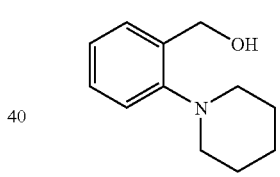

In the same manner as in Reference Example 51, the title compound was obtained from 2-fluorobenzaldehyde and piperidine. Yield 55%.

Oil.

$^1$H NMR: 1.54-1.62 (2H, m), 1.72-1.79 (4H, m), 2.92 (4H, t, J=5.1), 4.81 (2H, s), 6.07 (1H, brt), 7.04-7.42 (4H, m).

Reference Example 60

[3-(4-Chlorophenoxy)phenyl]methanol

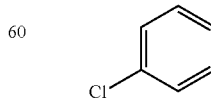

In the same manner as in Reference Example 23, the title compound was obtained from 3-(4-chlorophenoxy)benzaldehyde. Yield 86%.

Oil.

$^1$H NMR: 1.67 (1H, t, J=4.7), 4.68 (2H, d, J=4.7), 6.90-7.12 (5H, m), 7.26-7.36 (3H, m).

Reference Example 61

[3-(4-Methoxyphenoxy)phenyl]methanol

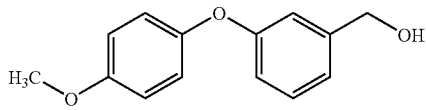

In the same manner as in Reference Example 23, the title compound was obtained from 3-(4-methoxyphenoxy)benzaldehyde. Quantitative.

Oil.

$^1$H NMR: 1.70 (1H, t, J=4.7), 3.81 (3H, s), 4.64 (2H, d, J=4.7), 6.85-7.05 (7H, m), 7.26-7.31 (1H, m).

Reference Example 62

[3-(4-Fluorophenoxy)phenyl]methanol

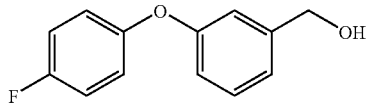

3-Hydroxybenzyl alcohol (3.0 g, 24.6 mmol) was dissolved in 1,3-dimethyl-2-imidazolidinone (50 mL). 4-Bromofluorobenzene (6.5 g, 36.9 mmol), potassium carbonate (2.0 g, 14.8 mmol), 8-quinolinol (71 mg, 0.5 mmol), and copper chloride(I) (49 mg, 0.5 mmol) were added thereto, and then the mixture was stirred at 150° C. for 2 days. To the reaction solution was added water, and the reaction mixture was extracted with ethyl acetate. The extract was dried, and then concentrated under reduced pressure. The residue was purified with silica gel column chromatography (hexane/ethyl acetate=90:10 to 80:20) to give the title compound (0.98 mg, yield 18%).

Oil.

$^1$H NMR: 1.64 (1H, t, J=6.0), 4.67 (2H, d, J=6.0), 6.87-7.09 (7H, m), 7.26-7.34 (1H, m).

Reference Example 63

3-(4-Methylphenoxy)benzaldehyde

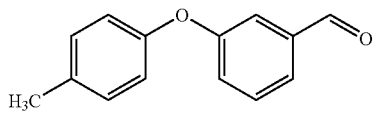

3-Hydroxybenzaldehyde (1.0 g, 8.2 mmol) was dissolved in dichloromethane (50 mL). (4-Methylphenyl)boronic acid (2.2 g, 16.4 mmol), triethylamine (5.7 mL, 41.0 mmol) and copper acetate(II) (1.5 g, 8.2 mmol) were added thereto, and then the mixture was stirred at room temperature for 2 days. The reaction solution was filtered, and concentrated under reduced pressure. The residue was purified with silica gel column chromatography (hexane/ethyl acetate=100:0 to 70:30) to give the title compound (324 mg, yield 19%).

Oil.

$^1$H NMR: 2.34 (3H, s), 6.93 (2H, d, J=8.5), 7.18 (2H, d, J=8.5), 7.23-7.28 (1H, m), 7.41-7.58 (3H, m), 9.94 (1H, s).

Reference Example 64

3-Phenoxyacetophenone

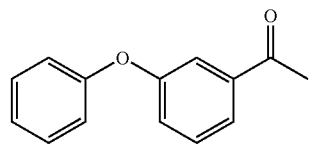

In the same manner as in Reference Example 63, the title compound was obtained from 3-hydroxyacetophenone and phenyl boronate. Yield 14%.

Oil.

$^1$H NMR: 2.58 (3H, s), 7.02 (2H, d, J=7.6), 7.12-7.26 (2H, m), 7.34-7.45 (3H, m), 7.57-7.69 (2H, m).

Reference Example 65

3-(Pyridin-2-yloxy)benzaldehyde

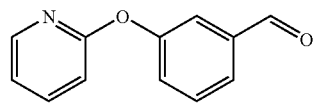

3-Hydroxybenzyl alcohol (1.0 g, 8.2 mmol) was dissolved in pyridine (20 mL). 2-Bromopyridine (1.6 g, 9.8 mmol) and potassium carbonate (2.3 g, 16.4 mmol) were added thereto, and then the mixture was stirred at 90° C. for 10 minutes. Copper oxide(II) (1.6 g, 20.5 mmol) was further added thereto, and the reaction mixture was heated under reflux for 2 days. The reaction solution was filtered, and concentrated under reduced pressure. To the residue was added water, and the mixture was extracted with ethyl acetate. The extract was dried, and then concentrated under reduced pressure. The residue was purified with silica gel column chromatography (hexane/ethyl acetate=100:0 to 70:30) to give the title compound (1.0 mg, yield 61%).

Oil.

$^1$H NMR: 6.97-7.08 (2H, m), 7.35-7.45 (1H, m), 7.57 (1H, dd, J=7.7, 7.7), 7.65-7.79 (3H, m), 8.10-8.20 (1H, m), 10.01 (1H, s).

Reference Example 66

[3-(Pyridin-2-yloxy)phenyl]methanol

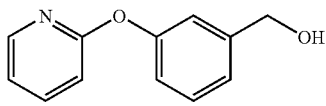

In the same manner as in Reference Example 23, the title compound was obtained from 3-(pyridin-2-yloxy)benzaldehyde. Quantitative.

Oil.

$^1$H NMR: 1.89 (1H, t, J=6.0), 4.70 (2H, d, J=6.0), 6.92 (1H, d, J=8.3), 6.97-7.07 (2H, m), 7.15-7.20 (2H, m), 7.38 (1H, dd, J=7.8, 7.8), 7.65-7.74 (1H, m), 8.18-8.20 (1H, m).

Reference Example 67

[3-(3-Thienyloxy)phenyl]methanol

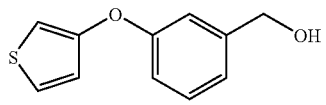

In the same manner as in Reference Example 62, the title compound was obtained from 3-hydroxybenzyl alcohol and 3-bromothiophene. Yield 19%.

Oil.

$^1$H NMR: 1.67 (1H, t, J=6.0), 4.68 (2H, d, J=6.0), 6.62 (1H, dd, J=1.5, 3.2), 6.85 (1H, dd, J=1.5, 5.3), 6.92-6.98 (1H, m), 7.06-7.10 (2H, m), 7.24-7.34 (2H, m).

Reference Example 68

[3-(2-Thienyloxy)phenyl]methanol

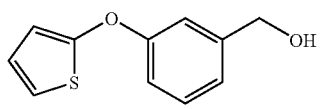

In the same manner as in Reference Example 62, the title compound was obtained from 3-hydroxybenzyl alcohol and 2-bromothiophene. Yield 4%.

Oil.

$^1$H NMR: 1.65 (1H, br), 4.68 (2H, s), 6.55 (1H, dd, J=2.6, 2.6), 6.75-6.90 (3H, m), 7.06-7.14 (2H, m), 7.21-7.32 (1H, m).

Reference Example 69

4-[3-(Hydroxymethyl)phenoxy]acetophenone

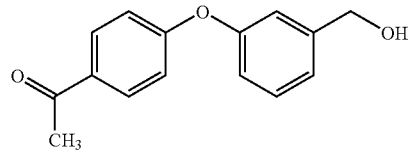

3-Hydroxybenzyl alcohol (894 mg, 7.2 mmol) was dissolved in DMF (50 mL). 4-Fluoroacetophenone (1.0 g, 7.2 mmol) and potassium carbonate (995 mg, 7.2 mmol) were added thereto, and then the mixture was stirred at 100° C. for 14 hours. To the reaction solution was added water, and the reaction mixture was extracted with ethyl acetate. The extract was dried, and then concentrated under reduced pressure. The residue was purified with silica gel column chromatography (hexane/ethyl acetate=100:0 to 70:30) to give the title compound (0.29 g, yield 17%).

Oil.

$^1$H NMR: 1.90 (1H, brt), 2.57 (3H, s), 4.72 (2H, d, J=3.9), 6.95-7.00 (3H, m), 7.09 (1H, s), 7.19 (1H, d, J=7.5), 7.39 (1H, dd, J=7.8, 7.8), 7.94 (2H, d, J=8.9).

Reference Example 70

[3-(1,3-Thiazol-2-yloxy)phenyl]methanol

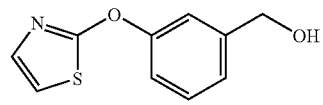

In the same manner as in Reference Example 62, the title compound was obtained from 3-hydroxybenzyl alcohol and 2-bromothiazole. Yield 39%.

Oil.

$^1$H NMR: 2.00 (1H, br), 4.72 (2H, s), 6.82 (1H, d, J=3.8), 7.17-7.26 (3H, m), 7.30 (1H, s), 7.40 (1H, dd, J=7.8, 7.8).

Reference Example 71

1-(3-Methylphenoxy)naphthalene

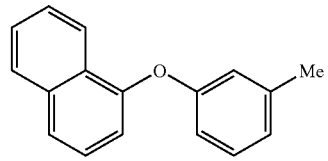

In the same manner as in Reference Example 62, the title compound was obtained from 1-naphthol and 3-bromotoluene. Yield 40%.

Oil.

¹H NMR: 2.32 (3H, s), 6.81-6.96 (4H, m), 7.19-7.25 (1H, m), 7.38 (1H, dd, J=7.8, 7.8), 7.44-7.55 (2H, m), 7.39 (1H, dd, J=7.8, 7.8), 7.86 (1H, d, J=7.3), 8.20-8.22 (1H, m).

Reference Example 72

1-[3-(Bromomethyl)phenoxy]naphthalene

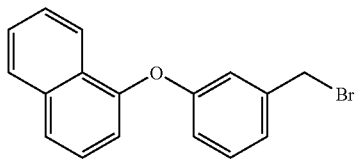

1-(3-Methylphenoxy)naphthalene (500 mg, 2.1 mmol) was dissolved in benzotrifluoride (30 mL), N-bromosuccinimide (417 mg, 2.3 mmol) and 2,2'-azobis(isobutyronitrile) (10 mg, 0.06 mmol) were added thereto, and then the mixture was stirred at 100° C. for 4 hours. The reaction solution was filtered, and concentrated under reduced pressure. The residue was purified with silica gel column chromatography (hexane/ethyl acetate=100:0 to 90:10) to give the title compound (481 mg, yield 73%).

Oil.

¹H NMR: 4.43 (2H, s), 6.80-7.70 (8H, m), 7.85-7.92 (1H, m), 8.11-8.28 (2H, m).

Reference Example 73

2-Phenoxyacetophenone

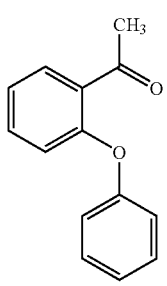

2-Fluoroacetophenone (2.0 mg, 14.5 mmol) was dissolved in DMF (50 mL), phenol (1.4 g, 14.5 mmol) and potassium carbonate (2.0 g, 14.5 mmol) were added thereto, and then the mixture was stirred at 120° C. for 7 hours. To the reaction solution was added water, and the reaction mixture was extracted with ethyl acetate. The extract was dried, and then concentrated under reduced pressure. The residue was purified with silica gel column chromatography (hexane/ethyl acetate=100:0 to 85:15) to give the title compound (2.0 g, yield 65%).

Oil.

¹H NMR: 2.65 (3H, s), 6.91 (1H, d, J=8.4), 7.01-7.04 (2H, m), 7.11-7.25 (2H, m), 7.35-7.59 (3H, m), 7.83-7.86 (1H, m).

Reference Example 74

1-(2-Phenoxyphenyl)ethanol

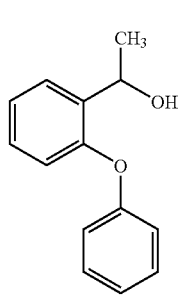

In the same manner as in Reference Example 23, the title compound was obtained from 2-phenoxyacetophenone. Yield 92%.

Oil.

¹H NMR: 1.53 (3H, d, J=6.6), 2.21 (1H, d, J=4.5), 5.18-5.21 (1H, m), 6.84 (1H, d, J=8.7), 6.96-7.36 (7H, m), 7.46-7.55 (1H, m).

Reference Example 75

1-(3-Phenoxyphenyl)ethanol

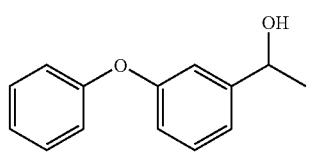

In the same manner as in Reference Example 23, the title compound was obtained from 3-phenoxyacetophenone. Yield 41%.

Oil.

$^1$H NMR: 1.48 (3H, d, J=6.3), 1.82 (1H, br), 4.87 (1H, q, J=6.3), 6.90 (1H, dd, J=2.4, 8.1), 7.00-7.13 (5H, m), 7.26-7.36 (3H, m).

Reference Example 76

2-(3-Isopropylphenoxy)benzaldehyde

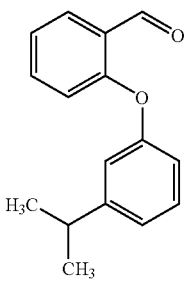

2-Fluorobenzaldehyde (1.0 mg, 8.1 mmol) was dissolved in DMF (20 mL), 3-isopropylphenol (1.1 g, 8.9 mmol) and potassium carbonate (1.1 g, 8.1 mmol) were added thereto, and then microwave was irradiated at 180° C. for 5 minutes. To the reaction solution was added water, and the reaction mixture was extracted with ethyl acetate. The extract was dried, and then concentrated under reduced pressure. The residue was purified with silica gel column chromatography (hexane/ethyl acetate=100:0 to 70:30) to give the title compound (1.1 g, yield 57%).

Oil.

$^1$H NMR: 1.24 (6H, d, J=7.2), 2.89-2.93 (1H, m), 6.84-6.97 (2H, m), 7.05 (1H, d, J=7.5), 7.14-7.32 (3H, m), 7.46-7.50 (1H, m), 7.93 (1H, dd, J=1.8, 7.8), 10.54 (1H, m).

Reference Example 77

[2-(3-Isopropylphenoxy)phenyl]methanol

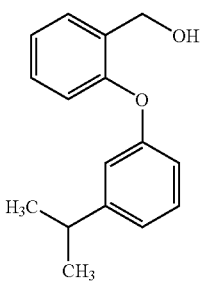

In the same manner as in Reference Example 23, the title compound was obtained from 2-(3-isopropylphenoxy)benzaldehyde. Yield 82%.

Oil.

$^1$H NMR: 1.24 (6H, d, J=6.9), 2.07 (1H, t, J=6.0), 2.84-2.93 (1H, m), 4.76 (2H, d, J=6.0), 6.75 (1H, dd, J=0.9, 2.4), 6.77-6.90 (2H, m), 6.98 (1H, d, J=7.8), 7.09-7.14 (1H, m), 7.22-7.27 (2H, m), 7.44 (1H, dd, J=1.5, 7.2).

Reference Example 78

2-(4-Isopropylphenoxy)benzaldehyde

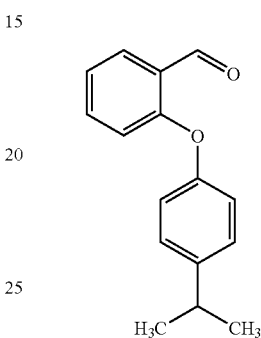

In the same manner as in Reference Example 76, the title compound was obtained from 2-fluorobenzaldehyde and 4-isopropylphenol. Yield 51%.

Oil.

$^1$H NMR: 1.26 (6H, d, J=6.9), 2.90-2.95 (1H, m), 6.89 (1H, d, J=8.1), 6.99 (2H, d, J=8.7), 7.13-7.26 (3H, m), 7.46-7.52 (1H, m), 7.93 (1H, dd, J=1.5, 7.5), 10.54 (1H, s).

Reference Example 79

[2-(4-Isopropylphenoxy)phenyl]methanol

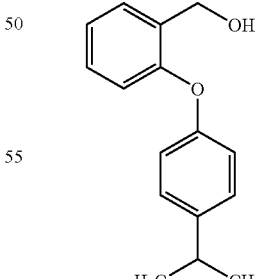

In the same manner as in Reference Example 23, the title compound was obtained from 2-(4-isopropylphenoxy)benzaldehyde. Yield 91%.

Oil.

¹H NMR: 1.24 (6H, d, J=6.9), 2.10 (1H, t, J=5.4), 2.85-2.95 (1H, m), 4.75 (2H, d, J=5.4), 6.83-6.94 (3H, m), 7.07-7.23 (4H, m), 7.43 (1H, dd, J=1.5, 7.5).

Reference Example 80

2-(2-Fluorophenoxy)benzaldehyde

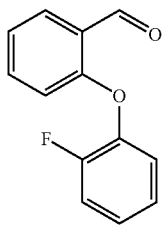

In the same manner as in Reference Example 76, the title compound was obtained from 2-fluorobenzaldehyde and 2-fluorophenol. Yield 71%.

Oil.

¹H NMR: 6.84 (1H, d, J=8.1), 7.02-7.26 (5H, m), 7.48-7.53 (1H, m), 7.93 (1H, dd, J=1.8, 7.85), 10.53 (1H, s).

Reference Example 81

[2-(2-Fluorophenoxy)phenyl]methanol

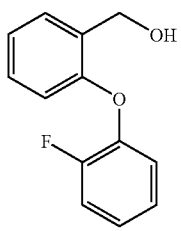

In the same manner as in Reference Example 23, the title compound was obtained from 2-(2-fluorophenoxy)benzaldehyde. Yield 90%.

Oil.

¹H NMR: 2.07 (1H, t, J=4.5), 4.75 (2H, d, J=4.5), 6.80 (1H, d, J=8.1), 6.92-7.14 (5H, m), 7.21-7.27 (1H, m), 7.45 (1H, dd, J=1.5, 7.5).

Reference Example 82

2-(2-Isopropylphenoxy)benzaldehyde

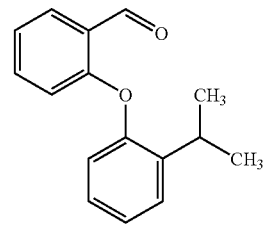

In the same manner as in Reference Example 76, the title compound was obtained from 2-fluorobenzaldehyde and 2-isopropylphenol. Yield 51%.

Oil.

¹H NMR: 1.23 (6H, d, J=6.9), 3.23-2.28 (1H, m), 6.75 (1H, d, J=6.9), 6.89-6.92 (1H, m), 7.10-7.22 (3H, m), 7.38-7.49 (2H, m), 6.94 (1H, dd, J=1.8, 7.8), 10.62 (1H, s).

Reference Example 83

[2-(2-Isopropylphenoxy)phenyl]methanol

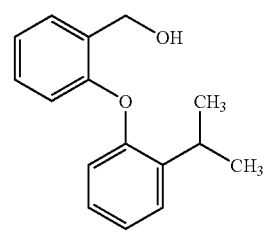

In the same manner as in Reference Example 23, the title compound was obtained from 2-(2-isopropylphenoxy)benzaldehyde. Yield 82%.

Oil.

$^1$H NMR: 1.24 (6H, d, J=6.9), 2.09 (1H, t, J=6.6), 3.22-2.31 (1H, m), 4.82 (2H, d, J=6.6), 6.68 (1H, dd, J=0.6, 8.1), 6.81-6.83 (1H, m), 7.04-7.22 (4H, m), 7.34-7.37 (1H, m), 7.43 (1H, dd, J=1.5, 7.5).

Reference Example 84

2-(3-Fluorophenoxy)benzaldehyde

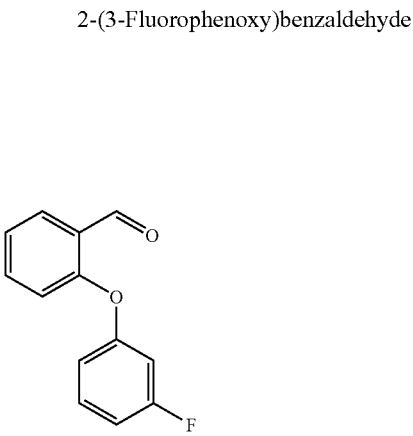

In the same manner as in Reference Example 76, the title compound was obtained from 2-fluorobenzaldehyde and 3-fluorophenol. Yield 93%.

Oil.

$^1$H NMR: 6.75-6.91 (3H, m), 6.98 (1H, d, J=8.4), 7.23-7.37 (2H, m), 7.54-7.59 (1H, m), 7.95 (1H, dd, J=1.8, 7.8), 10.45 (1H, s).

Reference Example 85

[2-(3-Fluorophenoxy)phenyl]methanol

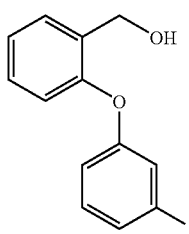

In the same manner as in Reference Example 23, the title compound was obtained from 2-(3-fluorophenoxy)benzaldehyde. Yield 93%.

Oil.

$^1$H NMR: 1.94 (1H, t, J=5.1), 4.51 (2H, d, J=5.1), 6.64-6.82 (3H, m), 6.93 (1H, d, J=7.8), 7.17-7.32 (3H, m), 7.49 (1H, d, J=7.5).

Reference Example 86

2-(4-Fluorophenoxy)benzaldehyde

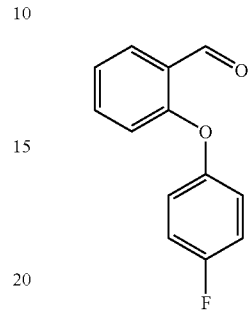

In the same manner as in Reference Example 76, the title compound was obtained from 2-fluorobenzaldehyde and 4-fluorophenol. Yield 75%.

Oil.

$^1$H NMR: 6.79 (1H, d, J=8.4), 7.13-7.26 (5H, m), 7.40-7.52 (1H, m), 7.94 (1H, dd, J=1.5, 7.5), 10.61 (1H, s).

Reference Example 87

[2-(4-Fluorophenoxy)phenyl]methanol

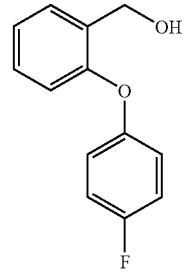

In the same manner as in Reference Example 23, the title compound was obtained from 2-(4-fluorophenoxy)benzaldehyde. Yield 88%.

Oil.

$^1$H NMR: 2.11 (1H, t, J=4.8), 4.82 (2H, d, J=5.1), 6.74 (1H, d, J=8.1), 7.01-7.26 (6H, m), 7.45 (1H, dd, J=1.5, 7.2).

Reference Example 88

{3-[4-(Trifluoromethyl)phenoxy]phenyl}methanol

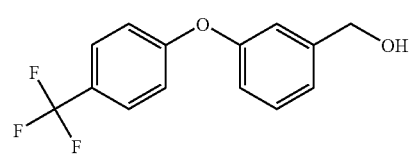

In the same manner as in Reference Example 62, the title compound was obtained from 3-hydroxybenzyl alcohol and 1-bromo-4-(trifluoromethyl)benzene. Yield 19%.

Oil.

¹H NMR: 2.07 (1H, br), 4.67 (2H, s), 6.95-6.96 (1H, m), 7.05-7.03 (3H, m), 7.16 (1H, d, J=7.5), 7.36 (1H, dd, J=7.8, 7.8), 7.56 (2H, d, J=8.4).

Reference Example 89

[3-(4-Propylphenoxy)phenyl]methanol

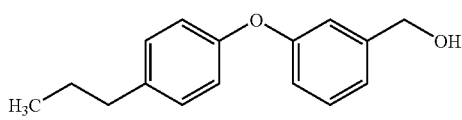

In the same manner as in Reference Example 62, the title compound was obtained from 3-hydroxybenzyl alcohol and 1-bromo-4-propylbenzene. Yield 15%.

Oil.

¹H NMR: 0.95 (3H, t, J=7.2), 1.58-1.70 (3H, m), 2.57 (2H, t, J=7.5), 4.65 (2H, d, J=5.7), 6.89-7.08 (7H, m), 7.30 (1H, dd, J=7.8, 7.8).

Reference Example 90

[3-(3,4-Dichlorophenoxy)phenyl]methanol

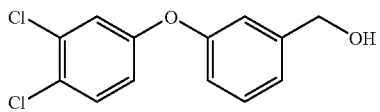

In the same manner as in Reference Example 62, the title compound was obtained from 3,4-dichlorophenol and 3-bromobenzyl alcohol. Yield 14%.

Oil.

¹H NMR: 1.81 (1H, br), 4.69 (2H, s), 6.84-6.95 (2H, m), 7.03-7.17 (3H, m), 7.32-7.39 (2H, m).

Reference Example 91

Ethyl 3-[3,5-difluoro-4-(2-naphthylmethoxy)phenyl]propanoate

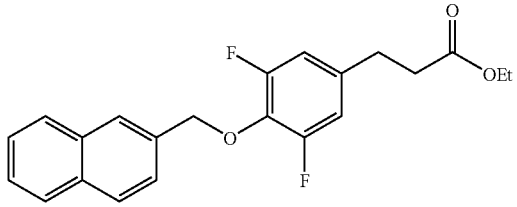

Ethyl 3,5-difluoro-4-hydroxybenzenepropanoate (200 mg, 0.87 mmol) was dissolved in DMF (10 mL). 2-(Bromomethyl)naphthalene (212 mg, 0.96 mmol) and potassium carbonate (132 mg, 0.96 mmol) were added thereto, and then the mixture was stirred at 80° C. for 4 hours. To the reaction solution was added water, and the reaction mixture was extracted with ethyl acetate. The extract was dried, and then concentrated under reduced pressure. The residue was purified with silica gel column chromatography (hexane/ethyl acetate=100:0 to 80:20) to give the title compound (298 mg, yield 93%).

Oil.

¹H NMR: 1.21 (3H, t, J=7.1), 2.56 (2H, t, J=7.7), 2.85 (2H, t, J=7.7), 4.11 (2H, q, J=7.1), 5.29 (2H, s), 6.71-6.74 (2H, m), 7.46-7.50 (2H, m), 7.59 (1H, dd, J=1.5, 8.6), 7.82-7.86 (4H, m).

Reference Example 92

3-[3,5-Difluoro-4-(2-naphthylmethoxy)phenyl]propanoic acid

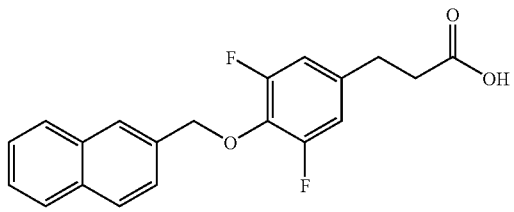

In the same manner as in Reference Example 5, the title compound was obtained from ethyl 3-[3,5-difluoro-4-(2-naphthylmethoxy)phenyl]propanoate. Yield 70%.

Melting point 130-131° C. (recrystallization from ethyl acetate-hexane)

¹H NMR: 2.63 (2H, t, J=7.5), 2.86 (2H, t, J=7.5), 5.29 (2H, s), 6.70-6.77 (2H, m), 7.46-7.49 (2H, m), 7.59 (1H, dd, J=1.0, 8.6), 7.82-7.86 (4H, m).

Reference Example 93

Ethyl 3-[3,5-difluoro-4-(1-naphthylmethoxy)phenyl]propanoate

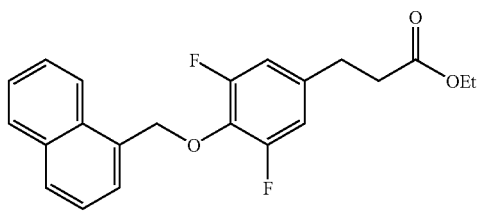

In the same manner as in Reference Example 89, the title compound was obtained from ethyl 3,5-difluoro-4-hydroxybenzenepropanoate and 1-(bromomethyl)naphthalene. Yield 92%.

Oil.

¹H NMR: 1.22 (3H, t, J=7.1), 2.57 (2H, t, J=7.7), 2.85 (2H, t, J=7.7), 4.12 (2H, q, J=7.1), 5.56 (2H, s), 6.70-6.77 (2H, m), 7.40-7.61 (4H, m), 7.86 (2H, dd, J=7.7, 7.7), 8.27 (1H, d, J=8.3).

Reference Example 94

3-[3,5-Difluoro-4-(1-naphthylmethoxy)phenyl]propanoic acid

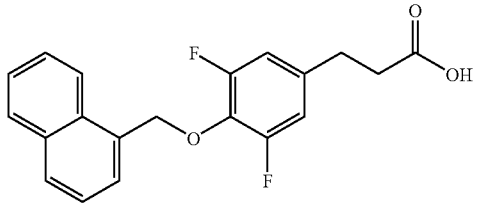

In the same manner as in Reference Example 5, the title compound was obtained from ethyl 3-[3,5-difluoro-4-(1-naphthylmethoxy)phenyl]propanoate. Yield 70%.

Melting point 111-112° C. (recrystallization from ethyl acetate-hexane)

¹H NMR: 2.65 (2H, t, J=7.5), 2.87 (2H, t, J=7.5), 5.57 (2H, s), 6.72-6.79 (2H, m), 7.41-7.61 (4H, m), 7.86 (2H, dd, J=7.6, 7.6), 8.27 (1H, d, J=8.3).

Reference Example 95

Ethyl 3-{4-[(5-chloro-1-benzothien-3-yl)methoxy]-3,5-difluorophenyl}propanoate

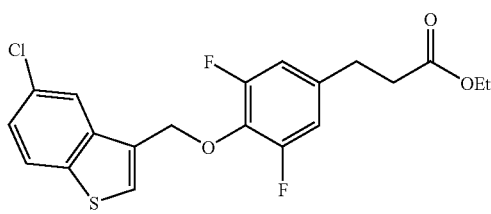

In the same manner as in Reference Example 91, the title compound was obtained from ethyl 3,5-difluoro-4-hydroxybenzenepropanoate and 3-(bromomethyl)-5-chloro-1-benzothiophene. Yield 90%.

Oil.

¹H NMR: 1.24 (3H, t, J=7.2), 2.58 (2H, t, J=7.7), 2.87 (2H, t, J=7.7), 4.12 (2H, q, J=7.2), 5.31 (2H, s), 6.72-6.78 (2H, m), 7.34 (1H, dd, J=2.0, 8.6), 7.55 (1H, s), 7.76 (1H, dd, J=8.6), 7.98 (1H, d, J=2.0).

Reference Example 96

3-{4-[(5-Chloro-1-benzothien-3-yl)methoxy]-3,5-difluorophenyl}propanoic acid

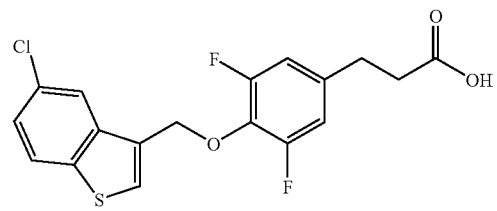

In the same manner as in Reference Example 5, the title compound was obtained from ethyl 3-{4-[(5-chloro-1-benzothien-3-yl)methoxy]-3,5-difluorophenyl}propanoate. Yield 83%.

Melting point 164-165° C. (recrystallization from ethyl acetate-hexane)

¹H NMR: 2.65 (2H, t, J=7.4), 2.89 (2H, t, J=7.4), 5.32 (2H, s), 6.75-6.78 (2H, m), 7.36 (1H, dd, J=2.0, 8.6), 7.55 (1H, s), 7.76 (1H, dd, J=8.6), 7.97 (1H, d, J=2.0).

Reference Example 97

Ethyl (E)-3-(2,5-difluoro-4-methoxyphenyl)acrylate

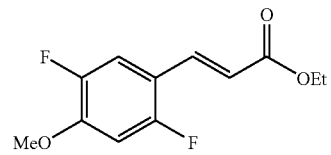

In the same manner as in Reference Example 12, the title compound was obtained from 1-bromo-2,5-difluoro-4-methoxybenzene and ethyl acrylate. Yield 44%.

Oil.

¹H NMR: 1.33 (3H, t, J=7.2), 3.91 (3H, s), 4.26 (2H, q, J=7.2), 6.36 (1H, d, J=15.9), 6.71 (1H, dd, J=6.9, 11.4), 7.25 (1H, dd, J=6.9, 11.4), 7.71 (1H, d, J=15.9).

Reference Example 98

Ethyl 3-(2,5-difluoro-4-methoxyphenyl)propanoate

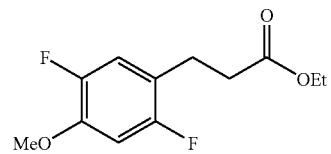

In the same manner as in Reference Example 41, the title compound was obtained from ethyl (E)-3-(2,5-difluoro-4-methoxyphenyl)acrylate. Yield 99%.

Oil.

$^1$H NMR: 1.24 (3H, t, J=7.2), 2.58 (2H, t, J=7.8), 2.88 (2H, t, J=7.8), 3.85 (3H, s), 4.13 (2H, q, J=7.2), 6.66 (1H, dd, J=7.2, 11.1), 6.92 (1H, dd, J=7.2, 11.1).

Reference Example 99

Ethyl 3-(2,5-difluoro-4-hydroxyphenyl)propanoate

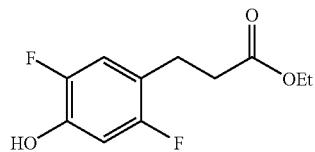

Ethyl 3-(2,5-difluoro-4-methoxyphenyl)propanoate (1.45 g, 5.9 mmol) was dissolved in dichloromethane (50 mL), a 1 M solution of boron tribromide in dichloromethane (7 mL) was added thereto, and the mixture was stirred at 0° C. for 4 hours. The reaction solution was concentrated under reduced pressure, water was added to the residue, and the reaction mixture was extracted with ethyl acetate. The extract was dried, and then concentrated under reduced pressure. The residue was purified with silica gel column chromatography (hexane/ethyl acetate=100:0 to 70:30) to give the title compound (387 mg, yield 29%).

Oil.

$^1$H NMR: 1.24 (3H, t, J=7.2), 2.58 (2H, t, J=6.6), 2.87 (2H, t, J=6.6), 4.13 (2H, q, J=7.2), 5.23 (1H, br), 6.70 (1H, dd, J=7.5, 10.5), 6.93 (1H, dd, J=7.5, 10.5).

Reference Example 100

Ethyl 3-{2,5-difluoro-4-[(3-phenoxybenzyl)oxy]phenyl}propanoate

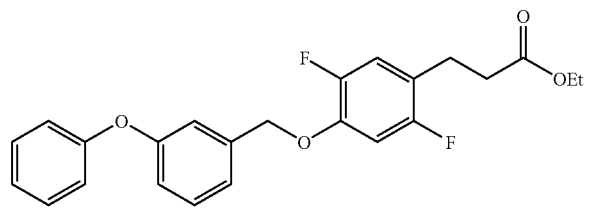

In the same manner as in Reference Example 1, the title compound was obtained from ethyl 3-(2,5-difluoro-4-hydroxyphenyl)propanoate and 3-phenoxybenzyl alcohol. Yield 39%.

Oil.

$^1$H NMR: 1.23 (3H, t, J=7.2), 2.57 (2H, t, J=7.8), 2.87 (2H, t, J=7.8), 4.12 (2H, q, J=7.2), 5.05 (2H, s), 6.67 (1H, dd, J=7.2, 10.8), 6.90-7.16 (7H, m), 7.31-7.37 (3H, m).

Reference Example 101

3-{2,5-Difluoro-4-[(3-phenoxybenzyl)oxy]phenyl}propanoic acid

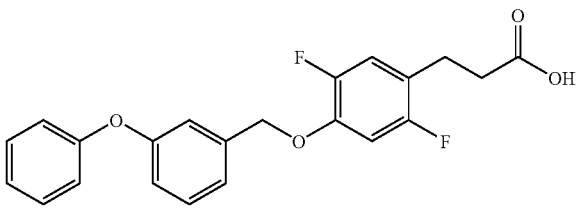

In the same manner as in Reference Example 5, the title compound was obtained from ethyl 3-{2,5-difluoro-4-[(3-phenoxybenzyl)oxy]phenyl}propanoate. Yield 80%.

Melting point 82-83° C. (recrystallization from ethyl acetate-hexane)

$^1$H NMR: 2.64 (2H, t, J=7.5), 2.89 (2H, t, J=7.5), 5.06 (2H, s), 6.68 (1H, dd, J=7.2, 10.8), 6.92-7.16 (7H, m), 7.32-7.37 (3H, m).

Reference Example 102

2-(3-Phenoxyphenyl)ethanol

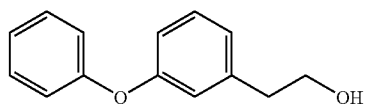

3-Phenoxyacetic acid (500 mg, 2.2 mmol) was dissolved in a 10% solution of hydrogen chloride in methanol (10 mL), and the mixture was stirred at room temperature for 4 hours. The reaction solution was concentrated under reduced pressure, water was added to the residue, and the mixture was extracted with ethyl acetate. The extract was dried, and then concentrated under reduced pressure. The residue was dissolved in tetrahydrofuran (20 mL), lithium boron hydride (144 mg, 6.6 mmol) was added thereto, and the mixture was stirred at room temperature for 2 days. The reaction solution was concentrated under reduced pressure, water was added to the residue, and the mixture was extracted with ethyl acetate. The extract was dried, and then concentrated under reduced pressure to give the title compound (370 mg, yield 78%).

Oil.

$^1$H NMR: 1.41 (1H, t, J=5.4), 2.85 (2H, t, J=6.6), 3.82-3.88 (2H, m), 6.85-6.90 (2H, m), 6.96-7.03 (3H, m), 7.08-7.03 (1H, m), 7.24-7.36 (3H, m).

Reference Example 103

Ethyl 3-{3-fluoro-4-[2-(3-phenoxyphenyl)ethoxy]phenyl}propanoate

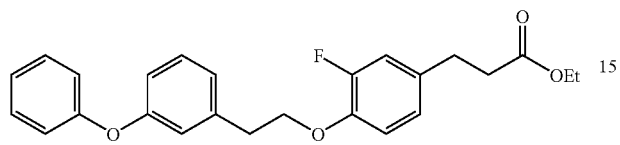

In the same manner as in Reference Example 1, the title compound was obtained from ethyl 3-fluoro-4-hydroxybenzenepropanoate and 2-(3-phenoxyphenyl)ethanol. Yield 79%.

Oil.

$^1$H NMR: 1.23 (3H, t, J=7.2), 2.57 (2H, t, J=7.8), 2.87 (2H, t, J=7.8), 3.08 (2H, t, J=6.9), 4.08-4.21 (4H, m), 6.76-7.13 (9H, m), 7.24-7.36 (3H, m).

Reference Example 104

3-{3-Fluoro-4-[2-(3-phenoxyphenyl)ethoxy]phenyl}propanoic acid

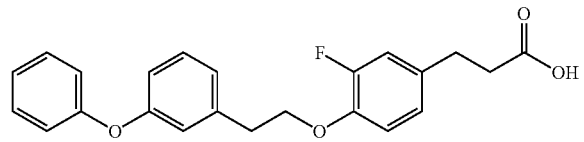

In the same manner as in Reference Example 5, the title compound was obtained from ethyl 3-{3-fluoro-4-[2-(3-phenoxyphenyl)ethoxy]phenyl}propanoate. Yield 99%.

Melting point 56-57° C. (recrystallization from ethyl acetate-hexane)

$^1$H NMR: 2.64 (2H, t, J=7.8), 2.88 (2H, t, J=7.8), 3.08 (2H, t, J=6.9), 4.19 (2H, t, J=6.9), 6.83-7.12 (7H, m), 7.24-7.36 (5H, m).

Reference Example 105

(4-Phenoxyphenyl)methanol

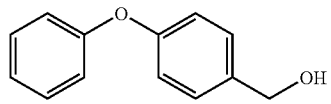

A solution of iodobenzene (2.0 g, 9.7 mmol), 4-hydroxybenzyl alcohol (1.0 g, 8.1 mmol), potassium carbonate (0.67 g, 4.8 mmol), copper chloride(I) (0.016 g, 0.16 mmol) and 8-quinolinol (0.023 g, 0.16 mmol) in 1,3-dimethyl-2-imidazolidinone (5 mL) was stirred at 170° C. for 20 hours. The reaction solution was filtered, extracted with ethyl acetate, and then concentrated under reduced pressure. The residue was purified with silica gel column chromatography (hexane/ethyl acetate=7:3) to give the title compound (0.12 g, yield 7%) as an oily matter.

$^1$H NMR: 1.60 (1H, t, J=5.8), 4.68 (2H, d, J=5.8), 6.95-7.16 (5H, m), 7.30-7.37 (4H, m).

Reference Example 106

Ethyl 3-[3-fluoro-4-(4-phenoxybenzyloxy)phenyl]propanoate

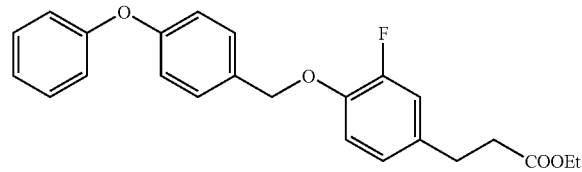

To a solution of ice-cooled ethyl 3-(3-fluoro-4-hydroxyphenyl)propanoate (0.19 g, 0.88 mmol), (4-phenoxyphenyl)methanol (0.12 g, 0.58 mmol) and triphenylphosphine (0.23 g, 0.88 mmol) in tetrahydrofuran (5 mL) was added dropwise diethyl azodicarboxylate (a 40% solution in toluene, 0.40 mL, 0.88 mmol), and the mixture was stirred at room temperature for 4 hours. To the reaction solution was added water, and the reaction mixture was extracted with ethyl acetate. The extract was washed with water, and then concentrated under reduced pressure. The residue was purified with silica gel column chromatography (hexane/ethyl acetate=8:2) to give the title compound (0.16 g, yield 71%) as an oily matter.

$^1$H NMR: 1.23 (3H, t, J=7.1), 2.58 (2H, t, J=7.7), 2.88 (2H, t, J=7.7), 4.13 (2H, q, J=7.1), 5.07 (2H, s), 6.81-7.04 (7H, m), 7.07-7.17 (1H, m), 7.28-7.44 (4H, m).

Reference Example 107

3-[3-Fluoro-4-(4-phenoxybenzyloxy)phenyl]propanoic acid

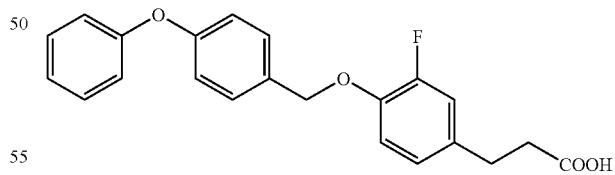

To a solution of ethyl 3-[3-fluoro-4-(4-phenoxybenzyloxy)phenyl]propanoate (0.16 g, 0.41 mmol) in ethanol (3 mL) was added a 2 N aqueous sodium hydroxide solution (3 mL), and the mixture was stirred at room temperature for 2 hours. To the reaction solution was added 2 N hydrochloric acid (3 mL), and the mixture was extracted with ethyl acetate. The extract was washed with water, and then concentrated under reduced pressure. The residue was recrystallized from ethyl acetate-hexane to give the title compound (0.14 g, yield 94%) as white powders.

Melting point 123-125° C.

¹H NMR: 2.62-2.69 (2H, m), 2.90 (2H, t, J=7.6), 5.07 (2H, s), 6.83-7.05 (7H, m), 7.06-7.15 (1H, m), 7.31-7.42 (4H, m).

Reference Example 108

Ethyl 3-[4-(4-ethoxy-benzyloxy)-3-fluorophenyl]propanoate

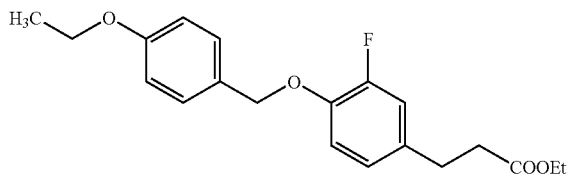

In the same manner as in Reference Example 106, the title compound as an oily matter was obtained from ethyl 3-(3-fluoro-4-hydroxyphenyl)propanoate and (4-ethoxyphenyl)methanol. Yield 77%.

¹H NMR: 1.23 (3H, t, J=7.1), 1.41 (3H, t, J=7.0), 2.57 (2H, t, J=7.7), 2.87 (2H, t, J=7.7), 4.03 (2H, q, J=7.0), 4.12 (2H, q, J=7.1), 5.03 (2H, s), 6.76-6.99 (5H, m), 7.34 (2H, d, J=8.6).

Reference Example 109

3-[4-(4-Ethoxybenzyloxy)-3-fluorophenyl]propanoic acid

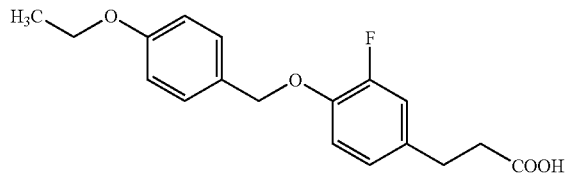

In the same manner as in Reference Example 107, the title compound as white powders was obtained from ethyl 3-[4-(4-ethoxybenzyloxy)-3-fluorophenyl]propanoate. Yield 80%.

Melting point 126-127° C.

¹H NMR: 1.41 (3H, t, J=7.0), 2.64 (2H, t, J=7.5), 2.88 (2H, t, J=7.6), 4.03 (2H, q, J=7.0), 5.03 (2H, s), 6.84-7.90 (5H, m), 7.34 (2H, d, J=8.5).

Reference Example 110

(4-Isopropoxyphenyl)methanol

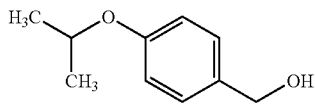

With ice cooling, to a solution of 4-isopropoxybenzaldehyde (0.93 g, 5.6 mmol) in methanol (20 mL) was added a solution of sodium tetrahydroborate (0.32 g, 11 mmol) in methanol (10 mL), and the mixture was stirred at room temperature for 4 hours. The mixture was acidified by adding 2 N hydrochloric acid to the reaction solution, and extracted with diethyl ether. The extract was washed with water, and then concentrated under reduced pressure. The residue was purified with silica gel column chromatography (hexane/ethyl acetate=7:3) to give the title compound (0.76 g, yield 81%) as an oily matter.

¹H NMR: 1.33 (6H, d, J=6.1), 4.55 (1H, quintet, J=6.1), 4.61 (2H, s), 6.85-6.91 (2H, m), 7.25-7.30 (2H, m).

Reference Example 111

Ethyl 3-[3-fluoro-4-(4-isopropoxybenzyloxy)phenyl]propanoate

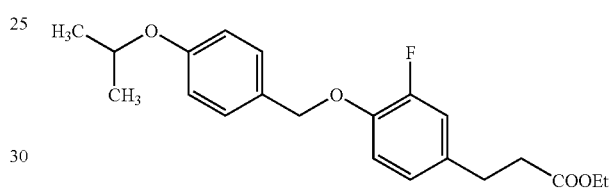

In the same manner as in Reference Example 106, the title compound as an oily matter was obtained from ethyl 3-(3-fluoro-4-hydroxyphenyl)propanoate and (4-isopropoxyphenyl)methanol. Yield 80%.

¹H NMR: 1.23 (3H, t, J=7.1), 1.33 (6H, d, J=6.1), 2.57 (2H, t, J=7.7), 2.87 (2H, t, J=7.7), 4.55 (1H, quintet, J=6.0), 5.02 (2H, s), 6.83-6.98 (5H, m), 7.30-7.36 (2H, m).

Reference Example 112

3-[3-Fluoro-4-(4-isopropoxybenzyloxy)phenyl]propanoic acid

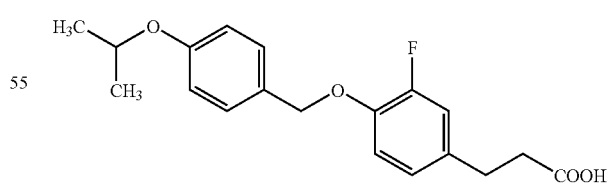

In the same manner as in Reference Example 107, the title compound as white powders was obtained from ethyl 3-[3-fluoro-4-(4-isopropoxybenzyloxy)phenyl]propanoate. Yield 79%.

Melting point 118.0-118.6° C.

¹H NMR: 1.33 (6H, d, J=6.1), 2.65 (2H, t, J=7.6), 2.89 (2H, t, J=7.6), 4.55 (1H, quintet, J=6.0), 5.02 (2H, s), 6.84-6.98 (5H, m), 7.31-7.36 (2H, m).

Reference Example 113

Methyl 3-hydroxy-5-(methoxymethoxy)benzoate

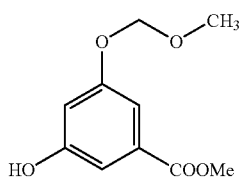

With ice cooling, to a solution of methyl 3,5-dihydroxybenzoate (14.0 g, 83.3 mmol) and N,N-diisopropylethylamine (11.0 g, 85.0 mmol) in dichloromethane (100 mL) was added dropwise chloromethylmethyl ether (6.84 g, 85.0 mmol), and the mixture was stirred at room temperature for 5 hours. The reaction mixture was diluted with dichloromethane (300 mL), and the organic layer was washed successively with a 3% aqueous hydrochloric acid solution, a saturated aqueous sodium bicarbonate solution and saturated brine, and then concentrated under reduced pressure. The residue was purified with silica gel column chromatography (hexane/ethyl acetate=4:6) to give the title compound (7.74 g, yield 44%) as an oily matter.

¹H NMR: 3.48 (3H, s), 3.90 (3H, s), 5.18 (2H, s), 5.35 (1H, brs), 6.76 (1H, t, J=2.3), 7.19 (1H, t, J=2.2), 7.27-7.29 (1H, m).

Reference Example 114

3-(Hydroxymethyl)-5-(methoxymethoxy)phenol

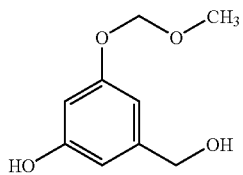

With ice cooling, to a solution of aluminum lithium hydride (1.80 g, 47.5 mmol) in tetrahydrofuran (50 mL) was added dropwise a solution of methyl 3-hydroxy-5-(methoxymethoxy)benzoate (7.74 g, 36.5 mmol) in tetrahydrofuran (50 mL), and the mixture was stirred at room temperature for 4 hours. To the reaction solution were successively added water (2 mL), a 15% aqueous sodium hydroxide solution (2 mL) and water (7 mL), and the mixture was further stirred for 2 hours. The reaction mixture was filtered, and the filtrate was concentrated under reduced pressure. The residue was purified with silica gel column chromatography (hexane/ethyl acetate=5:5) to give the title compound (4.46 g, yield 66%) as an oily matter.

¹H NMR: 2.34 (1H, brs), 3.46 (3H, s), 4.58 (2H, s), 5.13 (2H, s), 6.00 (1H, brs), 6.45-6.50 (2H, m), 6.58 (1H, s).

Reference Example 115

[3-(Methoxymethoxy)-5-phenoxyphenyl]methanol

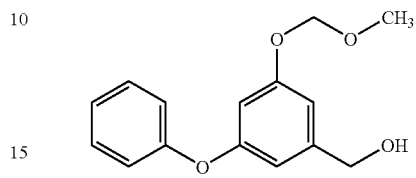

In the same manner as in Reference Example 105, the title compound as an oily matter was obtained from bromobenzene and 3-(hydroxymethyl)-5-(methoxymethoxy)phenol. Yield 72%.

¹H NMR: 1.66 (1H, t, J=6.1), 3.47 (3H, s), 4.63 (2H, d, J=6.1), 5.15 (2H, s), 6.62-6.64 (2H, m), 6.80 (1H, s), 7.01-7.05 (2H, m), 7.09-7.15 (1H, m), 7.31-7.38 (2H, m).

Reference Example 116

3-(Hydroxymethyl)-5-phenoxyphenol

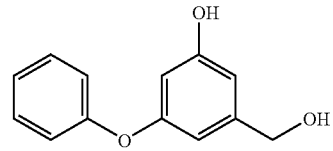

To a solution of [3-(methoxymethoxy)-5-phenoxyphenyl]methanol (0.75 g, 2.86 mmol) in ethanol (10 mL) was added concentrated hydrochloric acid (1 mL), and the mixture was stirred at 40° C. for 4 hours. The reaction solution was concentrated under reduced pressure, and the resulting residue was purified with silica gel column chromatography (hexane/ethyl acetate=5:5) to give the title compound (0.60 g, yield 96%) as an oily matter.

¹H NMR: 2.28 (2H, brs), 4.60 (2H, s), 6.40 (1H, t, J=2.2), 6.52-6.62 (2H, m), 7.00-7.05 (2H, m), 7.12 (1H, t, J=7.3), 7.32-7.37 (2H, m).

Reference Example 117

(3,5-Diphenoxyphenyl)methanol

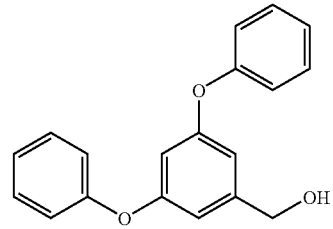

In the same manner as in Reference Example 105, the title compound as an oily matter was obtained from bromobenzene and 3-(hydroxymethyl)-5-phenoxyphenol. Yield 71%.

$^1$H NMR: 1.65 (1H, t, J=6.1), 4.61 (2H, d, J=6.0), 6.60 (1H, t, J=2.2), 6.72 (2H, d, J=2.2), 7.00-7.05 (4H, m), 7.08-7.16 (2H, m), 7.30-7.38 (4H, m).

Reference Example 118

[3-(2-Isopropylphenoxy)phenyl]methanol

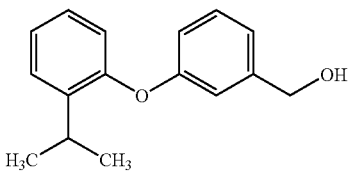

In the same manner as in Reference Example 105, the title compound as an oily matter was obtained from 3-bromobenzyl alcohol and 2-isopropylphenol.

$^1$H NMR: 1.22 (6H, d, J=6.9), 1.65 (1H, brs), 3.27 (1H, septet, J=6.9), 4.66 (2H, s), 6.79-6.92 (2H, m), 6.95 (1H, s), 7.04 (1H, d, J=7.5), 7.09-7.38 (4H, m).

Reference Example 119

[3-(3-Isopropylphenoxy)phenyl]methanol

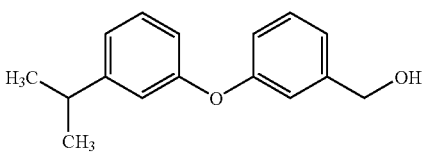

In the same manner as in Reference Example 105, the title compound as an oily matter was obtained from 3-bromobenzyl alcohol and 3-isopropylphenol.

$^1$H NMR: 1.24 (6H, d, J=6.9), 1.66 (1H, brs), 2.89 (1H, septet, J=6.9), 4.67 (2H, d, J=5.4), 6.79 (1H, m), 6.91-7.04 (3H, m), 7.09 (1H, d, J=7.5), 7.20-7.37 (3H, m).

Reference Example 120

[3-(4-Isopropylphenoxy)phenyl]methanol

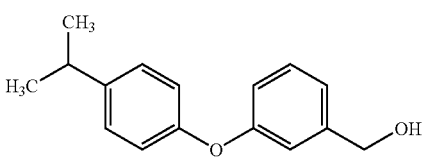

In the same manner as in Reference Example 105, the title compound as an oily matter was obtained from 3-bromobenzyl alcohol and 4-isopropylphenol.

$^1$H NMR: 1.25 (6H, d, J=6.9), 1.65 (1H, brs), 2.91 (1H, septet, J=6.9), 4.66 (2H, s), 6.89-6.97 (3H, m), 7.01 (1H, s), 7.07 (1H, d, J=7.8), 7.16-7.38 (3H, m).

Reference Example 121

[3-(2-Fluorophenoxy)phenyl]methanol

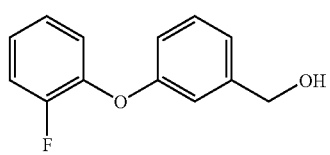

In the same manner as in Reference Example 105, the title compound as an oily matter was obtained from 3-bromobenzyl alcohol and 2-fluorophenol.

$^1$H NMR: 1.67 (1H, brs), 4.67 (2H, s), 6.90 (1H, dd, J=2.4, 8.1), 6.99 (1H, s), 7.03-7.41 (6H, m).

Reference Example 122

[3-(3-Fluorophenoxy)phenyl]methanol

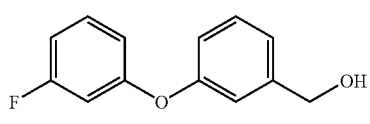

In the same manner as in Reference Example 105, the title compound as an oily matter was obtained from 3-bromobenzyl alcohol and 3-fluorophenol.

$^1$H NMR: 2.10 (1H, s), 4.70 (2H, s), 6.67-6.72 (1H, m), 6.76-6.83 (2H, m), 6.93-6.98 (1H, m), 7.06 (1H, s), 7.15 (1H, d, J=7.5), 7.20-7.40 (2H, m).

Reference Example 123

3-Ethoxy-2-methoxybenzaldehyde

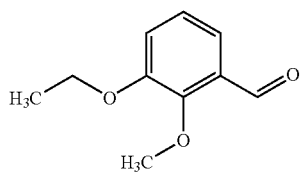

To a suspension of 3-ethoxysalicylaldehyde (1.00 g, 6.02 mmol) and potassium carbonate (3.33 g, 24.1 mmol) in N,N-dimethylformamide (10 mL) was added dimethyl sulfate (0.91 g, 7.22 mmol), and the mixture was stirred at 60° C. for 5 hours. The reaction mixture was diluted with ethyl acetate, filtered, and the filtrate was washed with water, and then concentrated under reduced pressure. The residue was purified with silica gel column chromatography (hexane/ethyl acetate=7:3) to give the title compound (1.10 g, yield 99%) as an oily matter.

¹H NMR: 1.49 (3H, t, J=7.1), 4.01 (3H, s), 4.12 (2H, q, J=7.0), 7.07-7.16 (2H, m), 7.41 (1H, dd, J=2.3, 7.1), 10.44 (1H, s).

Reference Example 124

(3-Ethoxy-2-methoxyphenyl)methanol

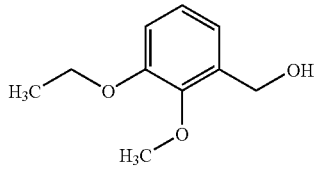

In the same manner as in Reference Example 110, the title compound as an oily matter was obtained from 3-ethoxy-2-methoxybenzaldehyde. Yield 84%.

¹H NMR: 1.46 (3H, t, J=7.0), 2.21 (1H, brs), 3.92 (3H, s), 4.09 (2H, q, J=7.0), 4.69 (2H, s), 6.89 (2H, td, J=1.6, 7.8), 7.02 (1H, t, J=7.8).

Reference Example 125

[3-(2-Methylphenoxy)phenyl]methanol

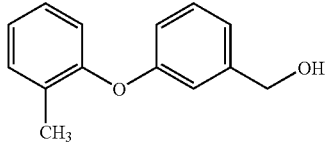

In the same manner as in Reference Example 105, the title compound as an oily matter was obtained from o-bromotoluene and 3-hydroxybenzyl alcohol. Yield 43%.

¹H NMR: 1.62 (1H, t, J=6.0), 2.24 (3H, s), 4.66 (2H, d, J=6.0), 6.82 (1H, dd, J=2.2, 8.0), 6.87-6.97 (2H, m), 7.03-7.22 (3H, m), 7.23-7.32 (2H, m).

Reference Example 126

[3-(3-Methylphenoxy)phenyl]methanol

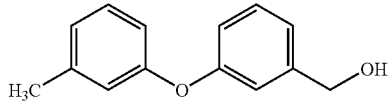

In the same manner as in Reference Example 105, the title compound as an oily matter was obtained from m-bromotoluene and 3-hydroxybenzyl alcohol. Yield 51%.

¹H NMR: 1.64 (1H, t, J=5.6), 2.33 (3H, s), 4.67 (2H, d, J=5.8), 6.73-6.86 (2H, m), 6.93 (2H, d, J=7.8), 7.01 (1H, s), 7.09 (1H, d, J=7.5), 7.22 (1H, t, J=7.7), 7.32 (1H, t, J=7.8).

Reference Example 127

[3-(4-Methylphenoxy)phenyl]methanol

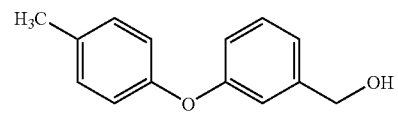

In the same manner as in Reference Example 105, the title compound as an oily matter was obtained from p-bromotoluene and 3-hydroxybenzyl alcohol. Yield 59%.

¹H NMR: 1.66 (1H, brs), 2.34 (3H, s), 4.66 (2H, d, J=5.9), 6.88-6.94 (3H, m), 6.99 (1H, s), 7.06 (1H, d, J=7.7), 7.14 (2H, d, J=8.4), 7.30 (1H, t, J=7.8).

Reference Example 128

[3-(Prop-2-yn-1-yloxy)phenyl]methanol

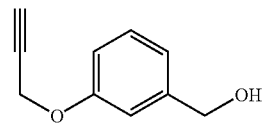

To an aqueous solution of 3-hydroxybenzyl alcohol (2.00 g, 16.1 mmol) in sodium hydroxide (35 mL, 1.5 M) was added propargyl bromide (2.11 g, 17.7 mmol), and the mixture was stirred at room temperature for 24 hours. The reaction mixture was extracted with diethyl ether and washed with a 1.5 M aqueous sodium hydroxide solution and saturated brine, and the organic layer was concentrated under reduced pressure. The resulting residue was purified with silica gel column chromatography (hexane/ethyl acetate=5:5) to give the title compound (0.82 g, yield 31%) as an oily matter.

¹H NMR: 1.67 (1H, t, J=5.7), 2.52 (1H, t, J=2.4), 4.67-4.81 (4H, m), 6.89-6.94 (1H, m), 6.97-7.01 (2H, m), 7.26-7.36 (1H, m).

Reference Example 129

Ethyl 3-hydroxy-2-methylbenzoate

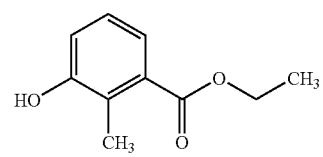

To a solution of 3-hydroxy-2-methylbenzoic acid (1.00 g, 6.57 mmol) in ethanol (10 mL) was added sulfuric acid (0.16 g, 1.64 mmol), and the mixture was heated under reflux for 12 hours. The reaction solution was cooled to room temperature, and one half of the solvent was concentrated under reduced pressure. Then, water (30 mL) was added thereto, and the mixture was neutralized with sodium carbonate. The mixture was extracted with diethyl ether, and the organic layer was washed with water, and then concentrated under reduced pressure. To the resulting residue was added hexane and crystallized to give the title compound (1.12 g, yield 95%).

$^1$H NMR: 1.39 (3H, t, J=7.2), 2.46 (3H, s), 4.36 (2H, q, J=7.1), 4.86 (1H, brs), 6.93 (1H, d, J=7.3), 7.11 (1H, t, J=7.9), 7.42 (1H, d, J=7.7).

Reference Example 130

Ethyl 3-ethoxy-2-methylbenzoate

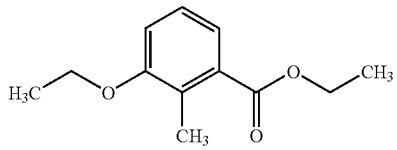

In the same manner as in Reference Example 106, the title compound as an oily matter was obtained from ethyl 3-hydroxy-2-methylbenzoate and ethanol. Yield 88%.

$^1$H NMR: 1.39 (3H, t, J=7.1), 1.44 (3H, t, J=7.0), 2.43 (3H, s), 4.04 (2H, q, J=6.9), 4.35 (2H, q, J=7.1), 6.94-6.97 (1H, m), 7.17 (1H, t, J=7.9), 7.38 (1H, dd, J=1.0, 7.8).

Reference Example 131

(3-Ethoxy-2-methylphenyl)methanol

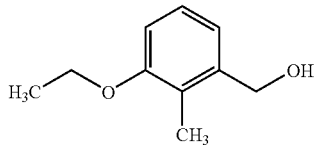

In the same manner as in Reference Example 115, the title compound as white powders was obtained from ethyl 3-ethoxy-2-methylbenzoate. Yield 95%.

$^1$H NMR: 1.43 (3H, t, J=7.0), 1.48 (1H, brs), 2.24 (3H, s), 4.03 (2H, q, J=7.0), 4.70 (2H, s), 6.81 (1H, d, J=8.1), 6.97 (1H, d, J=7.5), 7.15 (1H, t, J=7.9).

Reference Example 132

Ethyl 3-hydroxy-4-methylbenzoate

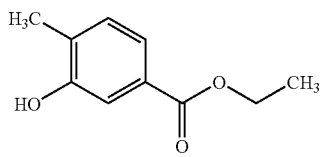

In the same manner as in Reference Example 129, the title compound as white powders was obtained from 3-ethoxy-4-methylbenzoic acid. Yield 98%.

$^1$H NMR: 1.38 (3H, t, J=7.1), 2.30 (3H, s), 4.35 (2H, q, J=7.1), 4.91 (1H, brs), 7.18 (1H, d, J=7.8), 7.46 (1H, s), 7.54 (1H, dd, J=1.5, 7.7).

Reference Example 133

Ethyl 3-ethoxy-4-methylbenzoate

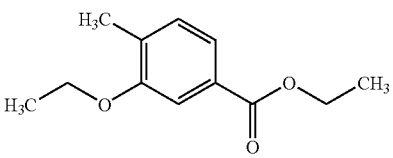

In the same manner as in Reference Example 106, the title compound as white powders was obtained from ethyl 3-hydroxy-4-methylbenzoate and ethanol. Yield 96%.

$^1$H NMR: 1.39 (3H, t, J=7.1), 1.44 (3H, t, J=7.1), 2.27 (3H, s), 4.10 (2H, q, J=7.0), 4.36 (2H, q, J=7.1), 7.16-7.19 (1H, m), 7.47 (1H, d, J=1.4), 7.55 (1H, dd, J=1.5, 7.7).

Reference Example 134

(3-Ethoxy-4-methylphenyl)methanol

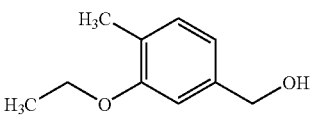

In the same manner as in Reference Example 115, the title compound as an oily matter was obtained from ethyl 3-ethoxy-4-methylbenzoate. Yield 89%.

$^1$H NMR: 1.43 (3H, t, J=7.0), 2.22 (3H, s), 4.05 (2H, q, J=7.0), 4.64 (2H, s), 6.81-6.85 (2H, m), 7.11 (1H, d, J=7.4).

Reference Example 135

Ethyl 3-{3-fluoro-4-[(3-phenoxybenzyl)oxy]phenyl}-2-methylpropanoate

A solution of N,N-diisopropylamide in THF (20 mL), which was prepared from n-butyllithium (a 1.6 M solution in hexane (2.3 mL, 3.7 mmol)) and diisopropylamine (0.79 mL, 5.58 mmol), was cooled to −70° C. A solution of the compound (1.0 g, 2.53 mmol) obtained in Example 11 in THF (5 mL) was added dropwise thereto. After stirring at the same temperature for 20 minutes, methane iodine (0.39 mL, 0.33 mmol) was added thereto. The reaction solution was stirred at −70° C. for 15 minutes, further stirred at room temperature for 30 minutes, and then a saturated aqueous ammonium chloride solution (1 mL) was added thereto. The mixture was diluted with ethyl acetate (30 mL), then washed with water and saturated brine, and dried over magnesium sulfate. The solvent was then distilled off under reduced pressure to give the title compound (250 mg, yield 25%) as an oily matter.

$^1$H NMR: 1.14 (3H, d, J=6.7), 1.19 (3H, t, J=7.1), 2.51-2.71 (2H, m), 2.92 (1H, m), 4.08 (2H, q, J=7.1), 5.07 (2H, s), 6.75-7.02 (6H, m), 7.05-7.21 (3H, m), 7.30-7.39 (3H, m).

Reference Example 136

3-{3-Fluoro-4-[(3-phenoxybenzyl)oxy]phenyl}-2-methylpropanoic acid

A mixture of ethyl 3-{3-fluoro-4-[(3-phenoxybenzyl)oxy]phenyl}-2-methylpropanoate (127 mg, 0.31 mmol), a 2 N aqueous sodium hydroxide solution (1 mL) and ethanol (2 mL) was stirred at 60° C. for 1.5 hours. The reaction solution was ice-cooled and acidified with 1 N hydrochloric acid, and then the solvent was distilled off under reduced pressure. The residue was dissolved in methylene chloride (5 mL), and the mixture was washed with water and saturated brine and dried over magnesium sulfate. The solvent was then distilled off under reduced pressure to give the title compound (93 mg, 78%) as an oily matter.

$^1$H NMR: 1.18 (3H, d, J=6.8), 2.52-2.78 (2H, m), 2.91-3.01 (1H, m), 5.07 (2H, s), 6.78-7.05 (6H, m), 7.06-7.20 (3H, m), 7.28-7.35 (3H, m).

Example 1

Ethyl 3,5-difluoro-4-[(3-phenoxyphenyl)methoxy]benzenepropanoate

In the same manner as in Reference Example 1, the title compound was obtained from ethyl 3,5-difluoro-4-hydroxybenzenepropanoate and 3-phenoxybenzyl alcohol. Yield 90%.

Oil.

$^1$H NMR (CDCl$_3$) δ 1.23 (3H, t, J=7.1 Hz), 2.57 (2H, t, J=7.5 Hz), 2.86 (2H, t, J=7.5 Hz), 4.12 (2H, q, J=7.1 Hz), 5.08 (2H, s), 6.68-6.78 (2H, m), 6.92-7.01 (3H, m), 7.06-7.18 (3H, m), 7.29-7.37 (3H, m).

Example 2

3,5-Difluoro-4-[(3-phenoxyphenyl)methoxy]benzenepropanoic acid

In the same manner as in Reference Example 5, the title compound was obtained from ethyl 3,5-difluoro-4-[(3-phenoxyphenyl)methoxy]benzenepropanoate. Yield 73%.

Melting point 71-72° C. (recrystallization from ethyl acetate-hexane).

$^1$H NMR (CDCl$_3$) δ 2.64 (2H, t, J=7.5 Hz), 2.87 (2H, t, J=7.5 Hz), 5.09 (2H, s), 6.67-6.77 (2H, m), 6.94-7.00 (3H, m), 7.09-7.19 (3H, m), 7.29-7.36 (3H, m).

Example 3

Methyl 3-chloro-4-[(3-phenoxyphenyl)methoxy]benzenepropanoate

In the same manner as in Reference Example 1, the title compound was obtained from methyl 3-chloro-4-hydroxybenzenepropanoate and 3-phenoxybenzyl alcohol. Yield 99%.

Oil.

$^1$H NMR (CDCl$_3$) δ 2.58 (2H, t, J=7.4 Hz), 2.86 (2H, t, J=7.4 Hz), 3.66 (3H, s), 5.09 (2H, s), 6.84 (1H, d, J=8.4 Hz), 6.92-7.02 (4H, m), 7.08-7.13 (2H, m), 7.16-7.22 (2H, m), 7.31-7.36 (3H, m).

Example 4

3-Chloro-4-[(3-phenoxyphenyl)methoxy]benzenepropanoic acid

In the same manner as in Reference Example 5, the title compound was obtained from methyl 3-chloro-4-[(3-phenoxyphenyl)methoxy]benzenepropanoate. Yield 62%.

Oil.

$^1$H NMR (CDCl$_3$) δ 2.63 (2H, t, J=7.4 Hz), 2.87 (2H, t, J=7.4 Hz), 5.09 (2H, s), 6.85 (1H, d, J=8.4 Hz), 6.91-7.03 (4H, m), 7.09-7.28 (4H, m), 7.30-7.36 (3H, m).

Example 5

Ethyl 3,5-difluoro-4-[(3-methoxyphenyl)methoxy]benzenepropanoate

In the same manner as in Reference Example 32, the title compound was obtained from 5-bromo-1,3-difluoro-2-[(3-methoxyphenyl)methoxy]benzene and acrolein diethyl acetal. Yield 40%.

Oil.

$^1$H NMR (CDCl$_3$) δ 1.23 (3H, t, J=7.1 Hz), 2.57 (2H, t, J=7.5 Hz), 2.86 (2H, t, J=7.5 Hz), 3.82 (3H, s), 4.12 (2H, q, J=7.1 Hz), 5.11 (2H, s), 6.67-6.79 (2H, m), 6.86 (1H, dd, J=1.9 Hz, 8.3 Hz), 6.98-7.02 (2H, m), 7.23-7.29 (1H, m).

Example 6

3,5-Difluoro-4-[(3-methoxyphenyl)methoxy]benzenepropanoic acid

In the same manner as in Reference Example 5, the title compound was obtained from ethyl 3,5-difluoro-4-[(3-methoxyphenyl)methoxy]benzenepropanoate. Yield 63%.

Melting point 59-60° C. (recrystallization from ethyl acetate-hexane).

$^1$H NMR (CDCl$_3$) δ 2.64 (2H, t, J=7.5 Hz), 2.86 (2H, t, J=7.5 Hz), 3.81 (3H, s), 5.11 (2H, s), 6.68-6.80 (2H, m), 6.86 (1H, dd, J=2.3 Hz, 8.5 Hz), 6.98-7.02 (2H, m), 7.23-7.29 (1H, m).

Example 7

Ethyl 4-[(3-ethoxyphenyl)methoxy]-3,5-difluorobenzenepropanoate

In the same manner as in Reference Example 32, the title compound was obtained from 5-bromo-2-[(3-ethoxyphenyl)methoxy]-1,3-difluorobenzene and acrolein diethyl acetal. Yield 37%.

Oil.

$^1$H NMR (CDCl$_3$) δ 1.23 (3H, t, J=7.1 Hz), 1.41 (3H, t, J=7.1 Hz), 2.57 (2H, t, J=7.6 Hz), 2.86 (2H, t, J=7.6 Hz), 4.04 (2H, q, J=7.1 Hz), 4.12 (2H, q, J=7.1 Hz), 5.09 (2H, s), 6.67-6.77 (2H, m), 6.84 (1H, dd, J=2.1 Hz, 8.3 Hz), 6.95-7.00 (2H, m), 7.22-7.27 (1H, m).

Example 8

4-[(3-Ethoxyphenyl)methoxy]-3,5-difluorobenzenepropanoic acid

In the same manner as in Reference Example 5, the title compound was obtained from ethyl 4-[(3-ethoxyphenyl)methoxy]-3,5-difluorobenzenepropanoate. Yield 78%.

Melting point 65-66° C. (recrystallization from ethyl acetate-hexane).

$^1$H NMR (CDCl$_3$) δ 1.41 (3H, t, J=7.1 Hz), 2.64 (2H, t, J=7.4 Hz), 2.86 (2H, t, J=7.4 Hz), 4.04 (2H, q, J=7.1 Hz), 5.10 (2H, s), 6.68-6.77 (2H, m), 6.85 (1H, dd, J=2.3 Hz, 8.5 Hz), 6.97-7.00 (2H, m), 7.22-7.27 (1H, m).

Example 9

Ethyl 3,5-difluoro-4-[3-(1-methylethoxy)phenyl]methoxy]benzenepropanoate

In the same manner as in Reference Example 32, the title compound was obtained from 5-bromo-1,3-difluoro-2-[[3-(1-methylethoxy)phenyl]methoxy]benzene and acrolein diethyl acetal. Yield 44%.

Oil.

$^1$H NMR (CDCl$_3$) δ 1.23 (3H, t, J=7.1 Hz), 1.32 (6H, t, J=6.1 Hz), 2.57 (2H, t, J=7.5 Hz), 2.85 (2H, t, J=7.5 Hz), 4.12 (2H, q, J=7.1 Hz), 4.56 (1H, septet, J=6.1 Hz), 5.09 (2H, s), 6.67-6.76 (2H, m), 6.83 (1H, dd, J=2.0 Hz, 8.3 Hz), 6.95-7.00 (2H, m), 7.21-7.26 (1H, m).

Example 10

3,5-Difluoro-4-[3-(1-methylethoxy)phenyl]methoxy]benzenepropanoic acid

In the same manner as in Reference Example 5, the title compound was obtained from ethyl 3,5-difluoro-4-[3-(1-methylethoxy)phenyl]methoxy]benzenepropanoate. Yield 77%.

Oil.

$^1$H NMR (CDCl$_3$) δ 1.32 (6H, d, J=6.1 Hz), 2.64 (2H, t, J=7.5 Hz), 2.86 (2H, t, J=7.5 Hz), 4.56 (1H, septet, J=6.1 Hz), 5.09 (2H, s), 6.67-6.75 (2H, m), 6.84 (1H, dd, J=2.3 Hz, 8.4 Hz), 6.94-6.99 (2H, m), 7.21-7.27 (1H, m).

Example 11

Ethyl 3-fluoro-4-[(3-phenoxyphenyl)methoxy]benzenepropanoate

In the same manner as in Reference Example 1, the title compound was obtained from ethyl 3-fluoro-4-hydroxybenzenepropanoate and 3-phenoxybenzyl alcohol. Yield 91%.

Oil.

$^1$H NMR (CDCl$_3$) δ 1.23 (3H, t, J=7.1 Hz), 2.57 (2H, t, J=7.4 Hz), 2.87 (2H, t, J=7.4 Hz), 4.12 (2H, q, J=7.1 Hz), 5.07 (2H, s), 6.81-7.02 (6H, m), 7.08-7.18 (3H, m), 7.30-7.36 (3H, m).

Example 12

3-Fluoro-4-[(3-phenoxyphenyl)methoxy]benzenepropanoic acid

In the same manner as in Reference Example 5, the title compound was obtained from ethyl 3-fluoro-4-[(3-phenoxyphenyl)methoxy]benzenepropanoate. Yield 88%.

Melting point 76-77° C. (recrystallization from ethyl acetate-hexane).

$^1$H NMR (CDCl$_3$) δ 2.63 (2H, t, J=7.4 Hz), 2.88 (2H, t, J=7.4 Hz), 5.07 (2H, s), 6.82-7.03 (6H, m), 7.06-7.18 (3H, m), 7.31-7.38 (3H, m).

Example 13

Methyl 3-methoxy-4-[(3-phenoxyphenyl)methoxy]benzenepropanoate

In the same manner as in Reference Example 1, the title compound was obtained from methyl 4-hydroxy-3-methoxybenzenepropanoate and 3-phenoxybenzyl alcohol. Yield 66%.

Oil.

$^1$H NMR (CDCl$_3$) δ 2.60 (2H, t, J=7.4 Hz), 2.89 (2H, t, J=7.4 Hz), 3.67 (3H, s), 3.84 (3H, s), 5.08 (2H, s), 6.64-6.70 (1H, m), 6.73-6.79 (2H, m), 6.89-6.94 (1H, m), 6.97-7.02 (2H, m), 7.07-7.18 (3H, m), 7.28-7.38 (3H, m).

Example 14

3-Methoxy-4-[(3-phenoxyphenyl)methoxy]benzenepropanoic acid

In the same manner as in Reference Example 5, the title compound was obtained from methyl 3-methoxy-4-[(3-phenoxyphenyl)methoxy]benzenepropanoate. Yield 82%.

Melting point 95-96° C. (recrystallization from ethyl acetate-hexane).

$^1$H NMR (CDCl$_3$) δ 2.65 (2H, t, J=7.4 Hz), 2.90 (2H, t, J=7.4 Hz), 3.84 (3H, s), 5.09 (2H, s), 6.65-6.70 (1H, m), 6.74-6.80 (2H, m), 6.87-6.93 (1H, m), 6.96-7.03 (2H, m), 7.06-7.18 (3H, m), 7.27-7.35 (3H, m).

Example 15

Ethyl 3,5-difluoro-4-[(2-phenoxyphenyl)methoxy]benzenepropanoate

In the same manner as in Reference Example 1, the title compound was obtained from ethyl 3,5-difluoro-4-hydroxybenzenepropanoate and 2-phenoxybenzyl alcohol. Yield 94%.

Oil.

$^1$H NMR (CDCl$_3$) δ 1.23 (3H, t, J=7.1 Hz), 2.56 (2H, t, J=7.5 Hz), 2.84 (2H, t, J=7.5 Hz), 4.12 (2H, q, J=7.1 Hz), 5.23 (2H, s), 6.66-6.71 (2H, m), 6.85 (1H, d, J=8.1 Hz), 6.92-6.95 (2H, m), 7.05-7.18 (2H, m), 7.25-7.34 (3H, m), 7.61 (1H, d, J=7.5 Hz).

Example 16

3,5-Difluoro-4-[(2-phenoxyphenyl)methoxy]benzenepropanoic acid

In the same manner as in Reference Example 5, the title compound was obtained from ethyl 3,5-difluoro-4-[(2-phenoxyphenyl)methoxy]benzenepropanoate. Yield 82%.

Melting point 78-79° C. (recrystallization from ethyl acetate-hexane).

$^1$H NMR (CDCl$_3$) δ 2.62 (2H, t, J=7.5 Hz), 2.85 (2H, t, J=7.5 Hz), 5.23 (2H, s), 6.62-6.73 (2H, m), 6.83-6.88 (1H, m), 6.91-6.96 (2H, m), 7.03-7.18 (2H, m), 7.24-7.34 (3H, m), 7.61 (1H, dd, J=1.4 Hz, 7.5 Hz).

Example 17

Ethyl 3-fluoro-4-[(2-phenoxyphenyl)methoxy]benzenepropanoate

In the same manner as in Reference Example 1, the title compound was obtained from ethyl 3-fluoro-4-hydroxybenzenepropanoate and 2-phenoxybenzyl alcohol. Yield 91%.
Oil.
$^1$H NMR (CDCl$_3$) δ 1.22 (3H, t, J=7.1 Hz), 2.56 (2H, t, J=7.5 Hz), 2.86 (2H, t, J=7.5 Hz), 4.11 (2H, q, J=7.1 Hz), 5.20 (2H, s), 6.80-6.99 (6H, m), 7.08-7.20 (2H, m), 7.26-7.38 (3H, m), 7.70-7.76 (1H, m).

Example 18

3-Fluoro-4-[(2-phenoxyphenyl)methoxy]benzenepropanoic acid

In the same manner as in Reference Example 5, the title compound was obtained from ethyl 3-fluoro-4-[(2-phenoxyphenyl)methoxy]benzenepropanoate. Yield 92%.
Melting point 103-104° C. (recrystallization from ethyl acetate-hexane).
$^1$H NMR (CDCl$_3$) δ 2.63 (2H, t, J=7.5 Hz), 2.87 (2H, t, J=7.5 Hz), 5.20 (2H, s), 6.81-6.98 (6H, m), 7.06-7.18 (2H, m), 7.25-7.38 (3H, m), 7.61 (1H, d, J=7.0 Hz).

Example 19

Ethyl 4-([1,1'-biphenyl]-2-ylmethoxy)-3,5-difluorobenzenepropanoate

In the same manner as in Reference Example 1, the title compound was obtained from ethyl 3,5-difluoro-4-hydroxybenzenepropanoate and 2-phenylbenzyl alcohol. Yield 94%.
Oil.
$^1$H NMR (CDCl$_3$) δ 1.23 (3H, t, J=7.1 Hz), 2.57 (2H, t, J=7.5 Hz), 2.85 (2H, t, J=7.5 Hz), 4.12 (2H, q, J=7.1 Hz), 5.00 (2H, s), 6.66-6.78 (2H, m), 7.29-7.47 (8H, m), 7.60-7.68 (1H, m).

Example 20

4-([1,1'-Biphenyl]-2-ylmethoxy)-3,5-difluorobenzenepropanoic acid

In the same manner as in Reference Example 5, the title compound was obtained from ethyl 4-([1,1'-biphenyl]-2-ylmethoxy)-3,5-difluorobenzenepropanoate. Yield 71%.
Melting point 78-79° C. (recrystallization from ethyl acetate-hexane).
$^1$H NMR (CDCl$_3$) δ 2.64 (2H, t, J=7.6 Hz), 2.86 (2H, t, J=7.6 Hz), 5.00 (2H, s), 6.65-6.74 (2H, m), 7.30-7.48 (8H, m), 7.59-7.67 (1H, m).

Example 21

Ethyl 4-([1,1'-biphenyl]-2-ylmethoxy)-3-fluorobenzenepropanoate

In the same manner as in Reference Example 1, the title compound was obtained from ethyl 3-fluoro-4-hydroxybenzenepropanoate and 2-phenylbenzyl alcohol. Yield 96%.
Oil.
$^1$H NMR (CDCl$_3$) δ 1.22 (3H, t, J=7.1 Hz), 2.55 (2H, t, J=7.5 Hz), 2.85 (2H, t, J=7.5 Hz), 4.11 (2H, q, J=7.1 Hz), 4.97 (2H, s), 6.70 (1H, t, J=8.4 Hz), 6.79 (1H, d, J=8.5 Hz), 6.91 (1H, dd, J=1.9 Hz, 12.1 Hz), 7.30-7.42 (8H, m), 7.62-7.66 (1H, m).

Example 22

4-([1,1'-Biphenyl]-2-ylmethoxy)-3-fluorobenzenepropanoic acid

In the same manner as in Reference Example 5, the title compound was obtained from ethyl 4-([1,1'-biphenyl]-2-ylmethoxy)-3-fluorobenzenepropanoate. Yield 90%.
Melting point 81-82° C. (recrystallization from ethyl acetate-hexane).
$^1$H NMR (CDCl$_3$) δ 2.62 (2H, t, J=7.6 Hz), 2.86 (2H, t, J=7.6 Hz), 4.97 (2H, s), 6.71 (1H, t, J=8.4 Hz), 6.80 (1H, d, J=8.4 Hz), 7.30-7.41 (8H, m), 7.62-7.65 (1H, m).

Example 23

Methyl 4-([1,1'-biphenyl]-2-ylmethoxy)-3-chlorobenzenepropanoate

In the same manner as in Reference Example 1, the title compound was obtained from methyl 3-chloro-4-hydroxybenzenepropanoate and 2-phenylbenzyl alcohol. Yield 95%.
Oil.
$^1$H NMR (CDCl$_3$) δ 2.57 (2H, t, J=7.5 Hz), 2.84 (2H, t, J=7.5 Hz), 3.66 (3H, s), 4.98 (2H, s), 6.65 (1H, d, J=8.4 Hz), 6.93 (1H, dd, J=2.0 Hz, 8.4 Hz), 7.20 (1H, d, J=2.0 Hz), 7.31-7.44 (8H, m), 7.68-7.71 (1H, m).

Example 24

4-([1,1'-Biphenyl]-2-ylmethoxy)-3-chlorobenzenepropanoic acid

In the same manner as in Reference Example 5, the title compound was obtained from methyl 4-([1,1'-biphenyl]-2-ylmethoxy)-3-chlorobenzenepropanoate. Yield 97%.
Melting point 111-112° C. (recrystallization from ethyl acetate-hexane).
$^1$H NMR (CDCl$_3$) δ 2.62 (2H, t, J=7.5 Hz), 2.85 (2H, t, J=7.5 Hz), 4.98 (2H, s), 6.66 (1H, d, J=8.4 Hz), 6.94 (1H, d, J=8.3 Hz), 7.21 (1H, s), 7.30-7.44 (8H, m), 7.67-7.70 (1H, m).

Structural formulas of the compounds obtained in Examples 1 to 12 are shown in Table 1.

TABLE 1

| Example No. | Structural formula |
|---|---|
| 1 |  |
| 2 |  |

TABLE 1-continued
| Example No. | Structural formula |
|---|---|
| 3 | 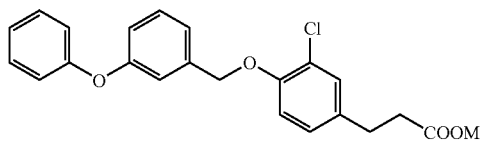 |
| 4 | 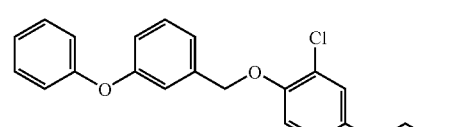 |
| 5 | 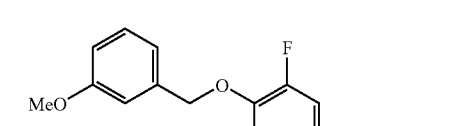 |
| 6 | 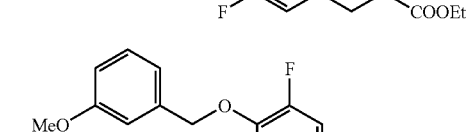 |
| 7 | 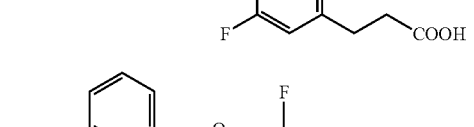 |
| 8 | 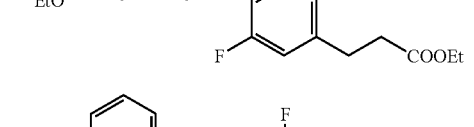 |
| 9 | 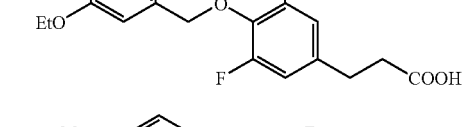 |
| 10 | 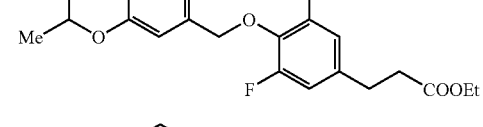 |
| 11 | 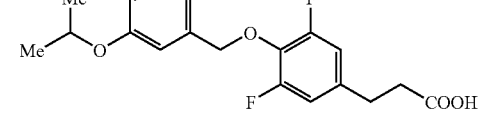 |
| 12 | 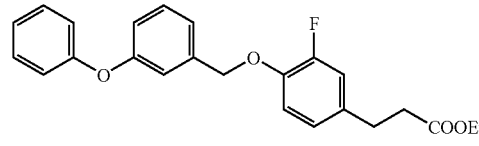 |
Structural formulas of the compounds obtained in Examples 13 to 24 are shown in Table 2.
TABLE 2
| Example No. | Structural formula |
|---|---|
| 13 | 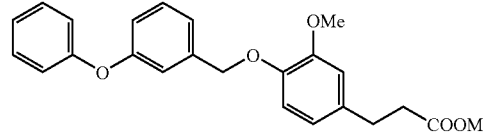 |
| 14 | 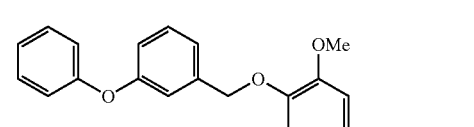 |
| 15 | 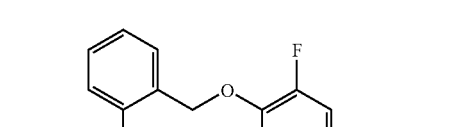 |
| 16 | 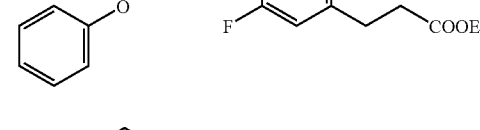 |
| 17 | 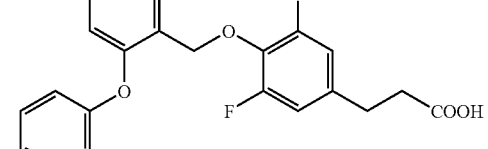 |
| 18 | 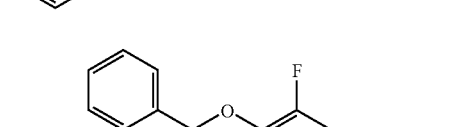 |
| 19 | 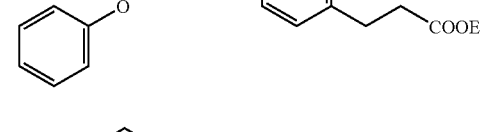 |

TABLE 2-continued

| Example No. | Structural formula |
|---|---|
| 20 | (biphenyl-CH2-O-(3,5-difluorophenyl)-CH2CH2-COOH) |
| 21 | (biphenyl-CH2-O-(3-fluorophenyl)-CH2CH2-COOEt) |
| 22 | (biphenyl-CH2-O-(3-fluorophenyl)-CH2CH2-COOH) |
| 23 | (biphenyl-CH2-O-(3-chlorophenyl)-CH2CH2-COOMe) |
| 24 | (biphenyl-CH2-O-(3-chlorophenyl)-CH2CH2-COOH) |

Examples 25 to 210 are shown as below. In Tables, unless specifically described, $^1$H NMR is measured using deuterated chloroform as a solvent. Further, chemical shift is a δ value (ppm), and the unit of coupling constants is Hz.

Example 25

Ethyl 3-{3,5-difluoro-4-[(2-methoxybenzyl)oxy]phenyl}propanoate

In the same manner as in Reference Example 1, the title compound was obtained from ethyl 3-(3,5-difluoro-4-hydroxyphenyl)propanoate and (2-methoxyphenyl)methanol. Yield 41%.

Similarly, the compounds shown in Examples 27, 29, 31, 33, 35, 39, 43, 45, 47, 49, 53, 59, 61, 63, 65, 67, 75, 77, 79, 81, 83, 85, 87, 89, 91 and 203 were synthesized using respectively corresponding raw material compounds.

Example 26

3-{3,5-Difluoro-4-[(2-methoxybenzyl)oxy]phenyl}propanoic acid

In the same manner as in Reference Example 5, the title compound was obtained from ethyl 3-{3,5-difluoro-4-[(2-methoxybenzyl)oxy]phenyl}propanoate. Yield 95%.

Similarly, the compounds shown in Examples 28, 30, 32, 34, 36, 38, 40, 42, 44, 46, 48, 52, 54, 56, 58, 60, 62, 64, 66, 68, 70, 72, 74, 76, 78, 80, 82, 84, 86, 88, 90, 92, 204 and 206 were synthesized using respectively corresponding raw material compounds.

Example 37

Ethyl 3-(4-{[2-(benzyloxy)benzyl]oxy}-3,5-difluorophenyl)propanoate 2-(Benzyloxy)benzaldehyde (274 mg, 1.3 mmol) dissolved in methanol (20 mL), sodium borohydride (73 mg, 1.9 mmol) was added thereto, and then the mixture was stirred with ice cooling for 2 hours. To the reaction solution was added water, and the reaction mixture was extracted with ethyl acetate. The extract was dried, and then concentrated under reduced pressure. The residue was dissolved in tetrahydrofuran (10 mL). Ethyl 3-(3,5-difluoro-4-hydroxyphenyl)propanoate (200 mg, 0.86 mmol), tributylphosphine (0.23 mL, 1.1 mmol) and azodicarbonyldipiperidine (282 mg, 1.1 mmol) were added thereto, and the mixture was stirred at room temperature for 12 hours. The reaction solution was purified with alumina column chromatography (ethyl acetate) and silica gel column chromatography (hexane/ethyl acetate=100:0 to 80:20) to give the title compound (162 mg, yield 29%) as an oily matter.

Similarly, the compounds shown in Examples 41, 55, 71 and 73 were synthesized using respectively corresponding raw material compounds.

Example 50

Ethyl 3-{3,5-difluoro-4-[(3-hydroxybenzyl)oxy]phenyl}propanoate

In the same manner as in Reference Example 39, the title compound was obtained from ethyl 3-(3,5-difluoro-4-{[3-(methoxymethoxy)benzyl]oxy}phenyl)propanoate. Yield 89%.

Example 51

Ethyl 3-(4-{[3-(cyclohexyloxy)benzyl]oxy}-3,5-difluorophenyl)propanoate

In the same manner as in Reference Example 1, the title compound was obtained from ethyl 3-{3,5-difluoro-4-[(3-hydroxybenzyl)oxy]phenyl}propanoate and cyclohexanol. Yield 15%.

Example 69

Ethyl 3-(3,5-difluoro-4-{[3-(1-naphthyloxy)benzyl]oxy}phenyl)propanoate

In the same manner as in Reference Example 91, the title compound was obtained from ethyl 3-{3,5-difluoro-4-[(3-hydroxybenzyl)oxy]phenyl}propanoate and 1-[3-(bromomethyl)phenoxy]naphthalene. Yield 94%.

Example 93

Ethyl 3-{4-[(3,5-dimethoxybenzyl)oxy]-3-fluorophenyl}propanoate

In the same manner as in Reference Example 106, the title compound as an oily matter was obtained from ethyl 3-(3-fluoro-4-hydroxyphenyl)propanoate and (3,5-dimethoxyphenyl)methanol. Yield 90%.

Similarly, the compounds shown in Examples 95, 99, 101, 103, 116, 121, 125, 138, 146, 148, 150, 152, 154, 156, 158, 160, 162, 164, 166, 168, 170, 172, 174, 179, 181, 183, 185, 187, 191, 193, 195, 197, 199, 201, 207 and 209 were synthesized using respectively corresponding raw material compounds.

Example 94

3-{4-[(3,5-Dimethoxybenzyl)oxy]-3-fluorophenyl}propanoic acid

In the same manner as in Reference Example 107, the title compound as white powders was obtained from ethyl 3-(4-[(3,5-dimethoxybenzyl)oxy]-3-fluorophenyl)propanoate. Yield 87%.

Similarly, the compounds shown in Examples 96, 100, 102, 107, 118, 120, 122, 124, 126, 137, 139, 142, 147, 149, 151, 153, 155, 157, 159, 161, 163, 165, 167, 169, 171, 173, 176, 178, 180, 182, 184, 186, 188, 190, 192, 194, 196, 198, 200, 202, 208 and 210 were synthesized using respectively corresponding raw material compounds.

Example 97

Ethyl 3-fluoro-4-[(2,4,6-trimethylphenyl)methoxy]benzenepropanoate

2-Chloromethyl-2,4,6-trimethylbenzene (397 mg, 2.4 mmol), ethyl 3-fluoro-4-hydroxybenzenepropanoate (500 mg, 2.4 mmol) and potassium carbonate (358 mg, 2.6 mmol) were stirred in DMF (8 mL) at 50° C. for 3 hours. The reaction solution was poured into water (30 mL) and the mixture was extracted with ethyl acetate. The ethyl acetate layer was washed with water and saturated brine, and dried over magnesium sulfate. Then, the solvent was distilled off under reduced pressure, and the residue was purified with silica gel column chromatography (hexane/ethyl acetate) to give the title compound (425 mg, yield 52%) as an oily matter.

Example 98

3-Fluoro-4-[(2,4,6-trimethylphenyl)methoxy]benzenepropanoic acid

A mixture of ethyl 3-fluoro-4-[(2,4,6-trimethylphenyl)methoxy]benzenepropanoate (363 mg, 1.1 mmol), a 2 N aqueous sodium hydroxide solution (1.5 mL) and ethanol (5 mL) was stirred at 60° C. for 1.5 hours. The reaction solution was ice-cooled and acidified with 1 N hydrochloric acid, and then the solvent was distilled off under reduced pressure. The residue was dissolved in methylene chloride, and the mixture was washed with water and saturated brine and dried over magnesium sulfate. Then, the solvent was distilled off under reduced pressure, and the resulting crystals were recrystallized from ethyl acetate/hexane (190 mg, yield 57%).

Example 104

Ethyl 3-{3-fluoro-4-[(3-hydroxybenzyl)oxy]phenyl}propanoate

In the same manner as in Reference Example 115, the title compound as an oily matter was obtained from ethyl 3-(3-fluoro-4-{[3-(methoxymethoxy)benzyl]oxy}phenyl)propanoate. Yield 96%.

Similarly, the compounds shown in Examples 117 and 175 were synthesized using respectively corresponding raw material compounds.

Example 105

Ethyl 3-(4-{[3-(2-tert-butoxy-2-oxoethoxy)benzyl]oxy}-3-fluorophenyl)propanoate

To a solution of ethyl 3-{3-fluoro-4-[(3-hydroxybenzyl)oxy]phenyl}propanoate (0.30 g, 0.94 mmol) and tert-butyl bromoacetate (0.92 g, 4.70 mmol) in N,N-dimethylformamide (10 mL) was added potassium carbonate (0.52 g, 3.76 mmol), and the mixture was stirred at 60° C. for 12 hours. The reaction mixture was diluted with ethyl acetate, filtered, washed with water, and then concentrated under reduced pressure. The resulting residue was purified with silica gel column chromatography (hexane/ethyl acetate=6:4) to give the title compound (0.43 g, yield 99%) as an oily matter.

Similarly, the compounds shown in Examples 108, 114, 123, 127, 136, 140, 143, 177 and 189 were synthesized using respectively corresponding raw material compounds.

Example 106

(3-{[4-(3-Ethoxy-3-oxopropyl)-2-fluorophenoxy]methyl}phenoxy)acetic acid

To a solution of ethyl 3-(4-{[3-(2-tert-butoxy-2-oxoethoxy)benzyl]oxy}-3-fluorophenyl)propanoate (0.43 g, 0.98 mmoL) in dichloromethane (15 mL) was added trifluoroacetic acid (1.1 g, 9.80 mmoL), and the mixture was stirred at 50° C. for, 1 hour. The reaction mixture was concentrated under reduced pressure, and the resulting residue was purified with silica gel column chromatography (hexane/ethyl acetate=9:1) to give the title compound (0.26 g, yield 72%) as white powders.

Similarly, the compound shown in Example 128 was synthesized using corresponding raw material compounds.

Example 109

3-(3-Fluoro-4-{[3-(2-oxopropoxy)benzyl]oxy}phenyl)propanoic acid

To a solution of ethyl 3-(3-fluoro-4-{[3-(2-oxopropoxy)benzyl]oxy}phenyl)propanoate (0.31 g, 0.82 mmol) in ethanol-water (2 mL-1 mL) was added lithium hydroxide mono- Similarly, the compounds shown in Examples 57 and 135 were synthesized using corresponding raw material compounds.

hydrate (0.052 g, 1.23 mmol), and the mixture was stirred at room temperature for 4 hours. To the reaction mixture was added 2 N hydrochloric acid (0.7 mL), and extracted with ethyl acetate. The extract was washed with water, and then concentrated under reduced pressure. The residue was recrystallized from ethyl acetate-hexane to give the title compound (0.047 g, yield 17%) as white powders.

Similarly, the compounds shown in Examples 111, 113, 115, 129, 131, 133 and 144 were synthesized using respectively corresponding raw material compounds.

Example 110

Ethyl 3-[3-fluoro-4-({3-[2-(methylamino)-2-oxoethoxy]benzyl}oxy)phenyl]propanoate A solution of (3-{[4-(3-ethoxy-3-oxopropyl)-2-fluorophenoxy]methyl}phenoxy)acetic acid (0.34 g, 0.90 mmol), methylamine hydrochloride (0.073 g, 1.08 mmol), triethylamine (0.22 g, 2.16 mmol), 1-ethyl-3-(3-dimethylaminopropyl)carbodiimide hydrochloride (0.21 g, 1.08 mmol) and 1-hydroxybenzotriazole (0.15 g, 1.08 mmol) in DMF (7 mL) was stirred at room temperature for 18 hours. Then, water was added to the reaction mixture and extracted with ethyl acetate. The organic layer was washed successively with saturated brine and water, and concentrated under reduced pressure. The resulting residue was purified with silica gel column chromatography (hexane/ethyl acetate=2:8) to give the title compound (0.34 g, yield 97%) as an oily matter.

Similarly, the compounds shown in Examples 112, 130 and 132 were synthesized using respectively corresponding raw material compounds.

Example 119

Ethyl 3-{3-fluoro-4-[(3-methoxy-5-phenoxybenzyl)oxy]phenyl}propanoate

To a solution of ethyl 3-{3-fluoro-4-[(3-hydroxy-5-phenoxybenzyl)oxy]phenyl}propanoate (0.30 g, 0.73 mmol) and methyl iodide (2.2 mL, 14.6 mmol) in acetone (10 mL) was added potassium carbonate (0.52 g, 3.76 mmol), and the mixture was heated under reflux and stirred for 4 hours. The reaction solution was diluted with ethyl acetate, filtered, washed with water, and then concentrated under reduced pressure. The resulting residue was purified with silica gel column chromatography (hexane/ethyl acetate=7:3) to give the title compound (0.31 g, yield 99%) as an oily matter.

Example 134

Ethyl 3-{3,5-difluoro-4-[(3-isobutoxybenzyl)oxy]phenyl}propanoate

Ethyl 3-{3,5-difluoro-4-[(3-hydroxybenzyl)oxy]phenyl}propanoate (200 mg, 0.59 mmol) was dissolved in DMF (10 mL), isobutyl iodide (339 μL, 3.0 mmol) and sodium hydride (47 mg, 1.2 mmol) were added thereto, and then the mixture was stirred at room temperature for 3 hours. To the reaction solution was added water, and the reaction mixture was extracted with ethyl acetate. The extract was dried, and then concentrated under reduced pressure. The residue was purified with silica gel column chromatography (hexane/ethyl acetate=100:0 to 80:20) to give the title compound (186 mg, yield 80%) as an oily matter.

Example 141

Ethyl 3-(3-fluoro-4-{[3-(2-hydroxyethoxy)-5-phenoxybenzyl]oxy}phenyl)propanoate Ethyl 3-(4-{[3-(2-{[tert-butyl(dimethyl)silyl]oxy}ethoxy)-5-phenoxybenzyl]oxy}-3-fluorophenyl)propanoate (0.43 g, 0.75 mmol) was dissolved in a solution of tetrabutylammonium fluoride in THF (3 mL, 3.00 mmol), and then the mixture was stirred at room temperature for 3 hours. The reaction mixture was diluted with ethyl acetate, washed with water, and concentrated under reduced pressure. The resulting residue was purified with silica gel column chromatography (hexane/ethyl acetate=5:5) to give the title compound (0.25 g, yield 74%) as an oily matter.

Example 145

3-(4-{[3-(2-Aminoethoxy)-5-phenoxybenzyl]oxy}-3-fluorophenyl)propanoic acid hydrochloride To 3-{4-[(3-{2-[(tert-butoxycarbonyl)amino]ethoxy}-5-phenoxybenzyl)oxy]-3-fluorophenyl}propanoic acid (0.20 g, 0.38 mmol) was added a solution of hydrochloric acid in ethyl acetate (4 N, 1 mL), and the mixture was stirred 15 hours. The reaction solution was concentrated under reduced pressure, and the resulting white powders were separated by filtration, washed with ethyl acetate and dried to give the title compound. Yield 89%.

TABLE 3

| Example No. | Structural formula | Chemical name | Property data |
| --- | --- | --- | --- |
| 25 (R = Et) | | ethyl 3-{3,5-difluoro-4-[(2-methoxybenzyl)oxy]phenyl}propanoate | Oily matter, $^1$H NMR: 1.24 (3H, t, J = 7.1), 2.57 (2H, t, J = 7.7), 2.86 (2H, t, J = 7.7), 3.81 (3H, s), 4.13 (2H, q, J = 7.1), 5.18 (2H, s), 6.68-6.75 (2H, m), 6.86-6.97 (2H, m), 7.27-7.32 (1H, m), 7.44 (1H, dd, J = 1.1, 7.3) |

TABLE 3-continued

| Example No. | Structural formula | Chemical name | Property data |
|---|---|---|---|
| 26 (R = H) | | 3-{3,5-difluoro-4-[(2-methoxybenzyl)oxy]-phenyl}propanoic acid | Colorless crystal, Melting point 66-67° C. (ethyl acetate-hexane), $^1$H NMR: 2.64 (2H, t, J = 7.6), 2.87 (2H, t, J = 7.6), 3.81 (3H, s), 5.18 (2H, s), 6.70-6.75 (2H, m), 6.86-6.98 (2H, m), 7.27-7.32 (1H, m), 7.45 (1H, dd, J = 1.5, 7.4) |
| 27 (R = Et) | | ethyl 3-(4-{[2-(cyclopentyloxy)benzyl]oxy}-3,5-difluorophenyl)-propanoate | Oily matter, $^1$H NMR: 1.23 (3H, t, J = 7.1), 1.60-1.88 (8H, m), 2.57 (2H, t, J = 7.5), 2.86 (2H, t, J = 7.5), 4.12 (2H, q, J = 7.1), 4.74-4.79 (1H, m), 5.13 (2H, s), 6.68-6.75 (2H, m), 6.84-6.94 (2H, m), 7.23-7.29 (1H, m), 7.47 (1H, dd, J = 1.3, 7.4) |
| 28 (R = H) | | 3-(4-{[2-(cyclopentyloxy)benzyl]oxy}-3,5-difluorophenyl)propanoic acid | Oily matter, $^1$H NMR: 1.56-1.86 (8H, m), 2.65 (2H, t, J = 7.6), 2.87 (2H, t, J = 7.6), 4.76-4.78 (1H, m), 5.14 (2H, s), 6.71-6.75 (2H, m), 6.84-6.95 (2H, m), 7.23-7.29 (1H, m), 7.47 (1H, dd, J = 1.6, 7.4) |

TABLE 4

| Example No. | Structural formula | Chemical name | Property data |
|---|---|---|---|
| 29 (R = Et) | | ethyl 3-{3,5-difluoro-4-[(2-morpholin-4-ylbenzyl)oxy]phenyl}-propanoate | Oily matter, $^1$H NMR: 1.24 (3H, t, J = 7.1), 2.59 (2H, t, J = 7.7), 2.88 (2H, t, J = 7.7), 2.99 (4H, t, J = 4.6), 3.84 (4H, t, J = 4.6), 4.13 (2H, q, J = 7.1), 5.21 (2H, s), 6.74-6.77 (2H, m), 7.14-7.16 (2H, m), 7.31-7.37 (1H, m), 7.53 (1H, dd, J = 1.6, 7.5) |
| 30 (R = H) | | 3-{3,5-difluoro-4-[(2-morpholin-4-ylbenzyl)oxy]phenyl}-propanoic acid | Colorless crystal, Melting point 113-114° C. (ethyl acetate-hexane), $^1$H NMR: 2.66 (2H, t, J = 7.4), 2.90 (2H, t, J = 7.4), 2.99 (4H, t, J = 4.6), 3.83 (4H, t, J = 4.6), 5.21 (2H, s), 6.74-6.80 (2H, m), 7.11-7.17 |

TABLE 4-continued

| Example No. | Structural formula | Chemical name | Property data |
|---|---|---|---|
| | | | (2H, m), 7.31-7.37 (1H, m), 7.54 (1H, d, J = 7.5) |
| 31 (R = Et) | 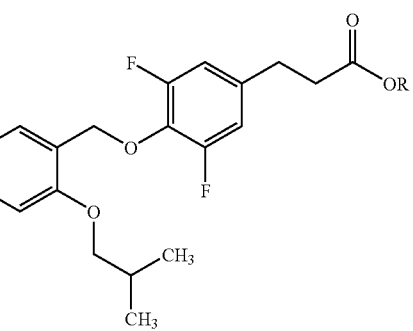 | ethyl 3-{3,5-difluoro-4-[(2-isobutoxybenzyl)oxy]-phenyl}propanoate | Oily matter, ¹H NMR: 1.01 (6H, d, J = 6.7), 1.24 (3H, t, J = 7.1), 2.03-2.12 (1H, m), 2.57 (2H, t, J = 7.8), 2.86 (2H, t, J = 7.8), 3.72 (2H, d, J = 6.4), 4.13 (2H, q, J = 7.1), 5.19 (2H, s), 6.71-6.73 (2H, m), 6.85 (1H, d, J = 8.3), 6.94 (1H, dd, J = 7.3, 7.5), 7.24-7.30 (1H, m), 7.48 (1H, dd, J = 1.6, 7.4) |
| 32 (R = H) | | 3-{3,5-difluoro-4-[(2-isobutoxybenzyl)oxy]-phenyl}propanoic acid | Oily matter, ¹H NMR: 1.01 (6H, d, J = 6.7), 2.03-2.11 (1H, m), 2.64 (2H, t, J = 7.4), 2.88 (2H, t, J = 7.4), 3.72 (2H, d, J = 6.4), 5.20 (2H, s), 6.70-6.75 (2H, m), 6.85 (1H, d, J = 8.2), 6.95 (1H, dd, J = 7.4, 7.4), 7.26-7.30 (1H, m), 7.49 (1H, d, J = 7.4) |

TABLE 5

| Example No. | Structural formula | Chemical name | Property data |
|---|---|---|---|
| 33 (R = Et) | 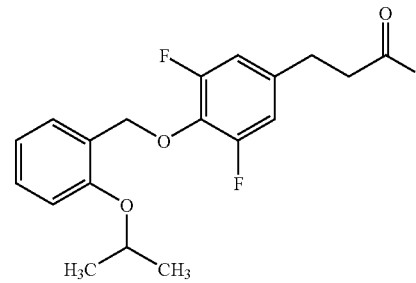 | ethyl 3-{3,5-difluoro-4-[(2-isopropoxybenzyl)oxy]-phenyl}propanoate | Oily matter, ¹H NMR: 1.23 (3H, t, J = 7.1), 1.28 (6H, d, J = 6.1), 2.57 (2H, t, J = 7.7), 2.86 (2H, t, J = 7.7), 4.13 (2H, q, J = 7.1), 4.51-4.59 (1H, m), 5.16 (2H, s), 6.71-6.76 (2H, m), 6.85-6.96 (2H, m), 7.23-7.29 (1H, m), 7.48 (1H, dd, J = 7.4) |
| 34 (R = H) | | 3-{3,5-difluoro-4-[(2-isopropoxybenzyl)oxy]-phenyl}propanoic acid | Oily matter, ¹H NMR: 1.28 (6H, d, J = 6.0), 2.65 (2H, t, J = 7.5), 2.87 (2H, t, J = 7.5), 4.51-4.59 (1H, m), 5.16 (2H, s), 6.70-6.77 (2H, m), 6.85-6.96 (2H, m), 7.23-7.29 (1H, m), 7.48 |

TABLE 5-continued

| Example No. | Structural formula | Chemical name | Property data |
|---|---|---|---|
| | | | (1H, dd, J = 1.5, 7.4) |
| 35 (R = Et) | | ethyl 3-(4-{[2-(cyclohexyloxy]benzyl]-oxy}-3,5-difluorophenyl)-propanoate | Oily matter, $^1$H NMR: 1.23 (3H, t, J = 7.1), 1.32-1.55 (6H, m), 1.73-1.78 (2H, m), 1.89-1.92 (2H, m), 2.57 (2H, t, J = 7.4), 2.86 (2H, t, J = 7.4), 4.13 (2H, q, J = 7.1), 4.24-4.31 (1H, m), 5.18 (2H, s), 6.70-6.75 (2H, m), 6.86-6.95 (2H, m), 7.22-7.28 (1H, m), 7.49 (1H, dd, J = 1.5, 7.5) |
| 36 (R = H) | | 3-(4-{[2-(cyclohexyloxy)benzyl]-oxy}-3,5-difluorophenyl)propanoic acid | Oily matter, $^1$H NMR: 1.32-1.54 (6H, m), 1.73-1.76 (2H, m), 1.89-1.92 (2H, m), 2.65 (2H, t, J = 7.6), 2.88 (2H, t, J = 7.6), 4.25-4.31 (1H, m), 5.18 (2H, s), 6.72-6.77 (2H, m), 6.86-6.96 (2H, m), 7.22-7.28 (1H, m), 7.49 (1H, dd, J = 1.6, 7.5) |

TABLE 6

| Example No. | Structural formula | Chemical name | Property data |
|---|---|---|---|
| 37 (R = Et) | | ethyl 3-(4-{[2-(benzyloxy)benzyl]oxy}-3,5-difluorophenyl)propanoate | Oily matter, $^1$H NMR: 1.23 (3H, t, J = 7.1), 2.56 (2H, t, J = 7.7), 2.85 (2H, t, J = 7.7), 4.13 (2H, q, J = 7.1), 5.09 (2H, s), 5.24 (2H, s), 6.68-6.71 (2H, m), 6.91-6.98 (2H, m), 7.27-7.52 (7H, m) |
| 38 (R = H) | | 3-(4-{[2-(benzyloxy)benzyl]oxy}-3,5-difluorophenyl)propanoic acid | Amorphous, $^1$H NMR: 2.63 (2H, t, J = 7.6), 2.85 (2H, t, J = 7.6), 5.09 (2H, s), 5.25 (2H, s), 6.68-6.71 (2H, m), 6.91-7.00 (2H, m), 7.28-7.51 (7H, m) |

TABLE 6-continued

| Example No. | Structural formula | Chemical name | Property data |
| --- | --- | --- | --- |
| 39 (R = Et) | | ethyl 3-(3,5-difluoro-4-{[2-(tetrahydrofuran-2-ylmethoxy)benzyl]oxy}-phenyl)propanoate | Oily matter, $^1$H NMR: 1.24 (3H, t, J = 7.1), 1.75-2.10 (4H, m), 2.57 (2H, t, J = 7.7), 2.86 (2H, t, J = 7.7), 3.80-4.27 (7H, m), 5.19 (2H, s), 6.69-6.76 (2H, m), 6.87-6.99 (2H, m), 7.27-7.30 (1H, m), 7.48 (1H, dd, J = 1.5, 7.5) |
| 40 (R = H) | | 3-(3,5-difluoro-4-([2-(tetrahydrofuran-2-ylmethoxy)benzyl]oxy}-phenyl)propanoic acid | Oily matter, $^1$H NMR: 1.75-2.10 (4H, m), 2.63 (2H, t, J = 7.4), 2.87 (2H, t, J = 7.4), 3.82-4.00 (4H, m), 4.21-4.24 (1H, m), 5.19 (2H, dd, J = 11.7, 14.8), 6.69-6.76 (2H, m), 6.86 (1H, d, J = 8.3), 6.97 (1H, dd, J = 7.4, 7.4), 7.26-7.31 (1H, m), 7.48 (1H, d, J = 6.4) |

TABLE 7

| Example No. | Structural formula | Chemical name | Property data |
| --- | --- | --- | --- |
| 41 (R = Et) | | ethyl 3-{3,5-difluoro-4-[(2-methylbenzyl)oxy]-phenyl}propanoate | Oily matter, $^1$H NMR: 1.24 (3H, t, J = 7.1), 2.45 (3H, s), 2.58 (2H, t, J = 7.7), 2.86 (2H, t, J = 7.7), 4.13 (2H, q, J = 7.1), 5.12 (2H, s), 6.72-6.75 (2H, m), 7.17-7.38 (4H, m) |
| 42 (R = H) | | 3-{3,5-difluoro-4-[(2-methylbenzyl)oxy]-phenyl}propanoic acid | Colorless crystal, Melting point 84-85° C. (ethyl acetate-hexane), $^1$H NMR: 2.45 (3H, s), 2.55 (2H, t, J = 7.5), 2.88 (2H, t, J = 7.5), 5.13 (2H, s,), 6.73-6.76 (2H, m), 7.18-7.26 (3H, m), 7.37 (1H, d, J = 7.2), |
| 43 (R = Et) | | ethyl 3-{3,5-difluoro-4-[(2-piperidin-1-ylbenzyl)oxy]phenyl}-propanoate | Oily matter, $^1$H NMR: 1.24 (3H, t, J = 7.1), 1.52-1.58 (2H, m), 1.64-1.71 (4H, m), 2.58 (2H, t, J = 7.7), 2.85-290 (6H, m), 4.13 (2H, q, J = 7.1), 5.21 (2H, s), 6.70-6.77 (2H, m), 7.06-7.11 (2H, m), 7.26-7.31 (1H, m), 7.57 (1H, d, J = 7.5) |

TABLE 7-continued

| Example No. | Structural formula | Chemical name | Property data |
|---|---|---|---|
| 44 (R = H) | | 3-{3,5-difluoro-4-[(2-piperidin-1-ylbenzyl)oxy]phenyl}-propanoic acid | Oily matter, $^1$H NMR: 1.54-1.57 (2H, m), 1.64-1.72 (4H, m), 2.66 (2H, t, J = 7.6), 2.85-2.91 (6H, m), 5.22 (2H, s), 6.73-6.79 (2H, m), 7.06-7.12 (2H, m), 7.26-7.32 (1H, m), 7.57 1H, d, J = 7.5) |
| 45 (R = Et) | | ethyl 3-(3,5-difluoro-4-{[3-(4-methoxyphenoxy)-benzyl]oxy}phenyl)-propanoate | Oily matter, $^1$H NMR: 1.23 (3H, t, J = 7.1), 2.57 (2H, t, J = 7.7), 2.86 (2H, t, J = 7.7), 3.81 (3H, s), 4.13 (2H, q, J = 7.1), 5.07 (2H, s), 6.71-6.74 (2H, m), 6.87-7.13 (7H, m), 7.25-7.36 (1H, m) |

TABLE 8

| Example No. | Structural formula | Chemical name | Property data |
|---|---|---|---|
| 46 (R = H) | | 3-(3,5-difluoro-4-{[3-(4-methoxyphenoxy)-benzyl]oxy}phenyl)-propanoic acid | Colorless crystal, Melting point 89-90° C. (ethyl acetate-hexane), $^1$H NMR: 2.64 (2H, t, J = 7.5), 2.87 (2H, t, J = 7.5), 3.81 (3H, s), 5.07 (2H, s), 6.72-6.75 (2H, m), 6.87-7.13 (7H, m), 7.26-7.31 (1H, m) |
| 47 (R = Et) | | ethyl 3-(4-{[3-(4-chlorophenoxy)-benzyl]oxy}-3,5-difluorophenyl)-propanoate | Oily matter, $^1$H NMR: 1.23 (3H, t, J = 7.1), 2.57 (2H, t, J = 7.7), 2.86 (2H, t, J = 7.7), 4.13 (2H, q, J = 7.1), 5.09 (2H, s), 6.71-6.74 (2H, m), 6.91-6.99 (3H, m), 7.09 (1H, s), 7.18 (2H, d, J = 7.6), 7.26-7.36 (2H, m) |
| 48 (R = H) | | 3-(4-{[3-(4-chlorophenoxy)-benzyl]oxy}-3,5-difluorophenyl)-propanoic acid | Colorless crystal, Melting point 79-80° C. (ethyl acetate-hexane), $^1$H NMR: 2.65 (2H, t, J = 7.5), 2.87 (2H, t, J = 7.5), 5.09 (2H, s), 6.71-6.77 (2H, m), 6.91-6.97 (3H, m), 7.09 (1H, s), 7.18 (2H, d, J = 7.6), 7.26-7.36 (2H, m) |
| 49 | | ethyl 3-(3,5-difluoro-4-{[3-(methoxymethoxy)-benzyl]oxy}phenyl)-propanoate | Oily matter, $^1$H NMR: 1.23 (3H, t, J = 7.1), 2.57 (2H, t, J = 7.7), 2.86 (2H, t, J = 7.7), 3.48 (3H, s), 4.13 (2H, q, J = 7.1), 5.10 (2H, s), 5.18 (2H, s), 6.71-6.75 (2H, m), 6.98-7.14 (3H, m), 7.25-7.30 (1H, m) |

TABLE 9

| Example No. | Structural formula | Chemical name | Property data |
|---|---|---|---|
| 50 | | ethyl 3-{3,5-difluoro-4-[(3-hydroxybenzyl)oxy]phenyl}propanoate | Oily matter, $^1$H NMR: 1.24 (3H, t, J = 7.1), 2.58 (2H, t, J = 7.5), 2.86 (2H, t, J = 7.5), 4.13 (2H, q, J = 7.1), 4.99 (1H, s), 5.07 (2H, s), 6.71-6.81 (3H, m), 6.89 (1H, d, J = 2.0), 6.98 (1H, d, J = 7.6), 7.20-7.26 (1H, m) |
| 51 (R = Et) | | ethyl 3-(4-{[3-(cyclohexyloxy)benzyl]oxy}-3,5-difluorophenyl)propanoate | Oily matter, $^1$H NMR: 1.23 (3H, t, J = 7.2), 1.32-1.60 (6H, m), 1.74-1.81 (2H, m), 1.96-1.98 (1H, m), 2.57 (2H, t, J = 7.6), 2.86 (2H, t, J = 7.6), 3.95-3.99 (1H, m), 4.13 (2H, q, J = 7.2), 4.20-4.35 (1H, m), 5.09 (2H, s), 6.71-6.74 (2H, m), 6.85 (1H, dd, J = 2.2, 8.3), 6.95-7.01 (2H, m), 7.21-7.26 (1H, m) |
| 52 (R = H) | | 3-(4-{[3-(cyclohexyloxy)benzyl]oxy}-3,5-difluorophenyl)propanoic acid | Oily matter, $^1$H NMR: 1.26-1.60 (6H, m), 1.74-1.81 (2H, m), 1.91-2.02 (1H, m), 2.64 (2H, t, J = 7.5), 2.87 (2H, t, J = 7.5), 3.95-3.99 (1H, m), 4.23-4.26 (1H, m), 5.09 (2H, s), 6.70-6.77 (2H, m), 6.85 (1H, dd, J = 1.7, 8.0), 6.96-7.00 (2H, m), 7.21-7.28 (1H, m) |
| 53 (R = Et) | | ethyl 3-(3,5-difluoro-4-{[3-(4-fluorophenoxy)benzyl]oxy}phenyl)propanoate | Oily matter, $^1$H NMR: 1.23 (3H, t, J = 7.1), 2.57 (2H, t, J = 7.6), 2.86 (2H, t, J = 7.6), 4.13 (2H, q, J = 7.1), 5.08 (2H, s), 6.71-6.74 (2H, m), 6.93-7.06 (5H, m), 7.15 (1H, d, J = 7.7), 7.26-7.34 (2H, m) |

TABLE 10

| Example No. | Structural formula | Chemical name | Property data |
|---|---|---|---|
| 54 (R = H) | | 3-(3,5-difluoro-4-{[3-(4-fluorophenoxy)benzyl]oxy}phenyl)propanoic acid | Colorless crystal, Melting point 82-83° C. (ethyl acetate-hexane), $^1$H NMR: 2.57 (2H, t, J = 7.4), 2.88 (2H, t, J = 7.4), 5.08 (2H, s), 6.72-6.75 (2H, m), 6.91-7.06 (5H, m), 7.15 (1H, d, J = 7.6), 7.26-7.34 (2H, m) |

TABLE 10-continued

| Example No. | Structural formula | Chemical name | Property data |
|---|---|---|---|
| 55 (R = Et) | | ethyl 3-(3,5-difluoro-4-{[3-(4-methylphenoxy)benzyl]oxy}phenyl)propanoate | Oily matter, $^1$H NMR: 1.23 (3H, t, J = 7.1), 2.34 (3H, s), 2.57 (2H, t, J = 7.7), 2.86 (2H, t, J = 7.7), 4.12 (2H, q, J = 7.1), 5.07 (2H, s), 6.71-6.73 (2H, m), 6.88-6.95 (3H, m), 7.06 (1H, d, J = 1.8), 7.12-7.15 (3H, m), 7.26-7.32 (1H, m) |
| 56 (R = H) | | 3-(3,5-difluoro-4-{[3-(4-methylphenoxy)benzyl]oxy}phenyl)propanoic acid | Colorless crystal, Melting point 91-92° C. (ethyl acetate-hexane), $^1$H NMR: 2.34 (3H, s), 2.64 (2H, t, J = 7.5), 2.87 (2H, t, J = 7.5), 5.08 (2H, s), 6.70-6.76 (2H, m), 6.88-6.94 (3H, m), 7.06 (1H, s), 7.12-7.15 (3H, m), 7.26-7.32 (1H, m) |
| 57 (R = Et) | | ethyl 3-(4-{[3-(cyclopentyloxy)-benzyl]oxy}-3,5-difluorophenyl)-propanoate | Oily matter, $^1$H NMR: 1.23 (3H, t, J = 7.1), 1.55-1.70 (2H, m), 1.75-1.96 (6H, m), 2.57 (2H, t, J = 7.7), 2.86 (2H, t, J = 7.7), 4.13 (2H, q, J = 7.1), 4.73-4.79 (1H, m), 5.09 (2H, s), 6.69-6.76 (2H, m), 6.83 (1H, dd, J = 2.2, 7.6), 6.94-6.98 (2H, m), 7.21-7.26 (1H, m) |

TABLE 11

| Example No. | Structural formula | Chemical name | Property data |
|---|---|---|---|
| 58 (R = H) | | 3-(4-{[3-(cyclopentyloxy)-benzyl]oxy}-3,5-difluorophenyl)-propanoic acid | Amorphous, $^1$H NMR: 1.55-1.69 (2H, m), 1.76-1.92 (6H, m), 2.64 (2H, t, J = 7.5), 2.87 (2H, t, J = 7.5), 4.75-4.79 (1H, m), 5.09 (2H, s), 6.68-6.77 (2H, m), 6.82 (1H, dd, J = 2.4, 7.4), 6.94-6.98 (2H, m), 7.21-7.26 (1H, m) |
| 59 (R = Et) | | ethyl 3-(3,5-difluoro-4-{[3-(pyridin-2-yloxy)benzyl]oxy}-phenyl)propanoate | Oily matter, $^1$H NMR: 1.23 (3H, t, J = 7.1), 2.57 (2H, t, J = 7.7), 2.86 (2H, t, J = 7.7), 4.12 (2H, q, J = 7.1), 5.13 (2H, s), 6.71-6.74 (2H, m), 6.88 (1H, d, J = 8.3), 6.97-7.14 (2H, m), 7.23-7.29 (2H, m), 7.39 (1H, dd, J = 7.8, 7.8), 7.64-7.73 (1H, m), 8.19-8.21 (1H, m) |
| 60 (R = H) | | 3-(3,5-difluoro-4-{[3-(pyridin-2-yloxy)benzyl]oxy}- | Oily matter, $^1$H NMR: 2.60 (2H, t, J = 7.2), 2.86 (2H, t, J = 7.2), |

TABLE 11-continued

| Example No. | Structural formula | Chemical name | Property data |
|---|---|---|---|
| | | phenyl)propanoic acid | 5.13 (2H, s), 6.70-6.73 (2H, m), 6.89 (1H, d, J = 8.3), 7.02-7.12 (2H, m), 7.26-7.29 (2H, m), 7.37 (1H, dd, J = 7.8, 7.8), 7.65-7.75 (1H, m), 8.23-8.25 (1H, m) |
| 61 (R = Et) | | ethyl 3-(3,5-difluoro-4-{[3-(3-thienyloxy)benzyl]oxy}phenyl)propanoate | Oily matter, $^1$H NMR: 1.23 (3H, t, J = 7.1), 2.57 (2H, t, J = 7.7), 2.86 (2H, t, J = 7.7), 4.12 (2H, q, J = 7.1), 5.09 (2H, s), 6.58 (1H, dd, J = 1.5, 3.3), 6.71-6.74 (2H, m), 6.84 (1H, dd, J = 1.5, 5.2), 6.95-7.01 (1H, m), 7.12-7.18 (2H, m), 7.23-7.32 (2H, m) |

TABLE 12

| Example No. | Structural formula | Chemical name | Property data |
|---|---|---|---|
| 62 (R = H) | | 3-(3,5-difluoro-4-{[3-(3-thienyloxy)benzyl]oxy}phenyl)propanoic acid | Colorless crystal, Melting point 45-46° C. (ethyl acetate-hexane), Oily matter, $^1$H NMR: 2.64 (2H, t, J = 7.5), 2.87 (2H, t, J = 7.5), 5.09 (2H, s), 6.58 (1H, dd, J = 1.5, 3.2), 6.71-6.74 (2H, m), 6.84 (1H, dd, J = 1.5, 5.2), 6.97-7.04 (1H, m), 7.12-7.17 (2H, m), 7.24-7.32 (2H, m) |
| 63 (R = Et) | | ethyl 3-(3,5-difluoro-4-{[3-(2-thienyloxy)benzyl]oxy}phenyl)propanoate | Oily matter, $^1$H NMR: 1.23 (3H, t, J = 7.1), 2.57 (2H, t, J = 7.5), 2.86 (2H, t, J = 7.5), 4.12 (2H, q, J = 7.1), 5.09 (2H, s), 6.52-6.54 (1H, m), 6.71-6.76 (2H, m), 6.82 (2H, d, J = 2.6), 6.95-7.04 (1H, m), 7.16-7.18 (2H, m), 7.28-7.34 (1H, m) |
| 64 (R = H) | | 3-(3,5-difluoro-4-{[3-(2-thienyloxy)benzyl]oxy}phenyl)propanoic acid | Oily matter, $^1$H NMR: 2.65 (2H, t, J = 7.4), 2.86 (2H, t, J = 7.4), 5.09 (2H, s), 6.53-6.54 (1H, m), 6.71-6.78 (2H, m), 6.82 (2H, d, J = 2.6), 7.01-7.08 (1H, m), 7.16-7.18 (2H, m), 7.29-7.34 (1H, m) |

TABLE 12-continued

| Example No. | Structural formula | Chemical name | Property data |
|---|---|---|---|
| 65 (R = Et) | | ethyl 3-(4-{[3-(4-acetylphenoxy)benzyl]oxy}-3,5-difluorophenyl)propanoate | Oily matter, $^1$H NMR: 1.23 (3H, t, J = 7.2), 2.55-2.60 (5H, m), 2.86 (2H, t, J = 7.4), 4.12 (2H, q, J = 7.2), 5.11 (2H, s), 6.71-6.75 (2H, m), 6.97-7.05 (3H, m), 7.17 (1H, d, J = 1.8), 7.25-7.27 (1H, m), 7.38 (1H, dd, J = 7.8, 7.8), 7.94 (2H, d, J = 8.9) |

TABLE 13

| Example No. | Structural formula | Chemical name | Property data |
|---|---|---|---|
| 66 (R = H) | | 3-(4-{[3-(4-acetylphenoxy)benzyl]oxy}-3,5-difluorophenyl)propanoic acid | Colorless crystal, Melting point 97-99° C. (ethyl acetate-hexane), $^1$H NMR: 2.58 (3H, s), 2.64 (2H, t, J = 7.5), 2.87 (2H, t, J = 7.5), 5.12 (2H, s), 6.72-6.76 (2H, m), 6.95-7.05 (3H, m), 7.16 (1H, s), 7.25-7.28 (1H, m), 7.39 (1H, dd, J = 7.8, 7.8), 7.94 (2H, d, J = 8.9) |
| 67 (R = Et) | | ethyl 3-(3,5-difluoro-4-{[3-(1,3-thiazol-2-yloxy)benzyl]oxy}-phenyl)propanoate | Oily matter, $^1$H NMR: 1.23 (3H, t, J = 7.1), 2.57 (2H, t, J = 7.7), 2.86 (2H, t, J = 7.7), 4.12 (2H, q, J = 7.1), 5.14 (2H, s), 6.71-6.75 (2H, m), 6.82 (1H, d, J = 3.8), 7.23-7.26 (2H, m), 7.35-7.44 (3H, m) |
| 68 (R = H) | | 3-(3,5-difluoro-4-{[3-(1,3-thiazol-2-yloxy)benzyl]oxy}-phenyl)propanoic acid | Oily matter, $^1$H NMR: 2.62 (2H, t, J = 7.3), 2.86 (2H, t, J = 7.3), 5.15 (2H, s), 6.71-6.74 (2H, m), 6.83 (1H, d, J = 3.8), 7.21-7.44 (5H, m) |
| 69 (R = Et) | | ethyl 3-(3,5-difluoro-4-{[3-(1-naphthyloxy)benzyl]oxy}phenyl)propanoate | Oily matter, $^1$H NMR: 1.25 (3H, t, J = 7.1), 2.57 (2H, t, J = 7.6), 2.86 (2H, t, J = 7.6), 4.12 (2H, q, J = 7.1), 5.09 (2H, s), 6.65-6.78 (2H, m), 6.91-7.03 (1H, m), 7.13-7.65 (7H, m), 7.85-7.90 (1H, m), 8.12-8.26 (2H, m) |
| 70 (R = H) | | 3-(3,5-difluoro-4-{[3-(1-naphthyloxy)benzyl]oxy}phenyl)propanoic acid | Oily matter, $^1$H NMR: 2.63 (2H, t, J = 7.5), 2.86 (2H, t, J = 7.5), 5.09 (2H, s), 6.63-6.80 (2H, m), 6.90-7.01 (1H, m), 7.15-7.67 (7H, m), 7.86-7.90 (1H, m), 8.17-8.26 (2H, m) |

TABLE 14

| Example No. | Structural formula | Chemical name | Property data |
|---|---|---|---|
| 71 (R = Et) | | ethyl 3-{3-fluoro-4-[1-(3-phenoxyphenyl)-ethoxy]phenyl}-propanoate | Oily matter, $^1$H NMR: 1.19 (3H, t, J = 7.5), 1.65 (3H, d, J = 6.3), 2.53 (2H, t, J = 7.2), 2.82 (2H, t, J = 7.2), 4.11 (2H, q, J = 7.5), 5.72 (1H, q, J = 6.3), 6.69-6.77 (2H, m), 6.84-7.00 (4H, m), 7.06-7.38 (5H, m), 7.57-7.62 (1H, m) |
| 72 (R = H) | | 3-(3-fluoro-4-[1-(3-phenoxyphenyl)-ethoxy]phenyl)-propanoic acid | Colorless crystal, Melting point 128-130° C. (ethyl acetate-hexane), $^1$H NMR: 1.64 (3H, d, J = 6.3), 2.60 (2H, t, J = 7.8), 2.83 (2H, t, J = 7.8), 5.72 (1H, q, J = 6.3), 6.70-6.79 (2H, m), 6.85-6.98 (4H, m), 7.08-7.37 (5H, m), 7.58 (1H, dd, J = 1.5, 7.5) |
| 73 (R = Et) | | ethyl 3-{3-fluoro-4-[1-(2-phenoxyphenyl)-ethoxy]phenyl}-propanoate | Oily matter, $^1$H NMR: 1.21 (3H, t, J = 6.9), 1.64 (3H, d, J = 6.6), 2.54 (2H, t, J = 7.8), 2.83 (2H, t, J = 7.8), 4.11 (2H, q, J = 6.9), 5.24 (1H, q, J = 6.9), 6.69-6.77 (2H, m), 6.86-6.98 (4H, m), 7.05-7.12 (3H, m), 7.28-7.34 (3H, m) |
| 74 (R = H) | | 3-{3-fluoro-4-[1-(2-phenoxyphenyl)-ethoxy]phenyl}-propanoic acid | Oily matter, $^1$H NMR: 1.64 (3H, d, J = 6.6), 2.61 (2H, t, J = 7.8), 2.85 (2H, t, J = 7.8), 5.25 (1H, q, J = 6.6), 6.70-6.78 (2H, m), 6.86-6.99 (4H, m), 7.05-7.12 (3H, m), 7.30-7.34 (3H, m) |

TABLE 15

| Example No. | Structural formula | Chemical name | Property data |
|---|---|---|---|
| 75 (R = Et) | | ethyl 3-(3-fluoro-4-{[2-(3-isopropylphenoxy)-benzyl]oxy}phenyl)-propanoate | Oily matter, $^1$H NMR: 1.20-1.25 (9H, m), 2.56 (2H, t, J = 7.8), 2.83-2.90 (3H, m), 4.12 (2H, q, J = 7.2), 5.21 (2H, s), 6.75-6.99 (7H, m), 7.14 (1H, dd, J = 6.6, 7.5), 7.21-7.29 (2H, m), 7.60 (1H, d, J = 6.3) |

TABLE 15-continued

| Example No. | Structural formula | Chemical name | Property data |
|---|---|---|---|
| 76 (R = H) | | 3-(3-fluoro-4-{[2-(3-isopropylphenoxy)-benzyl]oxy}phenyl)-propanoic acid | Colorless crystal, Melting point 85-86° C. (ethyl acetate-hexane), 1.23 (6H, d, J = 6.9), 2.62 (2H, t, J = 8.1), 2.83-2.90 (3H, m), 5.22 (2H, s), 6.75-6.99 (7H, m), 7.13 (1H, dd, J = 7.5, 7.5), 7.21-7.29 (2H, m), 7.60 (1H, dd, J = 1.5, 7.8) |
| 77 (R = Et) | | ethyl 3-(3-fluoro-4-{[2-(4-isopropylphenoxy)-benzyl]oxy}phenyl)-propanoate | Oily matter, $^1$H NMR: 1.20-1.25 (9H, m), 2.56 (2H, t, J = 8.1), 2.83-2.92 (3H, m), 4.12 (2H, q, J = 6.9), 5.21 (2H, s), 6.81-6.94 (6H, m), 7.09-7.27 (4H, m), 7.59 (1H, dd, J = 1.2, 7.5) |
| 78 (R = H) | | 3-(3-fluoro-4-{[2-(4-isopropylphenoxy)-benzyl]oxy}phenyl)-propanoic acid | Oily matter, $^1$H NMR: 1.24 (6H, d, J = 6.9), 2.63 (2H, t, J = 7.8), 2.85-2.92 (3H, m), 5.22 (2H, s), 6.82-6.95 (6H, m), 7.10-7.26 (4H, m), 7.60 (1H, d, J = 7.5) |
| 79 (R = Et) | | ethyl 3-(3-fluoro-4-{[2-(2-fluorophenoxy)benzyl]-oxy}phenyl)propanoate | Oily matter, $^1$H NMR: 1.22 (3H, t, J = 6.9), 2.56 (2H, t, J = 8.1), 2.86 (2H, t, J = 8.1), 4.12 (2H, q, J = 6.9), 5.19 (2H, s), 6.81-7.05 (8H, m), 7.11-7.29 (2H, m), 7.60 (1H, dd, J = 1.2, 7.5) |

TABLE 16

| Example No. | Structural formula | Chemical name | Property data |
|---|---|---|---|
| 80 (R = H) | | 3-(3-fluoro-4-{[2-(2-fluorophenoxy)benzyl]oxy}phenyl)propanoic acid | Colorless crystal, Melting point 88-89° C. ethyl acetate-hexane), ¹H NMR: 2.63 (2H, t, J = 7.5), 2.88 (2H, t, J = 7.5), 5.20 (2H, s), 6.81-7.32 (10H, m), 7.60 (1H, d, J = 7.2) |
| 81 (R = Et) | | ethyl 3-(3-fluoro-4-{[2-(2-isopropylphenoxy)-benzyl]oxy}phenyl)-propanoate | Oily matter, ¹H NMR: 1.20-1.27 (9H, m), 2.57 (2H, t, J = 7.8), 2.87 (2H, t, J = 7.8), 3.29 (1H, m), 4.12 (2H, q, J = 7.2), 5.26 (2H, s), 6.71 (1H, d, J = 8.1), 6.80-6.92 (4H, m), 7.06-7.36 (5H, m), 7.59 (1H, d, J = 8.4) |
| 82 (R = H) | | 3-(3-fluoro-4-{[2-(2-isopropylphenoxy)-benzyl]oxy}phenyl)-propanoic acid | Colorless crystal, Melting point 98-99° C. (ethyl acetate-hexane), ¹H NMR: 1.23 (6H, d, J = 6.9), 2.63 (2H, t, J = 8.1), 2.88 (2H, t, J = 8.1), 3.28 (1H, m), 5.27 (2H, s), 6.71 (1H, d, J = 8.1), 6.80-6.98 (4H, m), 7.06-7.36 (5H, m), 7.59 (1H, d, J = 7.5) |
| 83 (R = Et) | | ethyl 3-(3-fluoro-4-{[2-(3-fluorophenoxy)benzyl]oxy}phenyl)propanoate | Oily matter, ¹H NMR: 1.22 (3H, t, J = 7.2), 2.56 (2H, t, J = 7.8), 2.86 (2H, t, J = 7.8), 4.12 (2H, q, J = 7.2), 5.15 (2H, s), 6.64-6.97 (7H, m), 7.18-7.34 (3H, m), 7.61 (1H, d, J = 7.3) |
| 84 (R = H) | | 3-(3-fluoro-4-{[2-(3-fluorophenoxy)benzyl]oxy}phenyl)propanoic acid | Colorless crystal, Melting point 81-82° C. (ethyl acetate-hexane), ¹H NMR: 2.63 (2H, t, J = 7.8), 2.87 (2H, t, J = 7.8), 5.15 (2H, s), 6.63-6.97 (7H, m), 7.18-7.34 (3H, m), 7.61 (1H, d, J = 7.3) |

TABLE 17

| Example No. | Structural formula | Chemical name | Property data |
|---|---|---|---|
| 85 (R = Et) | | ethyl 3-(3-fluoro-4-{[2-(4-fluorophenoxy)benzyl]-oxy}phenyl)propanoate | Oily matter, $^1$H NMR: 1.22 (3H, t, J = 7.2), 2.57 (2H, t, J = 7.8), 2.86 (2H, t, J = 7.8), 4.12 (2H, q, J = 7.2), 5.28 (2H, s), 6.76-7.26 (10H, m), 7.60 (1H, dd, J = 1.2, 7.5) |
| 86 (R = H) | | 3-(3-fluoro-4-{[2-(4-fluorophenoxy)benzyl]-oxy}phenyl)propanoic acid | Colorless crystal, Melting point 68-70° C. (ethyl acetate-hexane), $^1$H NMR: 2.64 (2H, t, J = 7.8), 2.88 (2H, t, J = 7.8), 5.29 (2H, s), 6.76-7.24 (10H, m), 7.60 (1H, d, J = 7.5) |
| 87 (R = Et) | | ethyl 3-[3-fluoro-4-({3-[4-(trifluoromethyl)-phenoxy]benzyl}oxy)-phenyl]propanoate | Oily matter, $^1$H NMR: 1.23 (3H, t, J = 7.2), 2.57 (2H, t, J = 7.8), 2.88 (2H, t, J = 7.8), 4.12 (2H, q, J = 7.2), 5.10 (2H, s), 6.85-7.05 (6H, m), 7.14 (1H, d, J = 2.1), 7.25 (1H, d, J = 6.9), 7.39 (1H, dd, J = 7.8, 7.8), 7.57 (2H, d, J = 8.7) |
| 88 (R = H) | | 3-[3-fluoro-4-({3-[4-(trifluoromethyl)-phenoxy]benzyl}oxy)-phenyl]propanoic acid | Colorless crystal, Melting point 114-115° C. (ethyl acetate-hexane), $^1$H NMR: 2.64 (2H, t, J = 7.8), 2.89 (2H, t, J = 7.8), 5.10 (2H, s), 6.85-7.05 (6H, m), 7.14 (1H, s), 7.24 (1H, d, J = 6.6), 7.39 (1H, dd, J = 7.8, 7.8), 7.57 (2H, d, J = 8.4) |

TABLE 18

| Example No. | Structural formula | Chemical name | Property data |
|---|---|---|---|
| 89 (R = Et) | | ethyl 3-(3-fluoro-4-{[3-(4-propyl-phenoxy)benzyl]-oxy}phenyl) propanoate | Oily matter, $^1$H NMR: 0.95 (3H, t, J = 7.5), 1.23 (3H, t, J = 7.2), 1.63 (2H, qt, J = 7.5, 7.8), 2.57 (2H, t, J = 7.8), 2.57 (2H, t, J = 7.2), 2.88 (2H, t, J = 7.2), 4.12 (2H, q, J = 7.2), 5.07 (2H, s), 6.81-6.96 (6H, m), 7.06 (1H, s), 7.11-7.15 (3H, m), 7.31 (1H, dd, J = 7.8, 7.8) |

TABLE 18-continued

| Example No. | Structural formula | Chemical name | Property data |
|---|---|---|---|
| 90 (R = H) | | 3-(3-fluoro-4-{[3-(4-propylphenoxy)benzyl]-oxy}phenyl)propanoic acid | Colorless crystal, Melting point 83-84° C. (ethyl acetate-hexane), ¹H NMR: 0.95 (3H, t, J = 7.8), 1.63 (2H, qt, J = 7.8, 7.8), 2.57 (2H, t, J = 7.8), 2.64 (2H, t, J = 7.8), 2.88 (2H, t, J = 7.8), 5.07 (2H, s), 6.82-6.97 (6H, m), 7.06 (1H, s), 7.12-7.15 (3H, m), 7.31 (1H, dd, J = 7.8, 7.8) |
| 91 (R = Et) | 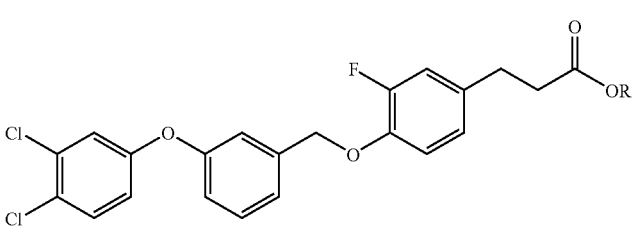 | ethyl 3-(4-{[3-(3,4-dichlorophenoxy)benzyl]oxy}-3-fluorophenyl)propanoate | Oily matter, ¹H NMR: 1.23 (3H, t, J = 7.2), 2.57 (2H, t, J = 7.2), 2.88 (2H, t, J = 7.2), 4.12 (2H, q, J = 7.2), 5.09 (2H, s), 6.83-6.97 (5H, m), 7.07-7.10 (2H, m), 7.21-7.26 (1H, m), 7.35-7.40 (2H, m) |
| 92 (R = H) | | 3-(4-{[3-(3,4-dichlorophenoxy)benzyl]oxy}-3-fluorophenyl)propanoic acid | Colorless crystal, Melting point 101-103° C. (ethyl acetate-hexane), ¹H NMR: 2.64 (2H, t, J = 7.5), 2.89 (2H, t, J = 7.5), 5.09 (2H, s), 6.83-6.97 (5H, m), 7.07-7.10 (2H, m), 7.21-7.26 (1H, m), 7.35-7.40 (2H, m) |

TABLE 19

| Example No. | Structural formula | Chemical name | Property data |
|---|---|---|---|
| 93 (R = Et) | 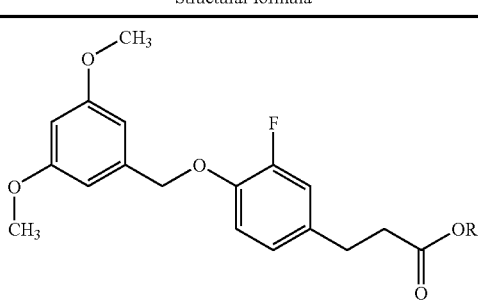 | ethyl 3-{4-[(3,5-dimethoxybenzyl)oxy]-3-fluorophenyl}propanoate | Oily matter, ¹H NMR: 1.23 (3H, t, J = 7.1 Hz), 2.57 (2H, t, J = 7.7 Hz), 2.87 (2H, t, J = 7.7 Hz), 3.79 (6H, s), 4.12 (2H, q, J = 7.1 Hz), 5.06 (2H, s), 6.40 (1H, t, J = 2.2 Hz), 6.58 (2H, d, J = 2.2 Hz), 6.82-6.97 (3H, m). |
| 94 (R = H) | | 3-{4-[(3,5-dimethoxybenzyl)oxy]-3-fluorophenyl}propanoic acid | White crystal, Melting point 109-110° C. (ethyl acetate-hexane), ¹H NMR: 2.64 (2H, t, J = 7.6 Hz), 2.88 (2H, t, J = 7.6 Hz), 3.79 (6H, s), 5.06 (2H, s), 6.41 (1H, t, J = 2.3 Hz), 6.58 (2H, d, J = 2.3 Hz), 6.83-6.98 (3H, m). |

TABLE 19-continued

| Example No. | Structural formula | Chemical name | Property data |
|---|---|---|---|
| 95 (R = Et) | | ethyl 3-{4-[(3,5-diethoxybenzyl)oxy]-3-fluorophenyl}propanoate | White crystal, Melting point 41-42° C. (ethyl acetate-hexane), $^1$H NMR: 1.23 (3H, t, J = 7.1 Hz), 1.39 (6H, t, J = 7.0 Hz), 2.57 (2H, t, J = 7.7 Hz), 2.86 (2H, t, J = 7.7 Hz), 4.01 (4H, q, J = 7.0 Hz), 4.12 (2H, q, J = 7.1 Hz), 5.04 (2H, s), 6.39 (1H, t, J = 2.2 Hz), 6.56 (2H, d, J = 2.2 Hz), 6.81-6.96 (3H, m). |
| 96 (R = H) | | 3-{4-[(3,5-diethoxybenzyl)oxy]-3-fluorophenyl}propanoic acid | White crystal, Melting point 93-95° C. (ethyl acetate-hexane), $^1$H NMR: 1.39 (6H, t, J = 7.0 Hz), 2.64 (2H, t, J = 7.6 Hz), 2.88 (2H, t, J = 7.6 Hz), 4.01 (4H, q, J = 7.0 Hz), 5.04 (2H, s), 6.39 (1H, t, J = 2.3 Hz), 6.56 (2H, d, J = 2.2 Hz), 6.82-6.98 (3H, m). |

TABLE 20

| Example No. | Structural formula | Chemical name | Property data |
|---|---|---|---|
| 97 (R = Et) | | ethyl 3-fluoro-4-[(2,4,6-trimethylphenyl)-methoxy]-benzenepropanoate | Oily matter, $^1$H NMR: 1.27 (3H, t, J = 7.2), 2.27 (3H, s), 2.37 (6H, s), 2.59 (2H, t, J = 7.5), 2.89 (2H, t, J = 7.5), 4.13 (2H, q, J = 7.2), 5.04 (2H, s), 6.85-7.06 (4H, m) |
| 98 (R = H) | | 3-fluoro-4-[(2,4,6-trimethylphenyl)-methoxy]-benzenepropanoic acid | Colorless crystal, Melting point 124-125° C. (ethyl acetate-hexane), $^1$H NMR: 2.28 (3H, s), 2.37 (6H, s), 2.66 (2H, t, J = 7.2), 2.91 (2H, t, J = 7.2), 5.04 (2H, s), 6.85-7.09 (5H, m) |
| 99 (R = Et) | | ethyl 3-[4-(1,3-benzodioxol-5-ylmethoxy)-3-fluorophenyl]-propanoate | Oily matter, $^1$H NMR: 1.23 (3H, t, J = 7.1 Hz), 2.57 (2H, t, J = 7.6 Hz), 2.87 (2H, t, J = 7.7 Hz), 4.12 (2H, q, J = 7.1 Hz), 5.00 (2H, s), 5.96 (2H, s), 6.77-6.96 (6H, m). |
| 100 (R = H) | | 3-[4-(1,3-benzodioxol-5-ylmethoxy)-3-fluorophenyl]-propanoic acid | White crystal, Melting point 137-138° C. (ethyl acetate-hexane), $^1$H NMR: 2.65 (2H, t, J = 7.6 Hz), 2.89 (2H, t, J = 7.6 Hz), 5.00 (2H, s), 5.96 (2H, s), 6.77-6.98 (6H, m). |

TABLE 21

| Example No. | Structural formula | Chemical name | Property data |
|---|---|---|---|
| 101 (R = Et) | | ethyl 3-[4-(1,3-benzodioxol-4-ylmethoxy)-3-fluorophenyl]-propanoate | Oily matter, $^1$H NMR: 1.23 (3H, t, J = 7.1 Hz), 2.57 (2H, t, J = 7.7 Hz), 2.87 (2H, t, J = 7.7 Hz), 4.12 (2H, q, J = 7.1 Hz), 5.09 (2H, s), 5.99 (2H, s), 6.80-6.98 (6H, m). |
| 102 (R = H) | | 3-[4-(1,3-benzodioxol-4-ylmethoxy)-3-fluorophenyl]-propanoic acid | White crystal, Melting point 131-133° C. (ethyl acetate-hexane), $^1$H NMR: 2.64 (2H, t, J = 7.6 Hz), 2.89 (2H, t, J = 7.6 Hz), 5.10 (2H, s), 5.99 (2H, s), 6.77-6.99 (6H, m). |
| 103 (R = MeOCH$_2$) | | ethyl 3-(3-fluoro-4-([3-(methoxymethoxy)-benzyl]oxy}phenyl)-propanoate | Oily matter, $^1$H NMR: 1.23 (3H, t, J = 7.1 Hz), 2.57 (2H, t, J = 7.7 Hz), 2.87 (2H, t, J = 7.7 Hz), 3.48 (3H, s), 4.12 (2H, q, J = 7.1 Hz), 5.08 (2H, s), 5.18 (2H, s), 6.79-7.12 (6H, m), 7.26-7.32 (1H, m). |
| 104 (R = H) | | ethyl 3-{3-fluoro-4-[(3-hydroxybenzyl)oxy]-phenyl}propanoate | Oily matter, $^1$H NMR: 1.23 (3H, t, J = 7.1 Hz), 2.57 (2H, t, J = 7.6 Hz), 2.87 (2H, t, J = 7.6 Hz), 4.12 (2H, q, J = 7.1 Hz), 4.83 (1H, brs), 5.07 (2H, s), 6.76-6.99 (6H, m), 7.21-7.26 (1H, m). |

TABLE 22

| Example No. | Structural formula | Chemical name | Property data |
|---|---|---|---|
| 105 (R = t-Bu) | | ethyl 3-(4-{[3-(2-tert-butoxy-2-oxoethoxy)benzyl]-oxy}-3-fluorophenyl)-propanoate | Oily matter, $^1$H NMR: 1.23 (3H, t, J = 7.1 Hz), 1.48 (9H, s), 2.57 (2H, t, J = 7.7 Hz), 2.87 (2H, t, J = 7.7 Hz), 4.12 (2H, q, J = 7.1 Hz), 4.52 (2H, s), 5.08 (2H, s), 6.79-7.05 (6H, m), 7.26-7.31 (1H, m). |
| 106 (R = H) | | (3-{[4-(3-ethoxy-3-oxopropyl)-2-fluorophenoxy]-methyl}phenoxy)-acetic acid | White crystal, Melting point 72-74° C. (ethyl acetate-hexane), $^1$H NMR: 1.23 (3H, t, J = 7.1 Hz), 2.59 (2H, t, J = 7.5 Hz), 2.87 (2H, t, J = 7.5 Hz), 4.12 (2H, q, J = 7.1 Hz), 4.68 (2H, s), 5.11 (2H, s), 6.80-6.98 (5H, m), 7.06 (1H, d, J = 7.6 Hz), 7.31 (1H, t, J = 7.9 Hz). |

TABLE 22-continued

| Example No. | Structural formula | Chemical name | Property data |
|---|---|---|---|
| 107 | | 3-(4-{[3-(carboxymethoxy)-benzyl]oxy}-3-fluorophenyl)-propanoic acid | White crystal, Melting point 150-151° C. (ethyl acetate-hexane), $^1$H NMR: 2.68 (2H, t, J = 7.1 Hz), 2.90 (2H, t, J = 7.1 Hz), 4.63 (2H, s), 5.22 (2H, s), 6.60 (1H, s), 6.69 (1H, t, J = 8.3 Hz), 6.77 (1H, d, J = 9.3 Hz), 6.90-6.97 (2H, m), 7.04 (1H, d, J = 7.4 Hz), 7.33 (1H, t, J = 7.7 Hz). |

TABLE 23

| Example No. | Structural formula | Chemical name | Property data |
|---|---|---|---|
| 108 (R = Et) | | ethyl 3-(3-fluoro-4-{[3-(2-oxopropoxy)-benzyl]oxy}-phenyl)propanoate | Oily matter, $^1$H NMR: 1.23 (3H, t, J = 7.1 Hz), 2.28 (3H, s), 2.57 (2H, t, J = 7.7 Hz), 2.87 (2H, t, J = 7.7 Hz), 4.12 (2H, q, J = 7.1 Hz), 4.55 (2H, s), 5.08 (2H, s), 6.76-7.09 (6H, m), 7.27-7.33 (1H, m). |
| 109 (R = H) | | 3-(3-fluoro-4-{[3-(2-oxopropoxy)-benzyl]oxy}-phenyl)propanoic acid | White crystal, Melting point 83-85° C. (ethyl acetate-hexane), $^1$H NMR: 2.28 (3H, s), 2.65 (2H, t, J = 7.5 Hz), 2.89 (2H, t, J = 7.5 Hz), 4.54 (2H, s), 5.09 (2H, s), 6.81-6.99 (5H, m), 7.05 (1H, d, J = 7.6 Hz), 7.30 (1H, t, J = 7.8 Hz). |
| 110 (R = Et) | | ethyl 3-[3-fluoro-4-({3-[2-(methylamino)-2-oxoethoxy]benzyl}-oxy)phenyl]-propanoate | Oily matter, $^1$H NMR: 1.23 (3H, t, J = 7.1 Hz), 2.58 (2H, t, J = 7.6 Hz), 2.84-2.93 (5H, m), 4.12 (2H, q, J = 7.1 Hz), 4.50 (2H, s), 5.09 (2H, s) 6.59 (1H, brs), 6.83-7.09 (6H, m), 7.32 (1H, t, J = 7.9 Hz). |
| 111 (R = H) | | 3-[3-fluoro-4-({3-[2-(methylamino)-2-oxoethoxy]benzyl}-oxy)phenyl]-propanoic acid | White crystal, Melting point 134-136° C. (ethyl acetate-hexane), $^1$H NMR: 2.66 (2H, t, J = 7.2 Hz), 2.86-2.93 (5H, m), 4.38 (2H, s), 5.10 (2H, s), 6.69 (1H, brs), 6.78-6.90 (4H, m), 6.98 (1H, dd, J = 2.0, 12.3 Hz), 7.07 (1H, d, J = 7.6 Hz), 7.32 (1H, t, J = 7.9 Hz) |

TABLE 24

| Example No. | Structural formula | Chemical name | Property data |
|---|---|---|---|
| 112 (R = Et) | | ethyl 3-[4-({3-[2-(dimethylamino)-2-oxoethoxy]-benzyl}oxy)-3-fluorophenyl]-propanoate | Oily matter, $^1$H NMR: 1.23 (3H, t, J = 7.1 Hz), 2.57 (2H, t, J = 7.7 Hz), 2.87 (2H, t, J = 7.7 Hz), 2.98 (3H, s), 3.09 (3H, s), 4.12 (2H, q, J = 7.1 Hz), 4.69 (2H, s), 5.08 (2H, s), 6.82-7.06 (6H, m), 7.26-7.32 (1H, m). |
| 113 (R = H) | | 3-[4-({3-[2-dimethylamino)-2-oxoethoxy]-benzyl}oxy)-3-fluorophenyl]-propanoic acid | White crystal, Melting point 178-179° C. (ethyl acetate-hexane), $^1$H NMR: 2.64 (2H, t, J = 7.3 Hz), 2.88 (2H, t, J = 7.3 Hz), 2.99 (3H, s), 3.09 (3H, s), 4.60 (2H, s), 5.09 (2H, s), 6.79-6.98 (5H, m), 7.05 (1H, d, J = 7.6 Hz), 7.26-7.32 (1H, m). |
| 114 (R = Et) | | ethyl 3-(4-{[3-(2-amino-2-oxoethoxy)-benzyl]oxy}-3-fluorophenyl)-propanoate | White crystal, Melting point 86-87° C. (ethyl acetate-hexane), $^1$H NMR: 1.23 (3H, t, J = 7.1 Hz), 2.58 (2H, t, J = 7.6 Hz), 2.88 (2H, t, J = 7.7 Hz), 4.12 (2H, q, J = 7.1 Hz), 4.51 (2H, s), 5.09 (2H, s), 5.60 (1H, brs), 6.54 (1H, brs), 6.80-7.00 (4H, m), 7.04 (1H, s), 7.09 (1H, d, J = 7.6 Hz), 7.33 (1H, t, J = 7.9 Hz). |

TABLE 25

| Example No. | Structural formula | Chemical name | Property data |
|---|---|---|---|
| 115 (R = H) | | 3-(4-{[3-(2-amino-2-oxoethoxy)benzyl]-oxy}-3-fluorophenyl)-propanoic acid | White crystal, Melting point 120-121° C. (ethyl acetate-hexane), $^1$H NMR (DMSO-$d_6$): 2.51 (2H, t, J = 7.5 Hz), 2.75 (2H, t, J = 7.5 Hz), 4.42 (1H, s), 4.64 (1H, s), 5.10 (2H, s), 6.83-7.17 (6H, m), 7.25-7.35 (1H, m), 7.38 (1H, brs), 7.53 (1H, brs), 12.78 (1H, brs). |
| 116 | | ethyl 3-(3-fluoro-4-{[3-(methoxy-methoxy)-5-phenoxybenzyl]oxy}-phenyl)propanoate | Oily matter, $^1$H NMR: 1.23 (3H, t, J = 7.1 Hz), 2.57 (2H, t, J = 7.7 Hz), 2.87 (2H, t, J = 7.7 Hz), 3.46 (3H, s), 4.12 (2H, q, J = 7.1 Hz), 5.02 (2H, s), 5.14 (2H, s), 6.65 (1H, t, J = 2.2 Hz), 6.71 (1H, s), 6.84-6.96 (6H, m), 7.12 (1H, t, J = 7.4 Hz), 7.30-7.37 (2H, m). |

TABLE 25-continued

| Example No. | Structural formula | Chemical name | Property data |
|---|---|---|---|
| 117 (R = Et) | | ethyl 3-{3-fluoro-4-[(3-hydroxy-5-phenoxybenzyl)oxy]-phenyl}propanoate | Oily matter, $^1$H NMR: 1.26 (3H, t, J = 7.2 Hz), 2.57 (2H, t, J = 7.6 Hz), 2.87 (2H, t, J = 7.6 Hz), 4.12 (2H, q, J = 7.1 Hz), 5.01 (2H, s), 5.11 (1H, s), 6.41 (1H, t, J = 2.2 Hz), 6.60-6.65 (2H, m), 6.80-7.16 (6H, m), 7.31-7.38 (2H, m). |

TABLE 26

| Example No. | Structural formula | Chemical name | Property data |
|---|---|---|---|
| 118 (R = H) | | 3-{3-fluoro-4-[(3-hydroxy-5-phenoxybenzyl)oxy]-phenyl}propanoic acid | White crystal, Melting point 172-173° C. (ethyl acetate-hexane), $^1$H NMR: 2.48 (2H, t, J = 7.5 Hz), 2.73 (2H, t, J = 7.5 Hz), 5.03 (2H, s), 6.28 (1H, t, J = 2.1 Hz), 6.47 (1H, s), 6.58 (1H, s), 6.91-7.16 (6H, m), 7.38 (2H, t, J = 8.0 Hz), 9.67 (1H, s), 12.08 (1H, brs). |
| 119 (R = Et) | | ethyl 3-{3-fluoro-4-[(3-methoxy-5-phenoxybenzyl)oxy]-phenyl}propanoate | Oily matter, $^1$H NMR: 1.23 (3H, t, J = 7.2 Hz), 2.57 (2H, t, J = 7.7 Hz), 2.87 (2H, t, J = 7.7 Hz), 3.77 (3H, s), 4.12 (2H, q, J = 7.2 Hz), 5.03 (2H, s), 6.50 (1H, t, J = 2.3 Hz), 6.65 (1H, s), 6.74 (1H, s), 6.81-7.04 (5H, m), 7.08-7.17 (1H, m), 7.30-7.38 (2H, m). |
| 120 (R = H) | | 3-{3-fluoro-4-[(3-methoxy-5-phenoxybenzyl)oxy]-phenyl}propanoic acid | White crystal, Melting point 94-96° C. (ethyl acetate-hexane), $^1$H NMR: 2.64 (2H, t, J = 7.5 Hz), 2.89 (2H, t, J = 7.5 Hz), 3.77 (3H, s), 5.04 (2H, s), 6.50 (1H, t, J = 2.3 Hz), 6.65 (1H, s), 6.74 (1H, s), 6.83-7.04 (5H, m), 7.12 (1H, t, J = 7.4 Hz), 7.34 (2H, t, J = 8.0 Hz). |

TABLE 27

| Example No. | Structural formula | Chemical name | Property data |
|---|---|---|---|
| 121 (R = Et) | | ethyl 3-{4-[(3-ethoxy-5-phenoxybenzyl)oxy]-3-fluorophenyl}-propanoate | Oily matter, $^1$H NMR: 1.23 (3H, t, J = 7.2 Hz), 1.38 (3H, t, J = 7.2 Hz), 2.57 (2H, t, J = 7.7 Hz), 2.87 (2H, t, J = 7.7 Hz), 3.99 (2H, q, J = 7.2 Hz), 4.12 (2H, q, J = 7.2 Hz), 5.03 (2H, s), 6.48 (1H, t, J = 2.3 Hz), 6.64 (1H, s), 6.73 (1H, s), 6.81-7.03 (5H, m), 7.08-7.14 (1H, m), 7.29-7.37 (2H, m). |
| 122 (R = H) | | 3-{4-[(3-ethoxy-5-phenoxybenzyl)oxy]-3-fluorophenyl}propanoic acid | Oily matter, $^1$H NMR: 1.38 (3H, t, J = 7.1 Hz), 2.64 (2H, t, J = 7.7 Hz), 2.88 (2H, t, J = 7.7 Hz), 3.99 (2H, q, J = 7.1 Hz), 5.03 (2H, s), 6.48 (1H, t, J = 2.3 Hz), 6.64 (1H, s), 6.73 (1H, s), 6.83-7.03 (5H, m), 7.08-7.18 (1H, m), 7.29-7.36 (2H, m). |
| 123 (R = Et) | | ethyl 3-{3-fluoro-4-[(3-isopropoxy-5-phenoxybenzyl)oxy]-phenyl}propanoate | Oily matter, $^1$H NMR: 1.23 (3H, t, J = 7.1 Hz), 1.30 (6H, d, J = 6.1 Hz), 2.57 (2H, t, J = 7.7 Hz), 2.87 (2H, t, J = 7.7 Hz), 4.12 (2H, q, J = 7.1 Hz), 4.50 (1H, septet, J = 6.1 Hz), 5.02 (2H, s), 6.47 (1H, t, J = 2.2 Hz), 6.62 (1H, s), 6.71 (1H, s), 6.81-7.03 (5H, m), 7.11 (1H, t, J = 7.4 Hz), 7.29-7.36 (2H, m). |

TABLE 28

| Example No. | Structural formula | Chemical name | Property data |
|---|---|---|---|
| 124 (R = H) | | 3-{3-fluoro-4-[(3-isopropoxy-5-phenoxybenzyl)oxy]-phenyl}propanoic acid | White crystal, Melting point 84-85° C. (ethyl acetate-hexane), $^1$H NMR: 1.30 (6H, d, J = 6.1 Hz), 2.64 (2H, t, J = 7.5 Hz), 2.88 (2H, t, J = 7.6 Hz), 4.50 (1H, septet, J = 6.1 Hz), 5.02 (2H, s), 6.47 (1H, t, J = 2.2 Hz), 6.62 (1H, s), 6.71 (1H, s), 6.85-7.16 (6H, m), 7.28-7.39 (2H, m). |

TABLE 28-continued

| Example No. | Structural formula | Chemical name | Property data |
|---|---|---|---|
| 125 (R = Et) | | ethyl 3-{4-[(3-butoxy-5-phenoxybenzyl)oxy]-3-fluorophenyl}propanoate | Oily matter, $^1$H NMR: 0.95 (3H, t, J = 7.4 Hz), 1.23 (3H, t, J = 7.1 Hz), 1.38-1.53 (2H, m), 1.68-1.78 (2H, m), 2.57 (2H, t, J = 7.7 Hz), 2.87 (2H, t, J = 7.7 Hz), 3.92 (2H, t, J = 6.5 Hz), 4.12 (2H, q, J = 7.1 Hz), 5.03 (2H, s), 6.49 (1H, t, J = 2.2 Hz), 6.63 (1H, s), 6.73 (1H, s), 6.81-7.14 (6H, m), 7.29-7.37 (2H, m). |
| 126 (R = H) | | 3-{4-[(3-butoxy-5-phenoxybenzyl)oxy]-3-fluorophenyl}propanoic acid | White crystal, Melting point 73-74° C. (ethyl acetate-hexane), $^1$H NMR: 0.95 (3H, t, J = 7.4 Hz), 1.39-1.53 (2H, m), 1.68-1.78 (2H, m), 2.64 (2H, t, J = 7.6 Hz), 2.88 (2H, t, J = 7.6 Hz), 3.92 (2H, t, J = 6.5 Hz), 5.03 (2H, s), 6.49 (1H, t, J = 2.2 Hz), 6.63 (1H, s), 6.73 (1H, s), 6.82-7.14 (6H, m), 7.30-7.36 (2H, m). |

TABLE 29

| Example No. | Structural formula | Chemical name | Property data |
|---|---|---|---|
| 127 (R = t-Bu) | | ethyl 3-(4-{[3-(2-tert-butoxy-2-oxoethoxy)-5-phenoxybenzyl]oxy}-3-fluorophenyl)-propanoate | Oily matter, $^1$H NMR: 1.23 (3H, t, J = 7.1 Hz), 1.46 (9H, s), 2.57 (2H, t, J = 7.7 Hz), 2.87 (2H, t, J = 7.7 Hz), 4.12 (2H, q, J = 7.1 Hz), 4.47 (2H, s), 5.02 (2H, s), 6.47 (1H, t, J = 2.3 Hz), 6.68 (1H, s), 6.72 (1H, s), 6.80-7.05 (5H, m), 7.08-7.16 (1H, m), 7.30-7.37 (2H, m). |
| 128 (R = H) | | (3-{[4-(3-ethoxy-3-oxopropyl)-2-fluorophenoxy]-methyl}-5-phenoxyphenoxy)-acetic acid | Oily matter, $^1$H NMR: 1.23 (3H, t, J = 7.1 Hz), 2.59 (2H, t, J = 7.4 Hz), 2.87 (2H, t, J = 7.5 Hz), 4.12 (2H, q, J = 7.1 Hz), 4.63 (2H, s), 5.06 (2H, s), 6.51 (1H, t, J = 2.3 Hz), 6.52-7.21 (8H, m), 7.30-7.41 (2H, m). |

TABLE 29-continued

| Example No. | Structural formula | Chemical name | Property data |
|---|---|---|---|
| 129 | 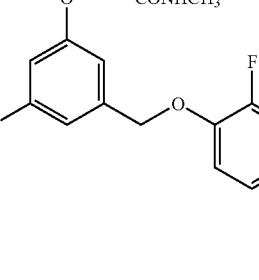 | 3-(4-{[3-(carboxymethoxy)-5-phenoxybenzyl]oxy}-3-fluorophenyl)-propanoic acid | White crystal, Melting point 122-124° C. (ethyl acetate-hexane), $^1$H NMR: 2.69 (2H, t, J = 7.1 Hz), 2.90 (2H, t, J = 7.1 Hz), 4.60 (2H, s), 5.13 (2H, s), 6.39 (1H, s), 6.53 (1H, t, J = 2.3 Hz), 6.66-7.18 (7H, m), 7.33-7.39 (2H, m). |

TABLE 30

| Example No. | Structural formula | Chemical name | Property data |
|---|---|---|---|
| 130 (R = Et) |  | ethyl 3-[3-fluoro-4-({3-[2-(methylamino)-2-oxoethoxy]-5-phenoxybenzyl}oxy)-phenyl]propanoate | White crystal, Melting point 95-96° C. (ethyl acetate-hexane), $^1$H NMR: 1.23 (3H, t, J = 7.1 Hz), 2.58 (2H, t, J = 7.6 Hz), 2.85-2.91 (5H, m), 4.12 (2H, q, J = 7.1 Hz), 4.45 (2H, s), 5.03 (2H, s), 6.48 (1H, t, J = 2.3 Hz), 6.55 (1H, brs), 6.72 (1H, s), 6.75 (1H, s), 6.85-7.19 (6H, m), 7.33-7.39 (2H, m). |
| 131 (R = H) | | 3-[3-fluoro-4-({3-[2-(methylamino)-2-oxoethoxy]-5-phenoxybenzyl}oxy)-phenyl]propanoic acid | White crystal, Melting point 153-154° C. (ethyl acetate-hexane), $^1$H NMR: 2.66 (2H, t, J = 7.1 Hz), 2.87-2.93 (5H, m), 4.29 (2H, s), 5.04 (2H, s), 6.42 (1H, s), 6.48 (1H, t, J = 2.2 Hz), 6.64 (1H, brs), 6.72 (1H, s), 6.77-7.21 (6H, m), 7.34-7.41 (2H, m). |
| 132 (R = Et) | 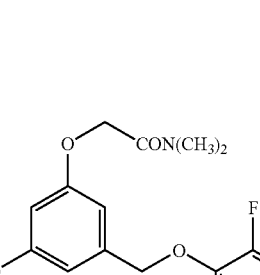 | ethyl 3-[4-({3-[2-(dimethylamino)-2-oxoethoxy]-5-phenoxybenzyl}oxy)-3-fluorophenyl]-propanoate | Oily matter, $^1$H NMR: 1.23 (3H, t, J = 7.1 Hz), 2.57 (2H, t, J = 7.7 Hz), 2.87 (2H, t, J = 7.7 Hz), 2.97 (3H, s), 3.05 (3H, s), 4.12 (2H, q, J = 7.1 Hz), 4.65 (2H, s), 5.02 (2H, s), 6.53 (1H, t, J = 2.2 Hz), 6.68 (1H, s), 6.76 (1H, s), 6.84-7.13 (6H, m), 7.31-7.37 (2H, m). |

TABLE 31

| Example No. | Structural formula | Chemical name | Property data |
|---|---|---|---|
| 133 (R = H) | | 3-[4-({3-[2-(dimethylamino)-2-oxoethoxy]-5-phenoxybenzyl}-oxy)-3-fluorophenyl]-propanoic acid | White crystal, Melting point 158-160° C. (ethyl acetate-hexane), $^1$H NMR: 2.64 (2H, t, J = 7.3 Hz), 2.88 (2H, t, J = 7.3 Hz), 2.98 (3H, s), 3.05 (3H, s), 4.56 (2H, s), 5.03 (2H, s), 6.51 (1H, t, J = 2.2 Hz), 6.57 (1H, s), 6.68 (1H, s), 6.78-7.16 (6H, m), 7.32-7.38 (2H, m). |
| 134 (R = Et) | | ethyl 3-{3,5-difluoro-4-[(3-isobutoxybenzyl)-oxy]phenyl}-propanoate | Oily matter, $^1$H NMR: 1.02 (6H, d, J = 6.6), 1.23 (3H, t, J = 7.1), 2.03-2.12 (1H, m), 2.57 (2H, t, J = 7.7), 2.86 (2H, t, J = 7.7), 3.73 (2H, d, J = 6.5), 4.13 (2H, q, J = 6.6), 5.09 (2H, s), 6.70-6.76 (2H, m), 6.85 (1H, dd, J = 1.7, 7.5), 6.99-7.01 (2H, m), 7.22-7.27 (1H, m) |
| 135 (R = H) | | 3-{3,5-difluoro-4-[(3-isobutoxybenzyl)-oxy]phenyl}propanoic acid | Amorphous, $^1$H NMR: 1.02 (6H, d, J = 6.7), 2.03-2.12 (1H, m), 2.64 (2H, t, J = 7.5), 2.87 (2H, t, J = 7.5), 3.73 (2H, d, J = 6.6), 5.10 (2H, s), 6.70-6.77 (2H, m), 6.86 (1H, dd, J = 2.5, 8.2), 6.97-7.01 (2H, m), 7.22-7.27 (1H, m) |

TABLE 32

| Example No. | Structural formula | Chemical name | Property data |
|---|---|---|---|
| 136 (R = Et) | | ethyl 3-(4-{[3-(benzyloxy)-5-phenoxybenzyl]oxy}-3-fluorophenyl)-propanoate | Oily matter, $^1$H NMR: 1.23 (3H, t, J = 7.1 Hz), 2.57 (2H, t, J = 7.7 Hz), 2.87 (2H, t, J = 7.7 Hz), 4.12 (2H, q, J = 7.1 Hz), 5.02 (2H, s), 5.03 (2H, s), 6.56 (1H, t, J = 2.2 Hz), 6.67 (1H, s), 6.82-7.03 (6H, m), 7.07-7.17 (1H, m), 7.30-7.44 (7H, m). |
| 137 (R = H) | | 3-(4-{[3-(benzyloxy)-5-phenoxybenzyl]oxy}-3-fluorophenyl)propanoic acid | White crystal, Melting point 73-75° C. (ethyl acetate-hexane), $^1$H NMR: 2.64 (2H, t, J = 7.6 Hz), 2.89 (2H, t, J = 7.6 Hz), 5.02 (2H, s), 5.03 (2H, s), 6.56 (1H, t, J = 2.2 Hz), 6.66 (1H, s), 6.82-7.02 (6H, m), 7.07-7.16 (1H, m), 7.29-7.41 (7H, m). |

TABLE 32-continued

| Example No. | Structural formula | Chemical name | Property data |
|---|---|---|---|
| 138 (R = Et) | | ethyl 3-(3-fluoro-4-{[3-phenoxy-5-(2-phenylethoxy)benzyl]-oxy}phenyl)propanoate | Oily matter, $^1$H NMR: 1.25 (3H, t, J = 7.2 Hz), 2.59 (2H, t, J = 7.7 Hz), 2.89 (2H, t, J = 7.7 Hz), 3.09 (2H, t, J = 7.2 Hz), 4.10-4.19 (4H, m), 5.04 (2H, s), 6.51 (1H, t, J = 2.1 Hz), 6.66 (1H, s), 6.76 (1H, s), 6.84-7.09 (5H, m), 7.13 (1H, t, J = 7.5 Hz), 7.24-7.39 (7H, m). |

TABLE 33

| Example No. | Structural formula | Chemical name | Property data |
|---|---|---|---|
| 139 (R = H) | | 3-(3-fluoro-4-{[3-phenoxy-5-(2-phenylethoxy)benzyl]-oxy}phenyl)propanoic acid | White crystal, Melting point 71-73° C. (ethyl acetate-hexane), $^1$H NMR: 2.64 (2H, t, J = 7.6 Hz), 2.88 (2H, t, J = 7.6 Hz), 3.06 (2H, t, J = 7.2 Hz), 4.13 (2H, t, J = 7.2 Hz), 5.02 (2H, s), 6.49 (1H, t, J = 2.1 Hz), 6.64 (1H, s), 6.73 (1H, s), 6.85-7.02 (5H, m), 7.11 (1H, t, J = 7.4 Hz), 7.22-7.36 (7H, m). |
| 140 | | ethyl 3-(4-{[3-(2-{[tert-butyl(dimethyl)-silyl]oxy}ethoxy)-5-phenoxybenzyl]oxy}-3-fluorophenyl)-propanoate | Oily matter, $^1$H NMR: 0.08 (6H, s), 0.89 (9H, s), 1.23 (3H, t, J = 7.2 Hz), 2.57 (2H, t, J = 7.7 Hz), 2.87 (2H, t, J = 7.7 Hz), 3.91-4.02 (4H, m), 4.12 (2H, q, J = 7.2 Hz), 5.03 (2H, s), 6.51 (1H, t, J = 2.1 Hz), 6.64 (1H, s), 6.74 (1H, s), 6.81-7.03 (5H, m), 7.11 (1H, t, J = 7.5 Hz), 7.30-7.36 (2H, m). |

TABLE 34

| Example No. | Structural formula | Chemical name | Property data |
|---|---|---|---|
| 141 (R = Et) | | ethyl 3-(3-fluoro-4-{[3-(2-hydroxyethoxy)-5-phenoxybenzyl]oxy}-phenyl)propanoate | Oily matter, $^1$H NMR: 1.23 (3H, t, J = 7.1 Hz), 1.94 (1H, t, J = 6.0 Hz), 2.57 (2H, t, J = 7.7 Hz), 2.87 (2H, t, J = 7.7 Hz), 3.90-3.96 (2H, m), 4.05 (2H, m), 4.12 (2H, q, J = 7.2 Hz), 5.03 (2H, s), 6.50 (1H, t, J = 2.1 Hz), 6.67 (1H, s), 6.76 (1H, s), 6.84-7.04 (5H, m), 7.13 (1H, t, J = 7.5 Hz), 7.31-7.38 (2H, m). |
| 142 (R = H) | | 3-(3-fluoro-4-{[3-(2-hydroxyethoxy)-5-phenoxybenzyl]oxy}-phenyl)propanoic acid | Oily matter, $^1$H NMR: 2.64 (2H, t, J = 7.5 Hz), 2.88 (2H, t, J = 7.5 Hz), 3.91-3.96 (2H, m), 3.99-4.04 (2H, m), 5.04 (2H, s), 6.50 (1H, t, J = 2.1 Hz), 6.66 (1H, s), 6.70 (1H, s), 6.81-7.03 (5H, m), 7.12 (1H, t, J = 7.4 Hz), 7.34 (2H, t, J = 8.0 Hz). |
| 143 (R = Et) | | ethyl 3-{4-[(3-{2-[(tert-butoxycarbonyl)amino]-ethoxy}-5-phenoxybenzyl)oxy]-3-fluorophenyl}propanoate | Oily matter, $^1$H NMR: 1.23 (3H, t, J = 7.1 Hz), 1.44 (9H, s), 2.57 (2H, t, J = 7.6 Hz), 2.87 (2H, t, J = 7.6 Hz), 3.43-3.57 (2H, m), 3.97 (2H, t, J = 5.1 Hz), 4.12 (2H, q, J = 7.1 Hz), 4.94 (1H, brs), 5.02 (2H, s), 6.47 (1H, t, J = 2.2 Hz), 6.66 (1H, s), 6.72 (1H, s), 6.84-7.03 (5H, m), 7.13 (1H, t, J = 7.4 Hz), 7.31-7.38 (2H, m). |

TABLE 35

| Example No. | Structural formula | Chemical name | Property data |
|---|---|---|---|
| 144 (R = H) | | 3-{4-[(3-{2-[(tert-butoxycarbonyl)amino]-ethoxy}-5-phenoxybenzyl)oxy]-3-fluorophenyl}propanoic acid | Oily matter, $^1$H NMR: 1.44 (9H, s), 2.64 (2H, t, J = 7.3 Hz), 2.88 (2H, t, J = 7.3 Hz), 3.47 (2H, brs), 3.92 (2H, brs), 4.98 (1H, brs), 5.05 (2H, s), 6.46 (1H, s), 6.64 (2H, s), 6.85 (2H, s), 6.93-7.04 (3H, m), 7.10-7.16 (1H, s), 7.32-7.38 (2H, m). |

TABLE 35-continued

| Example No. | Structural formula | Chemical name | Property data |
|---|---|---|---|
| 145 | 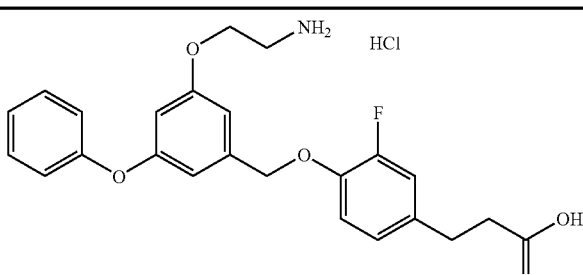 | 3-(4-{[3-(2-aminoethoxy)-5-phenoxybenzyl]oxy}-3-fluorophenyl)propanoic acid hydrochloride | White crystal, Melting point 182-183° C. (ethyl acetate-hexane), $^1$H NMR (DMSO-$d_6$): 2.76 (2H, t, J = 7.1 Hz), 3.13-3.26 (2H, m), 4.08-4.20 (2H, m), 5.12 (2H, s), 6.55 (1H, s), 6.71 (1H, s), 6.83 (1H, s), 6.94-7.22 (6H, m), 7.43 (2H, t, J = 7.8 Hz), 7.94 (3H, brs). |
| 146 (R = Et) | 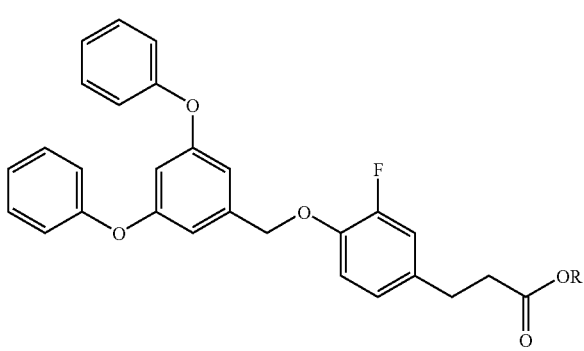 | ethyl 3-{4-[(3,5-diphenoxybenzyl)oxy]-3-fluorophenyl}propanoate | Oily matter, $^1$H NMR: 1.23 (3H, t, J = 7.1 Hz), 2.57 (2H, t, J = 7.7 Hz), 2.87 (2H, t, J = 7.7 Hz), 4.12 (2H, q, J = 7.1 Hz), 5.01 (2H, s), 6.60 (1H, t, J = 2.2 Hz), 6.79 (2H, d, J = 2.2 Hz), 6.83-7.15 (9H, m), 7.30-7.37 (4H, m). |
| 147 (R = H) | | 3-{4-[(3,5-diphenoxybenzyl)oxy]-3-fluorophenyl}propanoic acid | White crystal, Melting point 108-109° C. (ethyl acetate-hexane), $^1$H NMR: 2.64 (2H, t, J = 7.6 Hz), 2.88 (2H, t, J = 7.6 Hz), 5.01 (2H, s), 6.60 (1H, t, J = 2.2 Hz), 6.79 (2H, d, J = 2.2 Hz), 6.82-7.15 (9H, m), 7.29-7.37 (4H, m). |

TABLE 36

| Example No. | Structural formula | Chemical name | Property data |
|---|---|---|---|
| 148 (R = Et) | 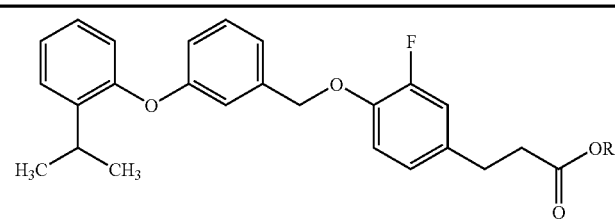 | ethyl 3-(3-fluoro-4-{[3-(2-isopropylphenoxy)-benzyl]oxy}phenyl)-propanoate | Oily matter, $^1$H NMR: 1.19-1.29 (9H, m), 2.57 (2H, t, J = 7.7 Hz), 2.87 (2H, t, J = 7.7 Hz), 3.26 (1H, septet, J = 6.9 Hz), 4.12 (2H, q, J = 7.2 Hz), 5.06 (2H, s), 6.79-7.01 (6H, m), 7.09-7.18 (3H, m), 7.29-7.38 (2H, m). |
| 149 (R = H) | | 3-(3-fluoro-4-{[3-(2-isopropylphenoxy)-benzyl]oxy}phenyl)-propanoic acid | White crystal, Melting point 51-52° C. (ethyl acetate-hexane), $^1$H NMR 1.21 (6H, d, J = 6.9 Hz), 2.64 (2H, t, J = 7.7 Hz), 2.89 (2H, t, J = 7.7 Hz), 3.26 (1H, |

TABLE 36-continued

| Example No. | Structural formula | Chemical name | Property data |
|---|---|---|---|
| | | | septet, J = 6.9 Hz), 5.06 (2H, s), 6.83-7.00 (6H, m), 7.09-7.18 (3H, m), 7.29-7.36 (2H, m). |
| 150 (R = Et) | | ethyl 3-(3-fluoro-4-{[3-(3-isopropylphenoxy)-benzyl]oxy}phenyl)-propanoate | Oily matter, $^1$H NMR: 1.20-1.29 (9H, m), 2.57 (2H, t, J = 7.7 Hz), 2.84-2.93 (3H, m), 4.12 (2H, q, J = 7.2 Hz), 5.07 (2H, s), 6.77-7.00 (7H, m), 7.09 (1H, s), 7.15 (1H, d, J = 8.1 Hz), 7.21-7.26 (1H, m), 7.32 (1H, t, J = 7.8 Hz). |
| 151 (R = H) | | 3-(3-fluoro-4-{[3-(3-isopropylphenoxy)-benzyl]oxy}phenyl)-propanoic acid | White crystal, Melting point 63-64° C. (ethyl acetate-hexane), $^1$H NMR 1.23 (6H, d, J = 6.9 Hz), 2.64 (2H, t, J = 7.7 Hz), 2.83-2.93 (3H, m), 5.08 (2H, s), 6.77-7.00 (7H, m), 7.08 (1H, s), 7.15 (1H, d, J = 8.1 Hz), 7.21-7.26 (1H, m), 7.33 (1H, t, J = 8.0 Hz). |

TABLE 37

| Example No. | Structural formula | Chemical name | Property data |
|---|---|---|---|
| 152 (R = Et) | | ethyl 3-(3-fluoro-4-{[3-(4-isopropylphenoxy)-benzyl]oxy}phenyl)-propanoate | Oily matter, $^1$H NMR: 1.16-1.28 (9H, m), 2.57 (2H, t, J = 7.7 Hz), 2.84-2.96 (3H, m), 4.12 (2H, q, J = 7.2 Hz), 5.07 (2H, s), 6.82-6.96 (6H, m), 7.07 (1H, s), 7.12-7.20 (3H, m), 7.31 (1H, t, J = 7.8 Hz). |
| 153 (R = H) | | 3-(3-fluoro-4-{[3-(4-isopropylphenoxy)-benzyl]oxy}phenyl)-propanoic acid | White crystal, Melting point 85-86° C. (ethyl acetate-hexane), $^1$H NMR: 1.25 (6H, d, J = 6.9 Hz), 2.64 (2H, t, J = 7.7 Hz), 2.85-2.96 (3H, m), 5.07 (2H, s), 6.82-6.98 (6H, m), 7.07 (1H, s), 7.12-7.21 (3H, m), 7.31 (1H, t, J = 7.8 Hz). |

TABLE 37-continued

| Example No. | Structural formula | Chemical name | Property data |
|---|---|---|---|
| 154 (R = Et) | | ethyl 3-(3-fluoro-4-{[3-(2-fluorophenoxy)benzyl]oxy}phenyl)propanoate | Oily matter, ¹H NMR: 1.23 (3H, t, J = 7.2 Hz), 2.57 (2H, t, J = 7.7 Hz), 2.87 (2H, t, J = 7.7 Hz), 4.12 (2H, q, J = 7.2 Hz), 5.07 (2H, s), 6.82-6.99 (4H, m), 7.00-7.24 (6H, m), 7.32 (1H, t, J = 8.1 Hz). |
| 155 (R = H) | | 3-(3-fluoro-4-{[3-(2-fluorophenoxy)benzyl]oxy}phenyl)propanoic acid | White crystal, Melting point 72-73° C. (ethyl acetate-hexane), ¹H NMR: 2.64 (2H, t, J = 7.7 Hz), 2.89 (2H, t, J = 7.7 Hz), 5.08 (2H, s), 6.83-6.98 (4H, m), 7.02-7.22 (6H, m), 7.32 (1H, t, J = 7.8 Hz). |

TABLE 38

| Example No. | Structural formula | Chemical name | Property data |
|---|---|---|---|
| 156 (R = Et) | | ethyl 3-(3-fluoro-4-{[3-(3-fluorophenoxy)benzyl]oxy}phenyl)propanoate | Oily matter, ¹H NMR: 1.23 (3H, t, J = 7.1 Hz), 2.57 (2H, t, J = 7.7 Hz), 2.87 (2H, t, J = 7.7 Hz), 4.12 (2H, q, J = 7.1 Hz), 5.09 (2H, s), 6.68 (1H, dt, J = 2.1, 10.2 Hz), 6.75-7.02 (6H, m), 7.11 (1H, s), 7.19-7.39 (3H, m). |
| 157 (R = H) | | 3-(3-fluoro-4-{[3-(3-fluorophenoxy)benzyl]oxy}phenyl)propanoic acid | White crystal, Melting point 61-62° C. (ethyl acetate-hexane), ¹H NMR: 2.64 (2H, t, J = 7.7 Hz), 2.89 (2H, t, J = 7.7 Hz), 5.08 (2H, s), 6.83-6.98 (4H, m), 7.02-7.22 (6H, m), 7.32 (1H, t, J = 7.8 Hz). |
| 158 (R = Et) | | ethyl 3-{4-[(3-ethoxy-2-methoxybenzyl)oxy]-3-fluorophenyl}propanoate | Oily matter, ¹H NMR: 1.23 (3H, t, J = 7.2 Hz), 1.47 (3H, t, J = 7.0 Hz), 2.57 (2H, t, J = 7.7 Hz), 2.87 (2H, t, J = 7.7 Hz), 3.89 (3H, s), 4.05-4.16 (4H, m), 5.15 (2H, s), 6.84-7.08 (6H, m). |
| 159 (R = H) | | 3-{4-[(3-ethoxy-2-methoxybenzyl)oxy]-3-fluorophenyl}propanoic acid | White crystal, Melting point 93-95° C. (ethyl acetate-hexane), ¹H NMR: 1.47 (3H, t, J = 7.1 Hz), 2.65 (2H, t, J = 7.6 Hz), |

TABLE 38-continued

| Example No. | Structural formula | Chemical name | Property data |
|---|---|---|---|
| | | | 2.89 (2H, t, J = 7.6 Hz), 3.89 (3H, s), 4.09 (2H, q, J = 7.1 Hz), 5.15 (2H, s), 6.86-7.08 (6H, m). |

TABLE 39

| Example No. | Structural formula | Chemical name | Property data |
|---|---|---|---|
| 160 (R = Et) | | ethyl 3-(3-fluoro-4-{[3-(4-fluorophenoxy)benzyl]oxy}phenyl)propanoate | Oily matter, $^1$H NMR: 1.23 (3H, t, J = 7.1 Hz), 2.57 (2H, t, J = 7.6 Hz), 2.87 (2H, t, J = 7.6 Hz), 4.12 (2H, q, J = 7.1 Hz), 5.07 (2H, s), 6.84-7.09 (9H, m), 7.15 (1H, d, J = 7.5 Hz), 7.32 (1H, t, J = 7.8 Hz). |
| 161 (R = H) | | 3-(3-fluoro-4-{[3-(4-fluorophenoxy)benzyl]oxy}phenyl)propanoic acid | White crystal, Melting point 108-108° C. (ethyl acetate-hexane), $^1$H NMR: 2.65 (2H, t, J = 7.6 Hz), 2.89 (2H, t, J = 7.6 Hz), 5.07 (2H, s), 6.82-7.08 (9H, m), 7.15 (1H, d, J = 7.4 Hz), 7.32 (1H, t, J = 7.8 Hz). |
| 162 (R = Et) | | ethyl 3-(3-fluoro-4-{[3-(4-chlorophenoxy)benzyl]oxy}phenyl)propanoate | Oily matter, $^1$H NMR: 1.23 (3H, t, J = 7.1 Hz), 2.57 (2H, t, J = 7.7 Hz), 2.88 (2H, t, J = 7.7 Hz), 4.12 (2H, q, J = 7.1 Hz), 5.08 (2H, s), 6.08-6.97 (6H, m), 7.07 (1H, s), 7.18 (1H, d, J = 7.7 Hz), 7.26-7.39 (3H, m). |
| 163 (R = H) | | 3-(3-fluoro-4-{[3-(4-chlorophenoxy)benzyl]oxy}phenyl)propanoic acid | White crystal, Melting point 119-119° C. (ethyl acetate-hexane), $^1$H NMR: 2.65 (2H, t, J = 7.6 Hz), 2.89 (2H, t, J = 7.6 Hz), 5.08 (2H, s), 6.82-6.98 (6H, m), 7.07 (1H, s), 7.18 (1H, d, J = 8.4 Hz), 7.26-7.40 (3H, m). |

TABLE 40

| Example No. | Structural formula | Chemical name | Property data |
|---|---|---|---|
| 164 (R = Et) | (structure) | ethyl 3-(3-fluoro-4-{[3-(4-methoxyphenoxy)benzyl]oxy}phenyl)propanoate | Oily matter, $^1$H NMR: 1.23 (3H, t, J = 7.1 Hz), 2.57 (2H, t, J = 7.7 Hz), 2.87 (2H, t, J = 7.7 Hz), 3.81 (3H, s), 4.12 (2H, q, J = 7.1 Hz), 5.06 (2H, s), 6.78-7.03 (9H, m), 7.11 (1H, d, J = 7.7 Hz), 7.26-7.32 (1H, m). |
| 165 (R = H) | | 3-(3-fluoro-4-{[3-(4-methoxyphenoxy)benzyl]oxy}phenyl)propanoic acid | White crystal, Melting paint 89-91° C. (ethyl acetate-hexane), $^1$H NMR: 2.65 (2H, t, J = 7.6 Hz), 2.89 (2H, t, J = 7.6 Hz), 3.81 (3H, s), 5.06 (2H, s), 6.78-7.03 (9H, m), 7.11 (1H, d, J = 7.6 Hz), 7.26-7.32 (1H, m). |
| 166 (R = Et) | (structure) | ethyl 3-(3-fluoro-4-{[3-(2-methylphenoxy)benzyl]oxy}phenyl)propanoate | Oily matter, $^1$H NMR: 1.23 (3H, t, J = 7.1 Hz), 2.22 (3H, s), 2.57 (2H, t, J = 7.7 Hz), 2.87 (2H, t, J = 7.7 Hz), 4.12 (2H, q, J = 7.1 Hz), 5.06 (2H, s), 6.74-7.00 (6H, m), 7.03-7.20 (3H, m), 7.24-7.35 (2H, m). |
| 167 (R = H) | | 3-(3-fluoro-4-{[3-(2-methylphenoxy)benzyl]oxy}phenyl)propanoic acid | White crystal, Melting point 53-54° C. (ethyl acetate-hexane), $^1$H NMR: 2.22 (3H, s), 2.65 (2H, t, J = 7.5 Hz), 2.89 (2H, t, J = 7.6 Hz), 5.06 (2H, s), 6.77-7.01 (6H, m), 7.02-7.22 (3H, m), 7.23-7.35 (2H, m). |

TABLE 41

| Example No. | Structural formula | Chemical name | Property data |
|---|---|---|---|
| 168 (R = Et) | (structure) | ethyl 3-(3-fluoro-4-{[3-(3-methylphenoxy)benzyl]oxy}phenyl)propanoate | Oily matter, $^1$H NMR: 1.23 (3H, t, J = 7.1 Hz), 2.33 (3H, s), 2.57 (2H, t, J = 7.7 Hz), 2.87 (2H, t, J = 7.7 Hz), 4.12 (2H, q, J = 7.1 Hz), 5.08 (2H, s), 6.75-7.01 (7H, m), 7.08 (1H, s), 7.11-7.26 (2H, m), 7.33 (1H, t, J = 7.9 Hz). |
| 169 (R = H) | | 3-(3-fluoro-4-{[3-(3-methylphenoxy)benzyl]oxy}phenyl)propanoic | White crystal, Melting point 65-67° C. (ethyl |

TABLE 41-continued

| Example No. | Structural formula | Chemical name | Property data |
|---|---|---|---|
| | | acid | acetate-hexane), $^1$H NMR: 2.33 (3H, s), 2.64 (2H, t, J = 7.6 Hz), 2.89 (2H, t, J = 7.6 Hz), 5.08 (2H, s), 6.75-7.00 (7H, m), 7.08 (1H, s), 7.12-7.25 (2H, m), 7.33 (1H, t, J = 7.9 Hz). |
| 170 (R = Et) | | ethyl 3-(3-fluoro-4-{[3-(4-methylphenoxy)benzyl]-oxy}phenyl)propanoate | Oily matter, $^1$H NMR: 1.23 (3H, t, J = 7.1 Hz), 2.34 (3H, s), 2.57 (2H, t, J = 7.7 Hz), 2.87 (2H, t, J = 7.7 Hz), 4.12 (2H, q, J = 7.1 Hz), 5.06 (2H, s), 6.79-6.98 (6H, m), 7.05 (1H, s), 7.14 (3H, d, J = 8.0 Hz), 7.31 (1H, t, J = 7.8 Hz). |
| 171 (R = H) | | 3-(3-fluoro-4-{[3-(4-methylphenoxy)benzyl]-oxy}phenyl)propanoic acid | White crystal, Melting point 102-103° C. (ethyl acetate-hexane), $^1$H NMR: 2.34 (3H, s), 2.64 (2H, t, J = 7.6 Hz), 2.89 (2H, t, J = 7.6 Hz), 5.07 (2H, s), 6.83-6.98 (6H, m), 7.05 (1H, d, J = 1.9 Hz), 7.14 (3H, d, J = 8.3 Hz), 7.31 (1H, t, J = 7.9 Hz). |

TABLE 42

| Example No. | Structural formula | Chemical name | Property data |
|---|---|---|---|
| 172 (R = Et) | | ethyl 3-(3-methyl-4-[(3-phenoxybenzyl)oxy]-phenyl)propanoate | Oily matter, $^1$H NMR: 1.23 (3H, t, J = 7.2 Hz), 2.21 (3H, s), 2.57 (2H, t, J = 7.8 Hz), 2.86 (2H, t, J = 7.8 Hz), 4.12 (2H, q, J = 7.2 Hz), 5.02 (2H, s), 6.76 (1H, d, J = 8.2 Hz), 6.92-7.17 (8H, m), 7.30-7.37 (3H, m). |
| 173 (R = H) | | 3-(3-methyl-4-[(3-phenoxybenzyl)oxy]-phenyl)propanoic acid | White crystal, Melting point 94-95° C. (ethyl acetate-hexane), $^1$H NMR: 2.22 (3H, s), 2.64 (2H, t, J = 7.7 Hz), 2.88 (2H, t, J = 7.7 Hz), 5.02 (2H, s), 6.77 (1H, d, J = 8.2 Hz), 6.93-7.20 (8H, m), 7.29-7.37 (3H, m). |

TABLE 42-continued

| Example No. | Structural formula | Chemical name | Property data |
|---|---|---|---|
| 174 | | ethyl 3-(4-{[3-(methoxymethoxy)benzyl]-oxy}-3-methylphenyl)propanoate | Oily matter, $^1$H NMR: 1.24 (3H, t, J = 7.1 Hz), 2.26 (3H, s), 2.55-2.61 (2H, m), 2.86 (2H, t, J = 7.5 Hz), 3.49 (3H, s), 4.13 (2H, q, J = 7.1 Hz), 5.03 (2H, s), 5.19 (2H, s), 6.78 (1H, d, J = 8.2 Hz), 6.94-7.00 (3H, m), 7.08 (1H, d, J = 7.6 Hz), 7.13 (1H, s), 7.26-7.32 (1H, m). |
| 175 (R = Et) | | ethyl 3-{4-[(3-hydroxybenzyl)oxy]-3-methylphenyl}propanoate | Oily matter, $^1$H NMR: 1.24 (3H, t, J = 7.1 Hz), 2.26 (3H, s), 2.58 (2H, t, J = 7.8 Hz), 2.86 (2H, t, J = 7.8 Hz), 4.13 (2H, q, J = 7.1 Hz), 4.84 (1H, s), 5.01 (2H, s), 6.75-6.80 (2H, m), 6.90-7.00 (4H, m), 7.21-7.27 (1H, m). |

TABLE 43

| Example No. | Structural formula | Chemical name | Property data |
|---|---|---|---|
| 176 (R = H) | | 3-{4-[(3-hydroxybenzyl)oxy]-3-methylphenyl}propanoic acid | White crystal, Melting paint 110-111° C. (ethyl acetate-hexane), $^1$H NMR: 2.26 (3H, s), 2.65 (2H, t, J = 7.7 Hz), 2.88 (2H, t, J = 7.7 Hz), 5.02 (2H, s), 6.76-6.79 (2H, m), 6.90-7.01 (4H, m), 7.22-7.28 (1H, m). |
| 177 (R = Et) | | ethyl 3-{4-[(3-isopropoxybenzyl)oxy]-3-methylphenyl}propanoate | Oily matter, $^1$H NMR: 1.24 (3H, t, J = 7.1 Hz), 1.34 (6H, d, J = 6.1 Hz), 2.26 (3H, s), 2.57 (2H, t, J = 7.8 Hz), 2.86 (2H, t, J = 7.8 Hz), 4.13 (2H, q, J = 7.1 Hz), 4.56 (1H, septet, J = 6.1 Hz), 5.01 (2H, s), 6.77-6.85 (2H, m), 6.94-7.00 (4H, m), 7.23-7.30 (1H, m). |
| 178 (R = H) | | 3-{4-[(3-isopropoxybenzyl)oxy]-3-methylphenyl}propanoic acid | White crystal, Melting point 78-79° C. (ethyl acetate-hexane), $^1$H NMR: 1.34 (6H, d, J = 6.1 Hz), 2.27 (3H, s), 2.65 (2H, t, J = 7.7 Hz), 2.88 (2H, t, J = 7.7 Hz), 4.56 (1H, septet, J = 6.1 Hz), 5.02 |

TABLE 43-continued

| Example No. | Structural formula | Chemical name | Property data |
|---|---|---|---|
| | | | (2H, s), 6.78-6.85 (2H, m), 6.96-7.01 (4H, m), 7.24-7.30 (1H, m). |

TABLE 44

| Example No. | Structural formula | Chemical name | Property data |
|---|---|---|---|
| 179 (R = Et) | | ethyl 3-{4-[(3-ethoxybenzyl)oxy]-3-methylphenyl}-propanoate | Oily matter, $^1$H NMR: 1.24 (3H, t, J = 7.1 Hz), 1.42 (3H, t, J = 7.1 Hz), 2.26 (3H, s), 2.58 (2H, t, J = 7.7 Hz), 2.86 (2H, t, J = 7.7 Hz), 4.05 (2H, q, J = 7.1 Hz), 4.13 (2H, q, J = 7.1 Hz), 5.02 (2H, s), 6.76-6.86 (2H, m), 6.94-7.00 (4H, m), 7.26-7.31 (1H, m). |
| 180 (R = H) | | 3-{4-[(3-ethoxybenzyl)oxy]-3-methylphenyl}propanoic acid | White crystal, Melting point 96-97° C. (ethyl acetate-hexane), $^1$H NMR: 1.42 (3H, t, J = 7.0 Hz), 2.27 (3H, s), 2.65 (2H, t, J = 7.7 Hz), 2.88 (2H, t, J = 7.7 Hz), 4.05 (2H, q, J = 7.0 Hz), 5.03 (2H, s), 6.77-6.86 (2H, m), 6.95-7.01 (4H, m), 7.25-7.31 (1H, m). |
| 181 (R = Et) | | ethyl 3-(4-{[3-(cyclohexyloxy)-benzyl]oxy}-3-methylphenyl)-propanoate | Oily matter, $^1$H NMR: 1.24 (3H, t, J = 7.1 Hz), 1.28-1.68 (6H, m), 1.70-1.88 (2H, m), 1.92-2.08 (2H, m), 2.26 (3H, s), 2.57 (2H, t, J = 7.8 Hz), 2.86 (2H, t, J = 7.8 Hz), 4.13 (2H, q, J = 7.1 Hz), 4.21-4.26 (1H, m), 5.01 (2H, s), 6.76-6.86 (2H, m), 6.94-7.00 (4H, m), 7.23-7.29 (1H, m). |

TABLE 45

| Example No. | Structural formula | Chemical name | Property data |
|---|---|---|---|
| 182 (R = H) | | 3-(4-{[3-(cyclohexyloxy)benzyl]oxy}-3-methylphenyl)propanoic acid | White crystal, Melting point 99-100° C. (ethyl acetate-hexane), $^1$H NMR: 1.23-1.65 (6H, m), 1.72-1.88 (2H, m), 1.94-2.07 (2H, m), 2.27 (3H, s), 2.65 (2H, t, J = 7.7 Hz), 2.88 (2H, t, J = 7.7 Hz), 4.20-4.30 (1H, m), 5.02 (2H, s), 6.77-6.88 (2H, m), 6.95-7.01 (4H, m), 7.23-7.29 (1H, m). |
| 183 (R = Et) | | ethyl 3-{4-[(3-butoxybenzyl)oxy]-3-methylphenyl}-propanoate | Oily matter, $^1$H NMR: 0.98 (3H, t, J = 7.3 Hz), 1.24 (3H, t, J = 7.1 Hz), 1.45-1.55 (2H, m), 1.72-1.82 (2H, m), 2.26 (3H, s), 2.57 (2H, t, J = 7.8 Hz), 2.86 (2H, t, J = 7.8 Hz), 3.97 (2H, t, J = 6.5 Hz), 4.13 (2H, q, J = 7.1 Hz), 5.02 (2H, s), 6.76-6.86 (2H, m), 6.94-7.00 (4H, m), 7.24-7.30 (1H, m). |
| 184 (R = H) | | 3-{4-[(3-butoxybenzyl)oxy]-3-methylphenyl}propanoic acid | White crystal, Melting point 75-76° C. (ethyl acetate-hexane), $^1$H NMR: 0.98 (3H, t, J = 7.4 Hz), 1.43-1.63 (2H, m), 1.72-1.82 (2H, m), 2.27 (3H, s), 2.65 (2H, t, J = 7.7 Hz), 2.88 (2H, t, J = 7.7 Hz), 3.97 (2H, t, J = 6.5 Hz), 5.02 (2H, s), 6.78-6.86 (2H, m), 6.96-7.01 (4H, m), 7.25-7.31 (1H, m). |

TABLE 46

| Example No. | Structural formula | Chemical name | Property data |
|---|---|---|---|
| 185 (R = Et) | | ethyl 3-(3-methyl-4-{[3-(2-morpholin-4-ylethoxy)benzyl]oxy}-phenyl)propanoate | Oily matter, $^1$H NMR: 1.24 (3H, t, J = 7.1 Hz), 2.26 (3H, s), 2.54-2.60 (6H, m), 2.78-2.89 (4H, m), 3.72-3.76 (4H, m), 4.08-4.17 (4H, m), 5.02 (2H, s), 6.77 (1H, d, J = 8.2 Hz), 6.83-6.87 (1H, m), 6.93-7.03 (4H, m), 7.28-7.31 (1H, m). |

TABLE 46-continued

| Example No. | Structural formula | Chemical name | Property data |
|---|---|---|---|
| 186 (R = H) | | 3-(3-methyl-4-{[3-(2-morpholin-4-ylethoxy)benzyl]oxy}-phenyl)propanoic acid | White crystal, Melting point 98-99° C. (ethyl acetate-hexane), $^1$H NMR: 2.05 (3H, s), 2.61-2.70 (6H, m), 2.79-2.88 (4H, m), 3.72-3.76 (6H, m), 5.12 (2H, s), 6.37 (1H, brs), 6.73-6.79 (2H, m), 6.96-7.00 (3H, m), 7.20-7.26 (1H, m). |
| 187 (R = Et) | | ethyl 3-{4-[(3-ethoxybenzyl)oxy]-3-fluorophenyl}-propanoate | Oily matter, $^1$H NMR: 1.23 (3H, t, J = 7.1 Hz), 1.41 (3H, t, J = 6.9 Hz), 2.57 (2H, t, J = 7.6 Hz), 2.87 (2H, t, J = 7.6 Hz), 4.04 (2H, q, J = 6.9 Hz), 4.12 (2H, q, J = 7.1 Hz), 5.08 (2H, s), 6.82-7.00 (6H, m), 7.24-7.30 (1H, m). |
| 188 (R = H) | | 3-{4-[(3-ethoxybenzyl)oxy]-3-fluorophenyl}propanoic acid | White crystal, Melting point 100-101° C. (ethyl acetate-hexane), $^1$H NMR: 1.41 (3H, t, J = 7.0 Hz), 2.64 (2H, t, J = 7.6 Hz), 2.88 (2H, t, J = 7.6 Hz), 4.04 (2H, q, J = 7.0 Hz), 5.09 (2H, s), 6.83-7.00 (6H, m), 7.24-7.30 (1H, m). |

TABLE 47

| Example No. | Structural formula | Chemical name | Property data |
|---|---|---|---|
| 189 (R = Et) | | ethyl 3-{3-fluoro-4-[(3-isopropoxy-benzyl)oxy]-phenyl}propanoate | Oily matter, $^1$H NMR: 1.23 (3H, t, J = 7.1 Hz), 1.33 (6H, d, J = 6.1 Hz), 2.57 (2H, t, J = 7.7 Hz), 2.87 (2H, t, J = 7.7 Hz), 4.12 (2H, q, J = 7.1 Hz), 4.56 (1H, septet, J = 6.1 Hz), 5.07 (2H, s), 6.80-6.98 (6H, m), 7.23-7.29 (1H, m). |
| 190 (R = H) | | 3-{3-fluoro-4-[(3-isopropoxybenzyl)oxy]-phenyl}propanoic acid | White crystal, Melting point 59-60° C. (ethyl acetate-hexane), $^1$H NMR: 1.33 (6H, d, J = 6.0 Hz), 2.64 (2H, t, J = 7.6 Hz), 2.89 (2H, t, J = 7.6 Hz), 4.56 (1H, septet, J = 6.0 Hz), 5.08 (2H, s), 6.82-6.98 (6H, m), 7.24-7.29 (1H, m). |

TABLE 47-continued

| Example No. | Structural formula | Chemical name | Property data |
|---|---|---|---|
| 191 (R = Et) | (morpholine-N-CH2CH2-O-phenyl-O-CH2-phenyl(F)-CH2CH2-C(O)OR) | ethyl 3-(3-fluoro-4-{[3-(2-morpholin-4-ylethoxy)benzyl]oxy}-phenyl)propanoate | Oily matter, ¹H NMR: 1.23 (3H, t, J = 7.2 Hz), 2.54-2.60 (6H, m), 2.80 (2H, t, J = 5.7 Hz), 2.87 (2H, t, J = 7.8 Hz), 3.72-3.76 (4H, m), 4.08-4.16 (4H, m), 5.08 (2H, s), 6.82-7.02 (6H, m), 7.25-7.31 (1H, m). |
| 192 (R = H) | | 3-(3-fluoro-4-{[3-(2-morpholin-4-ylethoxy)benzyl]oxy}-phenyl)propanoic acid | White crystal, Melting point 101-102° C. (ethyl acetate-hexane), ¹H NMR: 2.61-2.79 (6H, m), 2.80-2.89 (4H, m), 3.69-3.77 (6H, m), 5.12 (2H, s), 6.25 (1H, s), 6.66 (1H, t, J = 8.4 Hz), 6.77-6.86 (2H, m), 6.95-7.03 (2H, m), 7.23-7.29 (1H, m). |

TABLE 48

| Example No. | Structural formula | Chemical name | Property data |
|---|---|---|---|
| 193 (R = Et) | (H3C-CH2CH2CH2-O-phenyl-CH2-O-phenyl(F)-CH2CH2-C(O)OR) | ethyl 3-{4-[(3-butoxybenzyl)oxy]-3-fluorophenyl}-propanoate | Oily matter, ¹H NMR: 0.97 (3H, t, J = 7.4 Hz), 1.23 (3H, t, J = 7.1 Hz), 1.40-1.56 (2H, m), 1.71-1.83 (2H, m), 2.57 (2H, t, J = 7.7 Hz), 2.87 (2H, t, J = 7.7 Hz), 3.97 (2H, t, J = 6.5 Hz), 4.12 (2H, q, J = 7.1 Hz), 5.08 (2H, s), 6.82-6.99 (6H, m), 7.23-7.30 (1H, m). |
| 194 (R = H) | | 3-{4-[(3-butoxybenzyl)oxy]-3-fluorophenyl}propanoic acid | White crystal, Melting point 76-77° C. (ethyl acetate-hexane), ¹H NMR: 0.97 (3H, t, J = 7.4 Hz), 1.42-1.56 (2H, m), 1.71-1.81 (2H, m), 2.61-2.67 (2H, m), 2.89 (2H, t, J = 7.6 Hz), 3.97 (2H, t, J = 6.5 Hz), 5.08 (2H, s), 6.83-6.99 (6H, m), 7.24-7.30 (1H, m). |

TABLE 48-continued

| Example No. | Structural formula | Chemical name | Property data |
|---|---|---|---|
| 195 (R = Et) | | ethyl 3-(3-fluoro-4-{[3-(2-methoxyethoxy)benzyl]oxy}phenyl)propanoate | Oily matter, $^1$H NMR: 1.23 (3H, t, J = 7.1 Hz), 2.57 (2H, t, 7.7 Hz), 2.87 (2H, t, J = 7.7 Hz), 3.45 (3H, s), 3.73-3.77 (2H, m), 4.08-4.16 (4H, m), 5.08 (2H, s), 6.78-7.02 (6H, m), 7.24-7.30 (1H, m). |
| 196 (R = H) | | 3-(3-fluoro-4-{[3-(2-methoxyethoxy)benzyl]oxy}phenyl)propanoic acid | White crystal, Melting point 62-63° C. (ethyl acetate-hexane), $^1$H NMR: 2.64 (2H, t, 7.5 Hz), 2.88 (2H, t, J = 7.5 Hz), 3.45 (3H, s), 3.73-3.77 (2H, m), 4.08-4.12 (2H, m), 5.09 (2H, s), 6.84-7.02 (6H, m), 7.24-7.30 (1H, m). |

TABLE 49

| Example No. | Structural formula | Chemical name | Property data |
|---|---|---|---|
| 197 (R = Et) | | ethyl 3-(4-{[3-(cyclohexyloxy)benzyl]oxy}-3-fluorophenyl)propanoate | Oily matter, $^1$H NMR: 1.23 (3H, t, J = 7.1 Hz), 1.30-1.66 (6H, m), 1.70-1.87 (2H, m), 1.91-2.04 (2H, m), 2.57 (2H, t, J = 7.7 Hz), 2.87 (2H, t, J = 7.7 Hz), 4.12 (2H, q, J = 7.1 Hz), 4.20-4.30 (1H, m), 5.07 (2H, s), 6.82-6.98 (6H, m), 7.22-7.28 (1H, m). |
| 198 (R = H) | | 3-(4-{[3-(cyclohexyloxy)benzyl]oxy}-3-fluorophenyl)propanoic acid | White crystal, Melting point 86-87° C. (ethyl acetate-hexane), $^1$H NMR: 1.23-1.71 (6H, m), 1.73-1.87 (2H, m), 2.91-2.04 (2H, m), 2.64 (2H, t, J = 7.5 Hz), 2.89 (2H, t, J = 7.5 Hz), 4.19-4.30 (1H, m), 5.08 (2H, s), 6.83-6.98 (6H, m), 7.22-7.35 (1H, m). |
| 199 (R = Et) | | ethyl 3-(3-fluoro-4-{[3-(prop-2-yn-1-yloxy)benzyl]oxy}phenyl)propanoate | Oily matter, $^1$H NMR: 1.23 (3H, t, J = 7.2 Hz), 2.51 (1H, t, J = 2.1 Hz), 2.57 (2H, t, J = 7.7 Hz), 2.87 (2H, t, J = 7.7 Hz), 4.12 (2H, q, J = 7.2 Hz), 4.70 (2H, d, J = 2.1 Hz), 5.10 (2H, s), 6.82-6.97 (4H, m), 7.03-7.07 (2H, m), 7.26-7.33 (1H, m). |

TABLE 49-continued

| Example No. | Structural formula | Chemical name | Property data |
|---|---|---|---|
| 200 (R = H) | | 3-(3-fluoro-4-{[3-(prop-2-yn-1-yloxy)benzyl]oxy}-phenyl)propanoic acid | White crystal, Melting point 116-117° C. (ethyl acetate-hexane), $^1$H NMR: 2.51 (1H, t, J = 2.4 Hz), 2.64 (2H, t, J = 7.7 Hz), 2.88 (2H, t, J = 7.7 Hz), 4.70 (2H, d, J = 2.4 Hz), 5.10 (2H, s), 6.83-6.98 (4H, m), 7.03-7.07 (2H, m), 7.26-7.34 (1H, m). |

TABLE 50

| Example No. | Structural formula | Chemical name | Property data |
|---|---|---|---|
| 201 (R = Et) | | ethyl 3-(4-{[3-(4-fluorophenoxy)benzyl]-oxy}-3-methylphenyl)propanoate | Oily matter, $^1$H NMR: 1.26 (3H, t, J = 7.2 Hz), 2.21 (3H, s), 2.57 (2H, t, J = 7.5 Hz), 2.86 (2H, t, J = 7.5 Hz), 4.12 (2H, q, J = 7.1 Hz), 5.01 (2H, s), 6.75 (1H, d, J = 8.1 Hz), 6.86-7.10 (8H, m), 7.14 (1H, d, J = 7.5 Hz), 7.27-7.36 (1H, m). |
| 202 (R = H) | | 3-(4-{[3-(4-fluorophenoxy)benzyl]-oxy}-3-methylphenyl)propanoic acid | White crystal, Melting point 112-113° C. (ethyl acetate-hexane), $^1$H NMR: 2.21 (3H, s), 2.64 (2H, t, J = 7.8 Hz), 2.88 (2H, t, J = 7.8 Hz), 5.02 (2H, s), 6.76 (1H, d, J = 8.1 Hz), 6.87-7.09 (8H, m), 7.14 (1H, d, 7.5 Hz), 7.29-7.36 (1H, m). |
| 203 (R = Et) | | ethyl 3-[4-(2,3-dihydro-1H-inden-1-yloxy)-3-fluorophenyl]propanoate | Oily matter, $^1$H NMR: 1.24 (3H, t, J = 7.2), 2.21-2.32 (1H, m), 2.44-2.62 (3H, m), 2.85-2.95 (3H, m), 3.12-3.22 (1H, m), 4.13 (2H, q, J = 7.2), 5.72 (1H, dd, J = 4.2, 6.6), 6.88-7.03 (3H, m), 7.19-7.31 (3H, m), 7.40 (1H, d, J = 7.2) |
| 204 (R = H) | | 3-[4-(2,3-dihydro-1H-inden-1-yloxy)-3-fluorophenyl]propanoic acid | Colorless crystal, Melting point 91-92° C. (ethyl acetate-hexane), $^1$H NMR: 2.22-2.32 (1H, m), 2.45-2.56 (1H, m), 2.67 (2H, t, J = 7.2), 2.85-2.94 (3H, m), 3.12-3.22 (1H, m), 5.71 (1H, dd, J = 4.2, 6.6), 6.89- |

TABLE 50-continued

| Example No. | Structural formula | Chemical name | Property data |
|---|---|---|---|
| | | | 7.04 (3H, m), 7.19-7.31 (3H, m), 7.39 (1H, d, J = 7.2) |

TABLE 51

| Example No. | Structural formula | Chemical name | Property data |
|---|---|---|---|
| 205 (R = Et) | | ethyl 3-{4-[(2,2-dimethyl-2,3-dihydro-1H-inden-1-yl)oxy]-3-fluorophenyl}propanoate | Oily matter, $^1$H NMR: 1.18-1.27 (9H, m), 2.57-2.73 (3H, m), 2.87-2.95 (3H, m), 4.13 (2H, q, J = 7.2), 5.18 (1H, s), 6.86-7.03 (3H, m), 7.12-7.25 (4H, m) |
| 206 (R = H) | | 3-{4-[(2,2-dimethyl-2,3-dihydro-1H-inden-1-yl)oxy]-3-fluorophenyl}propanoic acid | Oily matter, $^1$H NMR: 1.19 (3H, s), 1.22 (3H, s), 2.65-2.73 (3H, m), 2.89-2.95 (3H, m), 5.18 (1H, s), 6.88-7.05 (3H, m), 7.14-7.26 (4H, m) |

TABLE 52

| Example No. | Structural formula | Chemical name | Property data |
|---|---|---|---|
| 207 (R = Et) | | ethyl 3-{4-[(3-ethoxy-2-methylbenzyl)oxy]-3-fluorophenyl}propanoate | Oily matter, $^1$H NMR: 1.23 (3H, t, J = 7.2 Hz), 1.43 (3H, t, J = 7.0 Hz), 2.25 (3H, s), 2.58 (2H, t, J = 7.7 Hz), 2.88 (2H, t, J = 7.7 Hz), 4.04 (2H, q, J = 7.0 Hz), 4.13 (2H, q, J = 7.2 Hz), 5.08 (2H, s), 6.82-7.04 (5H, m), 7.14 (1H, d, J = 7.9 Hz). |
| 208 (R = H) | | 3-{4-[(3-ethoxy-2-methylbenzyl)oxy]-3-fluorophenyl}propanoic acid | White crystal, Melting point 118-119° C. (ethyl acetate-hexane), $^1$H NMR: 1.43 (3H, t, J = 7.0 Hz), 2.25 (3H, s), 2.65 (2H, t, J = 7.6 Hz), 2.89 (2H, t, J = 7.6 Hz), 4.04 (2H, q, J = 7.0 Hz), 5.08 (2H, s), 6.82-7.04 (5H, m), 7.14 (1H, d, J = 7.9 Hz). |

TABLE 52-continued

| Example No. | Structural formula | Chemical name | Property data |
|---|---|---|---|
| 209 (R = Et) | | ethyl 3-{4-[(3-ethoxy-4-methylbenzyl)oxy]-3-fluorophenyl}propanoate | Oily matter, $^1$H NMR: 1.23 (3H, t, J = 7.1 Hz), 1.41 (3H, t, J = 7.0 Hz), 2.21 (3H, s), 2.57 (2H, t, J = 7.7 Hz), 2.87 (2H, t, J = 7.7 Hz), 4.04 (2H, q, J = 7.0 Hz), 4.12 (2H, q, J = 7.1 Hz), 5.06 (2H, s), 6.81-7.10 (5H, m), 7.11 (1H, d, J = 7.4 Hz). |
| 210 (R = H) | | 3-{4-[(3-ethoxy-4-methylbenzyl)oxy]-3-fluorophenyl}propanoic acid | White crystal, Melting point 106-107° C. (ethyl acetate-hexane), $^1$H NMR: 1.41 (3H, t, J = 7.1 Hz), 2.21 (3H, s), 2.64 (2H, t, J = 7.6 Hz), 2.88 (2H, t, J = 7.6 Hz), 4.04 (2H, q, J = 7.1 Hz), 5.06 (2H, s), 6.83-6.97 (5H, m), 7.11 (1H, d, J = 7.4 Hz). |

Preparation Example 1

| | | |
|---|---|---|
| (1) Compound of Example 1 | 10.0 g |
| (2) Lactose | 60.0 g |
| (3) Corn starch | 35.0 g |
| (4) Gelatin | 3.0 g |
| (5) Magnesium stearate | 2.0 g |

A mixture of 10.0 g of the compound obtained in Example 1, 60.0 g of lactose and 35.0 g of corn starch was granulated through a 1 mm-mesh sieve using 30 mL of a 10% by weight aqueous solution of gelatin (3.0 g as gelatin), and then dried at 40° C. and sieved. The obtained granules were mixed with 2.0 g of magnesium stearate and compressed. The obtained core tablets were sugar-coated with an aqueous suspension of sucrose, titanium dioxide, talc and gum Arabic. The thus-coated tablets were glazed with bees wax to obtain 1000 coated tablets.

Preparation Example 2

| | | |
|---|---|---|
| (1) Compound of Example 1 | 10.0 g |
| (2) Lactose | 70.0 g |
| (3) Corn starch | 50.0 g |
| (4) Soluble starch | 7.0 g |
| (5) Magnesium stearate | 3.0 g |

10.0 g of the compound obtained in Example 1 and 3.0 g of magnesium stearate were granulated with 70 mL (7.0 g as soluble starch) of an aqueous soluble starch solution, dried, and mixed with 70.0 g of lactose and 50.0 g of corn starch. The mixture was compressed to obtain 1000 tablets.

Test Example 1

Regulating Effect for 14273 Receptor Function (Agonist Effect)

CHO cell lines (No. 104) in which a human 14273 receptor has expressed was diluted to contain $3 \times 10^4/100$ μl cells, and dispensed in Black walled 96-well plate (Costar) at a density of 100 μl/well, followed by culturing overnight in a $CO_2$ incubator. A change in intracellular calcium level was measured using FLIPR (Molecular Device). The method is described as below. 50 μg of Fluo-3AM (DOJIN) was dissolved in 21 μl of DMSO (DOJIN) and an equal volume of 20% pluronic acid (Molecular Probes) was added thereto, followed by mixing them. The mixture was added to 10.6 ml of the assay buffer [which is prepared by adding 10 ml of a solution, which is prepared by adding 20 ml of 1 M HEPES (pH 7.4, DOJIN) to 1 L of HBSS (Invitrogen), dissolving 710 mg of probenecid (Sigma) in 5 ml of 1 N NaOH, and further adding 5 ml of the above-mentioned HBSS/HEPES solution and mixing it.] supplemented with 105 μl of fetal bovine serum to prepare a fluorescent dye solution. The medium of the cell plate was removed, the fluorescent dye solution was dispensed in 100 μl each per well. The culturing was performed in a $CO_2$ incubator for 1 hour to incorporate the fluorescent dye into the cells. The cells after culturing were washed with the assay buffer. The compounds to be added to the cells were diluted to each concentration with a buffer solution to which CHAPS (DOJIN) was added in 0.015%, and dispensed in a plate for the test sample. Following the pretreatment above, a change in intracellular calcium level after addition of the compound was determined with FLIPR to investigate the agonist effect. An $EC_{50}$ value was calculated from dose-reaction curve using the change of fluorescent intensity after 35 seconds from the reaction initiation.

The compounds obtained in Reference Examples 8, 14, 16, 18, 20, 25, 28, 30, 44, 47 and 50, and Examples 2, 4, 6, 8, 10, 12, 16, 18, 20, 22, 24, 28, 32, 34, 36, 42, 44, 46, 48, 52, 54, 56, 58, 60, 62, 64, 68, 94, 96, 102, 118, 124, 135, 161, 163, 169, 171, 173, 178, 180, 188 and 208 showed $EC_{50}$ value of 10 μM or less in this experimental system.

Test Example 2

Suppressing Effect of Lipolysis by Fatty Acids in 3T3-L1 Adipocytes

Figure 14:
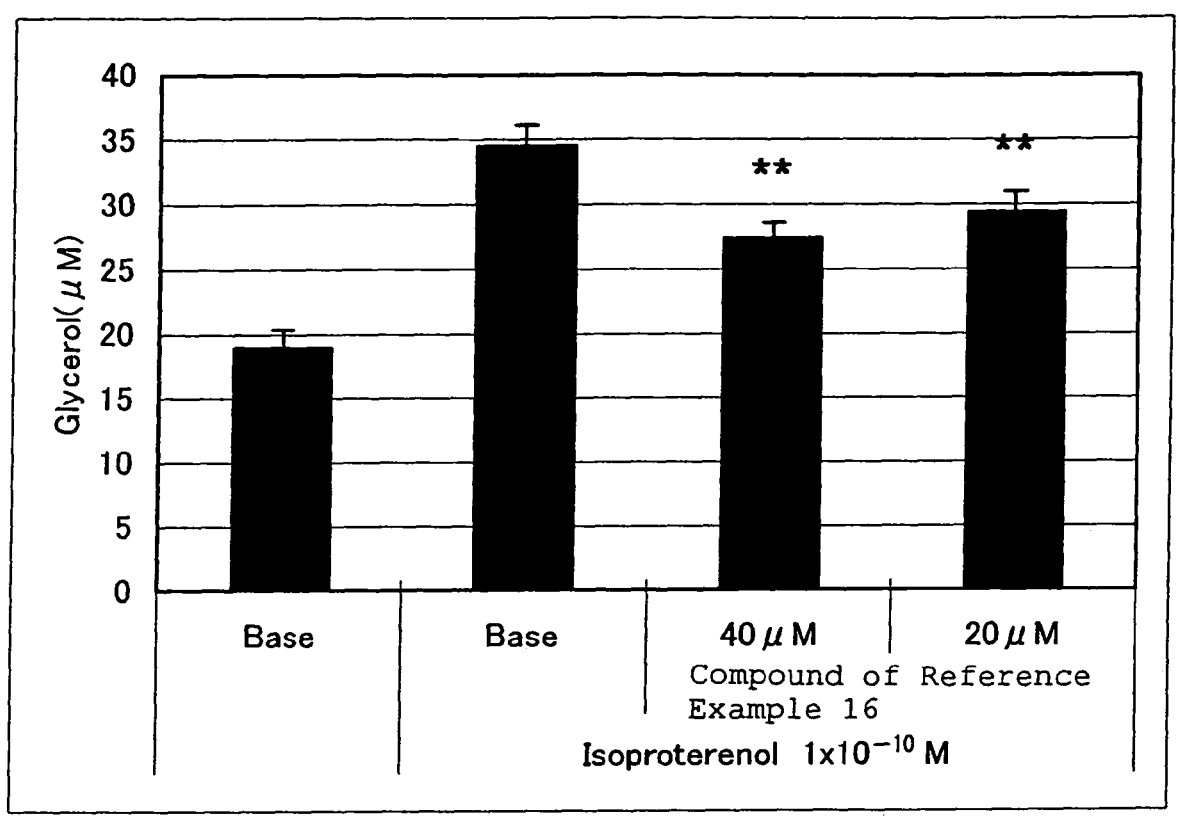
FIG. 14 shows the inhibitory effect of the compound obtained in Reference Example 16 on the lipolysis in differentiated 3T3-L1 adipocytes. The term Glyerol (μM) on the ordinate indicates the amount of glycerol production (μM). The term Base on the far left side of the abscissa indicates no addition. The $2^{nd}$ to $4^{th}$ terms from the left on the abscissa indicate the addition of $1 \times 10^{-10}$ M of isoproterenol. The second term Base from the left indicates the addition of $1 \times 10^{-10}$ M of isoproterenol only. The terms 40 μM and 20 μM on the abscissa indicate the respective added concentrations of the compound obtained in Reference Example 16. Symbol ** indicates significant inhibition compared to the base with isoproterenol (p<0.01).

Influence on lipolysis was investigated with use of mouse fibroblast-like cell line 3T3-L1 cells that can differentiate to adipocyte. As a medium, there was used a Dulbecco's Modified Eagle Medium (DMEM, Invitrogen) containing 4.5 g/l of glucose and being supplemented with 10% fetal bovine serum (FBS, Invitrogen), 100 units/ml of penicillin and 100 μg/ml of streptomycin. The 3T3-L cells were plated on a plate and cultured to become confluent. The cells were then treated for 48 hours in the medium containing 10 μg/ml of insulin, 0.5 mM of 3-isobutyl-1-methylxanthine (IBMX) and 2.5 μM of dexamethasone to induce differentiation into adipocytes. The culturing was continued for further 11 days. After the 3T3-L1 cells were differentiated into adipocytes, a change in the amount of glycerol produced after lipolysis was assayed. After the cells were washed with modified Krebs-Ringer buffer, they were treated with the compounds for 45 minutes, and the supernatant was then recovered. The glycerol content in the supernatant was determined using a Free Glycerol Determination Kit (Sigma). As a result, it was noted that addition of the compound obtained in Reference example 16, which is a compound having an agonist activity on the 14273 receptor, resulted in lowering the amount of the glycerol production increased by the isoproterenol stimulation (FIG. 14). From this, it was found that the compound of the invention, which has an agonist effect on the 14273 receptor, has lipolysis suppressing effect.

Test Example 3

Action for Suppressing Adrenocorticotropic Hormone (ACTH) Secretion in AtT-20 Cells Influence on ACTH secretion from mouse pituitary corticotrophic cell line AtT-20 cells was analyzed. The adherent substrain used in Reference Example A10 as cells was cultured in a medium composed of Dulbecco's Modified Eagle Medium (DMEM, Invitrogen) containing 4.5 g/l of glucose and supplemented with 10% fetal bovine serum (ThermoTrace), 100 U/ml of penicillin and 100 μg/ml of streptomycin. This adherent AtT-20 cell substrain was cultured on a poly-D-lysine-coated 48-well plate at a density of $1 \times 10^5$ cells/well for 2 nights, which was provided for assay. As a buffer for the assay, a Dulbecco's Modified Eagle Medium (DMEM, Invitrogen) containing 20 mM of HEPES (pH 7.4), 0.1% BSA and 1 g/l of glucose, was used. After washing the cells once with this buffer, a predetermined concentration of the compound was added thereto, followed by addition of a buffer containing 100 nM of a corticotropin-releasing factor (CRF), and followed by culturing at 37° C. for 90 minutes in a $CO_2$ incubator. Then, the plate was gently stirred, then centrifuged at 1200 rpm for 5 minutes at room temperature and the buffer was recovered from the intermediate layer. The ACTH concentration was determined using an ACTH assay kit (Mitsubishi Medical, ACTH IRMA "Yuka").

As results, the amount of ACTH secretion which had increased by CRF stimulation was lowered by 49% by addition of 10 μM of the compound obtained in Example 161, which has an agonist activity on the 14273 receptor.

INDUSTRIAL APPLICABILITY

The compound of the invention or the prodrug thereof has excellent regulating effect for the 14273 receptor function, and can be used as a preventing and/or treating agent for diabetes mellitus, hyperlipidemia, overweight, anorexia, etc., or a stress regulating agent.

Further, by using the compound of the invention or the prodrug thereof as a surrogate ligand, it is possible to screen the 14273 receptor agonist or the 14273 receptor antagonist in good efficiency.

In the above, some of embodiments of the invention have been illustrated in detail, but it will be apparent to those skilled in the art that various modifications and variations can be made to the embodiments shown specifically without departing from the teachings and advantages of the invention. Thus, it is intended that such modifications and variations are all covered in the spirit or scope of the invention, which is claimed in the following claims.

This application is based on a Japanese patent application No. 2003-394848 filed on Nov. 26, 2003, the contents of which are hereby incorporated by reference.

The invention claimed is:
1. A compound represented by the formula:

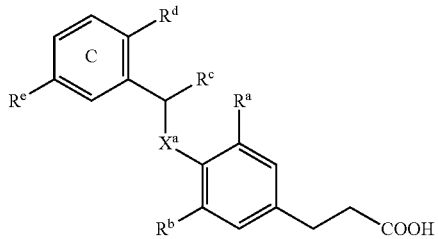

(II)

wherein $R^a$ is a fluorine atom, or a $C_{1-6}$ alkoxy group
$R^b$ is a hydrogen atom, or a fluorine atom;
$R^c$ is a hydrogen atom, or a $C_{1-6}$ alkyl group;
$X^a$ is an oxygen atom;
ring C is a benzene ring optionally having, in addition to $R^d$ and $R^e$, further substituent(s) selected from the group consisting of (i) a $C_{1-6}$ alkyl group, (ii) a hydroxy group, (iii) a $C_{1-6}$ alkoxy group having substituent(s) selected from the group consisting of hydroxy, amino, $C_{1-6}$ alkoxy-carbonyl-amino, carboxy, $C_{1-6}$ alkoxy-carbonyl, carbamoyl, mono-$C_{1-6}$ alkyl-carbamoyl, di-$C_{1-6}$ alkyl-carbamoyl, and tri-$C_{1-6}$ alkylsilyloxy, (iv) a $C_{6-14}$ aryloxy group, and (v) a $C_{7-16}$ aralkyloxy group; and
one of $R^d$ and $R^e$ is a hydrogen atom,
(1) when $R^d$ is a hydrogen atom,
then $R^e$ should be (i) a hydroxy group, (ii) a $C_{1-6}$ alkoxy group having substituent(s) selected from the group consisting of $C_{1-6}$ alkoxy, carboxy, $C_{1-6}$ alkoxy-carbonyl, $C_{1-6}$ alkyl-carbonyl, carbamoyl, mono-$C_{1-6}$ alkyl-carbamoyl, and di-$C_{1-6}$ alkyl-carbamoyl, (iii) a $C_{2-6}$ alkynyloxy group, (iv) a $C_{3-7}$ cycloalkyloxy group, (v) a $C_{6-14}$ aryloxy group optionally having substituent(s) selected from the group consisting of a halogen atom, $C_{1-6}$ alkyl, $C_{1-6}$ alkoxy, and $C_{1-6}$ alkyl-carbonyl, or (vi) a 5- to 10-membered heterocyclyl-oxy group containing, in addition to carbon atom(s), 1 to 4 heteroatoms of one or two kinds selected from a nitrogen atom, a sulfur atom and an oxygen atom;
(2) when $R^e$ is a hydrogen atom,
then $R^d$ should be, (i) a $C_{6-14}$ aryl group, (ii) a $C_{3-7}$ cycloalkyloxy group, (iii) a $C_{6-14}$ aryloxy group optionally having substituent(s) selected from the group consisting of a halogen atom and optionally halogenated $C_{1-6}$ alkyl, (iv) a $C_{7-16}$ aralkyloxy group, or (v) a 5- to 7-membered heterocyclic group containing, in addition to carbon atom(s), 1 to 4 heteroatoms of one or two kinds selected from a nitrogen atom, a sulfur atom, and an oxygen atom,
or a salt thereof.

2. The compound according to claim 1, wherein $R^c$ is a hydrogen atom; $R^d$ is a hydrogen atom; and $R^e$ is a $C_{6-14}$ aryloxy group optionally having substituent(s) selected from the group consisting of a halogen atom, $C_{1-6}$ alkyl, $C_{1-6}$ alkoxy and $C_{1-6}$ alkyl-carbonyl.

3. 3,5-Difluoro-4-[(3-phenoxyphenyl)methoxy]benzenepropanoic acid, or 3-fluoro-4-[(3-phenoxyphenyl)methoxy]benzenepropanoic acid, or a salt thereof.

4. 3-(4-{[3-(4-Chlorophenoxy)benzyl]oxy}-3,5-difluorophenyl)propanoic acid, 3-(3,5-difluoro-4-{[3-(4-fluorophenoxy)benzyl]oxy}phenyl)propanoic acid, 3-(3,5-difluoro-4-{[3-(4-methylphenoxy)benzyl]oxy}phenyl) propanoic acid, 3-(3-fluoro-4-{[3-(2-fluorophenoxy)benzyl]oxy}phenyl)propanoic acid, 3-(3-fluoro-4-{[3(3-fluorophenoxy)benzyl]-oxy}phenyl)propanoic acid, 3-(3-fluoro-4-{[3-(4-fluorophenoxy)benzyl]oxy}phenyl) propanoic acid, 3-(3-fluoro-4-{[3-(4-chlorophenoxy)benzyl]oxy}phenyl)propanoic acid, 3-(3-fluoro-4-{[3-(4-methylphenoxy)benzyl]oxy}phenyl)propanoic acid, 3-{3-methyl-4-[(3-phenoxybenzyl)oxy]phenyl}propanoic acid, or 3-(4-{[3-(4-fluorophenoxy)benzyl]oxy}-3-methylphenyl) propanoic acid, or a salt thereof.

5. A pharmaceutical agent comprising the compound according to claim 1, or a salt thereof.

* * * * *

SEQUENCE LISTING

```
<160> NUMBER OF SEQ ID NOS: 20

<210> SEQ ID NO 1
<211> LENGTH: 361
<212> TYPE: PRT
<213> ORGANISM: Human

<400> SEQUENCE: 1

Met Ser Pro Glu Cys Ala Arg Ala Ala Gly Asp Ala Pro Leu Arg Ser
                 5                  10                  15

Leu Glu Gln Ala Asn Arg Thr Arg Phe Pro Phe Phe Ser Asp Val Lys
            20                  25                  30

Gly Asp His Arg Leu Val Leu Ala Ala Val Glu Thr Thr Val Leu Val
        35                  40                  45

Leu Ile Phe Ala Val Ser Leu Leu Gly Asn Val Cys Ala Leu Val Leu
    50                  55                  60
```

| | | | | | | | | | | | |
|---|---|---|---|---|---|---|---|---|---|---|---|
| Val | Ala | Arg | Arg | Arg | Arg | Gly | Ala | Thr | Ala | Cys | Leu Val Leu Asn |
| 65 | | | | 70 | | | | 75 | | | 80 |

Val Ala Arg Arg Arg Arg Gly Ala Thr Ala Cys Leu Val Leu Asn
 65                  70                  75                  80

Leu Phe Cys Ala Asp Leu Leu Phe Ile Ser Ala Ile Pro Leu Val Leu
                 85                  90                  95

Ala Val Arg Trp Thr Glu Ala Trp Leu Leu Gly Pro Val Ala Cys His
            100                 105                 110

Leu Leu Phe Tyr Val Met Thr Leu Ser Gly Ser Val Thr Ile Leu Thr
        115                 120                 125

Leu Ala Ala Val Ser Leu Glu Arg Met Val Cys Ile Val His Leu Gln
    130                 135                 140

Arg Gly Val Arg Gly Pro Gly Arg Arg Ala Arg Ala Val Leu Leu Ala
145                 150                 155                 160

Leu Ile Trp Gly Tyr Ser Ala Val Ala Ala Leu Pro Leu Cys Val Phe
                165                 170                 175

Phe Arg Val Val Pro Gln Arg Leu Pro Gly Ala Asp Gln Glu Ile Ser
            180                 185                 190

Ile Cys Thr Leu Ile Trp Pro Thr Ile Pro Gly Glu Ile Ser Trp Asp
        195                 200                 205

Val Ser Phe Val Thr Leu Asn Phe Leu Val Pro Gly Leu Val Ile Val
    210                 215                 220

Ile Ser Tyr Ser Lys Ile Leu Gln Ile Thr Lys Ala Ser Arg Lys Arg
225                 230                 235                 240

Leu Thr Val Ser Leu Ala Tyr Ser Glu Ser His Gln Ile Arg Val Ser
                245                 250                 255

Gln Gln Asp Phe Arg Leu Phe Arg Thr Leu Phe Leu Leu Met Val Ser
            260                 265                 270

Phe Phe Ile Met Trp Ser Pro Ile Ile Thr Ile Leu Leu Ile Leu
        275                 280                 285

Ile Gln Asn Phe Lys Gln Asp Leu Val Ile Trp Pro Ser Leu Phe Phe
    290                 295                 300

Trp Val Val Ala Phe Thr Phe Ala Asn Ser Ala Leu Asn Pro Ile Leu
305                 310                 315                 320

Tyr Asn Met Thr Leu Cys Arg Asn Glu Trp Lys Lys Ile Phe Cys Cys
                325                 330                 335

Phe Trp Phe Pro Glu Lys Gly Ala Ile Leu Thr Asp Thr Ser Val Lys
            340                 345                 350

Arg Asn Asp Leu Ser Ile Ile Ser Gly
        355                 360

<210> SEQ ID NO 2
<211> LENGTH: 1083
<212> TYPE: DNA
<213> ORGANISM: Human

<400> SEQUENCE: 2
atgtcccctg aatgcgcgcg ggcagcgggc gacgcgccct tgcgcagcct ggagcaagcc      60
aaccgcaccc gctttccctt cttctccgac gtcaagggcg accaccggct ggtgctggcc     120
gcggtggaga caaccgtgct ggtgctcatc tttgcagtgt cgctgctggg caacgtgtgc     180
gccctggtgc tggtggcgcg ccgacgacgc gcggcgcga ctgcctgcct ggtactcaac     240
ctcttctgcg cggacctgct cttcatcagc gctatccctc tggtgctggc cgtgcgctgg     300
actgaggcct ggctgctggg ccccgttgcc tgccacctgc tcttctacgt gatgaccctg     360
agcggcagcg tcaccatcct cacgctggcc gcggtcagcc tggagcgcat ggtgtgcatc     420

```
gtgcacctgc agcgcggcgt gcgggtcct gggcggcggg cgcgggcagt gctgctggcg    480
ctcatctggg ctattcggc ggtcgccgct ctgcctctct gcgtcttctt ccgagtcgtc    540
ccgcaacggc tccccggcgc cgaccaggaa atttcgattt gcacactgat tggcccacc   600 attcctggag agatctcgtg ggatgtctct tttgttactt tgaacttctt ggtgccagga    660
ctggtcattg tgatcagtta ctccaaaatt ttacagatca caaaggcatc aaggaagagg    720
ctcacggtaa gcctggccta ctcggagagc caccagatcc gcgtgtccca gcaggacttc    780
cggctcttcc gcaccctctt cctcctcatg gtctccttct tcatcatgtg gagccccatc    840
atcatcacca tcctcctcat cctgatccag aacttcaagc aagacctggt catctggccg    900
tccctcttct tctgggtggt ggccttcaca tttgctaatt cagccctaaa ccccatcctc    960
tacaacatga cactgtgcag gaatgagtgg aagaaaattt tttgctgctt ctggttccca   1020
gaaaagggag ccattttaac agacacatct gtcaaaagaa atgacttgtc gattatttct   1080
ggc                                                                1083

<210> SEQ ID NO 3
<211> LENGTH: 361
<212> TYPE: PRT
<213> ORGANISM: Mouse

<400> SEQUENCE: 3

Met Ser Pro Glu Cys Ala Gln Thr Thr Gly Pro Gly Pro Ser His Thr
                 5                  10                  15

Leu Asp Gln Val Asn Arg Thr His Phe Pro Phe Phe Ser Asp Val Lys
             20                  25                  30

Gly Asp His Arg Leu Val Leu Ser Val Val Glu Thr Thr Val Leu Gly
         35                  40                  45

Leu Ile Phe Val Val Ser Leu Leu Gly Asn Val Cys Ala Leu Val Leu
     50                  55                  60

Val Ala Arg Arg Arg Arg Arg Gly Ala Thr Ala Ser Leu Val Leu Asn
 65                  70                  75                  80

Leu Phe Cys Ala Asp Leu Leu Phe Thr Ser Ala Ile Pro Leu Val Leu
                 85                  90                  95

Val Val Arg Trp Thr Glu Ala Trp Leu Leu Gly Pro Val Val Cys His
            100                 105                 110

Leu Leu Phe Tyr Val Met Thr Met Ser Gly Ser Val Thr Ile Leu Thr
        115                 120                 125

Leu Ala Ala Val Ser Leu Glu Arg Met Val Cys Ile Val Arg Leu Arg
    130                 135                 140

Arg Gly Leu Ser Gly Pro Gly Arg Arg Thr Gln Ala Ala Leu Leu Ala
145                 150                 155                 160

Phe Ile Trp Gly Tyr Ser Ala Leu Ala Ala Leu Pro Leu Cys Ile Leu
                165                 170                 175

Phe Arg Val Val Pro Gln Arg Leu Pro Gly Gly Asp Gln Glu Ile Pro
            180                 185                 190

Ile Cys Thr Leu Asp Trp Pro Asn Arg Ile Gly Glu Ile Ser Trp Asp
        195                 200                 205

Val Phe Phe Val Thr Leu Asn Phe Leu Val Pro Gly Leu Val Ile Val
    210                 215                 220

Ile Ser Tyr Ser Lys Ile Leu Gln Ile Thr Lys Ala Ser Arg Lys Arg
225                 230                 235                 240

Leu Thr Leu Ser Leu Ala Tyr Ser Glu Ser His Gln Ile Arg Val Ser
                245                 250                 255
```

```
Gln Gln Asp Tyr Arg Leu Phe Arg Thr Leu Phe Leu Leu Met Val Ser
            260                 265                 270
Phe Phe Ile Met Trp Ser Pro Ile Ile Thr Ile Leu Leu Ile Leu
        275                 280                 285
Ile Gln Asn Phe Arg Gln Asp Leu Val Ile Trp Pro Ser Leu Phe Phe
        290                 295                 300
Trp Val Val Ala Phe Thr Phe Ala Asn Ser Ala Leu Asn Pro Ile Leu
305                 310                 315                 320
Tyr Asn Met Ser Leu Phe Arg Asn Glu Trp Arg Lys Ile Phe Cys Cys
                325                 330                 335
Phe Phe Phe Pro Glu Lys Gly Ala Ile Phe Thr Asp Ser Val Arg
            340                 345                 350
Arg Asn Asp Leu Ser Val Ile Ser Ser
            355                 360

<210> SEQ ID NO 4
<211> LENGTH: 1083
<212> TYPE: DNA
<213> ORGANISM: Mouse

<400> SEQUENCE: 4
atgtcccctg agtgtgcaca gacgacgggc cctggcccct cgcacaccct ggaccaagtc      60
aatcgcaccc acttcccttt cttctcggat gtcaagggcg accacggtt ggtgttgagc     120
gtcgtggaga ccaccgttct ggggctcatc tttgtcgtct cactgctggg caacgtgtgt     180
gctctagtgc tggtggcgcg ccgtcggcgc cgtggggcga cagccagcct ggtgctcaac     240
ctcttctgcg cggatttgct cttccaccag gccatccctc tagtgctcgt cgtgcgctgg     300
actgaggcct ggctgttggg gcccgtcgtc tgccacctgc tcttctacgt gatgacaatg     360
agcggcagcg tcacgatcct cacactggcc gcggtcagcc tggagcgcat ggtgtgcatc     420
gtgcgcctcc ggcgcggctt gagcggcccg gggcggcgga ctcaggcggc actgctggct     480
ttcatatggg gttactcggc gctcgccgcg ctgcccctct gcatcttgtt ccgcgtggtc     540
ccgcagcgcc ttcccggcgg ggaccaggaa attccgattt gcacattgga ttggcccaac     600
cgcataggag aaatctcatg ggatgtgttt tttgtgactt tgaacttcct ggtgccggga     660
ctggtcattg tgatcagtta ctccaaaatt ttacagatca cgaaagcatc gcggaagagg     720
cttacgctga gcttggcata ctctgagagc caccagatcc gagtgtccca acaagactac     780
cgactcttcc gcacgctctt cctgctcatg gtttccttct tcatcatgtg gagtcccatc     840
atcatcacca tcctcctcat cttgatccaa aacttccggc aggacctggt catctggcca     900
tccctttct tctgggtggt ggccttcacg tttgccaact ctgccctaaa ccccatactg     960
tacaacatgt cgctgttcag gaacgaatgg aggaagattt tttgctgctt cttttttcca    1020
gagaagggag ccattttac agacacgtct gtcaggcgaa atgacttgtc tgttatttcc    1080
agc                                                                  1083

<210> SEQ ID NO 5
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 5
gctgtggcat gcttttaaac                                                  20
```

<210> SEQ ID NO 6
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 6
cgctgtggat gtctatttgc                                          20

<210> SEQ ID NO 7
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: probe

<400> SEQUENCE: 7
agttcatttc cagtaccctc catcagtggc                                30

<210> SEQ ID NO 8
<211> LENGTH: 361
<212> TYPE: PRT
<213> ORGANISM: Rat

<400> SEQUENCE: 8

```
Met Ser Pro Glu Cys Ala Gln Thr Thr Gly Pro Gly Pro Ser Arg Thr
  1               5                  10                  15

Pro Asp Gln Val Asn Arg Thr His Phe Pro Phe Phe Ser Asp Val Lys
             20                  25                  30

Gly Asp His Arg Leu Val Leu Ser Val Leu Glu Thr Thr Val Leu Gly
         35                  40                  45

Leu Ile Phe Val Val Ser Leu Leu Gly Asn Val Cys Ala Leu Val Leu
     50                  55                  60

Val Val Arg Arg Arg Arg Gly Ala Thr Val Ser Leu Val Leu Asn
 65                  70                  75                  80

Leu Phe Cys Ala Asp Leu Leu Phe Thr Ser Ala Ile Pro Leu Val Leu
                 85                  90                  95

Val Val Arg Trp Thr Glu Ala Trp Leu Leu Gly Pro Val Val Cys His
            100                 105                 110

Leu Leu Phe Tyr Val Met Thr Met Ser Gly Ser Val Thr Ile Leu Thr
        115                 120                 125

Leu Ala Ala Val Ser Leu Glu Arg Met Val Cys Ile Val Arg Leu Arg
    130                 135                 140

Arg Gly Leu Ser Gly Pro Gly Arg Arg Thr Gln Ala Ala Leu Leu Ala
145                 150                 155                 160

Phe Ile Trp Gly Tyr Ser Ala Leu Ala Ala Leu Pro Leu Cys Ile Leu
                165                 170                 175

Phe Arg Val Val Pro Gln Arg Leu Pro Gly Gly Asp Gln Glu Ile Pro
            180                 185                 190

Ile Cys Thr Leu Asp Trp Pro Asn Arg Ile Gly Glu Ile Ser Trp Asp
        195                 200                 205

Val Phe Phe Val Thr Leu Asn Phe Leu Val Pro Gly Leu Val Ile Val
    210                 215                 220

Ile Ser Tyr Ser Lys Ile Leu Gln Ile Thr Lys Ala Ser Arg Lys Arg
```

| | | | | | | | | | | | | | | |
|---|---|---|---|---|---|---|---|---|---|---|---|---|---|---|
| | | 225 | | | | 230 | | | | 235 | | | | 240 |
| Leu | Thr | Leu | Ser | Leu | Ala | Tyr | Ser | Glu | Ser | His | Gln | Ile | Arg | Val | Ser |
| | | | | | 245 | | | | | 250 | | | | | 255 |

Gln Gln Asp Tyr Arg Leu Phe Arg Thr Leu Phe Leu Leu Met Val Ser
            260                    265                    270

Phe Phe Ile Met Trp Ser Pro Ile Ile Thr Ile Leu Leu Ile Leu
        275                    280                    285

Ile Gln Asn Phe Arg Gln Asp Leu Val Ile Trp Pro Ser Leu Phe Phe
    290                    295                    300

Trp Val Val Ala Phe Thr Phe Ala Asn Ser Ala Leu Asn Pro Ile Leu
305                    310                    315                  320

Tyr Asn Met Ser Leu Phe Arg Ser Glu Trp Arg Lys Ile Phe Cys Cys
        325                    330                    335

Phe Phe Phe Pro Glu Lys Gly Ala Ile Phe Thr Glu Thr Ser Ile Arg
            340                    345                    350

Arg Asn Asp Leu Ser Val Ile Ser Thr
        355                    360

<210> SEQ ID NO 9
<211> LENGTH: 1083
<212> TYPE: DNA
<213> ORGANISM: Rat

<400> SEQUENCE: 9

| | | | | | |
|---|---|---|---|---|---|
| atgtccctg | agtgtgcgca | gacgacgggc | cctggcccct | cgcgcacccc | ggaccaagtc | 60 |
| aatcgcaccc | acttcccttt | cttctcggat | gtcaagggcg | accaccggct | ggtgctgagc | 120 |
| gtcctggaga | ccaccgttct | gggactcatc | tttgtggtct | cactgctggg | caacgtgtgt | 180 |
| gccctggtgc | tggtggtgcg | ccgtcggcgc | cgtggggcga | cagtcagctt | ggtgctcaac | 240 |
| ctcttctgcg | cggatttgct | cttcaccagc | gccatccctc | tagtgctcgt | ggtgcgctgg | 300 |
| actgaagcct | ggctgctggg | gcccgtcgtc | tgccacctgc | tcttctacgt | gatgaccatg | 360 |
| agcggcagcg | tcacgatcct | cacgctggcc | gcggtcagcc | tggagcgcat | ggtgtgcatc | 420 |
| gtgcgcctgc | ggcgcggctt | gagcggcccg | ggcggcgga | cgcaggcggc | gctgctggct | 480 |
| ttcatatggg | gttactcggc | gctcgccgcg | ctgcccctct | gcatcttgtt | ccgcgtggtc | 540 |
| ccgcagcgcc | ttcccggcgg | ggaccaggaa | attccgattt | gcacattgga | ttggcccaac | 600 |
| cgcataggag | aaatctcatg | ggatgtgttt | tttgtgactt | tgaacttcct | ggtaccagga | 660 |
| ctggtcattg | tgatcagcta | ctccaagatt | ttacagatca | cgaaagcctc | gcggaagagg | 720 |
| cttacgctga | gcttggcata | ctccgagagc | caccagatcc | gagtgtccca | gcaggactac | 780 |
| cggctcttcc | gaacgctctt | cctgctcatg | gtttccttct | tcatcatgtg | gagtcccatc | 840 |
| atcatcacca | tcctcctcat | cttgatccag | aacttccggc | aggacctggt | tatctggccg | 900 |
| tcccttttct | tctgggtggt | ggccttcacg | tttgccaact | ccgccctaaa | ccccattctg | 960 |
| tacaacatgt | cgctgttcag | gagcgagtgg | aggaagattt | tttgctgctt | cttttttccca | 1020 |
| gagaagggag | ccattttttac | agaaacgtct | atcaggcgaa | atgacttgtc | tgttatttcc | 1080 |
| acc | | | | | | 1083 |

<210> SEQ ID NO 10
<211> LENGTH: 19
<212> TYPE: DNA
<213> ORGANISM: Artificial Sequence
<220> FEATURE:
<221> NAME/KEY: misc_feature
<222> LOCATION: (1)..(19)

```
<223> OTHER INFORMATION: primer

<400> SEQUENCE: 10
gtggtggcct tcacgtttg                                                    19

<210> SEQ ID NO 11
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: primer

<400> SEQUENCE: 11
cgctcctgaa cagcgacat                                                    19

<210> SEQ ID NO 12
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: probe

<400> SEQUENCE: 12
caactccgcc ctaaacccca ttctgt                                            26

<210> SEQ ID NO 13
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer

<400> SEQUENCE: 13
gtcgacatgt cccctgagtg tgcgcagacg acg                                    33

<210> SEQ ID NO 14
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer

<400> SEQUENCE: 14
gctagcttag gtggaaataa cagacaagtc att                                    33

<210> SEQ ID NO 15
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: primer

<400> SEQUENCE: 15
tccgagtgtc ccaacaagac tac                                               23

<210> SEQ ID NO 16
<211> LENGTH: 24
<212> TYPE: DNA
```

```
<213> ORGANISM: Artificial Sequence
<220> FEATURE:
<221> NAME/KEY: misc_feature
<222> LOCATION: (1)..(24)
<223> OTHER INFORMATION: primer

<400> SEQUENCE: 16
gactccacat gatgaagaag gaaa                                              24

<210> SEQ ID NO 17
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: probe

<400> SEQUENCE: 17
ccgcacgctc ttcctgctca tg                                                22

<210> SEQ ID NO 18
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: primer

<400> SEQUENCE: 18
gtggtggcct tcacgtttg                                                    19

<210> SEQ ID NO 19
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: primer

<400> SEQUENCE: 19
cgctcctgaa cagcgacat                                                    19

<210> SEQ ID NO 20
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: probe

<400> SEQUENCE: 20
caactccgcc ctaaacccca ttctgt                                            26
```